(12) United States Patent
Johnson et al.

(10) Patent No.: US 10,793,683 B2
(45) Date of Patent: Oct. 6, 2020

(54) BLOCK CO-POLY(METAL ORGANIC NANOSTRUCTURES) (BCPMONS) AND USES THEREOF

(71) Applicant: Massachusetts Institute of Technology, Cambridge, MA (US)

(72) Inventors: Jeremiah A. Johnson, Boston, MA (US); Yufeng Wang, Hong Kong (CN); Michelle MacLeod, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/662,239

(22) Filed: Jul. 27, 2017

(65) Prior Publication Data

US 2018/0030213 A1 Feb. 1, 2018
US 2018/0258233 A9 Sep. 13, 2018

Related U.S. Application Data

(60) Provisional application No. 62/367,630, filed on Jul. 27, 2016.

(51) Int. Cl.
*C08J 3/075* (2006.01)
*C07F 15/00* (2006.01)
(Continued)

(52) U.S. Cl.
CPC .............. *C08J 3/075* (2013.01); *A61K 47/32* (2013.01); *C07F 3/06* (2013.01); *C07F 15/00* (2013.01);
(Continued)

(58) Field of Classification Search
CPC ....................................................... C08J 3/075
(Continued)

(56) References Cited

U.S. PATENT DOCUMENTS 9,447,129 B2 9/2016 Johnson et al.
9,822,216 B2 11/2017 Mahanthappa et al.
(Continued)

FOREIGN PATENT DOCUMENTS

WO WO 2016/023036 A1 2/2016

OTHER PUBLICATIONS

Zheng, J. Am. Chem. Soc. 2016, 138, 4927-4937.*
Zhang, Angew. Chem. Int. Ed. 2015, 54, 6152-6157 Published online: Apr. 29, 2015.*
Wang, Chemical Society Reviews (2009), 38(5), 1315-1329.*
Gadzikwa, Chem. Commun., 2008, 5493-5495 | 5493.*
Goto, J. Am. Chem. Soc. . 2008, 130, 14354-14355.*
Fenlon, Eur. J. Org. Chem. 2008, 3065-3068 p. 3067.*
Zhang, Coordination Chemistry Reviews 257 (2013), 1373-1408.*
International Search Report and Written Opinion for PCT/US2017/055145, dated Jan. 23, 2018.
International Search Report and Written Opinion for PCT/US2017/044259, dated Jan. 9, 2018.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
(Continued)

*Primary Examiner* — Nizal S Chandrakumar
(74) *Attorney, Agent, or Firm* — Wolf, Greenfield & Sacks, P.C.

(57) ABSTRACT

The present disclosure provides (block co-polymer)-(metal organic framework) conjugates (BCPMOFs), such as (block co-polymer)-(metal organic nanostructure) conjugates (BCPMONs), and thermoplastic elastomers, gels, and compositions thereof. Exemplary BCPMONs include (block co-polymer)-(metal organic cage) conjugates (BCPMOCs), (block co-polymer)-(metal organic paddlewheel) conjugates, and (block co-polymer)-(metal organic square) conjugates, such as BCPMONs of Formula (A), (B), or (C). Also described herein are macromonomers for preparing the BCPMONs; thermoplastic elastomers, gels, and compositions involving the BCPMONs; methods of preparing the BCPMONs, thermoplastic elastomers, gels, and compositions; and methods of using the BCPMONs, thermoplastic elastomers, gels, and compositions.

(A)

(B)

(Continued)

-continued

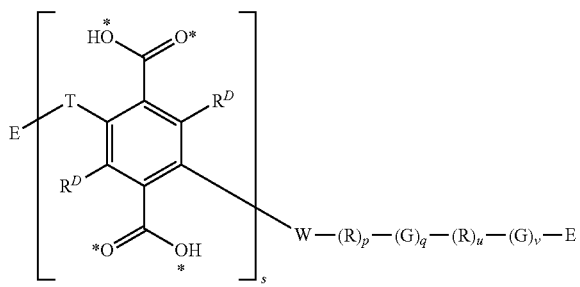

(C)

27 Claims, 35 Drawing Sheets

(51) Int. Cl.
C08G 83/00 (2006.01)
C07F 3/06 (2006.01)
A61K 47/32 (2006.01)
C08F 293/00 (2006.01)

(52) U.S. Cl.
CPC ...... C07F 15/0066 (2013.01); C08F 293/005 (2013.01); C08G 83/001 (2013.01); C08G 83/008 (2013.01)

(58) Field of Classification Search
USPC .......................................................... 546/255
See application file for complete search history.

(56) References Cited

U.S. PATENT DOCUMENTS

| | | | |
|---|---|---|---|
| 10,023,536 B2 | 7/2018 | Johnson et al. | |
| 10,153,513 B2 * | 12/2018 | Grubbs | C08G 81/00 |
| 2002/0183473 A1 | 12/2002 | Matyjaszewski et al. | |
| 2002/0198328 A1 | 12/2002 | L'Alloret | |
| 2003/0004364 A1 | 1/2003 | Yaghi et al. | |
| 2003/0065023 A1 | 4/2003 | Swindell et al. | |
| 2005/0109976 A1 | 5/2005 | Fuchs et al. | |
| 2011/0243848 A1 | 10/2011 | Appel et al. | |
| 2013/0029649 A1 | 1/2013 | Hanson et al. | |
| 2013/0296491 A1 | 11/2013 | Xia et al. | |
| 2013/0324666 A1 | 12/2013 | Yan et al. | |
| 2014/0142249 A1 | 5/2014 | Cho et al. | |
| 2015/0225438 A1 | 8/2015 | Johnson et al. | |
| 2016/0024246 A1 | 1/2016 | Mahanthappa et al. | |
| 2016/0289392 A1 | 10/2016 | Grubbs et al. | |
| 2016/0361702 A1 * | 12/2016 | Cohen | B01J 20/262 |
| 2017/0073311 A1 | 3/2017 | Johnson et al. | |
| 2018/0030213 A1 | 2/2018 | Johnson et al. | |
| 2018/0094099 A1 | 4/2018 | Johnson et al. | |
| 2019/0192672 A1 | 6/2019 | Johnson et al. | |

OTHER PUBLICATIONS

Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.
International Search Report and Written Opinion for PCT/US2017/048641, dated Nov. 9, 2017.
Invitation to Pay Additional Fees for PCT/US2017/044259, dated Nov. 8, 2017.
Allen et al., Chemically crosslinked isoreticular metal-organic frameworks. Chem Commun (Camb). Apr. 21, 2013;49(31):3200-2. doi: 10.1039/c3cc40635k. Epub Mar. 14, 2013.
Allen et al., Exploration of chemically cross-linked metal-organic frameworks. Inorg Chem. Jul. 7, 2014;53(13):7014-9. doi: 10.1021/ic500951b. Epub Jun. 19, 2014.
Altintas et al., ATRP-based polymers with modular ligation points under thermal and thermomechanical stress. Polym. Chem., Feb. 2015;6:2854-68.
Bates et al., Block Copolymers-Designer Soft Materials. Physics Today 1999;52(2):32.
Bates et al., Multiblock polymers: panacea or Pandora's box? Science. Apr. 27, 2012;336(6080):434-40. doi: 10.1126/science.1215368.
Bates et al., Polymer-polymer phase behavior. Science. Feb. 22, 1991;251(4996):898-905.
Binauld et al., Precise Synthesis of Molecularly Defined Oligomers and Polymers by Orthogonal Iterative Divergent/Convergent Approaches. Macromol. Rapid Commun., 32: 147-168. doi:10.1002/marc.201000548.
Brown et al., Halide-induced supramolecular ligand rearrangement. J Am Chem Soc. Nov. 10, 2004;126(44):14316-7.
Burnworth et al., Optically healable supramolecular polymers. Nature. Apr. 21, 2011;472(7343):334-7. doi: 10.1038/nature09963.
Burts et al., Using EPR to Compare PEG-branch-nitroxide "Bivalent-Brush Polymers" and Traditional PEG Bottle—Brush Polymers: Branching Makes a Difference. Macromolecules, Oct. 2012;45(20):8310-8318.
Calvez et al., One step synthesis of MOF-polymer composites. RSC Adv., 2016;6:17314-7.
Chakrabarty et al., Supramolecular coordination: self-assembly of finite two- and three-dimensional ensembles. Chem Rev. Nov. 9, 2011;111(11):6810-918. doi: 10.1021/cr200077m. Epub Aug. 24, 2011.
Cook et al., Biomedical and biochemical applications of self-assembled metallacycles and metallacages. Acc Chem Res. Nov. 19, 2013;46(11):2464-74. doi: 10.1021/ar400010v. Epub Jun. 20, 2013.
Cook et al., Metal-organic frameworks and self-assembled supramolecular coordination complexes: comparing and contrasting the design, synthesis, and functionality of metal-organic materials. Chem Rev. Jan. 9, 2013;113(1):734-77. doi: 10.1021/cr3002824. Epub Nov. 2, 2012.
Cook et al., Recent Developments in the Preparation and Chemistry of Metallacycles and Metallacages via Coordination. Chem Rev. Aug. 12, 2015;115(15):7001-45. doi: 10.1021/cr5005666. Epub Mar. 27, 2015.
De La Cruz et al., Theory of microphase separation in graft and star copolymers. Macromolecules, 1986;19(10):2501-8. DOI: 10.1021/ma00164a008.
Eryazici et al., Square-planar Pd(II), Pt(II), and Au(III) terpyridine complexes: their syntheses, physical properties, supramolecular constructs, and biomedical activities. Chem Rev. Jun. 2008;108(6):1834-95. doi: 10.1021/cr0781059.
Fujita et al., Coordination assemblies from a Pd(II)-cornered square complex. Acc Chem Res. Apr. 2005;38(4):371-80.
Fujita et al., Metal-directed self-assembly of two- and three-dimensional synthetic receptors. Chem. Soc. Rev., 1998;27:417-25. doi: 10.1039/A827417Z.
Fujita et al., Self-Assembly of M30L60 Icosidodecahedron. Chem 2016;1:91.
Fujita et al., Self-assembly of ten molecules into nanometre-sized organic host frameworks. Nature Nov. 1995;378:469-71. doi:10.1038/378469a0.
Furukawa et al., Structuring of metal-organic frameworks at the mesoscopic/macroscopic scale. Chem Soc Rev. Aug. 21, 2014;43(16):5700-34. doi: 10.1039/c4cs00106k.
Furukawa et al., The chemistry and applications of metal-organic frameworks. Science. Aug. 30, 2013;341:1230444. doi: 10.1126/science.1230444.
Gamage et al., MOF-5-Polystyrene: Direct Production from Monomer, Improved Hydrolytic Stability, and Unique Guest Adsorption. Angew Chem Int Ed Engl. Sep. 19, 2016;55(39):12099-103. doi: 10.1002/anie.201606926. Epub Aug. 24, 2016.
Gestwicki et al., Influencing Receptor-Ligand Binding Mechanisms with Multivalent Ligand Architecture. J. Am. Chem. Soc., 2002;124(50):14922-33. DOI: 10.1021/ja027184x.

(56) References Cited

OTHER PUBLICATIONS

Hardy et al., Generation of metallosupramolecular polymer gels from multiply functionalized grid-type complexes. New J. Chem., 2012;36:668-73.
Hoogenboom et al., L-Lactide Polymerization Utilizing a Hydroxy-Functionalized 3,6-Bis(2-pyridyl)pyridazine as Supramolecular (Co)initiator: Construction of Polymeric [2 × 2] Grids. Macromolecules, 2003;36(13):4743-9. DOI: 10.1021/ma034119e.
Hosono et al., Metal-Organic Polyhedral Core as a Versatile Scaffold for Divergent and Convergent Star Polymer Synthesis. J Am Chem Soc. May 25, 2016;138(20):6525-31. doi: 10.1021/jacs.6b01758. Epub May 11, 2016.
Jansze et al., Ligand Aspect Ratio as a Decisive Factor for the Self-Assembly of Coordination Cages. J Am Chem Soc. Feb. 17, 2016;138(6):2046-54. doi: 10.1021/jacs.5b13190. Epub Feb. 8, 2016.
Jiang et al., Iterative Exponential Growth Synthesis and Assembly of Uniform Diblock Copolymers. J Am Chem Soc. Aug. 3, 2016;138(30):9369-72. doi: 10.1021/jacs.6b04964. Epub Jul. 20, 2016.
Jiang et al., Thiophene-coated functionalized M12L24 spheres: synthesis, characterization, and electrochemical properties. Chem Asian J. Oct. 2012;7(10):2230-4. doi: 10.1002/asia.201200413. Epub Jul. 9, 2012.
Johnson et al., Construction of Linear Polymers, Dendrimers, Networks, and Other Polymeric Architectures by Copper-Catalyzed Azide-Alkyne Cycloaddition "Click" Chemistry. Macromol Rapid Commun Jul. 2008;29(12-13):1052-72.
Johnson et al., Synthesis of degradable model networks via ATRP and click chemistry. J Am Chem Soc. May 24, 2006;128(20):6564-5.
Kawamoto et al., Dual Role for 1,2,4,5-Tetrazines in Polymer Networks: Combining Diels-Alder Reactions and Metal Coordination to Generate Functional Supramolecular Gels. ACS Macro Letters 2015;4(4):458-61. doi: 10.1021/acsmacrolett.5b00221.
Kikuchi et al., Stepwise DNA condensation by a histone-mimic peptide-coated M12L24 spherical complex. Chem. Sci., 2014;5:3257-60.
Kuppler et al., Potential applications of metal-organic frameworks. Coord. Chem. Rev. 2009;253:3042-66.
Leibfarth et al., Scalable synthesis of sequence-defined, unimolecular macromolecules by Flow-IEG. Proc Natl Acad Sci U S A. Aug. 25, 2015;112(34):10617-22. doi: 10.1073/pnas.1508599112. Epub Aug. 12, 2015.
Li et al., Cross-linked supramolecular polymer gels constructed from discrete multi-pillar[5]arene metallacycles and their multiple stimuli-responsive behavior. J Am Chem Soc. Jun. 18, 2014;136(24):8577-89. doi: 10.1021/ja413047r. Epub Mar. 11, 2014.
Li et al., Design and synthesis of an exceptionally stable and highly porous metal-organic framework. Nature Nov. 1999;402:276-79. doi:10.1038/46248.
Li et al., Metallo/clusto hybridized supramolecular polymers. Soft Matter. Dec. 7, 2014;10(45):9038-53. doi: 10.1039/c4sm01684j.
Liu et al., Composites of metal-organic frameworks and carbon-based materials: preparations, functionalities and applications. J. Mater. Chem. A, 2016;4:3584-616.
Lutz et al., From precision polymers to complex materials and systems. Nat Rev Mat, 2016;1:1. doi:10.1038/natrevmats.2016.24.
Lynd et al., Influence of Polydispersity on the Self-Assembly of Diblock Copolymers. Macromolecules, 2005;38(21):8803-10.
Mai et al., Self-assembly of block copolymers. Chem Soc Rev. Sep. 21, 2012;41(18):5969-85. doi: 10.1039/c2cs35115c. Epub Jul. 9, 2012.
Matyjaszewski et al., Nanostructured functional materials prepared by atom transfer radical polymerization. Nat Chem. Jul. 2009;1(4):276-88. doi: 10.1038/nchem.257. Epub Jun. 22, 2009.
McConnell et al., Stimuli-Responsive Metal-Ligand Assemblies. Chem Rev. Aug. 12, 2015;115(15):7729-93. doi: 10.1021/cr500632f. Epub Apr. 16, 2015.

McDonald et al., Polymer@MOF@MOF: "grafting from" atom transfer radical polymerization for the synthesis of hybrid porous solids. Chem. Commun. 2015;51:11994-6.
Meng et al., Controlling the transmission of stereochemical information through space in terphenyl-edged Fe4L6 cages. J Am Chem Soc. Aug. 31, 2011;133(34):13652-60. doi: 10.1021/ja205254s. Epub Aug. 9, 2011.
Nese et al., Synthesis, Characterization, and Properties of Starlike Poly(n-butyl acrylate)-b-poly(methyl methacrylate) Block Copolymers. Macromolecules, 2010;43(3):1227-35. DOI: 10.1021/ma902447p.
Nitschke et al., Construction, substitution, and sorting of metalloorganic structures via subcomponent self-assembly. Acc Chem Res. Feb. 2007;40(2):103-12.
Olenyuk et al., Self-assembly of nanoscale cuboctahedra by coordination chemistry. Nature. Apr. 29, 1999;398(6730):796-9.
Oliveri et al., Heteroligated supramolecular coordination complexes formed via the halide-induced ligand rearrangement reaction. Acc Chem Res. Dec. 2008;41(12):1618-29. doi: 10.1021/ar800025w.
Pakula et al., Effect of chain topology on the self-organization and the mechanical properties of poly(n-butyl acrylate)-b-polystyrene block copolymers. Polymer, May 26, 2011;52(12):2576-83.
Pluth et al., Proton-mediated chemistry and catalysis in a self-assembled supramolecular host. Acc Chem Res. Oct. 20, 2009;42(10):1650-9. doi: 10.1021/ar900118t.
Pollino et al., Cross-linked and functionalized 'universal polymer backbones' via simple, rapid, and orthogonal multi-site self-assembly. Tetrahedron, 60(34), 7205-7215. DOI: 10.1016/j.tet.2004.05.055.
Reboul et al., Mesoscopic architectures of porous coordination polymers fabricated by pseudomorphic replication. Nat Mater. Jun. 24, 2012;11(8):717-23. doi: 10.1038/nmat3359.
Rodenas et al., Metal-organic framework nanosheets in polymer composite materials for gas separation. Nat Mater. Jan. 2015;14(1):48-55. doi: 10.1038/nmat4113. Epub Nov. 2, 2014.
Sato et al., Remarkable stabilization of M(12)L(24) spherical frameworks through the cooperation of 48 Pd(II)-pyridine interactions. J Am Chem Soc. May 6, 2009;131(17):6064-5. doi: 10.1021/ja900676f.
Seitz et al., Self-Assembly and Stress Relaxation in Acrylic Triblock Copolymer Gels. Macromolecules, 2007;40(4):1218-26.
Semino et al., Microscopic Model of the Metal-Organic Framework/Polymer Interface: A First Step toward Understanding the Compatibility in Mixed Matrix Membranes. ACS Appl Mater Interfaces. Jan. 13, 2016;8(1):809-19. doi: 10.1021/acsami.5b10150. Epub Dec. 22, 2015.
Seredyuk et al., Spin-crossover and liquid crystal properties in 2D cyanide-bridged Fe(II)-M(I/II) metalorganic frameworks. Inorg Chem. Nov. 1, 2010;49(21):10022-31. doi: 10.1021/ic101304v.
Shi et al., Producing Small Domain Features Using Miktoarm Block Copolymers with Large Interaction Parameters. ACS Macro Lett., 2015;4(11):1287-92. DOI: 10.1021/acsmacrolett.5b00712.
Smulders et al., Integrative self-sorting synthesis of a Fe8Pt6L24 cubic cage. Angew Chem Int Ed Engl. Jul. 2, 2012;51(27):6681-5. doi: 10.1002/anie.201202050. Epub Jun. 5, 2012.
Stadler et al., Formation of RACK- and grid-type metallosupramolecular architectures and generation of molecular motion by reversible uncoiling of helical ligand strands. Chemistry. Jun. 2, 2006;12(17):4503-22.
Stang et al., Self-Assembly, Symmetry, and Molecular Architecture: Coordination as the Motif in the Rational Design of Supramolecular Metallacyclic Polygons and Polyhedra. Acc. Chem. Res., 1997;30(12):502-18. DOI: 10.1021/ar9602011.
Stock et al., Synthesis of Metal-Organic Frameworks (MOFs): Routes to Various MOF Topologies, Morphologies, and Composites. Chem. Rev., 2012;112(2):933-69.
Uemura et al., Polymerization reactions in porous coordination polymers. Chem Soc Rev. May 2009;38(5):1228-36. doi: 10.1039/b802583p. Epub Feb. 3, 2009.
Van Genabeek et al., Synthesis and Self-Assembly of Discrete Dimethylsiloxane-Lactic Acid Diblock Co-oligomers: The

(56) References Cited

OTHER PUBLICATIONS

Dononacontamer and Its Shorter Homologues. J Am Chem Soc. Mar. 30, 2016;138(12):4210-8. doi: 10.1021/jacs.6b00629. Epub Mar. 21, 2016.
Verduzco et al., Structure, function, self-assembly, and applications of bottlebrush copolymers. Chem. Soc. Rev., 2015;44:2405-20.
Wang et al., A supramolecular approach to combining enzymatic and transition metal catalysis. Nat Chem. Feb. 2013;5(2):100-3. doi: 10.1038/nchem.1531. Epub Jan. 6, 2013.
Wang et al., Block Co-PolyMOCs by Stepwise Self-Assembly. J Am Chem Soc. Aug. 24, 2016;138(33):10708-15. doi: 10.1021/jacs. 6b06712. Epub Aug. 16, 2016.
Wang et al., Star PolyMOCs with Diverse Structures, Dynamics, and Functions by Three-Component Assembly. Angew Chem Int Ed Engl. Jan. 2, 2017;56(1):188-192. doi: 10.1002/anie.201609261. Epub Dec. 5, 2016.
Weng et al., Understanding the Mechanism of Gelation and Stimuli-Responsive Nature of a Class of Metallo-Supramolecular Gels. J. Am. Chem. Soc., 2006;128(35):11663-72. DOI: 10.1021/ja063408q.
Wood et al., Two-stage directed self-assembly of a cyclic [3]catenane. Nat Chem. Apr. 2015;7(4):354-8. doi: 10.1038/nchem.2205.
Xie et al., Construction of a highly symmetric nanosphere via a one-pot reaction of a tristerpyridine ligand with Ru(II). J Am Chem Soc. Jun. 11, 2014;136(23):8165-8. doi: 10.1021/ja502962j. Epub May 22, 2014.
Xie et al., Hydrophobic-Driven, Metallomacrocyclic Assembly—Towards Quantitative Construction. Eur. J. Inorg. Chem. 2016;11:1671-7.
Xie et al., Precise Molecular Fission and Fusion: Quantitative Self-Assembly and Chemistry of a Metallo-Cuboctahedron. Angew. Chem., 2015;54:9224-9.
Yamazaki et al., Dynamic Viscoelasticity of Poly(butyl acrylate) Elastomers Containing Dangling Chains with Controlled Lengths. Macromolecules, 2011;44(22):8829-34. DOI: 10.1021/ma201941v.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yang et al., Supramolecular Polymers: Historical Development, Preparation, Characterization, and Functions. Chem Rev. Aug. 12, 2015;115(15):7196-239. doi: 10.1021/cr500633b. Epub Mar. 13, 2015.
Zhang et al., Challenges and recent advances in MOF-polymer composite membranes for gas separation. Inorg. Chem. Front., 2016;3:896-909. DOI: 10.1039/C6QI00042H.
Zhang et al., Metal-organic gels: From discrete metallogelators to coordination polymers. Coordination Chemistry Reviews Apr. 2013;257(7-8):1373-1408.
Zhang et al., Polymer-Metal-Organic Frameworks (polyMOFs) as Water Tolerant Materials for Selective Carbon Dioxide Separations. J Am Chem Soc. Jan. 27, 2016;138(3):920-5. doi: 10.1021/jacs. 5b11034. Epub Jan. 13, 2016.
Zhao et al., Chiral amide directed assembly of a diastereo- and enantiopure supramolecular host and its application to enantioselective catalysis of neutral substrates. J Am Chem Soc. Dec. 18, 2013;135(50):18802-5. doi: 10.1021/ja411631v. Epub Dec. 5, 2013.
Zheng et al., Construction of Smart Supramolecular Polymeric Hydrogels Cross-linked by Discrete Organoplatinum(II) Metallacycles via Post-Assembly Polymerization. J Am Chem Soc. Apr. 13, 2016;138(14):4927-37. doi: 10.1021/jacs.6b01089. Epub Mar. 29, 2016.
Zhou et al., Introduction to metal-organic frameworks. Chem Rev. Feb. 8, 2012;112(2):673-4. doi: 10.1021/cr300014x. Epub Jan. 26, 2012.
Zhukhovitskiy et al., Highly branched and loop-rich gels via formation of metal-organic cages linked by polymers. Nat Chem. Jan. 2016;8(1):33-41. doi: 10.1038/nchem.2390. Epub Nov. 16, 2015.
Zhukhovitskiy et al., Polymer Structure Dependent Hierarchy in PolyMOC Gels. Macromolecules, 2016;49(18):6896-902.
Ayala et al., Hierarchical structure and porosity in UiO-66 polyMOFs. Chem Commun (Camb). Mar. 9, 2017;53(21):3058-3061. doi: 10.1039/c6cc10225e.
Laurier et al., Iron(III)-based metal-organic frameworks as visible light photocatalysts. J Am Chem Soc. Oct. 2, 2013;135(39):14488-91. doi: 10.1021/ja405086e. Epub Sep. 17, 2013.
Schukraft et al., Isoreticular expansion of polyMOFs achieves high surface area materials. Chem Commun (Camb). Sep. 26, 2017;53(77):10684-10687. doi: 10.1039/c7cc04222a.
International Search Report and Written Opinion for PCT/US2015/015032, dated May 8, 2015.
International Preliminary Report on Patentability for PCT/US2015/015032, dated Aug. 18, 2016.
Kim et al., Anion-directed self-assembly of coordination polymer into tunable secondary structure. J Am Chem Soc. Jun. 9, 2004;126(22):7009-14., with Supporting Information.
Tam et al., Recent advances in metallogels. Chem Soc Rev. Feb. 21, 2013;42(4):1540-67. doi: 10.1039/c2cs35354g. Epub Jan. 8, 2013.
International Preliminary Report on Patentability for PCT/US2017/044259, dated Feb. 7, 2019.
International Preliminary Report on Patentability for PCT/US2017/055145, dated Apr. 18, 2019.
International Preliminary Report on Patentability for PCT/US2017/048641, dated Mar. 7, 2019.
Bates et al., Polarity-switching top coats enable orientation of sub-10-nm block copolymer domains. Science. Nov. 9, 2012;338(6108):775-9. doi: 10.1126/science.1226046.
Bohbot-Raviv et al., Discovering new ordered phases of block copolymers. Phys Rev Lett. Oct. 16, 2000;85(16):3428-31.
Cheng et al., Well-defined diblock macromonomer with a norbornene group at block junction: anionic living linking synthesis and ring-opening metathesis polymerization. Macromol. Mar. 4, 2010;43(7):3153-5.
Dalsin et al., Bottlebrush block polymers: Quantitative theory and experiments. ACS Nano. Nov. 6, 2015;9(12):12233-45.
Davis et al., Atom transfer radical polymerization of tert-butyl acrylate and preparation of block copolymers. Macromol. May 30, 2000;33(11):4039-47.
Frechet, Functional polymers and dendrimers: reactivity, molecular architecture, and interfacial energy. Science. Mar. 25, 1994;263(5154):1710-5.
Grason et al., Geometric theory of diblock copolymer phases. Phys Rev Lett. Jul. 31, 2003;91(5):058304. 4 pages.
Gu et al., PolyMOF Nanoparticles: Dual Roles of a Multivalent polyMOF Ligand in Size Control and Surface Functionalization. Angewandte Chemie Int. Ed. 2019;58:2-8. Epub Sep. 10, 2019.
Hawker et al., Preparation of polymers with controlled molecular architecture. A new convergent approach to dendritic macromolecules. J Am Chem Soc. Oct. 1990;112(21):7638-47.
Heroguez et al., Novel Styrene-Butadiene Copolymers by Ring-Opening Metathesis Polymerization. Macromol. Oct. 3, 2000;33(20):7241-8.
Jakubowski et al., Activators regenerated by electron transfer for atom transfer radical polymerization of styrene. Macromol. Jan. 10, 2006;39(1):39-45.
Jeong et al., Highly tunable self-assembled nanostructures from a poly (2-vinylpyridine-b-dimethylsiloxane) block copolymer. Nano Lett. Sep. 27, 2011;11(10):4095-101.
Jiang et al., Morphology and Phase Diagram of Comb Block Copolymer a m+ 1 (BC) m. J Phys Chem B. May 7, 2009;113(21):7462-7.
Jung et al., Orientation-controlled self-assembled nanolithography using a polystyrene-polydimethylsiloxane block copolymer. Nano Lett. Jul. 11, 2007;7(7):2046-50.
Kale et al., Supramolecular assemblies of amphiphilic homopolymers. Langmuir. May 19, 2009;25(17):9660-70.
Kawamoto et al., Loops versus branch functionality in model click hydrogels. Macromol. Dec. 1, 2015;48(24):8980-8.
Lee et al., Novel phase morphologies in a microphase-separated dendritic polymer melt. Macromol. Jan. 12, 2009;42(3):849-59.
Li et al., Crosslinking-induced morphology change of latex nanoparticles: A study of RAFT-mediated polymerization in aqueous dispersed

(56) References Cited

OTHER PUBLICATIONS media using amphiphilic double-brush copolymers as reactive surfactants. J Polym Sci Part A: Polym Chem. Nov. 15, 2014;52(22):3250-9.

Li et al., Dynamic cylindrical assembly of triblock copolymers by a hierarchical process of covalent and supramolecular interactions. J Am Chem Soc. Jan. 4, 2011;133(5):1228-31.

Li et al., Efficient synthesis of narrowly dispersed amphiphilic double-brush copolymers through the polymerization reaction of macromonomer micelle emulsifiers at the oil-water interface. Polym Chem. 2016;7(27):4476-85.

Li et al., Facile syntheses of cylindrical molecular brushes by a sequential RAFT and ROMP "grafting-through" methodology. J Polym Sci A Polym Chem. Oct. 15, 2009;47(20):5557-5563.

Li et al., Synthesis of Hetero-Grafted Amphiphilic Diblock Molecular Brushes and Their Self-Assembly in Aqueous Medium. Macromolecules. 2010;43(3):1182-1184.

Li et al., Well-defined amphiphilic double-brush copolymers and their performance as emulsion surfactants. Macromol. May 18, 2012;45(11):4623-9.

Luo et al., Toroidal structures from brush amphiphiles. Chem Commun. 2014;50(5):536-8. Supporting information included.

Rangadurai et al., Temporal and triggered evolution of host-guest characteristics in amphiphilic polymer assemblies. J Am Chem Soc. Jun. 10, 2016;138(24):7508-11.

Rasmussen et al., Improved numerical algorithm for exploring block copolymer mesophases. J Polym Sci Part B: Poly Phys. Aug. 15, 2002;40(16):1777-83.

Runge et al., "Synthesis and Self-Assembly of Bottlebrush Block Copolymers" PMSEPreprints, 2005, 92, 5-6.

Rzayev, Synthesis of polystyrene—polylactide bottlebrush block copolymers and their melt self-assembly into large domain nanostructures. Macromol. Feb. 20, 2009;42(6):2135-41.

Sides et al., Parallel algorithm for numerical self-consistent field theory simulations of block copolymer structure. Polymer. Sep. 1, 2003;44(19):5859-66.

Sinturel et al., High $\chi$-low N block polymers: how far can we go?. ACS Macro Lett. Sep. 2, 2015;4:1044-50.

Sowers et al., Redox-responsive branched-bottlebrush polymers for in vivo MRI and fluorescence imaging. Nat Commun. Nov. 18, 2014;5:5460. 9 pages.

Theodorakis et al., Interplay between chain collapse and microphase separation in bottle-brush polymers with two types of side chains. Macromol. May 4, 2010;43(11):5137-48.

Yuan et al., One-pot syntheses of amphiphilic centipede-like brush copolymers via combination of ring-opening polymerization and "click" chemistry. Macromol. Jan. 27, 2010;43(4):1739-46.

Zhao et al., Polystyrene—Polylactide Bottlebrush Block Copolymer at the Air/Water Interface. Macromol. Sep. 28, 2009;42(22):9027-33.

Zheng et al., Morphology of ABC triblock copolymers. Macromol. Oct. 1995;28(21):7215-23.

Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.

Boyer, Glass temperatures of polyethylene. Macromolecules 1973;6(2):288-299.

* cited by examiner

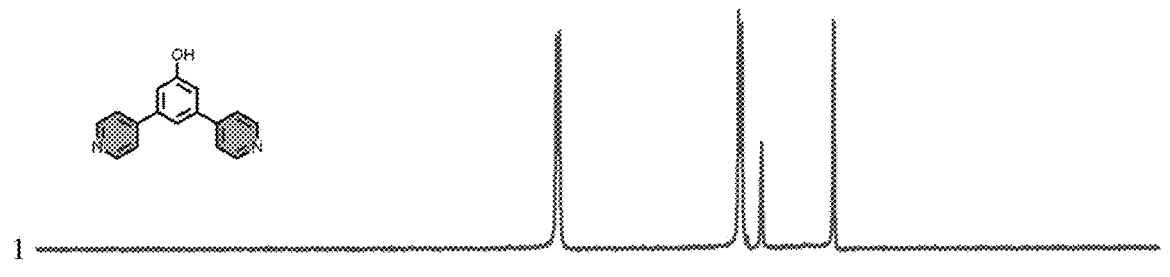
Figure 9A
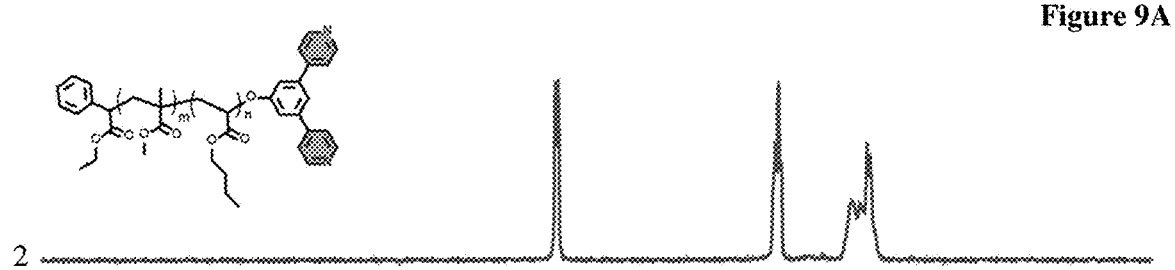
Figure 9B
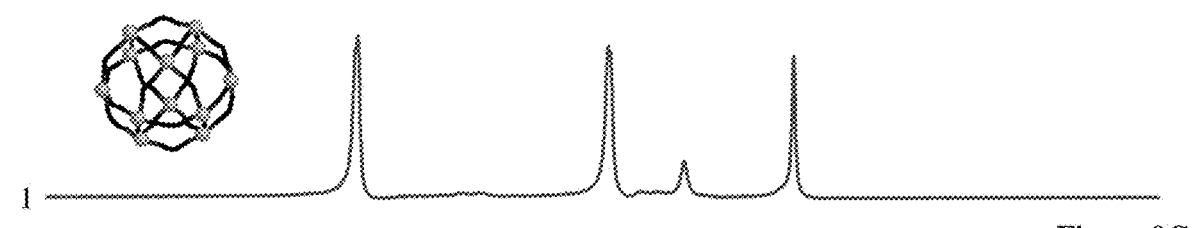
Figure 9C
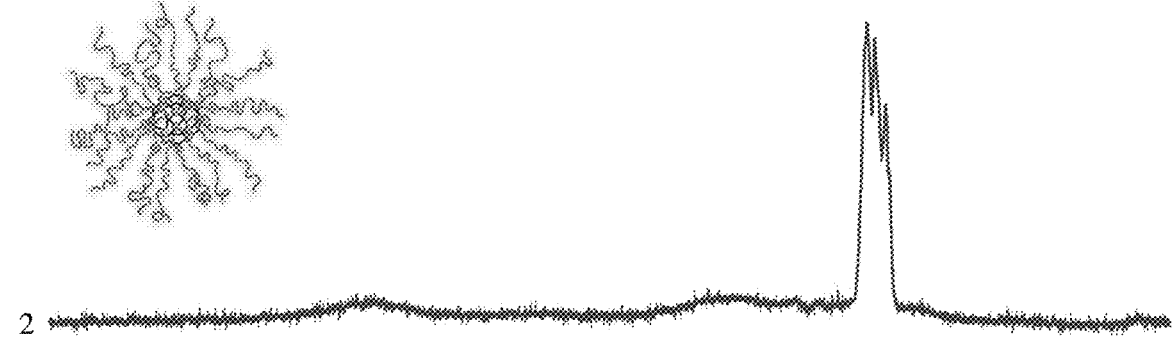
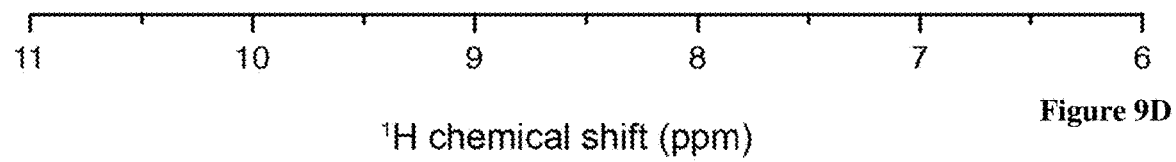
Figure 9D
¹H chemical shift (ppm)

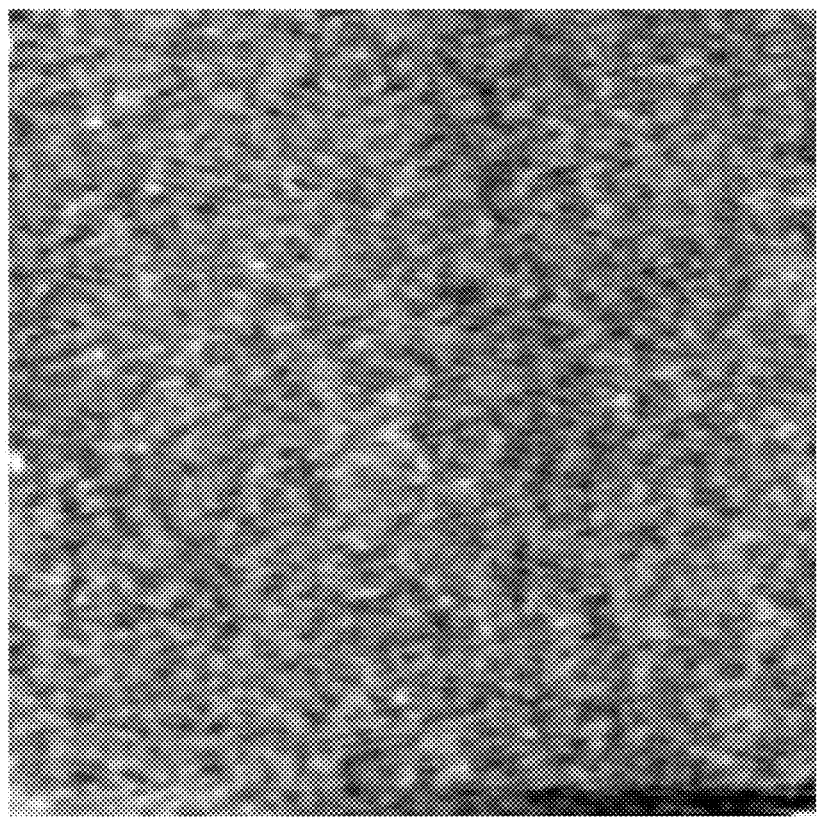
Figure 10
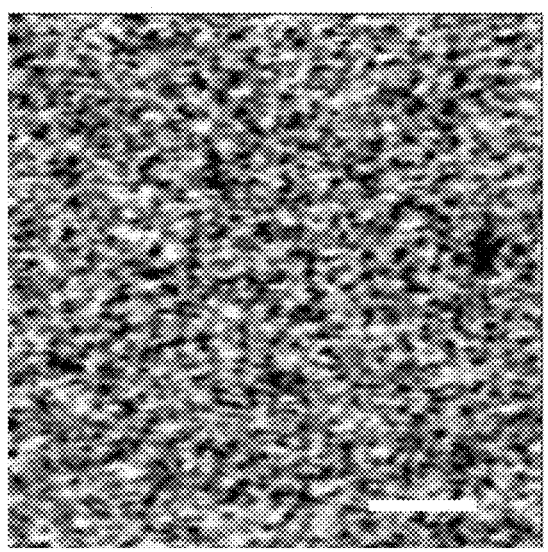 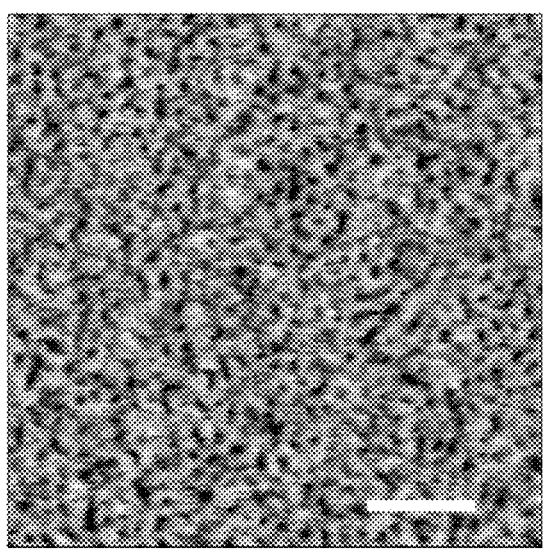
Figure 11A                                    Figure 11B

BLOCK CO-POLY(METAL ORGANIC NANOSTRUCTURES) (BCPMONS) AND USES THEREOF

RELATED APPLICATION

The present application claims priority under 35 U.S.C. § 119(e) to U.S. provisional application, U.S. Ser. No. 62/367,630, filed Jul. 27, 2016, which is incorporated herein by reference.

GOVERNMENT SUPPORT

This invention was made with Government support under Grant Nos. CHE-1334703 and CHE-1351646 awarded by the National Science Foundation. The Government has certain rights in the invention.

BACKGROUND OF THE DISCLOSURE

Coordination-directed self-assembly of metal ions and organic ligands is a powerful approach for the construction of two- and three-dimensional molecular architectures.[1-10] Examples of such structures range from discrete metal organic cycles and metal organic cages/polyhedra (MOCs/MOPs)[11-27] to infinite metal organic frameworks (MOFs)[28-31]. By rational design of the ligands and proper choice of the metal ions, these materials can feature well-defined sizes, shapes, geometries, and porosity, which enable applications in selective encapsulation, catalysis, sensing, etc.[32-40]

Inspired by the structural versatility as well as the dynamic nature of metal coordination, much effort has recently been devoted to the introduction of metal organic structures, which are generally rigid, into elastic polymer networks. The goal is to synthesize a new class of hybrid materials that have tunable viscoelastic properties and are capable of realizing multiple functions originally only possible for MOFs and MOCs.[41-46] For example, in 2015 the synthesis of polyethylene glycol (PEG) hydrogels cross-linked via metallosupramolecular assembly of $M_xL_y$ clusters (x metal ions and y ligands for each junction; $M_4L_4$ squares were targeted)[47] derived from bispyridyl tetrazine ligands bound to the ends of PEG chains and either $Fe^{2+}$ or $Ni^{2+}$ ions was reported on.[48] These gels were used as scaffolds for controlled photo-induced drug release and enzymatic reactions. In the same year, Nitschke and co-workers synthesized PEG hydrogels by crosslinking PEG chains with $M_4L_6$ pyramidal MOC junctions.[49] Small molecules—benzene and furan—could be encapsulated and released from the MOCs in these materials. In 2016, Yang and co-workers reported a post-assembly polymerization strategy to combine thermo-responsive polymers with small metallacyles to yield hydrogels with self-healing properties.[50] Later, Kitagawa and co-workers reported the synthesis of coordination star polymers containing copper-based MOCs using both divergent and convergent methods.[51]

Recently, the assembly of polymeric organogels connected with MOC junctions was described.[52] These 'poly-MOC' gels featured large cages, for instance, the $M_{12}L_{24}$ spherical 'Fujita cages', which served as crosslink junctions between linear polymer chains. Because the polymers used had ligands on both of their ends, the resulting network was assembled in one step, which produced polyMOCs with a high percentage of topological defects such as primary loops. However, the use of large cage junctions enabled the network to withstand those defects and at the same time allowed for the introduction of additional functionality via exchange of elastically inactive loops with functional free ligands.

SUMMARY OF THE DISCLOSURE

The merger of metal organic frameworks (MOFs), such as metal organic nanostructures (MONs) (e.g., metal organic cages (MOCs) and metal organic squares (MOSs)), was envisioned with a classic paradigm in polymer science: di-block copolymer (BCP) self-assembly.[53-55] BCP assembly is a widely employed "bottom-up" method for the fabrication of materials with periodic structures on the order of ~10 to 100 nm. Since MONs are generally an order of magnitude smaller than this size range, it was reasoned that hybrid materials based on MON assembly and BCP assembly could feature unique hierarchical structures with properties defined by order across various length scales. Such structural hierarchy is common in biomaterials, but is often more difficult to achieve in synthetic polymers.

Described herein are (block co-polymer)-(MON) conjugates (BCPMONs), and thermoplastic elastomers, gels, and compositions thereof. Also described herein are methods of preparing the BCPMONs, thermoplastic elastomers, gels, and compositions. In certain embodiments, the methods of preparing involve macromonomers. Also described herein are the macromonomers. Further described herein are methods of using the BCPMONs, thermoplastic elastomers, gels, and compositions, and uses of the BCPMONs, thermoplastic elastomers, gels, and compositions.

Certain MONs, and gels, compositions, methods, and uses thereof, are described in U.S. patent application publication, US 2015/0225438, which is incorporated by reference.

In certain embodiments, the BCPMONs are (block co-polymer)-(MOS) conjugates (BCPMOSs). In certain embodiments, the BCPMONs are (block co-polymer)-(MOC) conjugates (BCPMOCs). In certain embodiments, the BCPMONs are a class of materials derived from stepwise MON assembly and BCP phase separation. The BCP-MONs may be constructed from BCPs that feature one glassy block, one rubbery block, and a pyridyl ligand on the end of the rubbery block (FIG. 1A). These BCPs undergo metal-coordination driven assembly in solution to yield star polymers with well-defined ~1 to 4 nm MON cores and a precise number of polymer arms. When the solvent is removed, or a solvent that is selective for one block of the BCP is added, these materials may undergo phase separation and physical crosslinking by forming glassy polymer domains to yield BCPMONs as thermoplastic elastomers (TPE) or thermo-responsive organogels. The synthesis of BCPMONs with large (~3.5 nm) Fujita-sphere $M_{12}L_{24}$ MONs and small (~1.5 nm) paddlewheel $M_2L_4$ MONs was demonstrated. Since the conformations of attached BCP chains are restricted differently depending on the MON, BCPMONs derived from these two MONs have different microphase separated structures; e.g., MON assembly at short length scales impacts BCP assembly at longer length scales. Furthermore, it was shown that the structures and mechanical properties of BCPMONs may be highly tunable and directly related to the MON and the BCP.

This work represents the first example wherein MON assembly is merged with BCP phase separation to generate crosslinked materials. The versatility of MON assembly and the rich diversity of potential BCP structures provide great opportunities to develop novel BCPMONs with a range of properties. For example, herein it is shown that BCPs with a thermo-sensitive block can be employed to fabricate thermo-responsive BCPMON organogels. The described BCPMONs may also be useful for delivering an agent to a subject or cell, for treating a disease in a subject, for preventing a disease in a subject, or for enzymatic reactions.

In one aspect, the present disclosure provides (block co-polymer)-(metal organic nanostructure) conjugates (BCPMONs) comprising:
(a) a metal organic nanostructure comprising:
(i) x instances of a transition metal ion; and
(ii) 2x instances of a ligand of Formula (A):

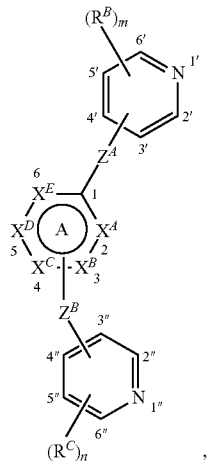

(A)

wherein each instance of the transition metal ion and two instances of the ligand of Formula (A) form through coordination bonds a coordination complex;
wherein each of the coordination bonds is formed between an instance of the transition metal ion and the nitrogen atom labeled with 1' or 1" of an instance of the ligand of Formula (A); and
wherein the maximum outer dimension of the metal organic nanostructure is between 1 nm and 100 nm, inclusive; and
(b) two or more instances of -L-(R)$_p$-(G)$_q$-(R)$_u$-(G)$_v$-E;
wherein:
each instance of -L-(R)$_p$-(G)$_q$-(R)$_u$-(G)$_v$-E is independently directly covalently attached to an instance of the ligand of Formula (A);
each two instances of -L-(R)$_p$-(G)$_q$-(R)$_u$-(G)$_v$-E are independently directly covalently attached to the same instance or two different instances of the ligand of Formula (A); and
the variables recited in this sentence are as described herein.

In another aspect, the present disclosure provides BCPMONs comprising:
(a) a metal organic nanostructure comprising:
(i) a transition metal ion; and
(ii) four instances of a ligand of Formula (B):

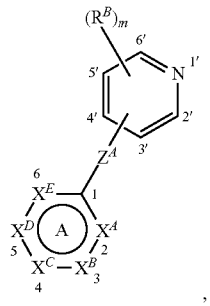

(B)

wherein the transition metal ion and the four instances of the ligand of Formula (B) form through coordination bonds a coordination complex;
wherein each of the coordination bonds is formed between the transition metal ion and the nitrogen atom labeled with 1' of each instance of the ligand of Formula (B); and
wherein the maximum outer dimension of the metal organic nanostructure is between about 1 nm and about 100 nm, inclusive; and
(b) two or more instances of -L-(R)$_p$-(G)$_q$-(R)$_u$-(G)$_v$-E,
wherein:
each instance of -L-(R)$_p$-(G)$_q$-(R)$_u$-(G)$_v$-E is independently directly covalently attached to an instance the ligand of Formula (B);
each two instances of -L-(R)$_p$-(G)$_q$-(R)$_u$-(G)$_v$-E are independently directly covalently attached to the same instance or two different instances of the ligand of Formula (B); and
the variables recited in this sentence are as described herein.

Another aspect of the present disclosure relates to thermoplastic elastomers comprising two or more instances of a BCPMON described herein.

Another aspect of the present disclosure relates to gels comprising two or more instances of a BCPMON described herein, and a fluid.

Another aspect of the present disclosure relates to macromonomers of Formula (L):

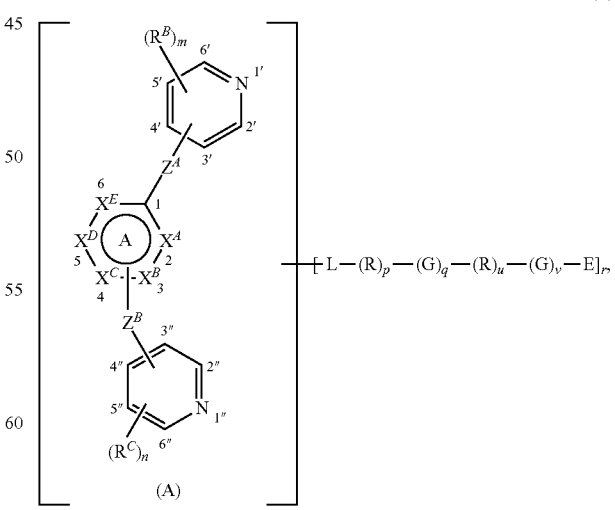

(L)

wherein the variables recited in this sentence are as described herein.

Another aspect of the present disclosure relates to macromonomers of Formula (M):

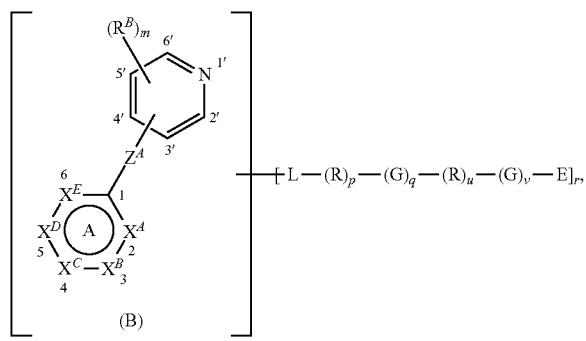

wherein the variables recited in this sentence are as described herein.

Also provided herein are (block co-polymer)-(metal organic framework) conjugates (BCPMOFs). In certain embodiments, a BCPMOF is a (block co-polymer)-(metal organic nanostructure) conjugate (BCPMON) (where the maximum outer dimension of the metal organic nanostructure (MON) of the BCPMON is not larger than 1 μm). In certain embodiments, the BCPMON is a assembly of polymer-polyMOF hybrids. The BCPMON may be prepared through iterative exponential growth and/or "click" chemistry. The BCPMON may comprise crystalline polyMOF domains embedded in an amorphous polymer (e.g., polystyrene (PS)) matrix.

Another aspect of the present disclosure relates to compositions comprising: a BCPMON, thermoplastic elastomer, gel, or macromonomer described herein; and optionally an excipient.

Another aspect of the present disclosure relates to methods of delivering an agent to a subject, the methods comprising administering to the subject a composition described herein.

Another aspect of the present disclosure relates to methods of delivering an agent to a cell, the methods comprising contacting the cell with a composition described herein.

Another aspect of the present disclosure relates to kits comprising: a macromonomer, BCPMON, thermoplastic elastomer, gel, or composition described herein; and instructions for using the macromonomer, BCPMON, thermoplastic elastomer, gel, or composition described herein.

Another aspect of the present disclosure relates to methods of preparing a BCPMON described herein comprising complexing a macromonomer described herein with a transition metal salt.

Another aspect of the present disclosure relates to methods of preparing a thermoplastic elastomer described herein comprising annealing two or more instances of a BCPMON described herein.

Another aspect of the present disclosure relates to methods of preparing a gel described herein comprising contacting two or more instances of a BCPMON described herein with a fluid.

Another aspect of the present disclosure relates to methods of preparing a composition described herein comprising complexing a macromonomer described herein with a transition metal salt in the presence of an agent.

Another aspect of the present disclosure relates to thermoplastic elastomers prepared by a method described herein.

Another aspect of the present disclosure relates to gels prepared by a method described herein.

The journal article MacLeod et al., *Polymer Chemistry*, 12 Jul. 2017 (DOI: 10.1039/C7PY00922D) may be related to the present disclosure and is incorporated herein by reference.

The details of one or more embodiments of the disclosure are set forth herein. Other features, objects, and advantages of the disclosure will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds (e.g., ligands, macromonomers, BCPMONs) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

"Alkyl" refers to a radical of a straight-chain or branched saturated hydrocarbon group. In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$), and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl" or "$C_{1-10}$ heteroalkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Alkenyl" refers to a radical of a straight-chain or branched hydrocarbon group having one or more carbon-carbon double bonds and no triple bonds. In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is unspecified (e.g., —CH=$CHCH_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl").

In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

"Alkynyl" refers to a radical of a straight-chain or branched hydrocarbon group having one or more carbon-carbon triple bonds and optionally one or more double bonds. In some embodiments, an alkynyl group has 2 to 20 carbon atoms ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-6}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-6}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl. The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(RC)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2,7-di-bromo)fluoroenylmethyl carbamate, 2,7-di-t-butyl-[9-(10,10-dioxo-0,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —C(=O) $SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$) $N(R^{bb})_2$, —S(=O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O) ($OR^{cc}$)$_2$, —P(=O)$_2N(R^{bb})_2$, and —P(=O)$(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis (4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

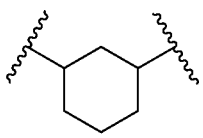 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

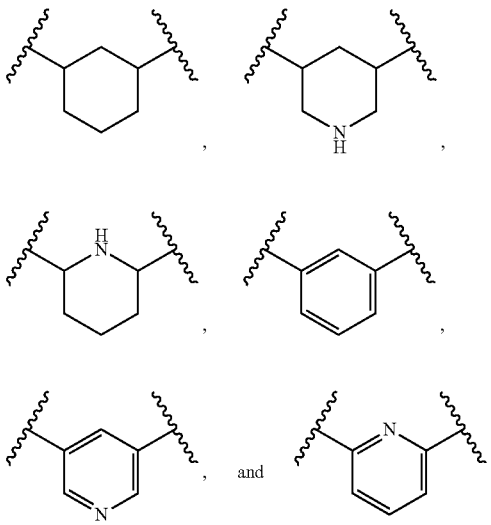 [SMILES: *C1CCCC(*)C1 ; *C1CNCC(*)C1 ; *C1CCCC(*)N1 ; *c1cccc(*)c1 ; *c1cncc(*)c1 ; *c1cccc(*)n1]

are all examples of a hydrocarbon chain. In contrast, in certain embodiments,

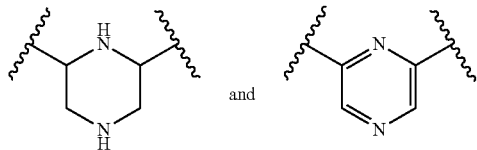 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

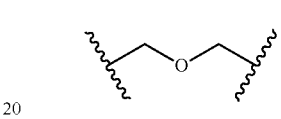

is a $C_3$ hydrocarbon chain wherein one chain atom is replaced with an oxygen atom.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least 1 and at most about 24 carbon atoms) are also within the scope of the disclosure. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

The term "polymer" refers to a compound comprising eleven or more covalently connected repeating units. In certain embodiments, a polymer is naturally occurring. In certain embodiments, a polymer is synthetic (i.e., not naturally occurring).

The term "polydispersity" refers to a measure of the distribution of molecular size in a mixture (e.g., a mixture of polymers), e.g., as determined by a chromatographic method, such as gel permeation chromatography or size exclusion chromatography, or through dynamic light scattering.

An "elastomer" is a polymer that displays rubber-like elasticity.

A "thermoplastic elastomer" is an elastomer comprising a thermoreversible network.

The "molecular weight" of a monovalent moiety —U is calculated by subtracting 1 from the molecular weight of the compound U—H. The "molecular weight" of a divalent moiety —V— is calculated by subtracting 2 from the molecular weight of the compound H—V—H.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present disclosure.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. The proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the subject will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., *Nature*, 290, 304-310, (1981); Yamamoto et al., *Cell*, 22, 787-797, (1980); Wagner et al., *Proc. Natl. Acad. Sci. U.S.A.* 78, 1441-1445, (1981); Brinster et al., *Nature* 296, 39-42, (1982)). Any type of plasmid, cosmid, yeast artificial chromosome, or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al., *Current Protocols in Molecular Biology*, Current Protocols (1989), and *DNA Cloning: A Practical Approach*, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design.

The term "pDNA," "plasmid DNA," or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1,000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

The term "cage" refers to a sphere or paddlewheel.

The term "sphere" or "spherical" refers to a cage-like structure, which is hollow and has at least one reflectional symmetry, rotational symmetry, or a combination thereof. The term "nanosphere" refers to a sphere, wherein the maximum outer dimension (e.g., diameter) of the sphere is between 1 nanometer (nm) and about 1 micrometer (μm) (e.g., between about 1 nm and about 300 nm, between about 1 nm and about 100 nm, between about 1 nm and about 30 nm, between about 1 nm and about 10 nm, or between about 1 nm and about 3 nm), inclusive).

The term "paddlewheel" or "paddle wheel" refers to a coordination complex comprising m instances of ligands and two metal centers (metal atoms or metal ions), wherein there is an axis of symmetry connecting the two metal centers, and the overall symmetry of the coordination complex falls into the Dmh point group. In certain embodiments, m is 4, and the point group is D4h (e.g., there is a four-fold axis of symmetry when looking down the metal centers). In certain embodiments, the geometry of each of the metal centers is substantially square planar. In certain embodiments, m is 3. The term "nano-paddlewheel" refers to a paddlewheel, wherein the maximum outer dimension (e.g., diameter) of the paddlewheel is between 1 nanometer (nm) and about 1 micrometer (μm) (e.g., between about 1 nm and about 300 nm, between about 1 nm and about 100 nm, between about 1 nm and about 30 nm, between about 1 nm and about 10 nm, or between about 1 nm and about 3 nm), inclusive). In certain embodiments, a nano-paddlewheel described herein is of the formula depicted in FIG. 42.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average (e.g., mean) characteristic dimension of about not more than 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having an average (e.g., mean) dimension (e.g., diameter) of between about 1 nanometer (nm) and about 1 micrometer (μm) (e.g., between about 1 nm and about 300 nm, between about 1 nm and about 100 nm, between about 1 nm and about 30 nm, between about 1 nm and about 10 nm, or between about 1 nm and about 3 nm), inclusive.

The term "microparticle" refers to a particle having an average (e.g., mean) dimension (e.g., diameter) of between about 1 micrometer (μm) and about 1 millimeter (mm) (e.g., between about 1 μm and about 100 μm, between about 1 μm and about 30 μm, between about 1 μm and about 10 μm, or between about 1 μm and about 3 μm), inclusive.

The term "fluid" refers to a substance that, under a shear stress at 25° C., continually flows (e.g., at a velocity of 1 millimeter per second) along a solid boundary. Examples of fluids include liquids (e.g., solvents and solutions), gases, and suspensions (where solids are suspended in a liquid or gas). In certain embodiments, a fluid is water. In certain embodiments, a fluid is DMSO or acetonitrile. In certain embodiments, a fluid is water, DMSO, acetonide, or a mixture thereof. A "nonfluid" is a substance that is not a fluid.

The term "gel" is a nonfluid colloidal network or nonfluid polymer network that is expanded throughout its whole volume by a fluid (e.g., a solvent (e.g., water) or a solution (e.g., an aqueous solution)). A gel has a finite, usually rather small, yield stress. A gel may contain: (i) a covalent molecular network (e.g., polymer network), e.g., a network formed by crosslinking molecules (e.g., polymers) or by nonlinear polymerization; (ii) a molecular network (e.g., polymer network) formed through non-covalent aggregation of molecules (e.g., polymers), caused by complexation (e.g., coordination bond formation between a ligand and a metal, the resulting gel referring to a "metallogel"), electrostatic interactions, hydrophobic interactions, hydrogen bonding, van der Waals interactions, π-π stacking, or a combination thereof, that results in regions of local order acting as the network junction points. The term "thermoreversible gel" refers to a gel where the regions of local order in the gel are thermally reversible; (iii) a polymer network formed through glassy junction points, e.g., one based on block copolymers. If the junction points are thermally reversible glassy domains, the resulting swollen network may also be termed a thermoreversible gel; (iv) lamellar structures including mesophases, e.g., soap gels, phospholipids, and clays; or (v) particulate disordered structures, e.g., a flocculent precipitate usually consisting of particles with large geometrical anisotropy, such as in $V_2O_5$ gels and globular or fibrillar protein gels. The term "hydrogel" refers to a gel, in which the fluid is water.

The term "interstructural" refers to a divalent linker Y directly covalently attached to two different instances of a metal organic nanostructure.

The term "intrastructural" refers to a divalent linker Y directly covalently attached to the same instance of a metal organic nanostructure.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "target tissue" refers to any biological tissue of a subject (including a group of cells, a body part, or an organ) or a part thereof, including blood and/or lymph vessels, which is the object to which a compound, particle, and/or composition of the disclosure is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. In certain embodiments, the target tissue is the spleen. A "non-target tissue" is any biological tissue of a subject (including a group of cells, a body part, or an organ) or a part thereof, including blood and/or lymph vessels, which is not a target tissue.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML)

(e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrdm's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomal-leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosus, rheumatoid, arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic *porphyria*, hepatic *porphyria* (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder;

cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, *cannabis* dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

The term "thermoplastic elastomer" refers to a material that is plasticized at a temperature higher than 20° C. (e.g., higher than 40° C., higher than 60° C., higher than 100° C., higher than 150° C., or higher than 200° C.), like plastics, and exhibits elastomeric (e.g., rubber-like) properties at about 20° C.

The term "conjugate" refers to the product formed by covalently attaching two substances. In certain embodiments, a hydrogen atom of the first substance is removed to form a first monoradical, a hydrogen atom of the second substance is removed to form a second monoradical, and the first monoradical and the second monoradical are directly connected to form the product.

The term "ambient conditions" refers to 20° C., 1 atmosphere, and 50% relative humidity.

BRIEF DESCRIPTION OF THE DRAWINGS

(FIG. 1A) Scheme showing the stepwise self-assembly of BCPMONs by MON formation followed by block copolymer phase separation. (FIG. 1B) Schematic and chemical structures of ligands employed to form MONs. (FIG. 1C) Schematic representation of the sizes and geometries metal-ligand assemblies investigated.

(FIG. 2A) Synthetic scheme of pyridyl ligand functionalized poly(methyl methacrylate)-block-poly (n-butyl acrylate) (PMMA-PBA)-L (-L1, -L2, or -L3). (FIG. 2B) $^1$H NMR characterization of the self-assembly of PMMA-PBA-L2 to form 4-arm star polymers containing a paddlewheel MON core. (FIG. 2C) $^1$H NMR characterization of the self-assembly of PMMA-PBA-L3 into 24-arm star polymers with a Fujita sphere MON core.

(FIG. 3A) Dynamic light scattering (DLS) histograms showing the size and size distribution of 4-arm (top) and 24-arm (bottom) star polymers assembled using PMMA-PBA-L2 and -L3. (FIG. 3B) Atomic force microscopy (AFM) height images showing the star polymers nanoparticle containing a Fujita sphere MON core. (FIG. 3B) Selected area is zoomed in and the height profile for a selected particle is depicted showing its width and height. (FIG. 3C) Transmission electron microscope image showing the same particles used in FIG. 3B. Scale bars, 200 nm.

(FIG. 4A) $PMMA_{4k}$-$PBA_{19k}$. (FIG. 4B) $PMMA_{8k}$-$PBA_{27k}$. (FIG. 4C) $PMMA_{8k}$-$PBA_{48k}$. Scale bars: 200 nm.

(FIG. 6A) The storage and loss moduli of BCPMON materials over different temperatures showing the transition between the gel and solution state. (FIG. 6B) SAXS profiles and pictures (inset) for BCPMONs in 2-ethyl hexanol at 25 and 50° C. (FIG. 6C) SAXS profiles showing the difference in the d-spacing of phase separation in gels with different MON cores. (FIG. 6D) The storage moduli and the solution-gel (sol-gel) transition temperature of gels with MON cores mixed at different ratios.

FIGS. 9A to 9D. $^1$H NMR spectra comparing the formation of Fujita sphere-like $M_{12}L_{24}$ MON based on small molecules DMSO-$d_6$ (1) and block copolymers acetonitrile-$d_3$ (2). Spectra before (FIGS. 9A and 9B) and after (FIGS. 9C and 9D) assembly are shown. Block copolymer $PMMA_{4k}$-$PBA_{19k}$-L3 was used to obtain the spectra. The molecular weight of the assembled star polymer (shown in FIG. 9D) is ~552,000 (23000×24) Da. Due to this large size, the aromatic resonances from the $M_{12}L_{24}$ cage are greatly broadened.

FIG. 10. Atomic force microscopy (AFM) height image of a linear block copolymer $PMMA_{4k}$-$PBA_{19k}$ coated on silicon wafer, which demonstrates that no nanoparticles were observed and rules out the possibility of micelle formation when sample was prepared (spin-coating a dilute solution).

FIGS. 11A and 11B. Atomic force microscopy (AFM) phase images of (FIG. 11A) the linear block copolymer $PMMA_{4k}$-$PBA_{19k}$ and (FIG. 11B) the star polymer with $M_{12}L_{24}$ MON core $PMMA_{4k}$-$PBA_{19k}$-L3 showing the effect of MON core on the phase separation behavior.

(FIG. 15A) Spectrum of paddle-wheel $M_2L_4$ MON; a small amount of extra free ligand was added to enhance ligand exchange (if any) purposely. (FIG. 15B) Spectrum of Fujita sphere $M_{12}L_{24}$ MON. (FIG. 15C) Spectrum of the mixture of FIGS. 15A and 15B. (FIG. 15D) Spectrum showing no changes after the mixture was heated at 50° C., which indicates that the MONs maintain their structures at this temperature. (FIG. 15E) New peaks developed after the mixture was heated at 80° C. overnight, suggesting possible ligand exchange or degradation to form ill-defined species.

(FIG. 18A) $L_2$-Zn. (FIG. 18B) $L_4$-Zn.

(FIG. 19A) Synthesis of BCPMON ligands L PS and L PS. (i) H, 1 eq. of 10% Pd/C; (ii) propargyl bromide, $K_2CO_3$, EtOH/DMF; (iii) CuBr, $Me_6$Tren, THF; (iv) KOH, DMSO/$H_2O$. (FIG. 19B) MALDI-TOF spectrum for $L_4$PS with selected peaks labeled. (FIG. 19C)$^1$H NMR (400 MHz) of $L_4$-PS in CDCl$_3$ (solvent labeled with "*").

(FIG. 22A) SEM image of $L_4$-Zn. (FIG. 22B) SEM image of $L_4$PS—Zn dried at RT. (FIG. 22C) Positively stained (RuO$_4$) TEM image of $L_4$PS—Zn dried at RT. (FIG. 22D) Schematic of $L_4$PS—Zn depicting a crystalline polyMOF domain embedded within a PS matrix.

DETAILED DESCRIPTION OF CERTAIN EMBODIMENTS OF THE DISCLOSURE

Figure 1A:
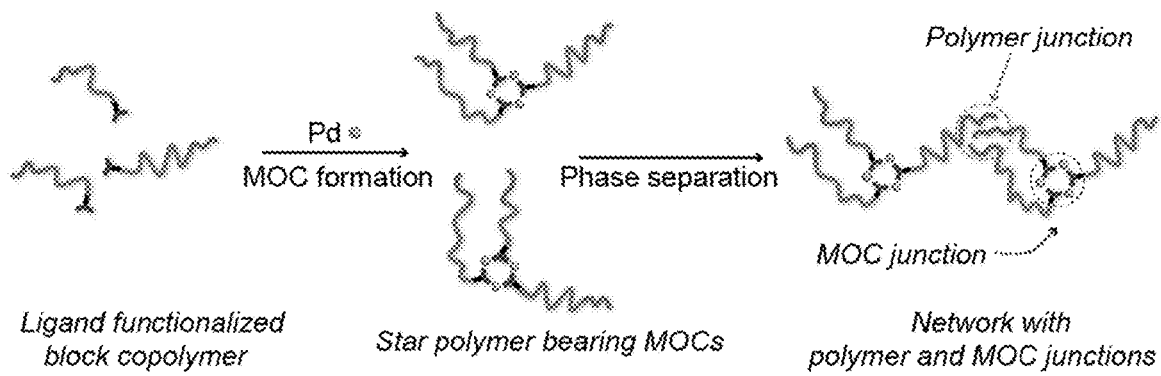
FIGS. 1A to 1C.

We report a stepwise assembly strategy for the integration of MONs into block copolymers (BCPs). This approach creates 'block co-polyMON' (BCPMON) materials whose microscopic structures and mechanical properties are readily tunable by adjusting the size and geometry of the MONs and the composition of the BCPs. In the first assembly step, BCPs functionalized with a pyridyl ligand on the chain end form star-shaped polymers triggered by metal-coordination-induced MON assembly. The type of MON junction employed precisely determines the number of arms for the star polymer. In the second step, microphase separation of the BCP is induced, physically crosslinking the star polymers and producing the desired BCPMON networks in the bulk (elastomers) or gel state (organogels). It is demonstrated that, through small changes programmed in the ligand design, large spherical (e.g., $M_{12}L_{24}$) cages, small paddle wheel-like (e.g., $M_2L_4$) cages, or a mixture of both can be incorporated into BCPMONs, precisely tailoring the microstructure of the materials including their branch functionality, phase separation and micro-domain spacing. This versatility enabled us to modulate the mechanical properties of the obtained materials. Given the synthetic and functional diversity of MONs and BCPs, the method described herein should give access to BCPMONs with a wide variety of properties.

Also provided herein are BCPMONs comprising a benzene dicarboxylate (BDC)-based oligomer, a polymer (e.g., PS), and a transition metal (e.g., Zn) ion. In certain embodiments, this BCPMON comprises a polyMOF domain embedded in a polymer (e.g., PS) matrix. This BCPMON may be the first demonstration that a BCP with a suitably designed polyMOF-forming block can form a composite material with both highly crystalline polyMOF domains and amorphous polymer domains.

The BCPMONs may be useful for gas and energy storage, catalysis, and/or gas separation.

BCPMOFs (e.g., BCPMONs) and Macromonomers

In one aspect, the present disclosure provides BCPMOFs (e.g., BCPMONs). In certain embodiments, the BCPMON comprises:

(a) a metal organic nanostructure comprising:
(i) x instances of a transition metal ion, wherein x is an integer between 2 and 60, inclusive; and
(ii) 2x instances of a ligand of Formula (A):

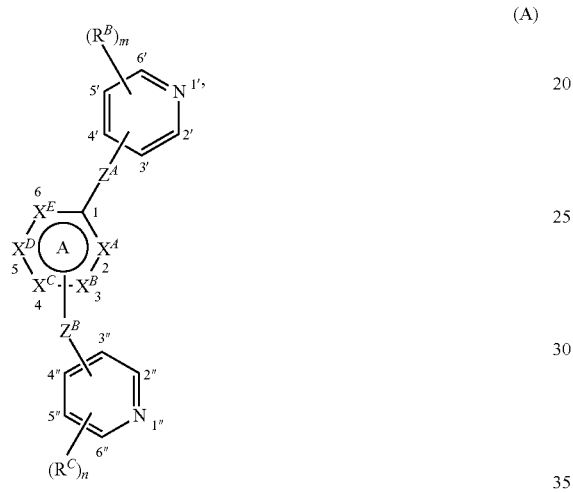

wherein:
Ring A is a substituted or unsubstituted phenyl ring or a substituted or unsubstituted, 5- or 6-membered, monocyclic heteroaryl ring;
each of $X^A$, $X^B$, $X^C$, and $X^D$ is independently O, S, N, $NR^{A1}$, C, or $CR^{A2}$;
$X^E$ is a bond, N, or $CR^{A2}$;
each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=O)R^a$, $-C(=O)OR^a$, $-C(=O)N(R^a)_2$, or a nitrogen protecting group;
each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;
each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;
each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;
m is 0, 1, 2, 3, or 4, as valency permits;
each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;
n is 0, 1, 2, 3, or 4, as valency permits;
$Z^A$ is a bond or a substituted or unsubstituted $C_{1-4}$ hydrocarbon chain, optionally wherein one or more chain atoms are independently replaced with $-C(=O)-$, $-O-$, $-S-$, $-NR^{ZA}-$, $-N=$, or $=N-$, wherein each instance of $R^{ZA}$ is independently hydrogen, substituted or unsubstituted $C_{1-6}$ alkyl, or a nitrogen protecting group; and
$Z^B$ is a bond or a substituted or unsubstituted $C_{1-4}$ hydrocarbon chain, optionally wherein one or more chain atoms are independently replaced with $-C(=O)-$, $-O-$, $-S-$, $-NR^{ZB}-$, $-N=$, or $=N-$, wherein each instance of $R^{ZB}$ is independently hydrogen, substituted or unsubstituted $C_{1-6}$ alkyl, or a nitrogen protecting group;
wherein each instance of the transition metal ion and two instances of the ligand of Formula (A) form through coordination bonds a coordination complex; and
wherein each of the coordination bonds is formed between an instance of the transition metal ion and the nitrogen atom labeled with 1' or 1" of an instance of the ligand of Formula (A); and
(b) two or more instances of $-L-(R)_p-(G)_q-(R)_u-(G)_v-E$, wherein:
each instance of L is independently a bond or a substituted or unsubstituted $C_{1-4}$ hydrocarbon chain, optionally wherein one or more chain atoms are independently replaced with $-C(=O)-$, $-O-$, $-S-$, $-NR^L-$, $-N=$, or $=N-$, wherein each instance of $R^L$ is independently hydrogen, substituted or unsubstituted $C_{1-6}$ alkyl, or a nitrogen protecting group;
each instance of R is independently a diradical of a first polymer, wherein:

the glass transition temperature ($T_g$) of each instance of the first polymer is not higher than 20° C.; and the number-average molecular weight ($M_n$) of the first polymer is between 1,000 g/mol and 1,000,000 g/mol, inclusive;

each instance of G is independently a diradical of a second polymer, wherein:

the $T_g$ of each instance of the second polymer is higher than 20° C.; and the $M_n$ of the second polymer is between 300 g/mol and 100,000 g/mol, inclusive;

each instance of p is independently 0, 1, 2, or 3;

each instance of q is independently 0, 1, 2, or 3, provided that at least one instance of p and q is 1, 2, or 3;

each instance of u is independently 0, 1, 2, or 3;

each instance of v is independently 0, 1, 2, or 3; and each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

wherein:

each instance of -L-(R)$_p$-(G)$_q$-(R)$_u$-(G)$_v$-E is independently directly covalently attached to an instance of the ligand of Formula (A); and each two instances of -L-(R)$_p$-(G)$_q$-(R)$_u$-(G)$_v$-E are independently directly covalently attached to the same instance or two different instances of the ligand of Formula (A).

In certain embodiments, the maximum outer dimension of the metal organic nanostructure is between 1 nm and 1,000 nm, inclusive. In certain embodiments, the maximum outer dimension of the metal organic nanostructure is between 1 nm and 100 nm, inclusive.

In certain embodiments, the BCPMON comprises:

(a) a metal organic nanostructure comprising:

(i) x instances of a transition metal ion, wherein x is an integer between 2 and 60, inclusive; and (ii) 2x instances of a ligand of Formula (A):

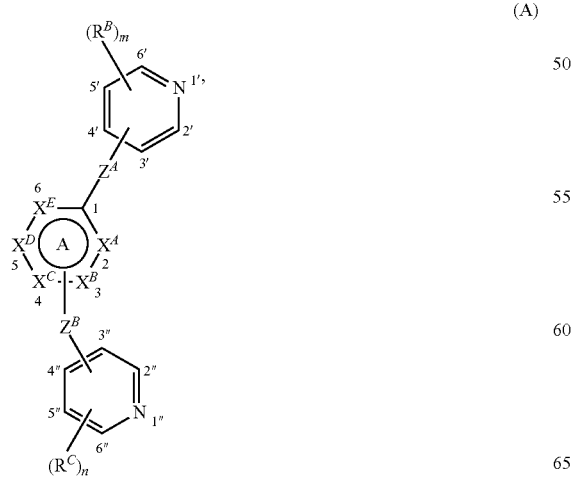

(A)

wherein:

Ring A is a substituted or unsubstituted phenyl ring or a substituted or unsubstituted, 5- or 6-membered, monocyclic heteroaryl ring;

each instance of $X^A$, $X^B$, $X^C$, and $X^D$ is independently O, S, N, NR$^{A1}$, C, or CR$^{A2}$;

$X^E$ is a bond, N, or CR$^{A2}$;

each instance of R$^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, or a nitrogen protecting group;

each instance of R$^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

each instance of R$^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

m is 0, 1, 2, 3, or 4, as valency permits;

each instance of R$^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

n is 0, 1, 2, 3, or 4, as valency permits;

$Z^A$ is a bond or a substituted or unsubstituted $C_{1-4}$ hydrocarbon chain, optionally wherein one or more chain atoms are independently replaced with —C(=O)—, —O—, —S—, —NR$^{ZA}$—, —N=, or =N—, wherein each instance of R$^{ZA}$ is independently hydrogen, substituted or unsubstituted C$_{1-6}$ alkyl, or a nitrogen protecting group; and Z$^B$ is a bond or a substituted or unsubstituted C$_{1-4}$ hydrocarbon chain, optionally wherein one or more chain atoms are independently replaced with —C(=O)—, —O—, —S—, —NR$^{ZB}$—, —N=, or =N—, wherein each instance of R$^{ZB}$ is independently hydrogen, substituted or unsubstituted C$_{1-6}$ alkyl, or a nitrogen protecting group;

wherein each instance of the transition metal ion and two instances of the ligand of Formula (A) form through coordination bonds a coordination complex;

wherein each of the coordination bonds is formed between an instance of the transition metal ion and the nitrogen atom labeled with 1' or 1" of an instance of the ligand of Formula (A); and wherein the maximum outer dimension of the metal organic nanostructure is between 1 nm and 100 nm, inclusive; and (b) two or more instances of -L-(R)$_p$-(G)$_q$-(R)$_u$-(G)$_v$-E, wherein:

each instance of L is independently a bond or a substituted or unsubstituted C$_{1-4}$ hydrocarbon chain, optionally wherein one or more chain atoms are independently replaced with —C(=O)—, —O—, —S—, —NR$^L$—, —N=, or =N—, wherein each instance of R$^L$ is independently hydrogen, substituted or unsubstituted C$_{1-6}$ alkyl, or a nitrogen protecting group;

each instance of R is independently a diradical of a first polymer, wherein:
  the glass transition temperature (T$_g$) of each instance of the first polymer is not higher than 20° C.; and
  the number-average molecular weight (M$_n$) of the first polymer is between 1,000 g/mol and 1,000,000 g/mol, inclusive;

each instance of G is independently a diradical of a second polymer, wherein:
  the T$_g$ of each instance of the second polymer is higher than 20° C.; and
  the M$_n$ of the second polymer is between 300 g/mol and 100,000 g/mol, inclusive;

each instance of p is independently 1, 2, or 3;
each instance of q is independently 1, 2, or 3;
each instance of u is independently 0, 1, 2, or 3;
each instance of v is independently 0, 1, 2, or 3; and
each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

wherein:
each instance of -L-(R)$_p$-(G)$_q$-(R)$_u$-(G)$_v$-E is independently directly covalently attached to an instance of the ligand of Formula (A); and each two instances of -L-(R)$_p$-(G)$_q$-(R)$_u$-(G)$_v$-E are independently directly covalently attached to the same instance or two different instances of the ligand of Formula (A).

In certain embodiments, the BCPMON comprises:
(a) a metal organic nanostructure comprising:
  (i) a transition metal ion; and
  (ii) four instances of a ligand of Formula (B):

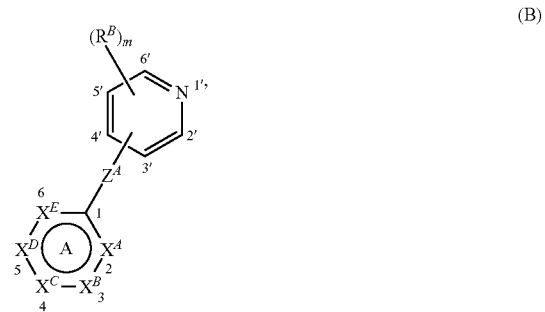

(B)

wherein:
Ring A is a substituted or unsubstituted phenyl ring or a substituted or unsubstituted, 5- or 6-membered, monocyclic heteroaryl ring;

each of X$^A$, X$^B$, X$^C$, and X$^D$ is independently O, S, N, NR$^{A1}$, C, or CR$^{A2}$;

X$^E$ is a bond, N, or CR$^{A2}$;

each instance of R$^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, or a nitrogen protecting group;

each instance of R$^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

m is 0, 1, 2, 3, or 4, as valency permits;

$Z^A$ is a bond or a substituted or unsubstituted $C_{1-4}$ hydrocarbon chain, optionally wherein one or more chain atoms are independently replaced with —C(=O)—, —O—, —S—, —$NR^{ZA}$—, —N=, or =N—, wherein each instance of $R^{ZA}$ is independently hydrogen, substituted or unsubstituted $C_{1-6}$ alkyl, or a nitrogen protecting group; and wherein the transition metal ion and the four instances of the ligand of Formula (B) form through coordination bonds a coordination complex;

wherein each of the coordination bonds is formed between the transition metal ion and the nitrogen atom labeled with 1' of each instance of the ligand of Formula (B); and wherein the maximum outer dimension of the metal organic nanostructure is between about 1 nm and about 100 nm, inclusive; and (b) two or more instances of -L-$(R)_p$-$(G)_q$-$(R)_u$-$(G)_v$-E, wherein:

each instance of L is independently a bond or a substituted or unsubstituted $C_{1-4}$ hydrocarbon chain, optionally wherein one or more chain atoms are independently replaced with —C(=O)—, —O—, —S—, —$NR^L$—, —N=, or =N—, wherein each instance of $R^L$ is independently hydrogen, substituted or unsubstituted $C_{1-6}$ alkyl, or a nitrogen protecting group;

each instance of R is independently a diradical of a first polymer, wherein:
the glass transition temperature ($T_g$) of each instance of the first polymer is not higher than 20° C.; and
the number-average molecular weight ($M_n$) of the first polymer is between 1,000 g/mol and 1,000,000 g/mol, inclusive;

each instance of G is independently a diradical of a second polymer, wherein:
the $T_g$ of each instance of the second polymer is higher than 20° C.; and
the $M_n$ of the second polymer is between 300 g/mol and 100,000 g/mol, inclusive;

each instance of p is independently 0, 1, 2, or 3;

each instance of q is independently 0, 1, 2, or 3, provided that at least one instance of p and q is 1, 2, or 3;

each instance of u is independently 0, 1, 2, or 3;

each instance of v is independently 0, 1, 2, or 3; and each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

wherein:
each instance of -L$(R)_p$-$(G)_q$-$(R)_u$-$(G)_v$-E is independently directly covalently attached to an instance the ligand of Formula (B); and
each two instances of -L-$(R)_p$-$(G)_q$-$(R)_u$-$(G)_v$-E are independently directly covalently attached to the same instance or two different instances of the ligand of Formula (B).

In certain embodiments, the BCPMON comprises:

(a) a metal organic nanostructure comprising:
(i) a transition metal ion; and
(ii) four instances of a ligand of Formula (B):

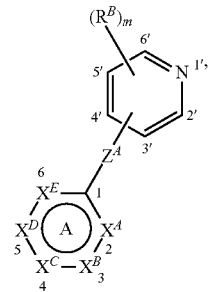

wherein:
Ring A is a substituted or unsubstituted phenyl ring or a substituted or unsubstituted, 5- or 6-membered, monocyclic heteroaryl ring;

each instance of $X^A$, $X^B$, $X^C$, and $X^D$ is independently O, S, N, $NR^{A1}$, C, or $CR^{A2}$;

$X^E$ is a bond, N, or $CR^{A2}$;

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)$OR^a$, —C(=O)$N(R^a)_2$, or a nitrogen protecting group;

each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

m is 0, 1, 2, 3, or 4, as valency permits;

$Z^A$ is a bond or a substituted or unsubstituted $C_{1-4}$ hydrocarbon chain, optionally wherein one or more chain atoms are independently replaced with —C(=O)—, —O—, —S—, —$NR^{ZA}$—, —N=, or =N—, wherein each instance of $R^{ZA}$ is independently hydrogen, substituted or unsubstituted $C_{1-6}$ alkyl, or a nitrogen protecting group; and wherein the transition metal ion and the four instances of at least one instance of the ligand of Formula (B) form through coordination bonds a coordination complex;

wherein each of the coordination bonds is formed between the transition metal ion and the nitrogen atom labeled with 1' of each instance of at least one instance of the ligand of Formula (B); and wherein the maximum outer dimension of the metal organic nanostructure is between about 1 nm and about 100 nm, inclusive; and (b) two or more instances of -L-$(R)_p$-$(G)_q$-$(R)_u$-$(G)_v$-E, wherein:

each instance of L is independently a bond or a substituted or unsubstituted $C_{1-4}$ hydrocarbon chain, optionally wherein one or more chain atoms are independently replaced with —C(=O)—, —O—, —S—, —$NR^L$—, —N=, or =N—, wherein each instance of $R^L$ is independently hydrogen, substituted or unsubstituted $C_{1-6}$ alkyl, or a nitrogen protecting group;

each instance of R is independently a diradical of a first polymer, wherein:
the glass transition temperature ($T_g$) of each instance of the first polymer is not higher than 20° C.; and
the number-average molecular weight ($M_n$) of the first polymer is between 1,000 g/mol and 1,000,000 g/mol, inclusive;

each instance of G is independently a diradical of a second polymer, wherein:
the $T_g$ of each instance of the second polymer is higher than 20° C.; and
the $M_n$ of the second polymer is between 300 g/mol and 100,000 g/mol, inclusive;

each instance of p is independently 1, 2, or 3;
each instance of q is independently 1, 2, or 3;
each instance of u is independently 0, 1, 2, or 3;
each instance of v is independently 0, 1, 2, or 3; and
each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

wherein:
each instance of -L-$(R)_p$-$(G)_q$-$(R)_u$-$(G)_v$-E is independently directly covalently attached to an instance of at least one instance of the ligand of Formula (B); and
each two instances of -L-$(R)_p$-$(G)_q$-$(R)_u$-$(G)_v$-E are independently directly covalently attached to the same instance or two different instances of at least one instance of the ligand of Formula (B).

In certain embodiments, the BCPMON comprises:
(i) y instances of a transition metal ion, wherein y is an integer between 1 and 1,000, inclusive; and
(ii) z instances of a ligand of Formula (C):

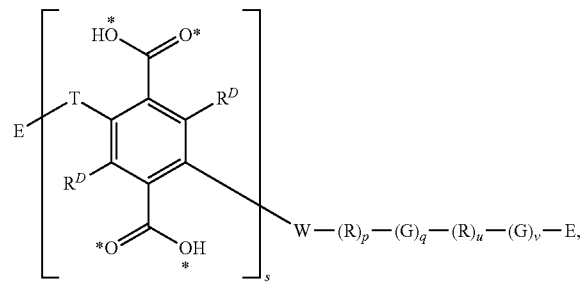

(C)

wherein:
z is is an integer between 2 and 200, inclusive;
s is an integer between 2 and 10, inclusive;
each instance of $R^D$ is independently hydrogen, halogen, substituted or unsubstituted $C_{1-6}$ alkyl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, or —OC(=O)$N(R^a)_2$;

each instance of T is independently a bond or a substituted or unsubstituted $C_{1-50}$ hydrocarbon chain, optionally wherein one or more chain atoms are independently replaced with —C(=O)—, —O—, —S—, —$NR^T$—, —N=, or =N—, wherein each instance of $R^T$ is independently hydrogen, substituted or unsubstituted $C_{1-6}$ alkyl, or a nitrogen protecting group;

W is substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene, wherein:
optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of R is independently a diradical of a first polymer, wherein:
the glass transition temperature ($T_g$) of each instance of the first polymer is not higher than 20° C.; and
the number-average molecular weight ($M_n$) of the first polymer is between 1,000 g/mol and 1,000,000 g/mol, inclusive;

each instance of G is independently a diradical of a second polymer, wherein:
the $T_g$ of each instance of the second polymer is higher than 20° C.; and
the $M_n$ of the second polymer is between 300 g/mol and 100,000 g/mol, inclusive;

each instance of p is independently 0, 1, 2, or 3;
each instance of q is independently 0, 1, 2, or 3, provided that at least one instance of p and q is 1, 2, or 3;
each instance of u is independently 0, 1, 2, or 3;
each instance of v is independently 0, 1, 2, or 3; and
each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

wherein each instance of the transition metal ion and at least one instance of the ligand of Formula (C) form through one or more coordination bonds a coordination complex; and wherein each of the coordination bonds is formed between an instance of the transition metal ion and an instance of the oxygen atom labeled with "*".

Another aspect of the present disclosure relates to macromonomers. In certain embodiments, the macromonomer is Formula (L):

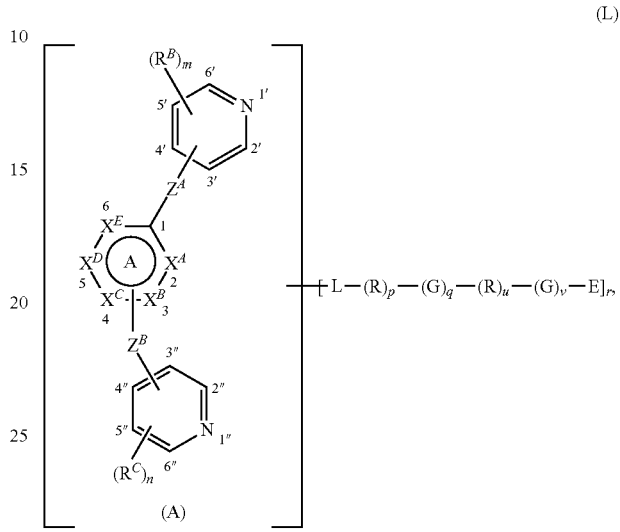

wherein:
Ring A is a substituted or unsubstituted phenyl ring or a substituted or unsubstituted, 5- or 6-membered, monocyclic heteroaryl ring;

each of X$^A$, X$^B$, X$^C$, and X$^D$ is independently O, S, N, NR$^{A1}$, C, or CR$^{A2}$;

X$^E$ is a bond, N, or CR$^{A2}$;

each instance of R$^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, or a nitrogen protecting group;

each instance of R$^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

m is 0, 1, 2, 3, or 4, as valency permits;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

n is 0, 1, 2, 3, or 4, as valency permits;

$Z^A$ is a bond or a substituted or unsubstituted $C_{1-4}$ hydrocarbon chain, optionally wherein one or more chain atoms are independently replaced with —C(=O)—, —O—, —S—, —$NR^{ZA}$—, —N=, or =N—, wherein each instance of $R^{ZA}$ is independently hydrogen, substituted or unsubstituted $C_{1-6}$ alkyl, or a nitrogen protecting group;

$Z^B$ is a bond or a substituted or unsubstituted $C_{1-4}$ hydrocarbon chain, optionally wherein one or more chain atoms are independently replaced with —C(=O)—, —O—, —S—, —$NR^{ZB}$—, —N=, or =N—, wherein each instance of $R^{ZB}$ is independently hydrogen, substituted or unsubstituted $C_{1-6}$ alkyl, or a nitrogen protecting group;

r is 1, 2, or 3;

each instance of L is independently a bond or a substituted or unsubstituted $C_{1-4}$ hydrocarbon chain, optionally wherein one or more chain atoms are independently replaced with —C(=O)—, —O—, —S—, —$NR^L$—, —N=, or =N—, wherein each instance of $R^L$ is independently hydrogen, substituted or unsubstituted $C_{1-6}$ alkyl, or a nitrogen protecting group;

each instance of R is independently a diradical of a first polymer, wherein:
  the glass transition temperature ($T_g$) of each instance of the first polymer is not higher than 20° C.; and
  the number-average molecular weight ($M_n$) of the first polymer is between 1,000 g/mol and 1,000,000 g/mol, inclusive;

each instance of G is independently a diradical of a second polymer, wherein:
  the $T_g$ of each instance of the second polymer is higher than 20° C.; and
  the $M_n$ of the second polymer is between 300 g/mol and 100,000 g/mol, inclusive;

each instance of p is independently 0, 1, 2, or 3;
each instance of q is independently 0, 1, 2, or 3, provided that at least one instance of p and q is 1, 2, or 3;
each instance of u is independently 0, 1, 2, or 3;
each instance of v is independently 0, 1, 2, or 3; and
each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$.

In certain embodiments, the macromonomer is of Formula (M):

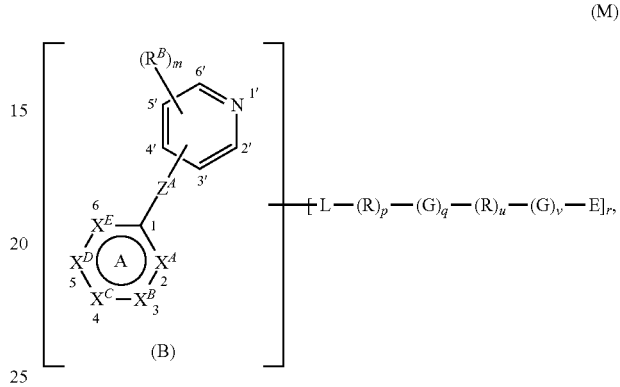

(M)

wherein:

Ring A is a substituted or unsubstituted phenyl ring or a substituted or unsubstituted, 5- or 6-membered, monocyclic heteroaryl ring;

each of $X^A$, $X^B$, $X^C$, and $X^D$ is independently O, S, N, $NR^{A1}$, C, or $CR^{A2}$;

$X^E$ is a bond, N, or $CR^{A2}$;

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)$OR^a$, —C(=O)N($R^a$)$_2$, or a nitrogen protecting group;

each instance of $R^{A2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

each instance of $R^B$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

m is 0, 1, 2, 3, or 4, as valency permits;

Z$^A$ is a bond or a substituted or unsubstituted C$_{1-4}$ hydrocarbon chain, optionally wherein one or more chain atoms are independently replaced with —C(=O)—, —O—, —S—, —NR$^{ZA}$—, —N=, or =N—, wherein each instance of R$^{ZA}$ is independently hydrogen, substituted or unsubstituted C$_{1-6}$ alkyl, or a nitrogen protecting group;

r is 1,2, or 3;

each instance of L is independently a bond or a substituted or unsubstituted C$_{1-4}$ hydrocarbon chain, optionally wherein one or more chain atoms are independently replaced with —C(=O)—, —O—, —S—, —NR$^L$—, —N=, or =N—, wherein each instance of R$^L$ is independently hydrogen, substituted or unsubstituted C$_{1-6}$ alkyl, or a nitrogen protecting group;

each instance of R is independently a diradical of a first polymer, wherein:
the glass transition temperature (T$_g$) of each instance of the first polymer is not higher than 20° C.; and
the number-average molecular weight (M$_n$) of the first polymer is between 1,000 g/mol and 1,000,000 g/mol, inclusive;

each instance of G is independently a diradical of a second polymer, wherein:
the T$_g$ of each instance of the second polymer is higher than 20° C.; and
the M$_n$ of the second polymer is between 300 g/mol and 100,000 g/mol, inclusive;

each instance of p is independently 0, 1, 2, or 3;

each instance of q is independently 0, 1, 2, or 3, provided that at least one instance of p and q is 1, 2, or 3;

each instance of u is independently 0, 1, 2, or 3;

each instance of v is independently 0, 1, 2, or 3; and each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$.

In certain embodiments, each instance of p is independently 1, 2, or 3; and each instance of q is independently 1, 2, or 3.

The BCPMONs described herein may include metal organic nanostructures, such as nanospheres, nano-paddlewheels, and nano-squares. Fujita et al. have reported banana-shaped organic molecules that self-organize into "Fujita spheres," which are finite, spherical coordination networks with a outer dimension in the order of nanometers (e.g., Tominaga et al., *Angew. Chem., Int. Ed.,* 2004, 43, 5621-5625; Bunzen et al. *Angew. Chem., Int. Ed.* 2012, 51, 3161; Sun et al., *Science,* 2010, 328, 1144). One of such reported Fujita spheres consists of 12 equivalents of a central metal ion (e.g., Pd(II)) and 24 equivalents of a bidentate ligand and has cuboctahedral symmetry. Hupp et al. has reported metal-organic frameworks prepared from a hexacarboxylated ligand and a transition metal ion (e.g., Cu(II) or Zn(II)) (Eryazici et al., *Crystal Growth & Design,* 2012, 12, 1075).

In certain embodiments, the x instances of the transition metal ion and the 2x instances of the ligand of Formula (A) form through the coordination bonds a substantially spherical structure (e.g., nanosphere). In certain embodiments, the nanosphere comprises:

(i) a plurality of a transition metal ion; and (ii) a plurality of a ligand;

wherein each instance of the transition metal ion and two or more instances of the ligand form through coordination bonds a coordination complex;

wherein the plurality of a transition metal ion and the plurality of a ligand form through the coordination bonds one substantially spherical structure; and wherein the maximum outer dimension of the nanosphere is between about 1 nm and about 100 nm, inclusive.

In certain embodiments, the the x instances of the transition metal ion and the 2x instances of the ligand of Formula (A) form through the coordination bonds a substantially paddlewheel structure (e.g., nano-paddlewheel). In certain embodiments, the nano-paddlewheel comprises:

(i) a plurality of a transition metal ion; and (ii) a plurality of a ligand;

wherein each instance of the transition metal ion and two or more instances of the ligand form through coordination bonds a coordination complex;

wherein the plurality of a transition metal ion and the plurality of a ligand form through the coordination bonds one substantially paddlewheel structure; and wherein the maximum outer dimension of the nano-paddlewheel is between about 1 nm and about 100 nm, inclusive.

the x instances of the transition metal ion and the 2x instances of the ligand of Formula (A) or (B) form through the coordination bonds a substantially square structure (e.g., nano-square). In certain embodiments, the nano-square comprises:

(i) a plurality of a transition metal ion; and (ii) a plurality of a ligand;

wherein each instance of the transition metal ion and two or more instances of the ligand form through coordination bonds a coordination complex;

wherein the plurality of a transition metal ion and the plurality of a ligand form through the coordination bonds one substantially square structure; and wherein the maximum outer dimension of the nano-square is between about 1 nm and about 100 nm, inclusive.

In certain embodiments, each instance of the ligand is a monodentate ligand. In certain embodiments, each instance of the ligand is a polydentate (e.g., bidentate, tridentate, or tetradentate) ligand. In certain embodiments, each instance of the ligand comprises two or more pyridinyl moieties. In certain embodiments, each instance of the ligand comprises at least a first pyridinyl moiety and second pyridinyl moiety, wherein the angle (bite angle) between (1) the lone electron pair of the nitrogen atom of the first pyridinyl moiety and (2) the lone electron pair of the nitrogen atom of the second pyridinyl moiety, along the long axes of the lone electron pairs, is between 30° and 180°, inclusive, when the ligand is in the minimum energy conformation. In certain embodiments, the bite angle is between 60° and 160°, inclusive (e.g., about 900, about 120°, about 127°, or about 149°). In certain embodiments, each instance of the ligand is a polydentate ligand, wherein the shortest distance between two chelation sites of the ligand is between about 5 Å and about 20 Å (e.g., between about 5 Å and about 10 Å), inclusive, when the ligand is in the minimum energy conformation.

In certain embodiments, a metal organic nanostructure described herein comprises x instances of a transition metal ion and 2x instances of a ligand of Formula (A):

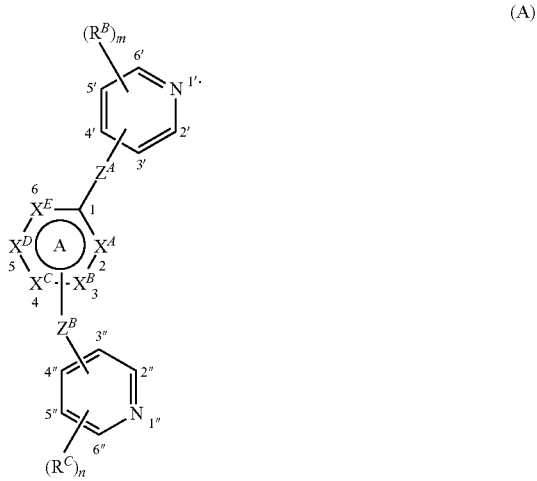

A metal organic nanostructure described herein includes x instances of a transition metal ion. In certain embodiments, all instances of the transition metal ion in a metal organic nanostructure are the same. In certain embodiments, x is an integer (e.g., an even integer) between 2 and 48, inclusive. In certain embodiments, x is an integer (e.g., an even integer) between 2 and 30, inclusive. In certain embodiments, x is an integer (e.g., an even integer) between 2 and 24, inclusive. In certain embodiments, x is an integer (e.g., an even integer) between 2 and 18, inclusive. In certain embodiments, x is 2. In certain embodiments, x is 4. In certain embodiments, x is 6. In certain embodiments, x is 12. In certain embodiments, x is 18. In certain embodiments, x is 24. In certain embodiments, x is 30. In certain embodiments, x is 48. In certain embodiments, x is 60. In certain embodiments, x is 12; and the nanostructure is a nanosphere. In certain embodiments, x is 24; and the nanostructure is a nanosphere. In certain embodiments, x is 2; and the nanostructure is a nano-paddlewheel.

In certain embodiments, each instance of the transition metal ion is the same. In certain embodiments, at least two instances of the transition metal ion or transition metal salt are different from each other. In certain embodiments, at least one instance of the transition metal ion or transition metal salt comprises Pd (e.g., Pd(II)). In certain embodiments, each instance of the transition metal ion or transition metal salt comprises Pd (e.g., Pd(II)). In certain embodiments, at least one instance of the transition metal ion or transition metal salt comprises Rh (e.g., Rh(I)). In certain embodiments, at least one instance of the transition metal ion or transition metal salt comprises Ir (e.g., Ir(I)). In certain embodiments, at least one instance of the transition metal ion or transition metal salt comprises Ni (e.g., Ni(II)). In certain embodiments, at least one instance of the transition metal ion or transition metal salt comprises Pt (e.g., Pt(II)). In certain embodiments, at least one instance of the transition metal ion or transition metal salt comprises Fe (e.g., Fe(II) or Fe(III)). In certain embodiments, at least one instance of the transition metal ion or transition metal salt comprises Au (e.g., Au(III)). In certain embodiments, at least one instance of the transition metal ion or transition metal salt comprises Cd (e.g., Cd(II)), Co (e.g., Co(III)), or Cu (e.g., Cu(I) or Cu(II)). In certain embodiments, at least one instance of the transition metal ion or transition metal salt comprises Zn(II). In certain embodiments, each instance of the transition metal ion or transition metal salt comprises Zn(II). In certain embodiments, at least one instance of the transition metal ion or transition metal salt does not comprise Zn(II).

In certain embodiments, all instances of the ligand of Formula (A) in a metal organic nanostructure are the same. In other embodiments, at least two instances of the ligand of Formula (A) in a metal organic nanostructure are different. In certain embodiments, all instances of the ligand of Formula (B) in a metal organic nanostructure are the same. In other embodiments, at least two instances of the ligand of Formula (B) in a metal organic nanostructure are different. In certain embodiments, all instances of the ligand of Formula (C) in a metal organic nanostructure are the same. In other embodiments, at least two instances of the ligand of Formula (C) in a metal organic nanostructure are different.

Formula (A) or (B) includes Ring A that includes $X^A$, $X^B$, $X^C$, $X^D$, and $X^E$ in the ring system and is unsubstituted (e.g., each instance of $R^{A1}$ and $R^{A2}$ is hydrogen) or substituted with one or more substituents $R^{A1}$ and/or $R^{A2}$ (e.g., at least one instance of $R^{A1}$ or $R^{A2}$ is not hydrogen). In certain embodiments, $X^E$ is a bond. In certain embodiments, $X^E$ is N, C, or $CR^{A2}$. In certain embodiments, each instance of $X^A$, $X^B$, $X^C$, $X^D$, and $X^E$ is independently C or $CR^{A2}$, and Ring A is a substituted or unsubstituted phenyl ring. In certain embodiments, Ring A is of the formula:

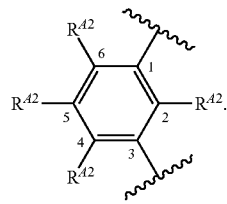

In certain embodiments, Ring A is of the formula:

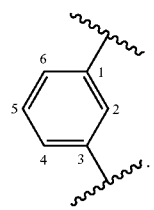 [SMILES: *c1cccc(*)c1]

In certain embodiments, Ring A is of the formula:

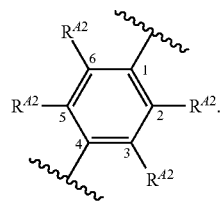

In certain embodiments, Ring A is of the formula:

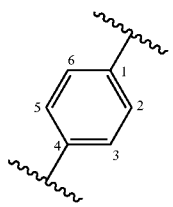

In certain embodiments, each instance of $X^A$, $X^B$, $X^C$, and $X^D$ is independently O, S, N, $NR^{A1}$, C, or $CR^{A2}$; at least one of $X^A$, $X^B$, $X^C$, and $X^D$ is not C or $CR^{A2}$; $X^E$ is a bond; and Ring A is a substituted or unsubstituted, 5-membered, monocyclic heteroaryl ring. In certain embodiments, Ring A is a substituted or unsubstituted furanyl, substituted or unsubstituted thienyl, or substituted or unsubstituted pyrrolyl ring. In certain embodiments, Ring A is of the formula:

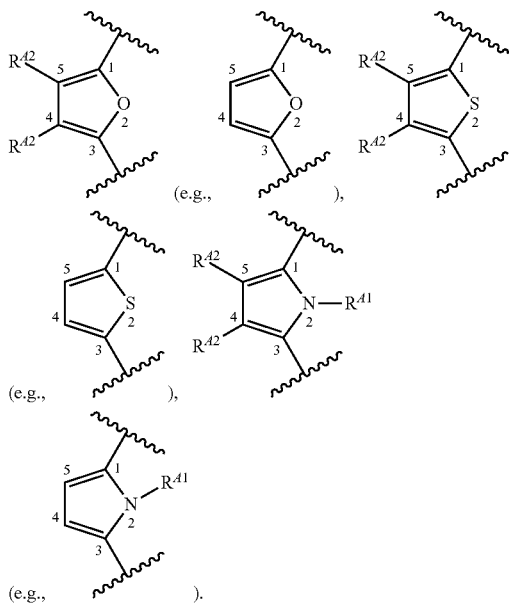

In certain embodiments, Ring A is a pyrazolyl, imidazolyl, oxazolyl, isoxazolyl, thiazolyl, or isothiazolyl ring, each of which is unsubstituted or substituted with $R^{A2}$. In certain embodiments, each instance of $X^A$, $X^B$, $X^C$, and $X^D$ is independently O, S, N, $NR^{A1}$, C, or $CR^{A2}$; $X^E$ is N, C, or $CR^{A2}$; at least one of $X^A$, $X^B$, $X^C$, $X^D$, and $X^E$ is not C or $CR^{A2}$; and Ring A is a substituted or unsubstituted, 6-membered, monocyclic heteroaryl ring. In certain embodiments, Ring A is a substituted or unsubstituted pyridyl ring. In certain embodiments, Ring A is of the formula:

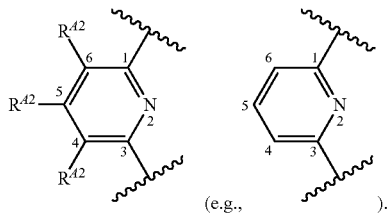

In certain embodiments, Ring A is a substituted or unsubstituted pyrazinyl, substituted or unsubstituted pyrimidinyl, or substituted or unsubstituted pyridazinyl ring. In certain embodiments, Ring A is of the formula:

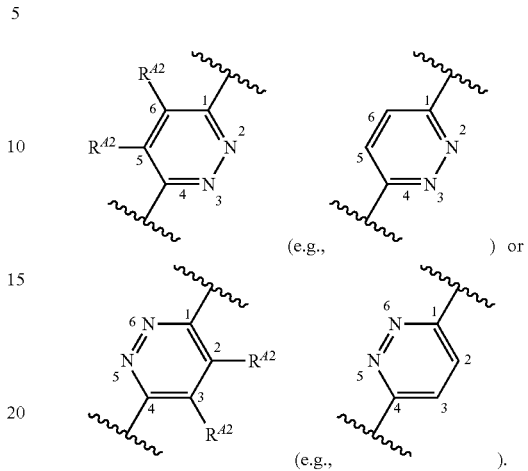

In certain embodiments, Ring A is of the formula:

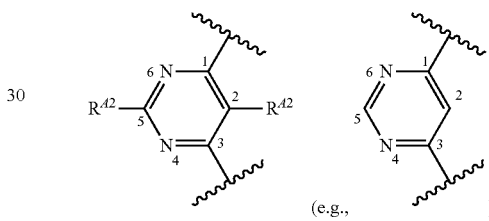

In certain embodiments, Ring A is of the formula:

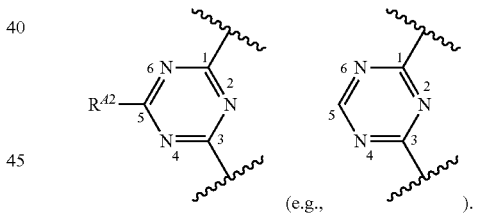

In certain embodiments, Ring A is of the formula:

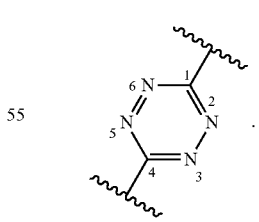

In certain embodiments, at least two instances of $R^{A1}$ are different from each other. In certain embodiments, all instances of $R^{A1}$ are the same. In certain embodiments, at least one instance of $R^{A1}$ is hydrogen. In certain embodiments, each instance of $R^{A1}$ is hydrogen. In certain embodiments, at least one instance of $R^{A1}$ is substituted alkyl. In certain embodiments, at least one instance of $R^{A1}$ is unsubstituted alkyl. In certain embodiments, at least one instance of $R^{41}$ is unsubstituted $C_{1-6}$ alkyl. In certain embodiments, all instances of $R^{41}$ are unsubstituted $C_{1-6}$ alkyl. In certain embodiments, at least one instance of $R^{41}$ is substituted $C_{1-6}$ alkyl. In certain embodiments, at least one instance of $R^{41}$ is $C_{1-6}$ alkyl substituted with at least one halogen. In certain embodiments, at least one instance of $R^{41}$ is —$CH_3$. In certain embodiments, all instances of $R^{41}$ are —$CH_3$. In certain embodiments, at least one instance of $R^{41}$ is substituted methyl. In certain embodiments, at least one instance of $R^{41}$ is —$CH_2F$, —$CHF_2$, or —$CF_3$. In certain embodiments, at least one instance of $R^{41}$ is ethyl, propyl, butyl, pentyl, or hexyl. In certain embodiments, at least one instance of $R^{41}$ is substituted alkenyl. In certain embodiments, at least one instance of $R^{41}$ is unsubstituted alkenyl. In certain embodiments, at least one instance of $R^{41}$ is substituted alkynyl. In certain embodiments, at least one instance of $R^{41}$ is unsubstituted alkynyl. In certain embodiments, at least one instance of $R^{41}$ is substituted carbocyclyl. In certain embodiments, at least one instance of $R^{41}$ is unsubstituted carbocyclyl. In certain embodiments, at least one instance of $R^{41}$ is saturated carbocyclyl. In certain embodiments, at least one instance of $R^{41}$ is unsaturated carbocyclyl. In certain embodiments, at least one instance of $R^{41}$ is monocyclic carbocyclyl. In certain embodiments, at least one instance of $R^{41}$ is 3- to 7-membered, monocyclic carbocyclyl. In certain embodiments, at least one instance of $R^{41}$ is substituted heterocyclyl. In certain embodiments, at least one instance of $R^{41}$ is unsubstituted heterocyclyl. In certain embodiments, at least one instance of $R^{41}$ is saturated heterocyclyl. In certain embodiments, at least one instance of $R^{41}$ is unsaturated heterocyclyl. In certain embodiments, at least one instance of $R^{41}$ is heterocyclyl, wherein one, two, or three atoms in the heterocyclic ring system are independently selected from the group consisting of nitrogen, oxygen, and sulfur. In certain embodiments, at least one instance of $R^{41}$ is monocyclic heterocyclyl. In certain embodiments, at least one instance of $R^{41}$ is 3- to 7-membered, monocyclic heterocyclyl. In certain embodiments, at least one instance of $R^{41}$ is substituted aryl. In certain embodiments, at least one instance of $R^{41}$ is unsubstituted aryl. In certain embodiments, at least one instance of $R^{41}$ is 6- to 10-membered aryl. In certain embodiments, at least one instance of $R^{41}$ is substituted phenyl. In certain embodiments, at least one instance of $R^{41}$ is unsubstituted phenyl. In certain embodiments, at least one instance of $R^{41}$ is substituted heteroaryl. In certain embodiments, at least one instance of $R^{41}$ is unsubstituted heteroaryl. In certain embodiments, at least one instance of $R^{41}$ is heteroaryl, wherein one, two, three, or four atoms in the heteroaryl ring system are independently selected from the group consisting of nitrogen, oxygen, and sulfur. In certain embodiments, at least one instance of $R^{41}$ is monocyclic heteroaryl. In certain embodiments, at least one instance of $R^{41}$ is 5-membered, monocyclic heteroaryl. In certain embodiments, at least one instance of $R^{41}$ is 6-membered, monocyclic heteroaryl. In certain embodiments, at least one instance of $R^{41}$ is bicyclic heteroaryl, wherein the point of attachment may be on any atom of the bicyclic heteroaryl ring system, as valency permits. In certain embodiments, at least one instance of $R^{41}$ is 9- or 10-membered, bicyclic heteroaryl. In certain embodiments, at least one instance of $R^{41}$ is —C(=O)$R^a$ (e.g., —C(=O)(substituted or unsubstituted $C_{1-6}$ alkyl)), —C(=O)O$R^a$ (e.g., —C(=O)O(substituted or unsubstituted $C_{1-6}$ alkyl)), or —C(=O)N($R^a$)$_2$ (e.g., —C(=O)NH$_2$, —C(=O)NH(substituted or unsubstituted $C_{1-6}$ alkyl), or —C(=O)N(substituted or unsubstituted $C_{1-6}$ alkyl)-(substituted or unsubstituted $C_{1-6}$ alkyl)). In certain embodiments, at least one instance of $R^{41}$ is a nitrogen protecting group. In certain embodiments, at least one instance of $R^{41}$ is Bn, Boc, Cbz, Fmoc, trifluoroacetyl, triphenylmethyl, acetyl, or Ts.

Each instance of $R^{41}$, $R^{42}$, $R^B$, and $R^C$ may independently include one or more substituents $R^a$. In certain embodiments, all instances of $R^a$ are the same. In certain embodiments, at least two instances of $R^a$ are different from each other. In certain embodiments, at least one instance of $R^a$ is H. In certain embodiments, each instance of $R^a$ is H. In certain embodiments, at least one instance of $R^a$ is substituted or unsubstituted acyl (e.g., acetyl). In certain embodiments, at least one instance of $R^a$ is substituted or unsubstituted alkyl (e.g., substituted or unsubstituted $C_{1-6}$ alkyl). In certain embodiments, at least one instance of $R^a$ is —$CH_3$. In certain embodiments, at least one instance of $R^a$ is —$CF_3$, unsubstituted ethyl, perfluoroethyl, unsubstituted propyl, perfluoropropyl, unsubstituted butyl, or perfluorobutyl. In certain embodiments, at least one instance of $R^a$ is substituted or unsubstituted alkenyl (e.g., substituted or unsubstituted $C_{1-6}$ alkenyl). In certain embodiments, at least one instance of $R^a$ is substituted or unsubstituted alkynyl (e.g., substituted or unsubstituted $C_{1-6}$ alkynyl). In certain embodiments, at least one instance of $R^a$ is substituted or unsubstituted carbocyclyl (e.g., substituted or unsubstituted, monocyclic, 3- to 7-membered carbocyclyl). In certain embodiments, at least one instance of $R^a$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted phenyl. In certain embodiments, at least one instance of $R^a$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^a$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^a$ are joined to form a substituted or unsubstituted heterocyclic ring (e.g., substituted or unsubstituted, monocyclic, 5- to 6-membered heterocyclic ring, wherein one, two, or three atoms in the heterocyclic ring system are independently nitrogen, oxygen, or sulfur). In certain embodiments, two instances of $R^a$ are joined to form a substituted or unsubstituted heteroaryl ring (e.g., substituted or unsubstituted, monocyclic, 5- to 6-membered heteroaryl ring, wherein one, two, three, or four atoms in the heteroaryl ring system are independently nitrogen, oxygen, or sulfur).

In certain embodiments, at least two instances of $R^{42}$ are different from each other. In certain embodiments, all instances of $R^{42}$ are the same. In certain embodiments, at least one instance of $R^{42}$ is hydrogen. In certain embodiments, each instance of $R^{42}$ is hydrogen. In certain embodiments, at least one instance of $R^{42}$ is halogen. In certain embodiments, at least one instance of $R^{A2}$ is F. In certain embodiments, at least one instance of $R^{A2}$ is Cl. In certain embodiments, at least one instance of $R^{A2}$ is Br. In certain embodiments, at least one instance of $R^{A2}$ is I (iodine). In certain embodiments, at least one instance of $R^{A2}$ is substituted alkyl. In certain embodiments, at least one instance of $R^{A2}$ is unsubstituted alkyl. In certain embodiments, at least one instance of $R^{A2}$ is unsubstituted $C_{1-6}$ alkyl. In certain embodiments, all instances of $R^{A2}$ are unsubstituted $C_{1-6}$ alkyl. In certain embodiments, at least one instance of $R^{A2}$ is substituted $C_{1-6}$ alkyl. In certain embodiments, at least one instance of $R^{A2}$ is $C_{1-6}$ alkyl substituted with at least one halogen. In certain embodiments, at least one instance of $R^{A2}$ is —$CH_3$. In certain embodiments, all instances of $R^{A2}$ are —$CH_3$. In certain embodiments, at least one instance of $R^{A2}$ is substituted methyl. In certain embodiments, at least one instance of $R^{A2}$ is —$CH_2F$, —$CHF_2$, or —$CF_3$. In certain embodiments, at least one instance of $R^{A2}$ is ethyl, propyl, butyl, pentyl, or hexyl. In certain embodiments, at least one instance of $R^{A2}$ is substituted alkenyl. In certain embodiments, at least one instance of $R^{A2}$ is unsubstituted alkenyl. In certain embodiments, at least one instance of $R^{A2}$ is substituted alkynyl. In certain embodiments, at least one instance of $R^{A2}$ is unsubstituted alkynyl. In certain embodiments, at least one instance of $R^{A2}$ is substituted carbocyclyl. In certain embodiments, at least one instance of $R^{A2}$ is unsubstituted carbocyclyl. In certain embodiments, at least one instance of $R^{A2}$ is saturated carbocyclyl. In certain embodiments, at least one instance of $R^{A2}$ is unsaturated carbocyclyl. In certain embodiments, at least one instance of $R^{A2}$ is monocyclic carbocyclyl. In certain embodiments, at least one instance of $R^{A2}$ is 3- to 7-membered, monocyclic carbocyclyl. In certain embodiments, at least one instance of $R^{A2}$ is substituted heterocyclyl. In certain embodiments, at least one instance of $R^{A2}$ is unsubstituted heterocyclyl. In certain embodiments, at least one instance of $R^{A2}$ is saturated heterocyclyl. In certain embodiments, at least one instance of $R^{A2}$ is unsaturated heterocyclyl. In certain embodiments, at least one instance of $R^{A2}$ is heterocyclyl, wherein one, two, or three atoms in the heterocyclic ring system are independently selected from the group consisting of nitrogen, oxygen, and sulfur. In certain embodiments, at least one instance of $R^{A2}$ is monocyclic heterocyclyl. In certain embodiments, at least one instance of $R^{A2}$ is 3- to 7-membered, monocyclic heterocyclyl. In certain embodiments, at least one instance of $R^{A2}$ is substituted aryl. In certain embodiments, at least one instance of $R^{A2}$ is unsubstituted aryl. In certain embodiments, at least one instance of $R^{A2}$ is 6- to 10-membered aryl. In certain embodiments, at least one instance of $R^{A2}$ is substituted phenyl. In certain embodiments, at least one instance of $R^{A2}$ is unsubstituted phenyl. In certain embodiments, at least one instance of $R^{A2}$ is substituted heteroaryl. In certain embodiments, at least one instance of $R^{A2}$ is unsubstituted heteroaryl. In certain embodiments, at least one instance of $R^{A2}$ is heteroaryl, wherein one, two, three, or four atoms in the heteroaryl ring system are independently selected from the group consisting of nitrogen, oxygen, and sulfur. In certain embodiments, at least one instance of $R^{A2}$ is monocyclic heteroaryl. In certain embodiments, at least one instance of $R^{A2}$ is 5-membered, monocyclic heteroaryl. In certain embodiments, at least one instance of $R^{A2}$ is 6-membered, monocyclic heteroaryl. In certain embodiments, at least one instance of $R^{A2}$ is bicyclic heteroaryl, wherein the point of attachment may be on any atom of the bicyclic heteroaryl ring system, as valency permits. In certain embodiments, at least one instance of $R^{A2}$ is 9- or 10-membered, bicyclic heteroaryl. In certain embodiments, at least one instance of $R^{A2}$ is —$OR^a$. In certain embodiments, at least one instance of $R^{A2}$ is —OH. In certain embodiments, at least one instance of $R^{A2}$ is —O(substituted or unsubstituted $C_{1-6}$ alkyl). In certain embodiments, at least one instance of $R^{A2}$ is —OMe. In certain embodiments, at least one instance of $R^{A2}$ is —OEt, —OPr, or —OBu. In certain embodiments, at least one instance of $R^{A2}$ is —OBn or —OPh. In certain embodiments, at least one instance of $R^{A2}$ is —$SR^a$. In certain embodiments, at least one instance of $R^{A2}$ is —SH. In certain embodiments, at least one instance of $R^{A2}$ is —SMe. In certain embodiments, at least one instance of $R^{A2}$ is —N($R^a$)$_2$. In certain embodiments, at least one instance of $R^{A2}$ is —$NH_2$. In certain embodiments, at least one instance of $R^{A2}$ is —NHMe. In certain embodiments, at least one instance of $R^{A2}$ is —$NMe_2$. In certain embodiments, at least one instance of $R^{A2}$ is —CN. In certain embodiments, at least one instance of $R^{A2}$ is —SCN. In certain embodiments, at least one instance of $R^{A2}$ is —C(=$NR^a$)$R^a$, —C(=$NR^a$)$OR^a$, or —C(=$NR^a$)N($R^a$)$_2$. In certain embodiments, at least one instance of $R^{A2}$ is —C(=O)$R^a$ or —C(=O)$OR^a$. In certain embodiments, at least one instance of $R^{A2}$ is —C(=O)N($R^a$)$_2$. In certain embodiments, at least one instance of $R^{A2}$ is —C(=O)$NMe_2$, —C(=O)NHMe, or —C(=O)$NH_2$. In certain embodiments, at least one instance of $R^{A2}$ is —$NO_2$. In certain embodiments, at least one instance of $R^{A2}$ is —$NR^a$C(=O)$R^a$, —$NR^a$C(=O)$OR^a$, or —$NR^a$C(=O)N($R^a$)$_2$. In certain embodiments, at least one instance of $R^{A2}$ is —OC(=O)$R^a$, —OC(=O)$OR^a$, or —OC(=O)N($R^a$)$_2$.

Formula (A) or (B) includes as Ring B a pyridyl ring that is unsubstituted (e.g., when m is 0) or substituted with one or more substituents $R^B$ (e.g., when m is 1, 2, 3, or 4). In certain embodiments, Ring B is of the formula:

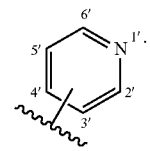

In certain embodiments, Ring B is of the formula:

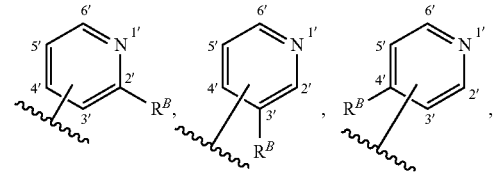

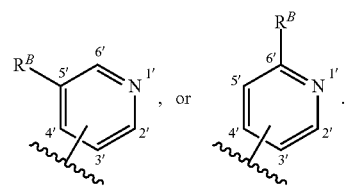

In certain embodiments, Ring B is of the formula:

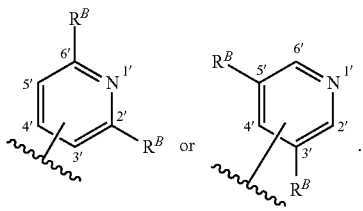

In certain embodiments, Ring B is of the formula:

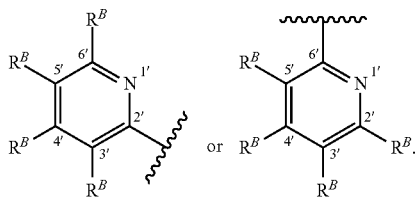

In certain embodiments, Ring B is of the formula:

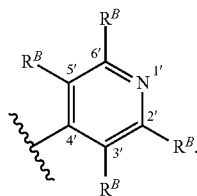

In certain embodiments, Ring B is of the formula:

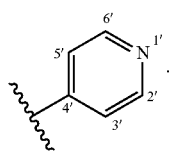

In certain embodiments, Ring B is of the formula:

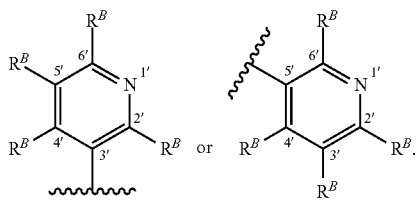

In certain embodiments, Ring B is of the formula:

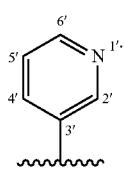

In certain embodiments, at least two instances of $R^B$ are different from each other. In certain embodiments, all instances of $R^B$ are the same. In certain embodiments, at least one instance of $R^B$ is halogen. In certain embodiments, at least one instance of $R^B$ is F. In certain embodiments, at least one instance of $R^B$ is Cl. In certain embodiments, at least one instance of $R^B$ is Br. In certain embodiments, at least one instance of $R^B$ is I (iodine). In certain embodiments, at least one instance of $R^B$ is substituted alkyl. In certain embodiments, at least one instance of $R^B$ is unsubstituted alkyl. In certain embodiments, at least one instance of $R^B$ is unsubstituted $C_{1-6}$ alkyl. In certain embodiments, all instances of $R^B$ are unsubstituted $C_{1-6}$ alkyl. In certain embodiments, at least one instance of $R^B$ is substituted $C_{1-6}$ alkyl. In certain embodiments, at least one instance of $R^B$ is $C_{1-6}$ alkyl substituted with at least one halogen. In certain embodiments, at least one instance of $R^B$ is —$CH_3$. In certain embodiments, all instances of $R^B$ are —$CH_3$. In certain embodiments, at least one instance of $R^B$ is substituted methyl. In certain embodiments, at least one instance of $R^B$ is —$CH_2F$, —$CHF_2$, or —$CF_3$. In certain embodiments, at least one instance of $R^B$ is ethyl, propyl, butyl, pentyl, or hexyl. In certain embodiments, at least one instance of $R^B$ is substituted alkenyl. In certain embodiments, at least one instance of $R^B$ is unsubstituted alkenyl. In certain embodiments, at least one instance of $R^B$ is substituted alkynyl. In certain embodiments, at least one instance of $R^B$ is unsubstituted alkynyl. In certain embodiments, at least one instance of $R^B$ is substituted carbocyclyl. In certain embodiments, at least one instance of $R^B$ is unsubstituted carbocyclyl. In certain embodiments, at least one instance of $R^B$ is saturated carbocyclyl. In certain embodiments, at least one instance of $R^B$ is unsaturated carbocyclyl. In certain embodiments, at least one instance of $R^B$ is monocyclic carbocyclyl. In certain embodiments, at least one instance of $R^B$ is 3- to 7-membered, monocyclic carbocyclyl. In certain embodiments, at least one instance of $R^B$ is substituted heterocyclyl. In certain embodiments, at least one instance of $R^B$ is unsubstituted heterocyclyl. In certain embodiments, at least one instance of $R^B$ is saturated heterocyclyl. In certain embodiments, at least one instance of $R^B$ is unsaturated heterocyclyl. In certain embodiments, at least one instance of $R^B$ is heterocyclyl, wherein one, two, or three atoms in the heterocyclic ring system are independently selected from the group consisting of nitrogen, oxygen, and sulfur. In certain embodiments, at least one instance of $R^B$ is monocyclic heterocyclyl. In certain embodiments, at least one instance of $R^B$ is 3- to 7-membered, monocyclic heterocyclyl. In certain embodiments, at least one instance of $R^B$ is substituted aryl. In certain embodiments, at least one instance of $R^B$ is unsubstituted aryl. In certain embodiments, at least one instance of $R^B$ is 6- to 10-membered aryl. In certain embodiments, at least one instance of $R^B$ is substituted phenyl. In certain embodiments, at least one instance of $R^B$ is unsubstituted phenyl. In certain embodiments, at least one instance of $R^B$ is substituted heteroaryl. In certain embodiments, at least one instance of $R^B$ is unsubstituted heteroaryl. In certain embodiments, at least one instance of $R^B$ is heteroaryl, wherein one, two, three, or four atoms in the heteroaryl ring system are independently selected from the group consisting of nitrogen, oxygen, and sulfur. In certain embodiments, at least one instance of $R^B$ is monocyclic heteroaryl. In certain embodiments, at least one instance of $R^B$ is 5-membered, monocyclic heteroaryl. In certain embodiments, at least one instance of $R^B$ is 6-membered, monocyclic heteroaryl. In certain embodiments, at least one instance of $R^B$ is bicyclic heteroaryl, wherein the point of attachment may be on any atom of the bicyclic heteroaryl ring system, as valency permits. In certain embodiments, at least one instance of $R^B$ is 9- or 10-membered, bicyclic heteroaryl. In certain embodiments, at least one instance of $R^B$ is —$OR^a$. In certain embodiments, at least one instance of $R^B$ is —OH. In certain embodiments, at least one instance of $R^B$ is —O(substituted or unsubstituted $C_{1-6}$ alkyl). In certain embodiments, at least one instance of $R^B$ is —OMe. In certain embodiments, at least one instance of $R^B$ is —OEt, —OPr, or —OBu. In certain embodiments, at least one instance of $R^B$ is —OBn or —OPh. In certain embodiments, at least one instance of $R^B$ is —$SR^a$. In certain embodiments, at least one instance of $R^B$ is —SH. In certain embodiments, at least one instance of $R^B$ is —SMe. In certain embodiments, at least one instance of $R^B$ is —N$(R^a)_2$. In certain embodiments, at least one instance of $R^B$ is —$NH_2$. In certain embodiments, at least one instance of $R^B$ is —NHMe. In certain embodiments, at least one instance of $R^B$ is —$NMe_2$. In certain embodiments, at least one instance of $R^B$ is —CN. In certain embodiments, at least one instance of $R^B$ is —SCN. In certain embodiments, at least one instance of $R^B$ is —C(=$NR^a$)$R^a$, —C(=$NR^a$)$OR^a$, or —C(=$NR^a$)N$(R^a)_2$. In certain embodiments, at least one instance of $R^B$ is —C(=O)$R^a$ or —C(=O)$OR^a$. In certain embodiments, at least one instance of $R^B$ is —C(=O)N$(R^a)_2$. In certain embodiments, at least one instance of $R^B$ is —C(=O)$NMe_2$, —C(=O)NHMe, or —C(=O)$NH_2$. In certain embodiments, at least one instance of $R^B$ is —$NO_2$. In certain embodiments, at least one instance of $R^B$ is —$NR^a$C(=O)$R^a$, —$NR^a$C(=O)$OR^a$, or —$NR^a$C(=O)N$(R^a)_2$. In certain embodiments, at least one instance of $R^B$ is —OC(=O)$R^a$, —OC(=O)$OR^a$, or —OC(=O)N$(R^a)_2$.

In certain embodiments, m is 0. In certain embodiments, m is 1. In certain embodiments, m is 2. In certain embodiments, m is 3. In certain embodiments, m is 4.

Formula (A) includes as Ring C a pyridyl ring that is unsubstituted (e.g., when n is 0) or substituted with one or more substituents $R^C$ (e.g., when n is 1, 2, 3, or 4). In certain embodiments, Ring C is of the formula:

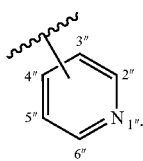

In certain embodiments, Ring C is of the formula:

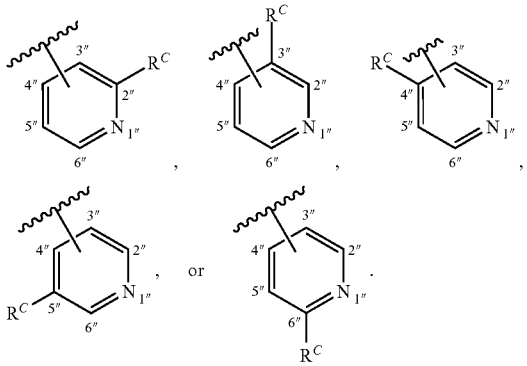

In certain embodiments, Ring C is of the formula:

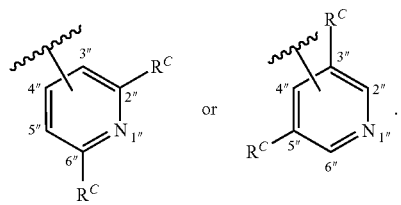

In certain embodiments, Ring C is of the formula:

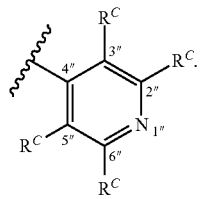

In certain embodiments, Ring C is of the formula:

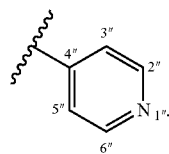 [SMILES: *c1ccncc1]

In certain embodiments, Ring C is of the formula:

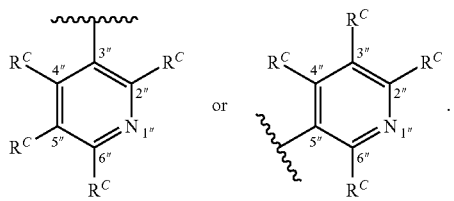

In certain embodiments, Ring C is of the formula:

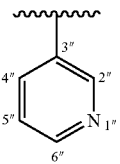

In certain embodiments, at least two instances of $R^C$ are different from each other. In certain embodiments, all instances of $R^C$ are the same. In certain embodiments, at least one instance of $R^C$ is halogen. In certain embodiments, at least one instance of $R^C$ is F. In certain embodiments, at least one instance of $R^C$ is Cl. In certain embodiments, at least one instance of $R^C$ is Br. In certain embodiments, at least one instance of $R^C$ is I (iodine). In certain embodiments, at least one instance of $R^C$ is substituted alkyl. In certain embodiments, at least one instance of $R^C$ is unsubstituted alkyl. In certain embodiments, at least one instance of $R^C$ is unsubstituted $C_{1-6}$ alkyl. In certain embodiments, all instances of $R^C$ are unsubstituted $C_{1-6}$ alkyl. In certain embodiments, at least one instance of $R^C$ is substituted $C_{1-6}$ alkyl. In certain embodiments, at least one instance of $R^C$ is $C_{1-6}$ alkyl substituted with at least one halogen. In certain embodiments, at least one instance of $R^C$ is —$CH_3$. In certain embodiments, all instances of $R^C$ are —$CH_3$. In certain embodiments, at least one instance of $R^C$ is substituted methyl. In certain embodiments, at least one instance of $R^C$ is —$CH_2F$, —$CHF_2$, or —$CF_3$. In certain embodiments, at least one instance of $R^C$ is ethyl, propyl, butyl, pentyl, or hexyl. In certain embodiments, at least one instance of $R^C$ is substituted alkenyl. In certain embodiments, at least one instance of $R^C$ is unsubstituted alkenyl. In certain embodiments, at least one instance of $R^C$ is substituted alkynyl. In certain embodiments, at least one instance of $R^C$ is unsubstituted alkynyl. In certain embodiments, at least one instance of $R^C$ is substituted carbocyclyl. In certain embodiments, at least one instance of $R^C$ is unsubstituted carbocyclyl. In certain embodiments, at least one instance of $R^C$ is saturated carbocyclyl. In certain embodiments, at least one instance of $R^C$ is unsaturated carbocyclyl. In certain embodiments, at least one instance of $R^C$ is monocyclic carbocyclyl. In certain embodiments, at least one instance of $R^C$ is 3- to 7-membered, monocyclic carbocyclyl. In certain embodiments, at least one instance of $R^C$ is substituted heterocyclyl. In certain embodiments, at least one instance of $R^C$ is unsubstituted heterocyclyl. In certain embodiments, at least one instance of $R^C$ is saturated heterocyclyl. In certain embodiments, at least one instance of $R^C$ is unsaturated heterocyclyl. In certain embodiments, at least one instance of $R^C$ is heterocyclyl, wherein one, two, or three atoms in the heterocyclic ring system are independently selected from the group consisting of nitrogen, oxygen, and sulfur. In certain embodiments, at least one instance of $R^C$ is monocyclic heterocyclyl. In certain embodiments, at least one instance of $R^C$ is 3- to 7-membered, monocyclic heterocyclyl. In certain embodiments, at least one instance of $R^C$ is substituted aryl. In certain embodiments, at least one instance of $R^C$ is unsubstituted aryl. In certain embodiments, at least one instance of $R^C$ is 6- to 10-membered aryl. In certain embodiments, at least one instance of $R^C$ is substituted phenyl. In certain embodiments, at least one instance of $R^C$ is unsubstituted phenyl. In certain embodiments, at least one instance of $R^C$ is substituted heteroaryl. In certain embodiments, at least one instance of $R^C$ is unsubstituted heteroaryl. In certain embodiments, at least one instance of $R^C$ is heteroaryl, wherein one, two, three, or four atoms in the heteroaryl ring system are independently selected from the group consisting of nitrogen, oxygen, and sulfur. In certain embodiments, at least one instance of $R^C$ is monocyclic heteroaryl. In certain embodiments, at least one instance of $R^C$ is 5-membered, monocyclic heteroaryl. In certain embodiments, at least one instance of $R^C$ is 6-membered, monocyclic heteroaryl. In certain embodiments, at least one instance of $R^C$ is bicyclic heteroaryl, wherein the point of attachment may be on any atom of the bicyclic heteroaryl ring system, as valency permits. In certain embodiments, at least one instance of $R^C$ is 9- or 10-membered, bicyclic heteroaryl. In certain embodiments, at least one instance of $R^C$ is —$OR^a$. In certain embodiments, at least one instance of $R^C$ is —OH. In certain embodiments, at least one instance of $R^C$ is —O(substituted or unsubstituted $C_{1-6}$ alkyl). In certain embodiments, at least one instance of $R^C$ is —OMe. In certain embodiments, at least one instance of $R^C$ is —OEt, —OPr, or —OBu. In certain embodiments, at least one instance of $R^C$ is —OBn or —OPh. In certain embodiments, at least one instance of $R^C$ is —$SR^a$. In certain embodiments, at least one instance of $R^C$ is —SH. In certain embodiments, at least one instance of $R^C$ is —SMe. In certain embodiments, at least one instance of $R^C$ is —$N(R^a)_2$. In certain embodiments, at least one instance of $R^C$ is —$NH_2$. In certain embodiments, at least one instance of $R^C$ is —NHMe. In certain embodiments, at least one instance of $R^C$ is —$NMe_2$. In certain embodiments, at least one instance of $R^C$ is —CN. In certain embodiments, at least one instance of $R^C$ is —SCN. In certain embodiments, at least one instance of $R^C$ is —$C(=NR^a)R^a$, —$C(=NR^a)OR^a$, or —$C(=NR^a)N(R^a)_2$. In certain embodiments, at least one instance of $R^C$ is —$C(=O)R^a$ or —$C(=O)OR^a$. In certain embodiments, at least one instance of $R^C$ is —$C(=O)N(R^a)_2$. In certain embodiments, at least one instance of $R^C$ is —$C(=O)NMe_2$, —$C(=O)NHMe$, or —$C(=O)NH_2$. In certain embodiments, at least one instance of $R^C$ is —$NO_2$. In certain embodiments, at least one instance of $R^C$ is —$NR^aC(=O)R^a$, —$NR^aC(=O)OR^a$, or —$NR^aC(=O)N(R^a)_2$. In certain embodiments, at least one instance of $R^C$ is —$OC(=O)R^a$, —$OC(=O)OR^a$, or —$OC(=O)N(R^a)_2$.

In certain embodiments, n is 0. In certain embodiments, n is 1. In certain embodiments, n is 2. In certain embodiments, n is 3. In certain embodiments, n is 4.

In certain embodiments, at least one instance of $R^B$ and at least one instance of $R^C$ are different from each other. In certain embodiments, the instance of $R^B$ at the carbon atom labeled with w' is the same as the instance of $R^C$ at the carbon atom labeled with w'', wherein w is 2, 3, 4, 5, or 6. In certain embodiments, m and n are different from each other. In certain embodiments, m and n are the same. In certain embodiments, each of m and n is 0.

Formula (A) or (B) includes a divalent linker $Z^A$ that directly covalently connects Ring A and Ring B. In certain embodiments, $Z^A$ is a bond. In certain embodiments, $Z^A$ is a substituted or unsubstituted $C_{1-4}$ hydrocarbon chain, optionally wherein one or more chain atoms are independently replaced with —C(=O)—, —O—, —S—, —$NR^{ZA}$—, —N=, or =N—. In certain embodiments, when $Z^A$ is a substituted or unsubstituted $C_{1-4}$ hydrocarbon chain, $Z^A$ consists of a chain, and optionally one or more hydrogen atoms and/or one or more substituents (e.g., =O) on the chain, where any two substituents may optionally be joined to form a ring. In certain embodiments, $Z^A$ does not include unsaturated bonds in the chain. In certain embodiments, $Z^A$ consists of one or two unsaturated bonds in the chain. In certain embodiments, $Z^A$ is a substituted (e.g., substituted with at least one instance of halogen) $C_{1-4}$ hydrocarbon chain. In certain embodiments, $Z^A$ is an unsubstituted $C_{1-4}$ hydrocarbon chain. In certain embodiments, the molecular weight of $Z^A$ is not more than 150 g/mol, not more than 100 g/mol, not more than 80 g/mol, not more than 50 g/mol, or not more than 30 g/mol. In certain embodiments, $Z^A$ consists of not more than 50 atoms, not more than 40 atoms, not more than 30 atoms, not more than 20 atoms, or not more than 10 atoms. In certain embodiments, $Z^A$ is —C≡C— or —C≡C—C≡C—. In certain embodiments, $Z^A$ is of the formula:

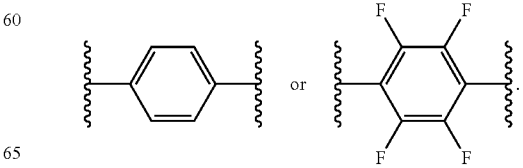

In certain embodiments, all instances of $R^{ZA}$ are the same. In certain embodiments, at least two instances of $R^{ZA}$ are different from each other. In certain embodiments, at least one instance of $R^{ZA}$ is hydrogen. In certain embodiments, all instances of $R^{ZA}$ are hydrogen. In certain embodiments, at least one instance of $R^{ZA}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of $R^{ZA}$ is a nitrogen protecting group (e.g., Bn, Boc, Cbz, Fmoc, trifluoroacetyl, triphenylmethyl, acetyl, or Ts).

In certain embodiments, $Z^A$ is directly covalently attached to the carbon atom labeled with 2' or 6' of Ring B. In certain embodiments, $Z^A$ is directly covalently attached to the carbon atom labeled with 3' or 5' of Ring B. In certain embodiments, $Z^A$ is directly covalently attached to the carbon atom labeled with 4' of Ring B.

Formula (A) includes a divalent linker $Z^B$ that directly covalently connects Ring A and Ring C. In certain embodiments, $Z^B$ is a bond. In certain embodiments, $Z^B$ is a substituted or unsubstituted $C_{1-4}$ hydrocarbon chain, optionally wherein one or more chain atoms are independently replaced with —C(=O)—, —O—, —S—, —NR$^{ZB}$—, —N=, or =N—. In certain embodiments, when $Z^B$ is a substituted or unsubstituted $C_{1-4}$ hydrocarbon chain, $Z^B$ consists of a chain, and optionally one or more hydrogen atoms and/or one or more substituents (e.g., =O) on the chain, where any two substituents may optionally be joined to form a ring. In certain embodiments, $Z^B$ does not include unsaturated bonds in the chain. In certain embodiments, $Z^B$ consists of one or two unsaturated bonds in the chain. In certain embodiments, $Z^B$ is a substituted (e.g., substituted with at least one instance of halogen) $C_{1-4}$ hydrocarbon chain. In certain embodiments, $Z^B$ is an unsubstituted $C_{1-4}$ hydrocarbon chain. In certain embodiments, the molecular weight of $Z^B$ is not more than 150 g/mol, not more than 100 g/mol, not more than 80 g/mol, not more than 50 g/mol, or not more than 30 g/mol. In certain embodiments, $Z^B$ consists of not more than 50 atoms, not more than 40 atoms, not more than 30 atoms, not more than 20 atoms, or not more than 10 atoms. In certain embodiments, $Z^B$ is —C≡C— or —C≡C—C≡C—. In certain embodiments, $Z^B$ is of the formula:

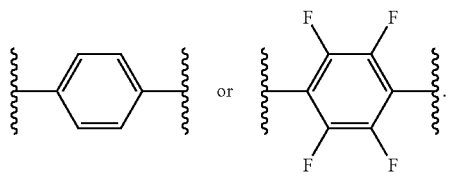 [SMILES: *c1ccc(*)cc1 ; *c1c(F)c(F)c(*)c(F)c1F]

In certain embodiments, all instances of $R^{ZB}$ are the same. In certain embodiments, at least two instances of $R^{ZB}$ are different from each other. In certain embodiments, at least one instance of $R^{ZB}$ is hydrogen. In certain embodiments, all instances of $R^{ZB}$ are hydrogen. In certain embodiments, at least one instance of $R^{ZB}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of $R^{ZB}$ is a nitrogen protecting group (e.g., Bn, Boc, Cbz, Fmoc, trifluoroacetyl, triphenylmethyl, acetyl, or Ts).

In certain embodiments, $Z^B$ is directly covalently attached to the carbon atom labeled with 2 or 6 of Ring A. In certain embodiments, $Z^B$ is directly covalently attached to the carbon atom labeled with 3 or 5 of Ring A. In certain embodiments, $Z^B$ is directly covalently attached to the carbon atom labeled with 4 of Ring A.

In certain embodiments, $Z^B$ is directly covalently attached to the carbon atom labeled with 2" or 6" of Ring C. In certain embodiments, ZB is directly covalently attached to the carbon atom labeled with 3" or 5" of Ring C. In certain embodiments, $Z^B$ is directly covalently attached to the carbon atom labeled with 4" of Ring C.

In certain embodiments, ZA and $Z^B$ are different from each other. In certain embodiments, $Z^A$ and $Z^B$ are the same. In certain embodiments, each of $Z^A$ and $Z^B$ is a bond.

In certain embodiments, $Z^A$ is directly covalently attached to the carbon atom labeled with 2' or 6' of Ring B; and $Z^B$ is directly covalently attached to the carbon atom labeled with 2" or 6" of Ring C. In certain embodiments, $Z^A$ is directly covalently attached to the carbon atom labeled with 3' or 5' of Ring B; and $Z^B$ is directly covalently attached to the carbon atom labeled with 3" or 5" of Ring C. In certain embodiments, $Z^A$ is directly covalently attached to the carbon atom labeled with 4' of Ring B; and $Z^B$ is directly covalently attached to the carbon atom labeled with 4" of Ring C.

In certain embodiments, the ligand of Formula (A) is of the formula:

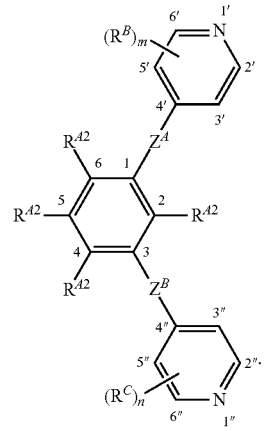

In certain embodiments, the ligand of Formula (A) is of the formula:

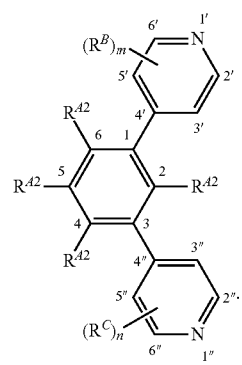

In certain embodiments, the ligand of Formula (A) is of the formula:

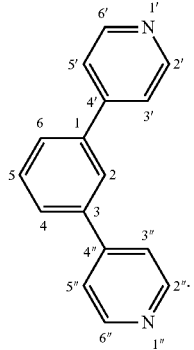

In certain embodiments, the ligand of Formula (A) is of the formula:

(A-1)

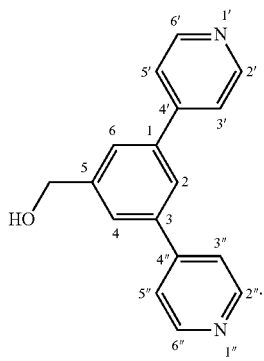

In certain embodiments, the ligand of Formula (A) is of the formula:

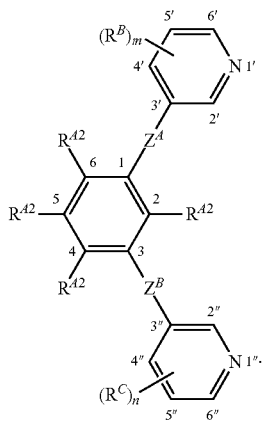

In certain embodiments, the ligand of Formula (A) is of the formula:

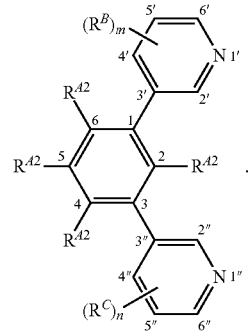

In certain embodiments, the ligand of Formula (A) is of the formula:

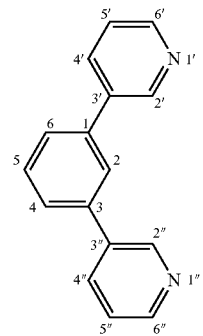

In certain embodiments, the ligand of Formula (A) is of the formula:

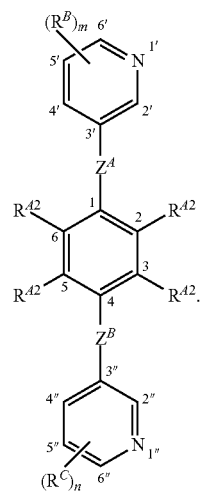

In certain embodiments, the ligand of Formula (A) is of the formula:
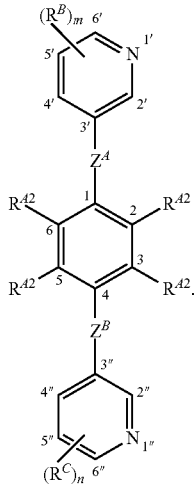
In certain embodiments, the ligand of Formula (A) is of the formula:
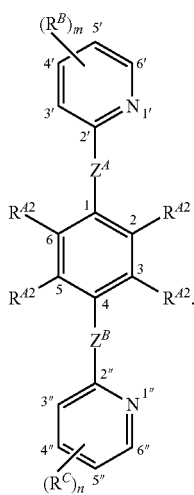
In certain embodiments, the ligand of Formula (A) is of the formula:
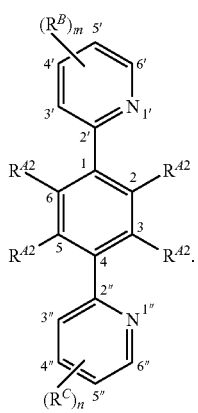
In certain embodiments, the ligand of Formula (A) is of the formula:
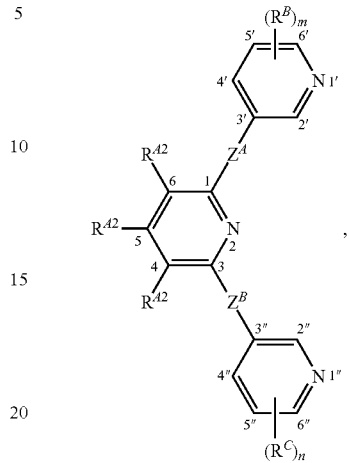
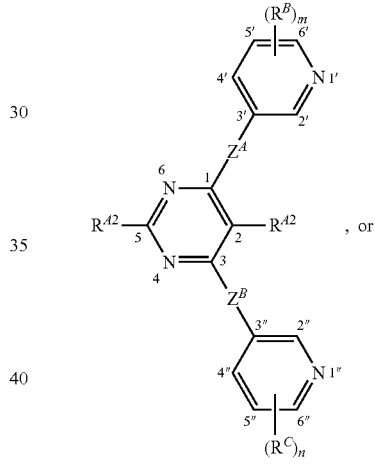, or
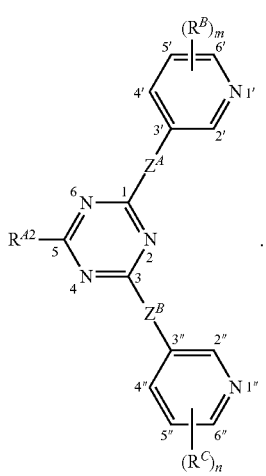

In certain embodiments, the ligand of Formula (A) is of the formula:
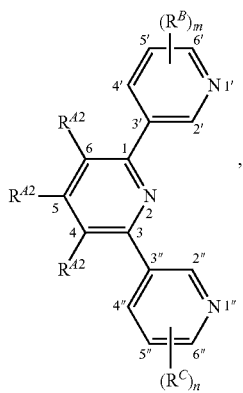
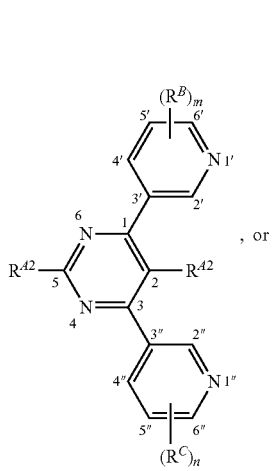
, or
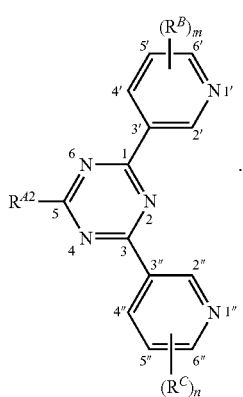
In certain embodiments, the ligand of Formula (A) is of the formula:
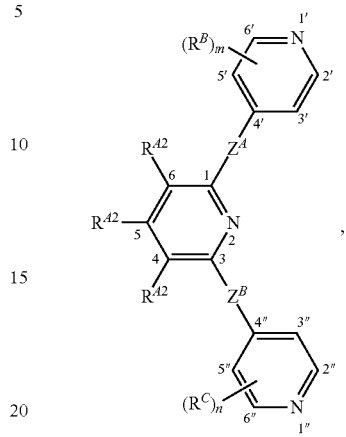
, or
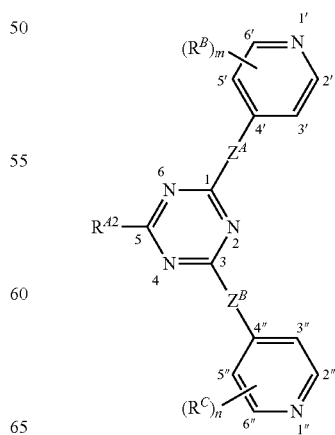

In certain embodiments, the ligand of Formula (A) is of the formula:
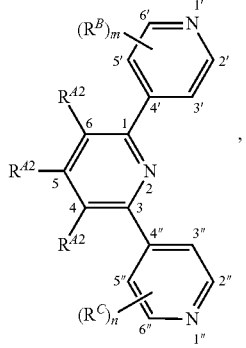
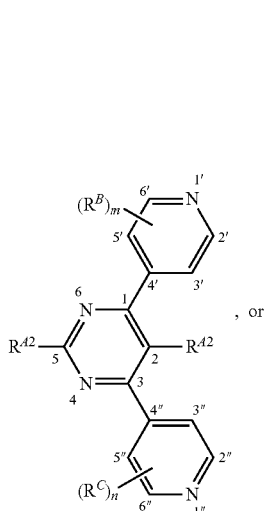
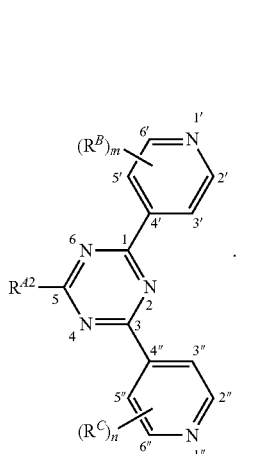
In certain embodiments, the ligand of Formula (A) is of the formula:
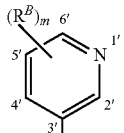 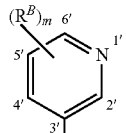
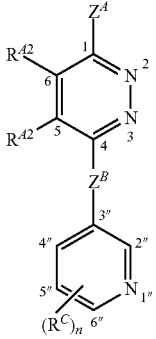 or 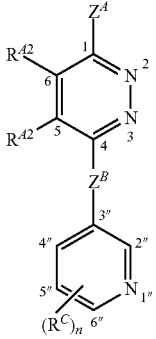
In certain embodiments, the ligand of Formula (A) is of the formula:
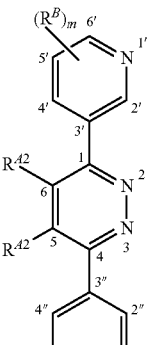 or 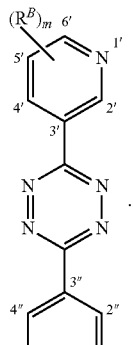
In certain embodiments, the ligand of Formula (A) is of the formula:
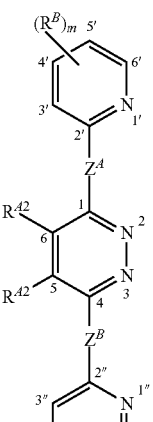 or 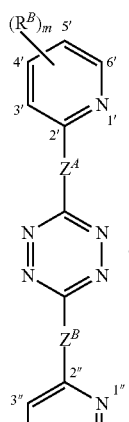
In certain embodiments, the ligand of Formula (A) is of the formula:

In certain embodiments, the ligand of Formula (A) is of the formula:

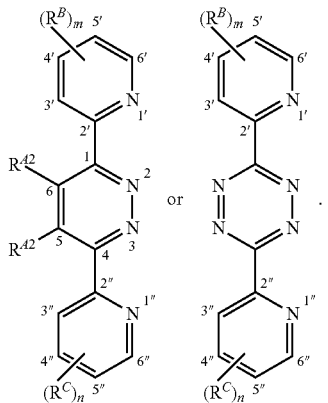

or

In certain embodiments, the ligand of Formula (A) is of the formula:

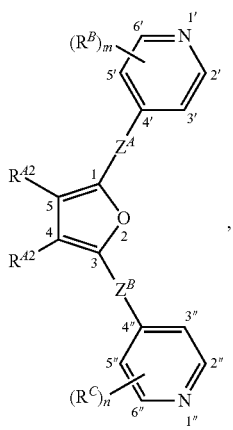

,

In certain embodiments, the ligand of Formula (A) is of the formula:

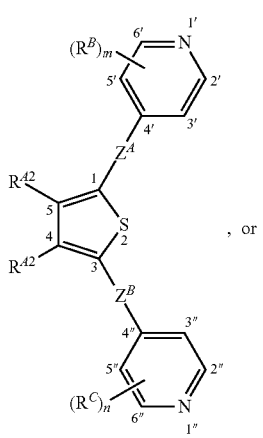

, or

In certain embodiments, the ligand of Formula (A) is of the formula:

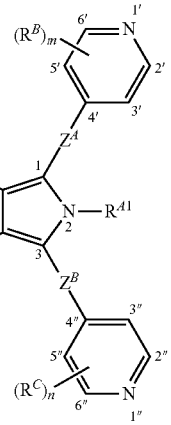

,

In certain embodiments, the ligand of Formula (A) is of the formula:

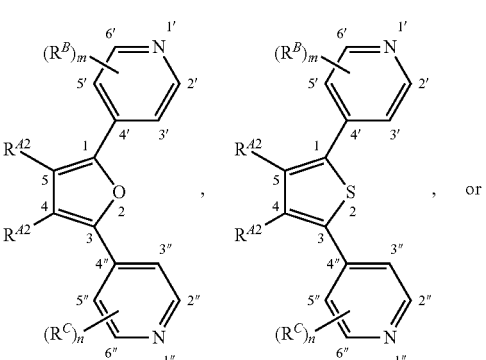

, or

In certain embodiments, the ligand of Formula (A) is of the formula:

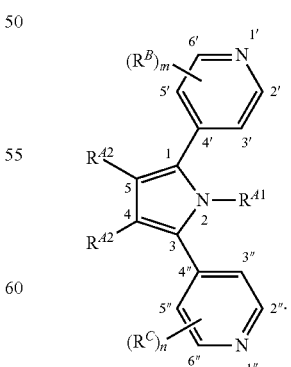

.

In certain embodiments, the ligand of Formula (A) is of the formula:

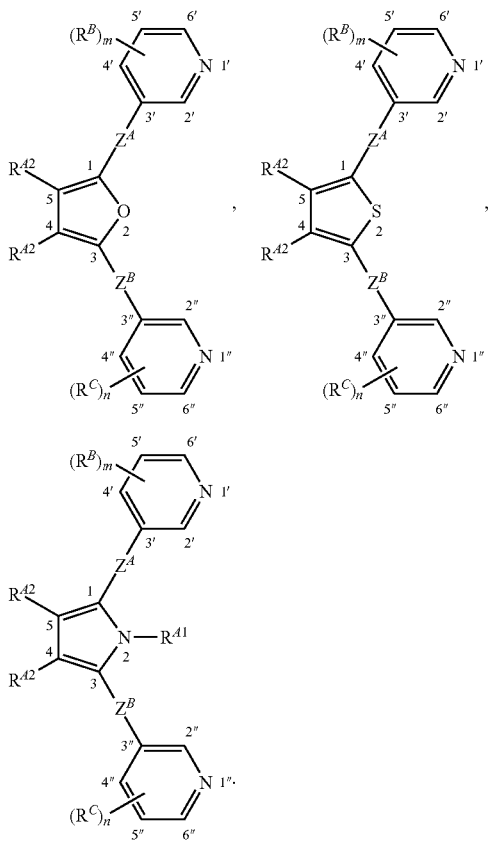
In certain embodiments, the ligand of Formula (A) is of the formula:
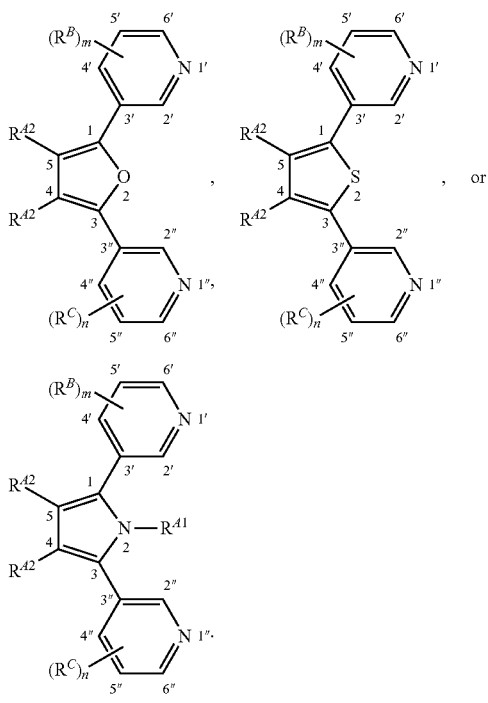
In certain embodiments, at least one instance of the ligand of Formula (B) is of the formula:
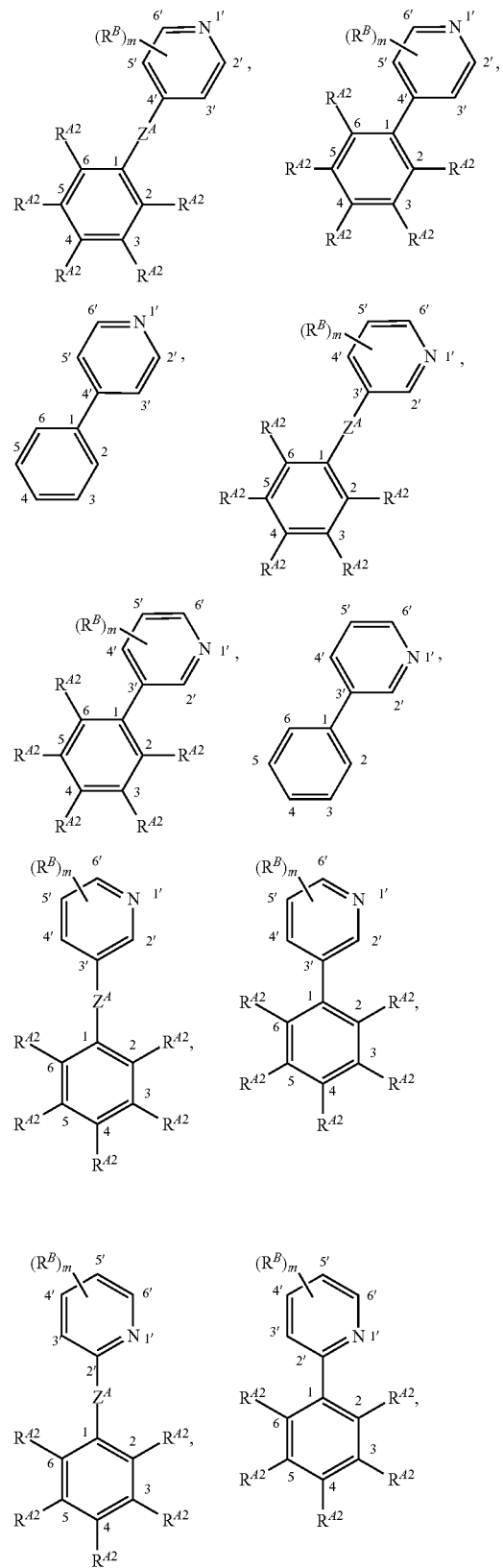

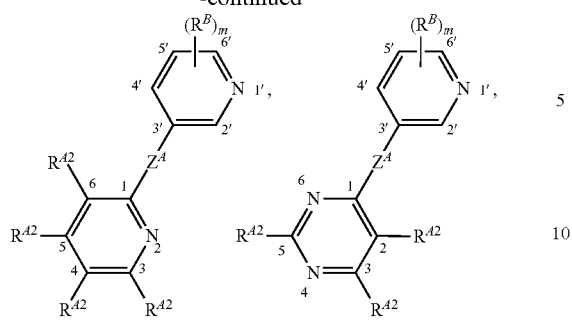
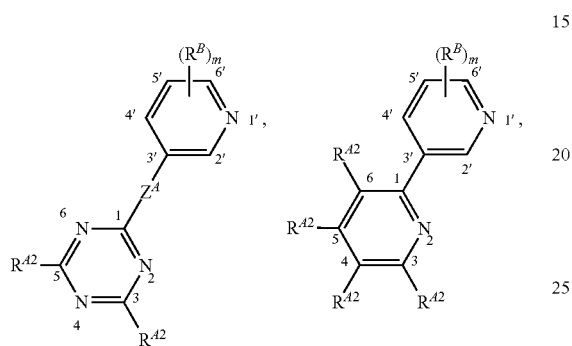
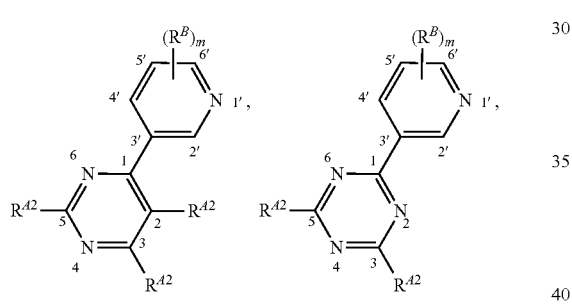
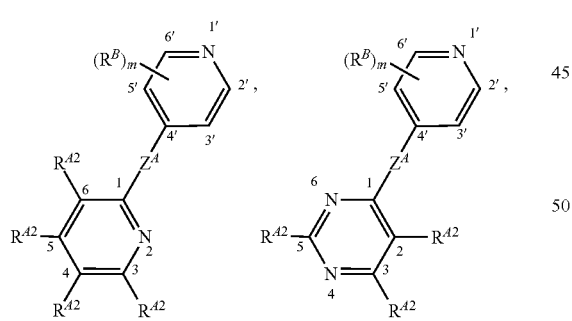
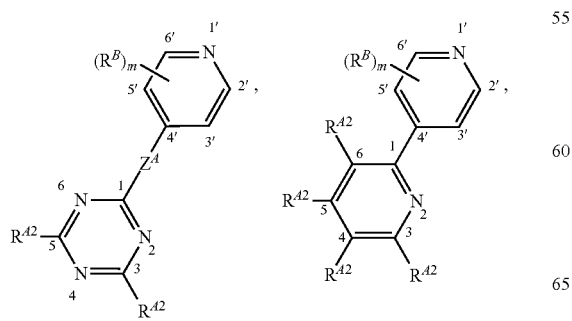
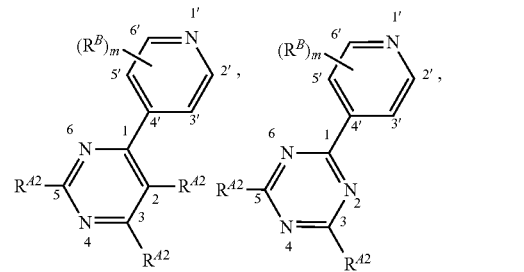
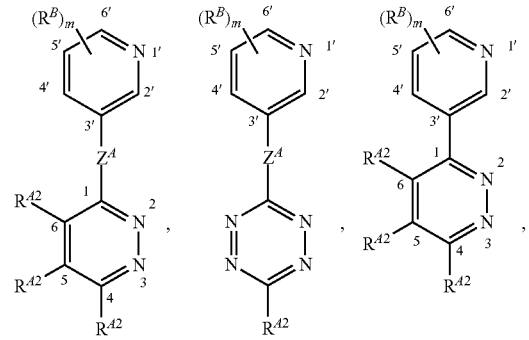
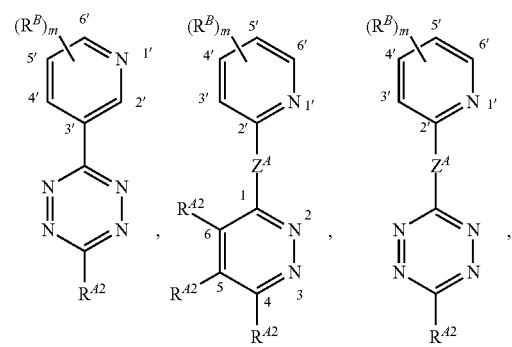
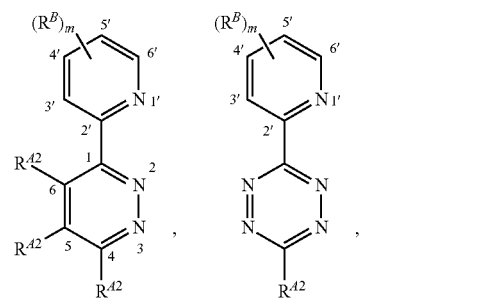
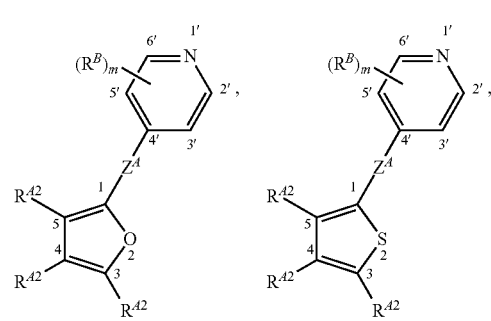

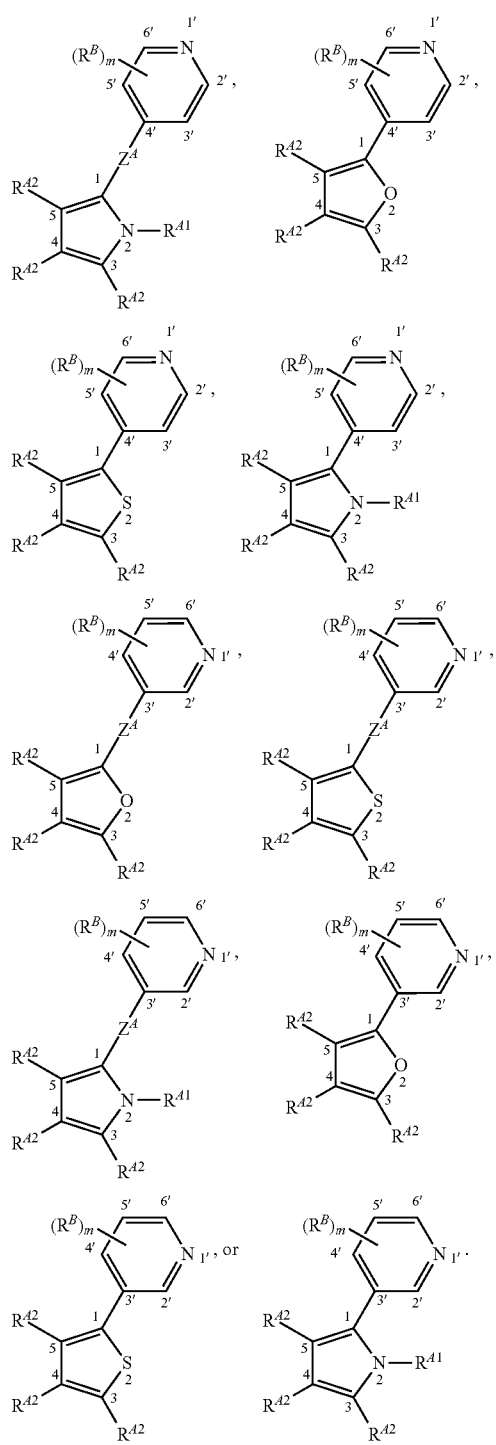

In certain embodiments, each instance of the ligand of Formula (A) or (B) forms through coordination bonds a coordination complex with one instance of the transition metal ion. In certain embodiments, an instance of the coordination bonds is formed between an instance of the transition metal ion and the nitrogen atom labeled with 1' of an instance of the ligand of Formula (A) or (B). In certain embodiments, an instance of the coordination bonds is formed between an instance of the transition metal ion and the nitrogen atom labeled with 1" of an instance of the ligand of Formula (A) or (B). In certain embodiments, an instance of the coordination bonds is formed between an instance of the transition metal ion and the nitrogen atom labeled with 1' of an instance of the ligand of Formula (A) or (B), and another instance of the coordination bonds is formed between the instance of the transition metal ion and the nitrogen atom labeled with 1" of the instance of the ligand of Formula (A) or (B).

In certain embodiments, at least one instance of the transition metal ion and at least two instances of the ligand of Formula (C) form through two or more coordination bonds coordination complex(es). In certain embodiments, at least 30%, at least 40%, at least 50%, at least 60%, at least 70%, or at least 80% of all instances of the oxygen atom labeled with "*" of a ligand of Formula (C) form coordination bonds with one or more instances of the transition metal ion.

In certain embodiments, at least one instance of the metal organic nanostructure (e.g., coordination complex) is in a square planar molecular geometry. In certain embodiments, at least one instance of the metal organic nanostructure (e.g., coordination complex) is in a pseudo square planar molecular geometry. The metal organic nanostructure may be a nanosphere. In certain embodiments, the metal organic nanostructure has cuboctahedral symmetry. In certain embodiments, the metal organic nanostructure has quasi-regular polyhedral symmetry, icosidodecahedral symmetry, or regular polyhedral symmetry (e.g., cubic (regular hexahedral) or dodecahedral symmetry). In certain embodiments, the metal organic nanostructure is a nano-paddlewheel. In certain embodiments, the metal organic nanostructure is a nano-square.

A metal organic nanostructure described herein is hollow (e.g., including a cavity). In certain embodiments, the maximum outer dimension (e.g., diameter) of a metal organic nanostructure described herein is not more than 100 nm, not more than 60 nm, not more than 30 nm, not more than 10 nm, not more than 5 nm, not more than 3 nm, or not more than 1 nm. In certain embodiments, the maximum outer dimension of the a metal organic nanostructure described herein is at least 1 nm, at least 2 nm, at least 5 nm, at least 10 nm, at least 30 nm, at least 60 nm, or at least 100 nm. Combinations of the above ranges (e.g., at least 1 nm and not more than 100 nm or at least 1 nm and not more than 10 nm) are also within the scope of the present disclosure. The minimum inner dimension (e.g., diameter) of a metal organic nanostructure described herein is the minimum dimension of the cavity of the nanostructure. In certain embodiments, the minimum inner dimension of a metal organic nanostructure described herein is not more than 100 nm, not more than 60 nm, not more than 30 nm, not more than 10 nm, not more than 5 nm, not more than 3 nm, or not more than 1 nm. In certain embodiments, the minimum inner dimension of the nanostructure described herein is at least 1 nm, at least 2 nm, at least 5 nm, at least 10 nm, at least 30 nm, at least 60 nm, or at least 100 nm. Combinations of the above ranges (e.g., at least 1 nm and not more than 60 nm or at least 1 nm and not more than 5 nm) are also within the scope of the present disclosure.

In certain embodiments, a metal organic nanostructure described herein is not a polymer or does not include a polymeric moiety.

Figures 40A, 40B:
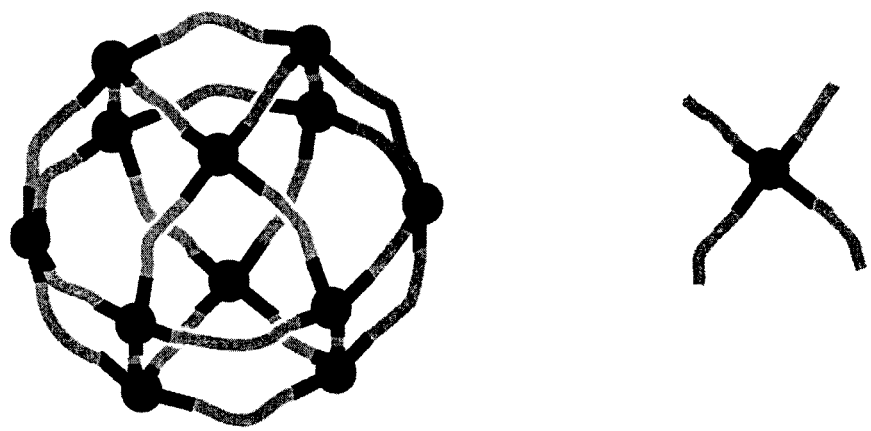
FIG. 40A. A schematic of a metal organic nanostructure of Formula (I-A).
FIG. 40B. A schematic of a moiety of a metal organic nanostructure of Formula (I-A).
Figure 41:
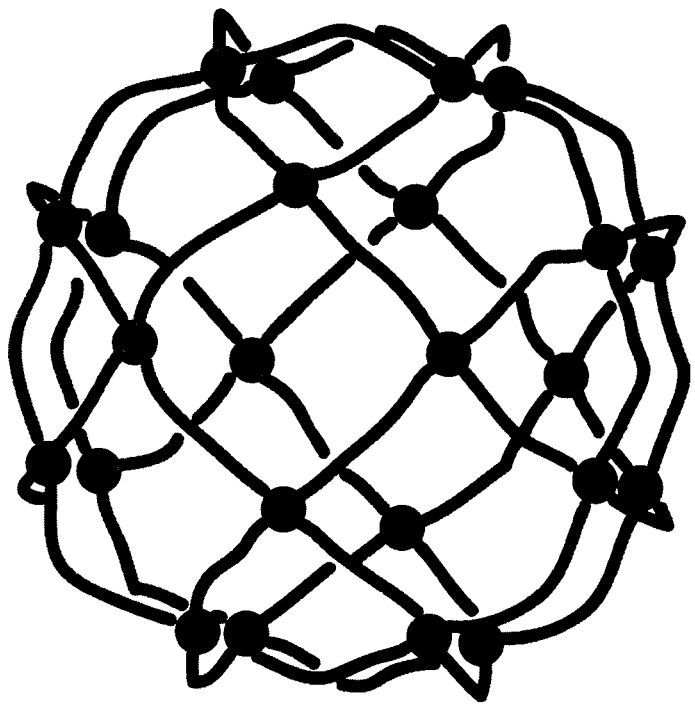
FIG. 41. A schematic of a metal organic nanostructure of Formula (I-B).
Figure 42:
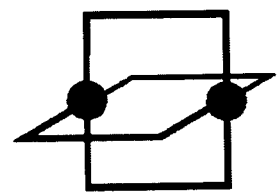
FIG. 42. A schematic of a metal organic nanostructure of Formula (I-C).

In certain embodiments, a nanosphere described herein is of Formula (I-A) as shown in FIG. 40A, or a salt thereof, wherein each instance of the black dots is the transition metal ion; each instance of the grey lines is the ligand of Formula (A); and each instance of the black lines is the coordination bond. In certain embodiments, a nanosphere described herein is of Formula (I-B) as shown in FIG. 41, or a salt thereof, wherein each instance of the black dots is the transition metal ion; and each instance of the grey lines is the ligand of Formula (A). In certain embodiments, a nano-paddlewheel described herein is of Formula (I-C) as shown in FIG. 42, or a salt thereof, wherein each instance of the dots is the transition metal ion; and each instance of the U-shaped lines is the ligand of Formula (A). In certain embodiments, a nano-square described herein is of Formula (II-A) as shown in the second view of FIG. 1C, or a salt thereof, the dot is the transition metal ion; and each instance of the lines is the ligand of Formula (B). In certain embodiments, a nanosphere described herein (nanosphere I-1) is of Formula (I-A), wherein each instance of the gray lines is ligand A-1. In Formula (I-A), each instance of the moiety shown in FIG. 40B is of the formula:

embodiments, two or more instances of the ligand of Formula (A) are different from each other. In certain embodiments, each instance of the ligand of Formula (B) is the same. In certain embodiments, two or more instances of the ligand of Formula (B) are different from each other.

In certain embodiments, a BCPMON described herein also includes two or more instances of -L-(R)$_p$-(G)$_q$-(R)$_u$-(G)$_v$-E. In certain embodiments, all instances of -L-(R)$_p$-(G)$_q$-(R)$_u$-(G)$_v$-E are the same. In certain embodiments, at least two instances of -L-(R)$_p$-(G)$_q$-(R)$_u$-(G)$_v$-E are different from each other. In certain embodiments, at least one instance of L is a bond. In certain embodiments, each instance of L is a bond. In certain embodiments, at least one instance of L is substituted or unsubstituted $C_{1-4}$ hydrocarbon chain. In certain embodiments, at least one instance of L is substituted or unsubstituted $C_{1-4}$ hydrocarbon chain, wherein one or more chain atoms are independently replaced

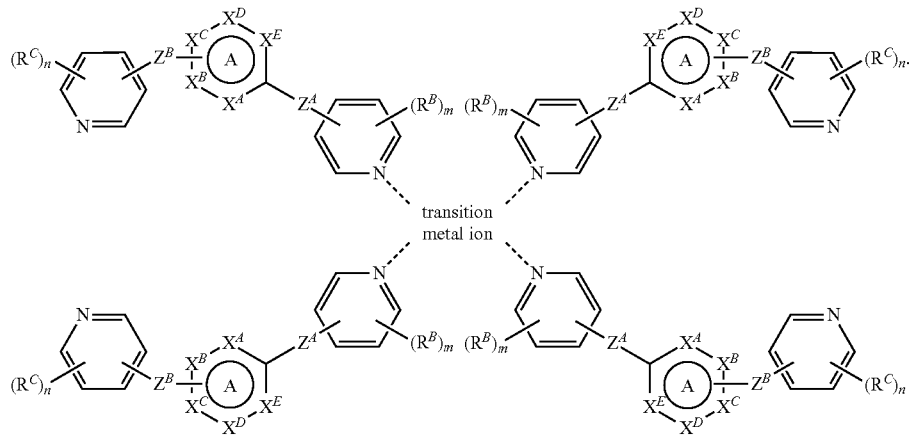

In certain embodiments, each instance of the moiety shown in FIG. 40B is of the formula:

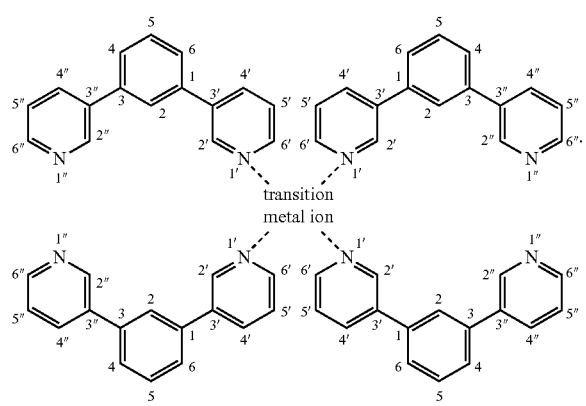

In certain embodiments, each instance of the metal organic nanostructure is the same. In certain embodiments, two or more instances of the metal organic nanostructure are different from each other. In certain embodiments, the variables x of all instances of the metal organic nanostructure are the same. In certain embodiments, the variables x of two or more instances of the metal organic nanostructure are different from each other. In certain embodiments, each instance of the ligand of Formula (A) is the same. In certain with —C(=O)—, —O—, —S—, —NR$^L$—, —N=, or =N—. In certain embodiments, at least one instance of L is —O—.

In certain embodiments, all instances of R$^L$ are the same. In certain embodiments, at least two instances of R$^L$ are different from each other. In certain embodiments, at least one instance of R$^L$ is hydrogen. In certain embodiments, each instance of R$^L$ is hydrogen. In certain embodiments, at least one instance of R$^L$ is substituted or unsubstituted $C_{1-6}$ alkyl or a nitrogen protecting group. In certain embodiments, at least one instance of R$^L$ is $C_{1-6}$ alkyl substituted with at least one halogen. In certain embodiments, at least one instance of R$^L$ is —CH$_3$. In certain embodiments, all instances of R$^L$ are —CH$_3$. In certain embodiments, at least one instance of R$^L$ is substituted methyl. In certain embodiments, at least one instance of R$^L$ is —CH$_2$F, —CHF$_2$, or —CF$_3$. In certain embodiments, at least one instance of R$^L$ is Et, Pr, Bu, unsubstituted pentyl, or unsubstituted hexyl. In certain embodiments, at least one instance of R$^L$ is a nitrogen protecting group (e.g., Bn, Boc, Cbz, Fmoc, trifluoroacetyl, triphenylmethyl, acetyl, or Ts).

In certain embodiments, all instances of R are the same. In certain embodiments, at least two instances of R are different from each other. In certain embodiments, the glass transition temperature (T$_g$) of each instance of the first polymer is not higher than 20° C. (e.g., not higher than 10° C., not higher than 0° C., not higher than −10° C., not higher than −20° C., not higher than −40° C., or not higher than −60° C.).

In certain embodiments, at least one instance of the first polymer is a poly(alkyl acrylate), a poly(hydroxyalkyl acrylate), poly(haloalkyl acrylate), polymethacrylate, a poly(alkyl methacrylate), a poly(hydroxyalkyl methacrylate), or a poly(haloalkyl methacrylate). In certain embodiments, at least one instance of the first polymer is poly(n-butyl acrylate) (PBA). In certain embodiments, at least one instance of the first polymer is polydimethylsiloxane, polybutadiene, or polyisoprene. In certain embodiments, each instance of the first polymer has the same repeating unit. In certain embodiments, at least two instances of the first polymer have different repeating units.

In certain embodiments, the number-average molecular weight ($M_n$) of the first polymer is between 1,000 g/mol and 1,000,000 g/mol, inclusive (e.g., between 3,000 g/mol and 300,000 g/mol, between 3,000 g/mol and 100,000 g/mol, between 10,000 g/mol and 300,000 g/mol, or between 10,000 g/mol and 100,000 g/mol).

In certain embodiments, all instances of G are the same. In certain embodiments, at least two instances of G are different from each other. In certain embodiments, the $T_g$ of each instance of the second polymer is higher than 20° C. (e.g., higher than 40° C., higher than 60° C., higher than 80° C., higher than 100° C., higher than 120° C., higher than 140° C., higher than 160° C., or higher than 180° C.).

In certain embodiments, the $M_n$ of the second polymer is between 300 g/mol and 100,000 g/mol, inclusive (e.g., between 1,000 g/mol and 30,000 g/mol, between 1,000 g/mol and 10,000 g/mol, between 3,000 g/mol and 30,000 g/mol, or between 3,000 g/mol and 10,000 g/mol, inclusive).

In certain embodiments, at least one instance of the second polymer is a poly(alkyl acrylate), a poly(hydroxyalkyl acrylate), poly(haloalkyl acrylate), polymethacrylate, a poly(alkyl methacrylate), a poly(hydroxyalkyl methacrylate), or a poly(haloalkyl methacrylate). In certain embodiments, at least one instance of the second polymer is poly(methyl methacrylate) (PMMA). In certain embodiments, at least one instance of the second polymer is polystyrene or polyethylene.

In certain embodiments, at least one instance of the first polymer or second polymer is an addition polymer (e.g., polyethylene, poly(tetrafluoroethylene), polypropylene, polyisobutylene, polystyrene, polyacrylonitrile, poly(vinyl chloride), poly(methyl acrylate), poly(methyl methacrylate), polybutadiene, polychloroprene, poly(cis-1,4-isoprene), or poly(trans-1,4-isoprene)). In certain embodiments, at least one instance of the first polymer or second polymer is an condensation polymer (e.g., polyamide, polyaramide, polyester, polycarbonate, or silicone). In certain embodiments, at least one instance (e.g., each instance) of the first polymer is different from at least one instance (e.g., each instance) of the second polymer.

In certain embodiments, at least one instance of the second polymer is a semi-crystalline polymer (e.g., a semi-crystalline polymer under ambient conditions) whose melting temperature (e.g., melting temperature under 1 atmosphere) is higher than 20° C. (e.g., higher than 40, higher than 60, higher than 80, higher than 100, higher than 150, higher than 200, or higher than 300° C.). In certain embodiments, each instance of the second polymer has the same repeating unit. In certain embodiments, at least two instances of the second polymer have different repeating units.

In some embodiments, the polydispersity of the polymer (e.g., first polymer or second polymer) is less than about 0.5 (e.g., less than about 0.4, about 0.35, about 0.3, about 0.25, about 0.2, about 0.15, or less). In some embodiments, the polydispersity of the polymer is less than about 0.3. In some embodiments, the polydispersity of the polymer is less than about 0.2. In some embodiments, the polymer is monodisperse. In some embodiments, the polymer is about 50% monodisperse (e.g., about 55%, about 60%, about 65%, about 70%, about 75%, about 80%, about 85%, about 90%, about 95%, about 99%, or about 99.9% monodisperse).

In certain embodiments, ratio of the $M_n$ of the first polymer to the $M_n$ of the second polymer is between 100:1 and 1:1, between 30:1 and 1:1, between 10:1 and 1:1, between 3:1 and 1:1, between 100:1 and 3:1, between 30:1 and 3:1, between 10:1 and 3:1, between 100:1 and 10:1, or between 30:1 and 10:1, inclusive.

In certain embodiments, at least one instance of p is 1, 2, or 3. In certain embodiments, each instance of p is 1.

In certain embodiments, at least one instance of q is 1, 2, or 3. In certain embodiments, each instance of q is 1.

In certain embodiments, each instance of p is 1, and each instance of q is 0. In certain embodiments, each instance of p is 0, and each instance of q is 1.

In certain embodiments, at least one instance of u is 1, 2, or 3. In certain embodiments, each instance of u is 0.

In certain embodiments, at least one instance of v is 1, 2, or 3. In certain embodiments, each instance of v is 0.

In certain embodiments, each instance of E is the same. In certain embodiments, at least two instances of E are different from each other. In certain embodiments, at least one instance of E is hydrogen. In certain embodiments, each instance of E is hydrogen. In certain embodiments, at least one instance of E is hydrogen or substituted or unsubstituted $C_{1-6}$ alkyl. In certain embodiments, at least one instance of E is substituted or unsubstituted alkyl, substituted or unsubstituted alkenyl, or substituted or unsubstituted alkynyl. In certain embodiments, at least one instance of E is substituted or unsubstituted carbocyclyl, substituted or unsubstituted heterocyclyl, substituted or unsubstituted aryl, or substituted or unsubstituted heteroaryl. In certain embodiments, at least one instance of E is —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$.

In certain embodiments, no two or more instances of -L-(R)$_p$-(G)$_q$-(R)$_u$-(G)$_v$-E are directly covalently attached to the same instance of the ligand of Formula (A) or (B). In certain embodiments, at least one instance (e.g., each instance) of -L-(R)$_p$-(G)$_q$-(R)$_u$-(G)$_v$-E is directly covalently attached to the 5-position of an instance of the ligand of Formula (A) or (B). In certain embodiments, at least one instance (e.g., each instance) of -L-(R)$_p$-(G)$_q$-(R)$_u$-(G)$_v$-E is directly covalently attached to the 4-position of an instance of the ligand of Formula (A) or (B). In certain embodiments, each instance of the ligand of Formula (A) or (B) is directly covalently attached to one instance of -L-(R)$_p$-(G)$_q$-(R)$_u$-(G)$_v$-E.

Figure 43:
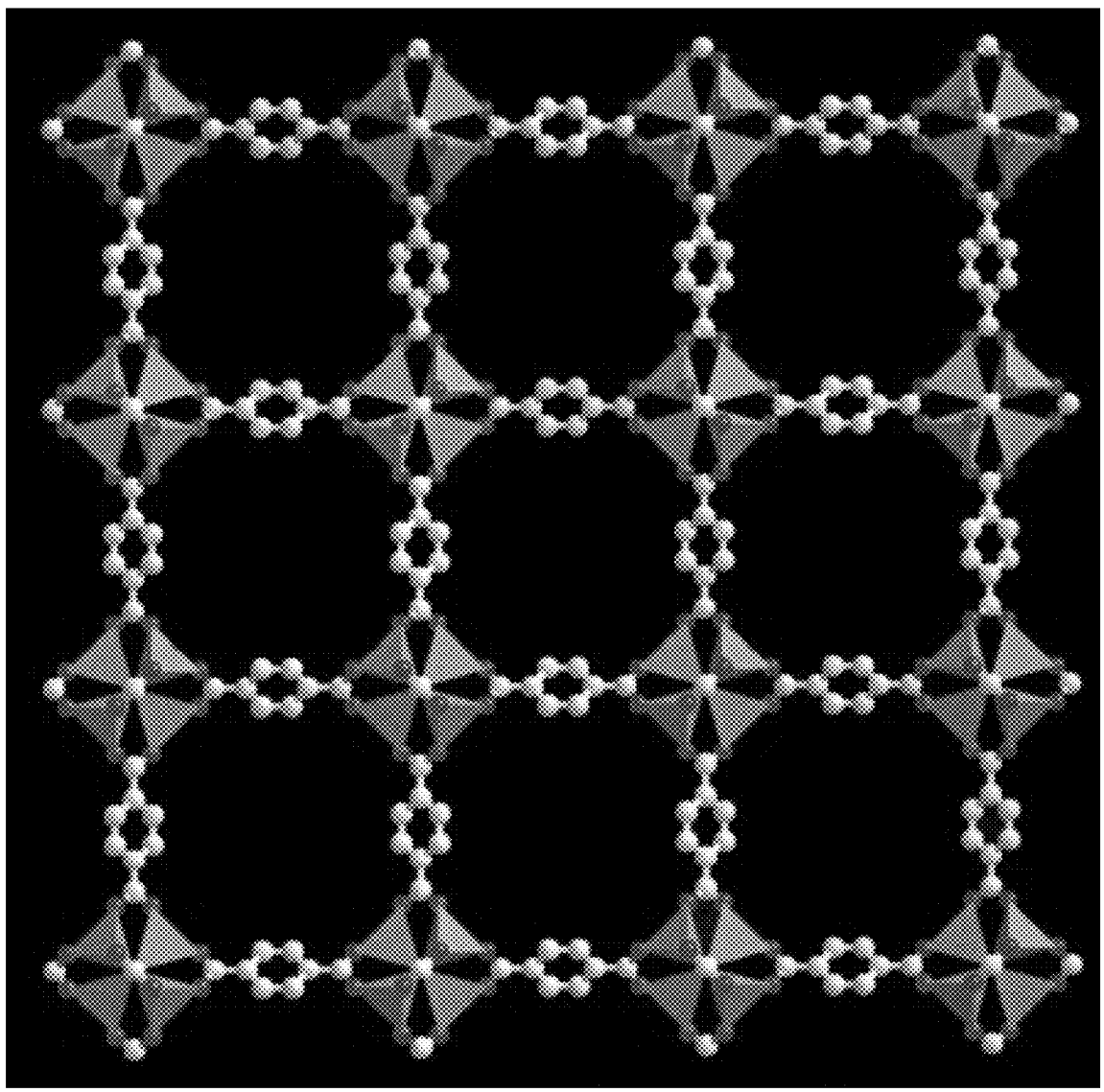
FIG. 43. Representation of a {100} layer of the MOF-5 framework shown along the a-axis (light grey dots: carbon atoms; dark grey dots: oxygen atoms; tetrahedra: (transition metal ion)O$_4$) (Li et al., Nature, 1999, 402, 276).

In certain embodiments, at least one instance of the coordination complex is substantively of a framework described in U.S. patent application publication, US 2003/0004364, which is incorporated herein by reference. In certain embodiments, at least one instance (e.g., each instance) of the coordination complex is substantively of the MOF-5 framework as shown in FIG. 43.

In certain embodiments, the BCPMON further comprises:
a first phase, wherein the first phase comprises more than 50% (e.g., more than 60%, more than 70%, more than 80%, or more than 90%) of all instances of the coordination complexes;

a second phase, wherein the second phase comprises more than 50% (e.g., more than 60%, more than 70%, more than 80%, or more than 90%) of all instances of —$(R)_p$-$(G)_q$-$(R)_u$-$(G)_v$-E; and optionally a third phase;

wherein, compared to the second phase, the first phase is the inner phase of the BCPMON and is more crystalline under ambient conditions.

In certain embodiments, the first phase is crystalline under ambient conditions. In certain embodiments, the first phase is semi-crystalline under ambient conditions. In certain embodiments, the second phase is semi-crystalline or not crystalline, under ambient conditions. In certain embodiments, the second phase is amorphous under ambient conditions.

In certain embodiments, the maximum outer dimension of the first phase is between 1 nm and 1,000 nm, between 1 nm and 100 nm, between 1 nm and 10 nm, between 10 nm and 1,000 nm, between 10 nm and 100 nm, or between 100 nm and 1,000 nm, inclusive. In certain embodiments, the maximum outer dimension of the first phase is between 1 nm and 100 nm, inclusive.

In certain embodiments, y is an integer between 1 and 100, between 1 and 10, between 10 and 1,000, between 10 and 100, or between 100 and 1,000, inclusive. In certain embodiments, y is an integer between 10 and 100, inclusive.

In certain embodiments, z is an integer between 2 and 50, between 2 and 10, between 10 and 200, between 10 and 50, or between 50 and 200, inclusive. In certain embodiments, z is an integer between 2 and 20, inclusive.

In certain embodiments, s is 2. In certain embodiments, s is an integer between 3 and 10, inclusive. In certain embodiments, s is 3, 4, or 5. In certain embodiments, s is 4.

In certain embodiments, each instance of $R^D$ is the same. In certain embodiments, at least two instances of $R^D$ are different from each other. In certain embodiments, at least one instance of $R^D$ is hydrogen. In certain embodiments, each instance of $R^D$ is hydrogen. In certain embodiments, at least one instance of RD is halogen. In certain embodiments, at least one instance of $R^D$ is substituted or unsubstituted $C_{1-6}$ alkyl (e.g., Me). In certain embodiments, at least one instance of $R^D$ is —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$.

In certain embodiments, each instance of T is the same. In certain embodiments, at least two instances of T are different from each other. In certain embodiments, at least one instance of T is a bond. In certain embodiments, at least one instance of (e.g., each instance) of T is independently a substituted or unsubstituted $C_{1-50}$ hydrocarbon chain, wherein one or more (e.g., 2) chain atoms are independently replaced with —C(=O)—, —O—, —S—, —$NR^T$—, —N=, or =N—. In certain embodiments, at least one instance of (e.g., each instance) of T is independently a substituted or unsubstituted $C_{5-20}$ hydrocarbon chain, wherein one or more (e.g., 2) chain atoms are independently replaced with —C(=O)—, —O—, —S—, or —$NR^T$—. In certain embodiments, at least one instance of (e.g., each instance) of T is independently —O—$(CH_2)_t$—O—, wherein t is an integer between 4 and 16, inclusive.

In certain embodiments, W is substituted or unsubstituted, $C_{2-200}$ alkynylene. In certain embodiments, W is substituted or unsubstituted, $C_{2-200}$ heteroalkynylene. In certain embodiments, W is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with substituted or unsubstituted heteroarylene. In certain embodiments, W is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with

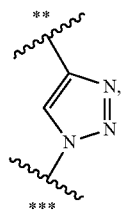 [SMILES: *c1cn(*)nn1]

wherein —$(R)_p$-$(G)_q$-$(R)_u$-$(G)_v$-E is closer to the attachment point labeled with "*" than the attachment point labeled with "". In certain embodiments, W is substituted or unsubstituted, $C_{2-200}$ heteroalkylene, wherein one carbon or one heteroatom, of the substituted or unsubstituted, $C_{2-200}$ heteroalkylene, is replaced with

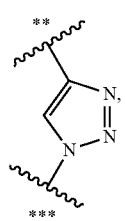 [SMILES: *c1cn(*)nn1]

wherein —$(R)_p$-$(G)_q$-(R)-$(G)_v$-E is closer to the attachment point labeled with "*" than the attachment point labeled with "".

In certain embodiments, W comprises

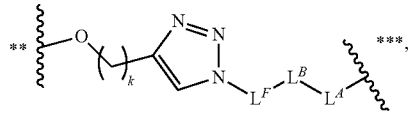

wherein:

each instance of k is independently an integer from 1 to 10, inclusive;

each instance of $L^F$ is independently substituted or unsubstituted, $C_{2-180}$ heteroalkylene;

each instance of -$L^B$-$L^A$- is independently —C(=O)O—, —OC(=O)—, —C(=O)$NR^E$—, or —$NR^E$C(=O)—, wherein each instance of $R^E$ is independently hydrogen, substituted or unsubstituted, $C_{1-6}$ alkyl, or a nitrogen protecting group; and —$(R)_p$-$(G)_q$-$(R)_u$-$(G)_v$-E is closer to the attachment point labeled with "*" than the attachment point labeled with "".

In certain embodiments, W is

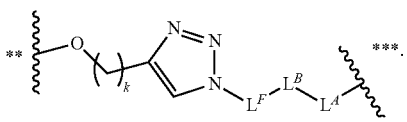

In certain embodiments, W comprises

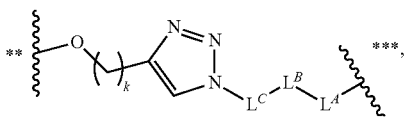

wherein:
each instance of k is independently an integer from 1 to 10, inclusive;
each instance of $L^C$ is independently substituted or unsubstituted, $C_{1-180}$ alkylene;
each instance of $-L^B-L^A-$ is independently —C(=O)O—, —OC(=O)—, —C(=O)NR$^E$—, or —NR$^E$C(=O)—, wherein each instance of $R^E$ is independently hydrogen, substituted or unsubstituted, $C_{1-6}$ alkyl, or a nitrogen protecting group; and
—(R)$_p$-(G)$_q$-(R)$_u$-(G)$_v$-E is closer to the attachment point labeled with "*" than the attachment point labeled with "".

In certain embodiments, W is

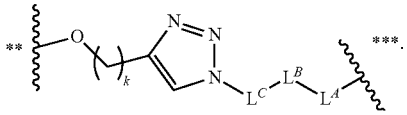

In certain embodiments, each instance of $L^C$ is independently $C_{1-180}$ alkylene substituted with one or more instances of: substituted or unsubstituted phenyl and/or substituted or unsubstituted, $C_{1-6}$ alkyl.

In certain embodiments, W comprises a polymer (e.g., substituted or unsubstituted polyethylene (e.g., unsubstituted polystyrene), optionally wherein the $M_n$ of the polymer is between 300 and 10,000, between 300 and 3,000, between 300 and 1,000, between 1,000 and 10,000, between 1,000 and 3,000, or between 3,000 and 10,000, inclusive, g/mol.

In certain embodiments, W comprises a natural amino acid, an unnatural amino acid, or a peptide, optionally wherein the peptide consists of between 3 and 60, between 3 and 30, between 3 and 10, between 10 and 60, between 10 and 30, or between 30 and 60, inclusive, amino acids.

In certain embodiments, W is cleavable by ultraviolet irradiation. In certain embodiments, W is cleavable by hydrolysis, reduction, or oxidation. In certain embodiments, W is cleavable by contacting with an enzyme. In certain embodiments, at least 50% of all instances of W that is cleavable is cleaved after 10 minutes, 1 hour, 6 hours, 12 hours, 1 day, 2 days, 3 days, 5 days, or 7 days of the ultraviolet irradiation, hydrolysis, reduction, oxidation, or contact with the enzyme. In certain embodiments, W is stable (e.g., having a half life of at least 1 day, 3 days, 7 days, 1 month, 3 months, 6 months, or 1 year) under ambient conditions.

In certain embodiments, r is 1. In certain embodiments, r is 2 or 3.

In certain embodiments, the macromonomer is a ligand of Formula (A)

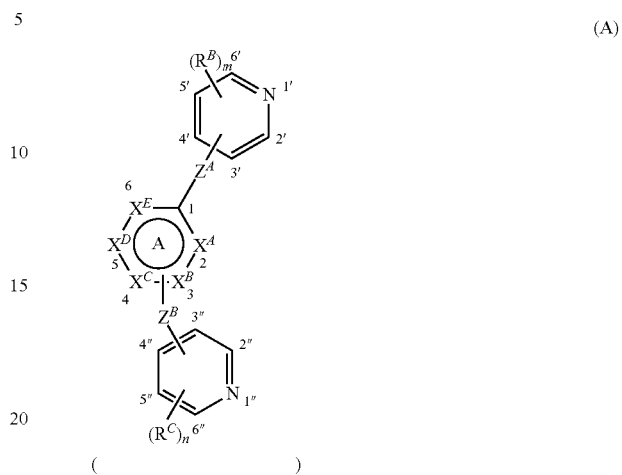

(A)

covalently attached to r instances of -L-(R)$_p$-(G)$_q$-(R)$_u$-(G)$_v$-E. In certain embodiments, the macromonomer is a ligand of Formula (B)

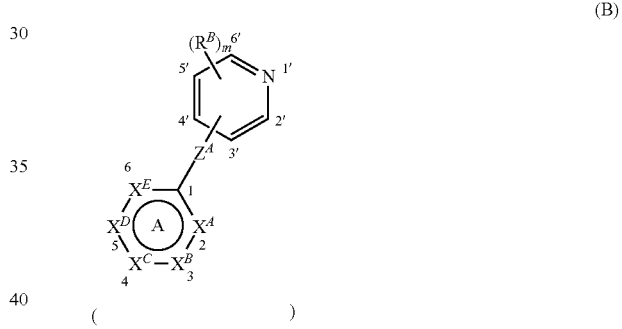

(B)

covalently attached to r instances of -L-(R)$_p$-(G)$_q$-(R)$_u$-(G)$_v$-E. In certain embodiments, r instances of hydrogen atom are removed from a ligand of Formula (A) or (B) to form the attachment points.

In certain embodiments, the macromonomer is of the formula:

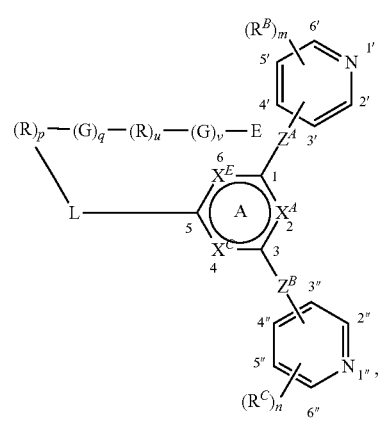

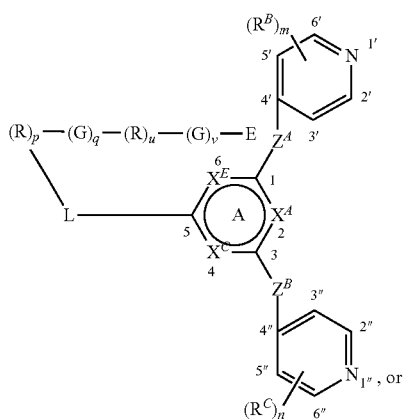
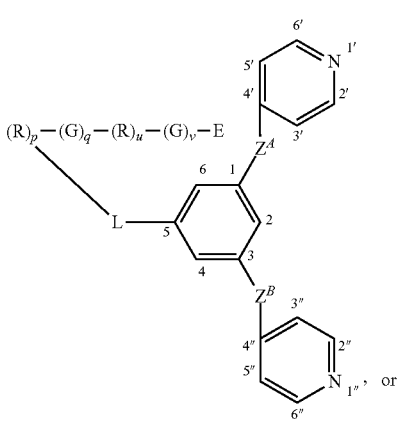
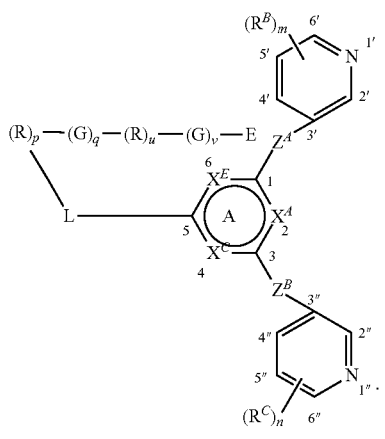
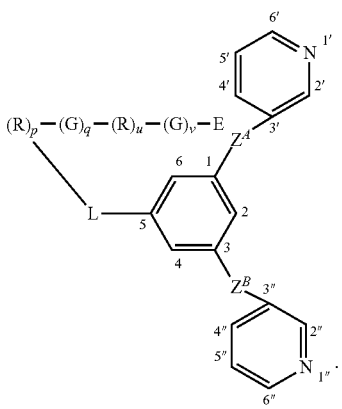
In certain embodiments, the macromonomer is of the formula:
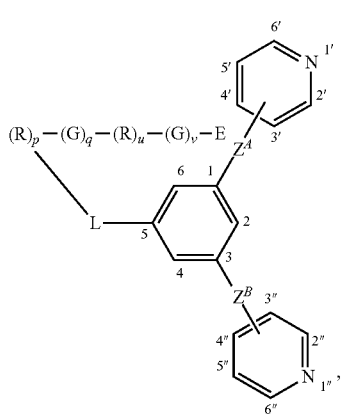
In certain embodiments, the macromonomer is of the formula:
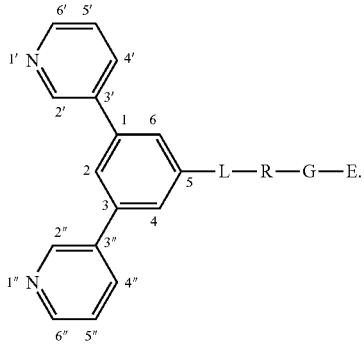

In certain embodiments, the macromonomer is of the formula:

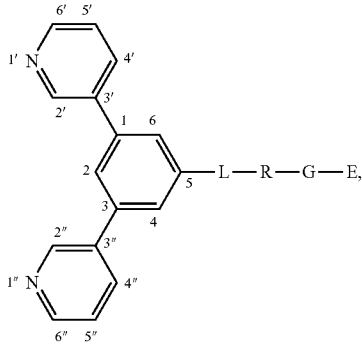

wherein the first polymer is poly(n-butyl acrylate) (PBA), and the second polymer is poly(methyl methacrylate) (PMMA).

In certain embodiments, the macromonomer is of the formula:

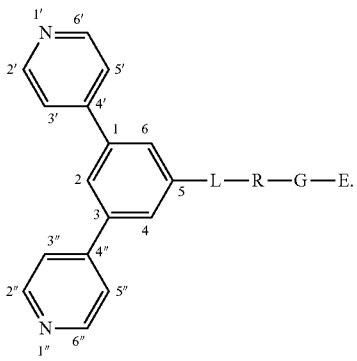

In certain embodiments, the macromonomer is of the formula:

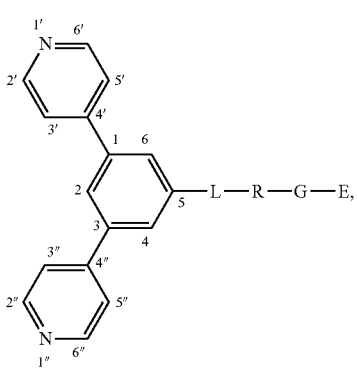

wherein the first polymer is poly(n-butyl acrylate) (PBA), and the second polymer is poly(methyl methacrylate) (PMMA).

In certain embodiments, the macromonomer is of the formula:

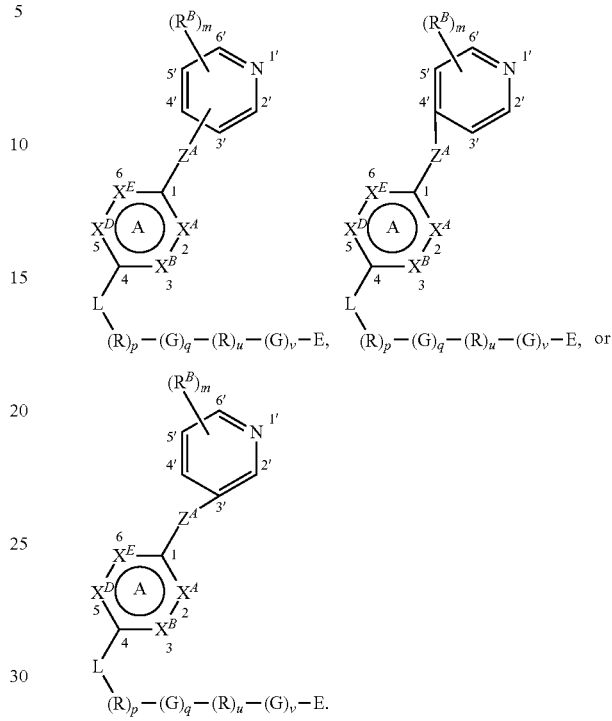

In certain embodiments, the macromonomer is of the formula:

In certain embodiments, the macromonomer is of the formula:

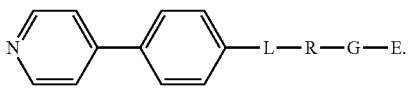

In certain embodiments, the macromonomer is of the formula:

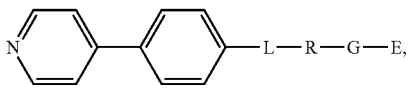

wherein the first polymer is poly(n-butyl acrylate) (PBA), and the second polymer is poly(methyl methacrylate) (PMMA).

In certain embodiments, the BCPMON further comprises at least one instance of an anionic counterion. The anionic counterions may reduce the overall electric charge of the BCPMON, each of which includes transition metal ions that are positively charged. In certain embodiments, at least two instances of the anionic counterion are different. In certain embodiments, all instances of the anionic counterion are the same. In certain embodiments, the BCPMON is substantially electrically neutral. In certain embodiments, the BCPMON is slightly positively charged. In certain embodiments, the ξ-potential of the BCPMON is between about 0 and about +30 mV, inclusive (e.g., between about 0 and about 10 mV, inclusive). In certain embodiments, the BCPMON is slightly negatively charged. In certain embodiments, the ξ-potential of the BCPMON is between about −30 and about 0 mV, inclusive (e.g., between about −10 and about 0 mV, inclusive). In certain embodiments, at least one instance of the anionic counterion is a non-coordinating anionic counterion (e.g., $ClO_4^-$, $NO_3^-$, $TfO^-$, $BF_4^-$, $PF_4^-$, $PF_6^-$, $AsF_6^-$, or $SbF_6^-$). In certain embodiments, at least one instance (e.g., each instance) of the anionic counterion is $NO_3^-$. In certain embodiments, at least one instance of the anionic counterion is $AcO^-$, $F^-$, $Cl^-$, $Br^-$, or $I^-$. In certain embodiments, at least one instance of the anionic counterion is a coordinating anionic counterion. In certain embodiments, at least one instance (e.g., each instance) of the anionic counterion is at the outer surface of at least one instance of the BCPMON. In certain embodiments, at least one instance of the anionic counterion is encapsulated by at least one instance of the BCPMON.

Thermoplastic Elastomers

Another aspect of the present disclosure relates to thermoplastic elastomers comprising two or more instances of a BCPMON described herein.

Thermoplastic elastomers, such as styrene-butadiene block copolymers, thermoplastic polyurethanes, polyester amides, polyether amides, thermoplastic copolyester elastomers and polyolefin alloys with elastomers, are known (Rader, C., Kunststoffe 83 (1993) 10, 777-781, Kunststoffe 86, (1996) 12, 1845-1851). The thermoplastic elastomers described herein may be advantageous over known thermoplastic elastomers in that one or more of the properties (e.g., tensile modulus, tensile strength, tensile elongation, nominal tensile strain at break, flexural modulus, flexural stress, taber abrasion resistance, tensile set, tensile stress, tear strength, compression set, hardness, deflection temperature under load, continuous use temperature, brittleness temperature, Vicat softening temperature, RTI Elec, RTI Str, change in volume) are tunable (e.g., by changing the framework type of the MOFs) and/or reversible (e.g., by subjecting the BCPMONs to different conditions). In certain embodiments, each instance of the ligand of Formula (A) is the same. In certain embodiments, two or more instances of the ligand of Formula (A) are different from each other. In certain embodiments, each instance of the ligand of Formula (B) is the same. In certain embodiments, two or more instances of the ligand of Formula (B) are different from each other. In certain embodiments, each instance of the transition metal ion or transition metal salt is the same. In certain embodiments, two or more instances of the transition metal ion or transition metal salt are different from each other.

Compositions

In another aspect, the present disclosure provides compositions comprising a MON described herein and optionally an excipient. A composition described herein may further comprise a solvent (e.g., a suitable solvent described herein, such as water or DMSO). The solvent may be encapsulated inside a MON and/or be present outside of any MON in the composition.

In still another aspect, the present disclosure provides compositions comprising a BCPMON described herein and optionally an excipient. In another aspect, the present disclosure provides compositions comprising a thermoplastic elastomer described herein and optionally an excipient. In another aspect, the present disclosure provides compositions comprising a macromonomer described herein and optionally an excipient.

The excipient included in a composition described herein may be a pharmaceutically acceptable excipient, cosmetically acceptable excipient, dietarily acceptable excipient, or nutraceutically acceptable excipient.

A composition described herein may further comprise an agent (e.g., a pharmaceutical agent or diagnostic agent). In a composition described herein, an agent may form an adduct (e.g., through covalent attachment and/or non-covalent interactions) with a MON described herein (including a MON moiety of a BCPMON described herein). In certain embodiments, a composition described herein is useful in the delivery of the agent (e.g., an effective amount of the agent) to a subject, tissue, or cell.

A composition described herein may further comprise a fluid (e.g., a solvent, e.g., water, DMSO, acetonitrile, or a mixture thereof)

Compositions of the disclosure may improve or increase the delivery of an agent described herein to a subject, tissue, or cell. In certain embodiments, the compositions increase the delivery of the agent to a target tissue or target cell. In certain embodiments, the target tissue is liver, spleen, or lung. In certain embodiments, the target tissue is pancreas, kidney, uterus, ovary, heart, thymus, fat, or muscle. In certain embodiments, the target cell is a liver cell, spleen cell, lung cell, pancreas cell, kidney cell, uterus cell, ovary cell, heart cell, thymus cell, or muscle cell. In certain embodiments, the compositions selectively deliver the agent to the target tissue or target cell (e.g., the compositions deliver the agent to the target tissue in a greater quantity in unit time than to a non-target tissue or deliver the agent to the target cell in a greater quantity in unit time than to a non-target cell).

The delivery of an agent described herein may be characterized in various ways, such as the exposure, concentration, and bioavailability of the agent. The exposure of an agent in a subject, tissue, or cell may be defined as the area under the curve (AUC) of the concentration of the agent in the subject, tissue, or cell after administering or dosing the agent. In general, an increase in exposure may be calculated by first taking the difference in: (1) a first AUC, which is the AUC measured in a subject, tissue, or cell administered or dosed with a composition described herein; and (2) a second AUC, which is the AUC measured in a subject, tissue, or cell administered or dosed with a control composition; and then by dividing the difference by the second AUC. Exposure of an agent may be measured in an appropriate animal model. The concentration of an agent and, when appropriate, its metabolite(s), in a subject, tissue, or cell is measured as a function of time after administering or dosing the agent.

Concentration of an agent, and, when appropriate, of its metabolite(s), in a subject, tissue, or cell, may be measured as a function of time in vivo using an appropriate animal model. In certain embodiments, the concentration of the agent is the concentration of the agent in a target tissue or target cell. One exemplary method of determining the concentration of an agent involves dissecting of a tissue. The concentration of the agent may be determined by HPLC or LC/MS analysis.

In some embodiments, a composition of the disclosure increases the delivery of an agent described herein to a subject, tissue, or cell due to the presence of a MON described herein. In some embodiments, a composition of the disclosure increases the delivery of an agent described herein to a subject, tissue, or cell due to the presence of a BCPMON described herein. In some embodiments, the composition increases the delivery of the agent due to the presence of an adduct formed between the MON (including a MON moiety of a BCPMON) and the agent. In some embodiments, the presence of a MON or BCPMON described herein increase the delivery of the agent by at least 10%, at least 20%, at least 30%, at least 40%, at least 50%, at least 100%, at least 2-fold, at least 3-fold, at least 10-fold, at least 30-fold, at least 100-fold, at least 300-fold, or at least 1000-fold. In certain embodiments, a MON or BCPMON described herein is present in the composition in an amount sufficient to increase the delivery of the agent by an amount described herein when administered in the composition compared to the delivery of the agent when administered in the absence of the MON or BCPMON.

Compositions described herein may deliver an agent selectively to a tissue or cell. In certain embodiments, the tissue or cell to which the agent is selectively delivered is a target tissue or target cell, respectively. In certain embodiments, the compositions deliver at least 10%, at least 20%, at least 30%, at least 40%, at least 50%, at least 70%, at least 100%, at least 3-fold, at least 10-fold, at least 30-fold, at least 100-fold, at least 300-fold, or at least 1000-fold more amount of the agent in unit time to a target tissue than to a non-target tissue or to a target cell than to a non-target cell. The amount of agent may be measured by the exposure, concentration, and/or bioavailability of the agent in a tissue or cell as described herein.

The compositions described herein (e.g., pharmaceutical compositions) including one or more agents (e.g., pharmaceutical agents) may be useful in treating and/or preventing a disease. In certain embodiments, the compositions are useful in gene therapy. In certain embodiments, the compositions are useful for treating and/or preventing a genetic disease. In certain embodiments, the compositions are useful for treating and/or preventing a proliferative disease. In certain embodiments, the compositions are useful for treating and/or preventing cancer. In certain embodiments, the compositions are useful for treating and/or preventing a benign neoplasm. In certain embodiments, the compositions are useful for treating and/or preventing pathological angiogenesis. In certain embodiments, the compositions are useful for treating and/or preventing an inflammatory disease. In certain embodiments, the compositions are useful for treating and/or preventing an autoimmune disease. In certain embodiments, the compositions are useful for treating and/or preventing a hematological disease. In certain embodiments, the compositions are useful for treating and/or preventing a neurological disease. In certain embodiments, the compositions are useful for treating and/or preventing a gastrointestinal disease. In certain embodiments, the compositions are useful for treating and/or preventing a liver disease. In certain embodiments, the compositions are useful for treating and/or preventing a spleen disease. In certain embodiments, the compositions are useful for treating and/or preventing a respiratory disease. In certain embodiments, the compositions are useful for treating and/or preventing a lung disease. In certain embodiments, the compositions are useful for treating and/or preventing hepatic carcinoma, hypercholesterolemia, refractory anemia, or familial amyloid neuropathy. In certain embodiments, the compositions are useful for treating and/or preventing a painful condition. In certain embodiments, the compositions are useful for treating and/or preventing a genitourinary disease. In certain embodiments, the compositions are useful for treating and/or preventing a musculoskeletal condition. In certain embodiments, the compositions are useful for treating and/or preventing an infectious disease. In certain embodiments, the compositions are useful for treating and/or preventing a psychiatric disorder. In certain embodiments, the compositions are useful for treating and/or preventing a metabolic disorder.

The agents may be provided in an effective amount in a composition described herein. In certain embodiments, the effective amount is a therapeutically effective amount. In certain embodiments, the effective amount is a prophylactically effective amount. In certain embodiments, the effective amount is an amount effective for treating a disease described herein. In certain embodiments, the effective amount is an amount effective for preventing a disease described herein.

An effective amount of an agent may vary from about 0.001 mg/kg to about 1000 mg/kg in one or more dose administrations for one or several days (depending on the mode of administration). In certain embodiments, the effective amount per dose varies from about 0.001 to about 1000 mg/kg, from about 0.01 to about 750 mg/kg, from about 0.1 to about 500 mg/kg, from about 1.0 to about 250 mg/kg, and from about 10.0 to about 150 mg/kg.

In certain embodiments, a composition described herein is in the form of gels. In certain embodiments, the gels result from self-assembly of the components of the composition. The agent to be delivered by the gel may be in the form of a gas, liquid, or solid. The MONs and/or BCPMONs described herein may be combined with polymers (synthetic or natural), surfactants, cholesterol, carbohydrates, proteins, lipids, lipidoids, etc. to form gels. The gels may be further combined with an excipient to form the composition. The gels are described in more detail herein.

The compositions described herein (e.g., pharmaceutical compositions) can be prepared by any method known in the art (e.g., pharmacology). In certain embodiments, such preparatory methods include the steps of bringing a MON or BCPMON described herein into association with an agent described herein (i.e., the "active ingredient"), optionally with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. A unit dose is a discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the excipient (e.g., the pharmaceutically or cosmetically acceptable excipient), and/or any additional ingredients in a composition described herein will vary, depending upon the identity, size, and/or condition of the subject to whom the composition is administered and further depending upon the route by which the composition is to be administered. The composition may comprise between 0.1% and 100% (w/w) active ingredient.

Excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, and mixtures thereof.

Exemplary chelating agents include ethylenediaminetetraacetic acid (EDTA) and salts and hydrates thereof (e.g., sodium edetate, disodium edetate, trisodium edetate, calcium disodium edetate, and dipotassium edetateke), citric acid and salts and hydrates thereof (e.g., citric acid monohydrate), fumaric acid and salts and hydrates thereof, malic acid and salts and hydrates thereof, phosphoric acid and salts and hydrates thereof, tartaric acid and salts and hydrates thereof, and mixtures thereof.

Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, thimerosal, and mixtures thereof.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, sorbic acid, and mixtures thereof.

Exemplary alcohol preservatives include ethanol, polyethylene glycol, phenol, phenolic compounds, bisphenol, chlorobutanol, hydroxybenzoate, phenylethyl alcohol, and mixtures thereof.

Exemplary acidic preservatives include vitamin A, vitamin C, vitamin E, beta-carotene, citric acid, acetic acid, dehydroacetic acid, ascorbic acid, sorbic acid, phytic acid, and mixtures thereof.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, Euxyl®, and mixtures thereof.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Additionally, the composition may further comprise an apolipoprotein. Previous studies have reported that Apolipoprotein E (ApoE) was able to enhance cell uptake and gene silencing for a certain type of materials. See, e.g., Akinc, A., et al., *Targeted delivery of RNAi therapeutics with endogenous and exogenous ligand-based mechanisms.* Mol Ther. 18(7): p. 1357-64. In certain embodiments, the apolipoprotein is ApoA, ApoB, ApoC, ApoE, or ApoH, or an isoform thereof.

Liquid dosage forms for oral and parenteral administration include emulsions, microemulsions, solutions, suspensions, syrups and elixirs. In certain embodiments, the emulsions, microemulsions, solutions, suspensions, syrups and elixirs are or cosmetically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, excipient or carrier (e.g., pharmaceutically or cosmetically acceptable excipient or carrier) such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the formulation art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a composition of this disclosure may include ointments, pastes, creams, lotions, gels, powders, solutions, sprays, inhalants, and/or patches. Generally, the active ingredient is admixed under sterile conditions with a carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the agent in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the active ingredient. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A composition described herein can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Metal organic nanostructures and BCPMONs described herein are typically formulated in dosage unit form for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease being treated and the severity of the disorder, the activity of the specific active ingredient employed, the specific composition employed, the age, body weight, general health, sex, and diet of the subject, the time of administration, route of administration, and rate of excretion of the specific active ingredient employed, the duration of the treatment, drugs used in combination or coincidental with the specific active ingredient employed, and like factors well known in the medical arts.

The compositions described herein can be administered by any suitable route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In certain embodiments, the compositions are administered by oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of an agent required to achieve an effective amount will vary from subject to subject, depending, for example, on species, age, and general condition of a subject, severity of the side effects or disorder, identity of the particular agent, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an agent for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an agent per unit dosage form.

In certain embodiments, the agents described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided compositions to an adult. The amount to be administered to, for example, a child or an adolescent can be determined by a medical practitioner or person skilled in the art and can be lower or the same as that administered to an adult.

Compositions described herein may further include a hydrophilic polymer (e.g., polyethylene glycol (PEG)). The compositions described herein may further include a lipid (e.g., a steroid, a substituted or unsubstituted cholesterol, or a polyethylene glycol (PEG)-containing material). In certain embodiments, the lipid included in the compositions is a triglyceride, a driglyceride, a PEGylated lipid, dimyristoyl-PEG2000 (DMG-PEG2000), a phospholipid (e.g., 1,2-distearoyl-sn-glycero-3-phosphocholine (DSPC)), dioleoyl-phosphatidylethanolamine (DOPE), a substituted or unsubstituted cholesterol, a steroid an apolipoprotein, or a combination thereof. In certain embodiments, the compositions include two components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include three components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include at least four components selected from the group consisting of the following components: a hydrophilic polymer, a triglyceride, a driglyceride, a PEGylated lipid, a phospholipid, a steroid, a substituted or unsubstituted cholesterol, and an apolipoprotein. In certain embodiments, the compositions include a hydrophilic polymer, a phospholipid, a steroid, and a substituted or unsubstituted cholesterol. In certain embodiments, the compositions include PEG, DSPC, and substituted or unsubstituted cholesterol. In certain embodiments, the additional materials are approved by a regulatory agency, such as the U.S. FDA, for human and/or veterinary use.

Compositions described herein may be useful in other applications, e.g., non-medical applications. Nutraceutical compositions described herein may be useful in the delivery of an effective amount of a nutraceutical, e.g., a dietary supplement, to a subject in need thereof. Cosmetic compositions described herein may be formulated as a cream, ointment, balm, paste, film, or liquid, etc., and may be useful in the application of make-up, hair products, and materials useful for personal hygiene, etc. Compositions described herein may be useful for other non-medical applications, e.g., such as an emulsion, emulsifier, or coating, useful, for example, as a food component, for extinguishing fires, for disinfecting surfaces, for oil cleanup, and/or as a bulk material.

Agents (Agents to be Delivered)

Agents that are delivered by the systems (e.g., pharmaceutical compositions) described herein may be pharmaceutical (e.g., therapeutic or prophylactic), diagnostic, cosmetic, or nutraceutical agents. Any chemical compound to be administered to a subject or to be contacted with a tissue or cell may be delivered using the MONs, BCPMONs, and/or compositions described herein. The agent may be a small molecule (e.g., a small organic molecule or small inorganic molecule), protein, peptide, polynucleotide, targeting agent, isotopically labeled chemical compound, vaccine, or immunological agent. The agent may be an agent useful in bioprocessing (e.g., intracellular manufacturing of proteins, such as a cell's bioprocessing of a commercially useful chemical or fuel). For example, intracellular delivery of an agent may be useful in bioprocessing by maintaining the cell's health and/or growth, e.g., in the manufacturing of proteins. Any chemical compound to be administered to a subject or contacted with a tissue or cell may be delivered to the subject, tissue, or cell using the compositions described herein.

Exemplary agents that may be included in a composition described herein include, but are not limited to, small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, agents useful in bioprocessing, and mixtures thereof. The targeting agents are described in more detail herein. In certain embodiments, the agents are nutraceutical agents. In certain embodiments, the agents are pharmaceutical agents (e.g., a therapeutic or prophylactic agent). In certain embodiments, the agent is an antibiotic agent (e.g., an anti-bacterial, anti-viral, or anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, and Freund's adjuvant, etc. In certain embodiments, the agent is a small molecule. In certain embodiments, the agent is an anti-cancer agent (e.g., an anti-cancer agent disclosed in U.S. Patent Application Publication No. US 2003/065023). In certain embodiments, the agent is doxorubicin.

In certain embodiments, an agent described herein is a polynucleotide. In certain embodiments, the agent is plasmid DNA (pDNA). In certain embodiments, the agent is single-stranded DNA (ssDNA), double-stranded DNA (dsDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, the agent is RNA. In certain embodiments, the agent is small interfering RNA (siRNA). In certain embodiments, the agent is messenger RNA (mRNA). In certain embodiments, the agent is single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, the agent is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, upon delivery of an RNA into a subject, tissue, or cell, the RNA is able to interfere with the expression of a specific gene in the subject, tissue, or cell. In certain embodiments, the agent is a pDNA, siRNA, mRNA, or a combination thereof.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1): 31-44, 1999; Crooke, "Evaluating the mechanism of action of anti-proliferative antisense drugs," *Antisense Nucleic Acid Drug Dev.* 10(2):123-126, discussion 127, 2000; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

The RNA and/or RNAi described herein can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271.

The polynucleotide included in a composition described herein may be of any size or sequence, and they may be single- or double-stranded. In certain embodiments, the polynucleotide includes at least 30, at least 100, at least 300, at least 1,000, at least 3,000, or at least 10,000 base pairs. In certain embodiments, the polynucleotide includes not more than 10,000, not more than 3,000, not more than 1,000, not more than 300, not more than 100, or not more than 30 base pairs. Combinations of the above ranges (e.g., at least 100 and not more than 1,000) are also within the scope of the disclosure. The polynucleotide may be provided by any suitable means known in the art. In certain embodiments, the polynucleotide is engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least 50%, at least 60%, at least 70%, at least 80%, at least 90%, at least 95%, or at least 99% free of impurities.

The polynucleotide may be modified by physical, chemical, and/or biological means. The modifications include methylation, phosphorylation, and/or end-capping, etc. In certain embodiments, the modifications lead to increased stability of the polynucleotide.

Wherever a polynucleotide is employed in the present disclosure, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any suitable means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, or an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, or insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from bacterial organisms, such as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi*, and *Camphylobacter jejuni*; from viruses, such as smallpox virus, influenza A virus, influenza B virus, respiratory syncytial virus, parainfluenza virus, measles virus, HIV virus, varicella-zoster virus, herpes simplex 1 virus, herpes simplex 2 virus, cytomegalovirus, Epstein-Barr virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus, Rift Valley fever virus, hepatitis A virus, hepatitis B virus, hepatitis C virus, hepatitis D virus, and hepatitis E virus; and from fungal, protozoan, or parasitic organisms, such as *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis,*

*Plasmodium falciparum, Trypanosoma brucei, Entamoeba histolytica, Toxoplasma gondii, Trichomonas vaginalis*, and *Schistosoma mansoni*.

An agent described herein may be covalently or non-covalently attached to (e.g., complexed to and/or encapsulated in) a MON or BCPMON (e.g., attached to a MON of the BCPMON) described herein, or included in a composition described herein. In certain embodiments, at least one instance of the MON encapsulates the agent. In certain embodiments, at least one molecule of the agent is not encapsulated in any instance of the MON. In certain embodiments, upon delivery of the agent into a cell, the agent is able to interfere with the expression of a specific gene in the cell.

In certain embodiments, an agent described herein may be a mixture of two or more agents that may be useful as, e.g., combination therapies. A composition including the mixture can be used to achieve a synergistic effect. In certain embodiments, the composition including the mixture can be used to improve the activity and/or bioavailability, reduce and/or modify the metabolism, inhibit the excretion, and/or modify the distribution of at least one of the two or more agents in a subject, tissue, or cell to which the mixture is administered or dosed. It will also be appreciated that the composition including the mixture may achieve a desired effect for the same disorder, and/or it may achieve different effects. The two or more agents in the mixture may be useful for treating and/or preventing a same disease or different diseases described herein.

The compositions (e.g., pharmaceutical compositions) described herein can be administered concurrently with, prior to, or subsequent to the one or more agents (e.g., pharmaceutical agents). Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, a composition described herein may further include targeting moieties or targeting agents. In certain embodiments, a MON described herein (including a MON moiety of a BCPMON described herein) is modified to include targeting moieties or targeting agents. For example, a targeting moiety or targeting agent may be included throughout a MON or BCPMON (e.g., throughout a MON of the BCPMON) described herein or may be only at the surface (e.g., outer or inner surface) of the MON or BCPMON (e.g., at the surface of a MON of the BCPMON). A targeting agent may be a protein, peptide, carbohydrate, glycoprotein, lipid, small molecule, or polynucleotide, and a targeting moiety may be a fragment of the targeting agent. The targeting moiety or targeting agent may be used to target specific cells or tissues or may be used to promote endocytosis or phagocytosis of the MON and/or BCPMON. The targeting moieties or targeting agents include the ones known in the art. See, e.g., Cotten et al., *Methods Enzym.* 217:618, 1993. Examples of the targeting moieties and targeting agents include, but are not limited to, antibodies, proteins, peptides, carbohydrates, small molecules, metals, receptor ligands, sialic acid, aptamers, and fragments thereof. If a targeting moiety or targeting agent is included throughout a MON or BCPMON, the targeting agent may be included in the mixture that is used to form the MON or BCPMON. If the targeting agent is only on the surface of a MON or BCPMON, the targeting agent may be associated with (e.g., by covalent or non-covalent (e.g., electrostatic, hydrophobic, hydrogen bonding, van der Waals, π-π stacking) interactions) the MON or BCPMON using standard chemical techniques.

Adducts of a MON and an Agent

The present disclosure contemplates that the MONs described herein (including the MON moieties of the BCPMONs described herein) are useful in the delivery of an agent described herein (e.g., a small molecule, peptide, protein, or a polynucleotide) to a subject, tissue, or cell. Without wishing to be bound by any particular theory, the MONs have several desirable properties that make a composition that includes the MONs and an agent suitable for delivering the agent to a subject, tissue, or cell. Encapsulation of an agent within a MON described herein may have desirable properties for delivering an agent to a subject, tissue, or cell, including protection from degradation of the agent by ubiquitous nucleases, passive and active targeting, and/or evasion of endosomal Toll-like receptors. Other desirable properties include: 1) the ability of the MONs to form an adduct with and "protect" the agent that may otherwise be labile (e.g., labile at least due to chemical and/or enzymatical (e.g., by nucleases) degradation); 2) the ability of the MONs to buffer the pH in an endosome of the cell; 3) the ability of the MONs to act as a "proton sponge" and cause endosomolysis; and 4) the ability of the MONs to substantially neutralize the negative or positive charges of the agent. Challenges to the efficient delivery of an agent exist, including particle dissociation via serum proteins, cellular uptake, endosomal escape, and appropriate intracellular disassembly. To address some of these challenges, single parameter studies that evaluate the effect of chemical structure on a single biological property or on delivery performance have been reported. Furthermore, high-throughput synthetic methods have been exploited for the accelerated discovery of potent lipid nanoparticles (LNPs) and evaluation of structure activity relationships (SARs). In spite of these efforts, the relationships between physico-chemical properties of nanoparticles and biological barriers, and that between biological barriers and gene silencing activity remain unclear. This lack of clarity has also resulted in poor in vitro-in vivo translation.

In certain embodiments, a MON described herein encapsulates an agent described herein. In certain embodiments, the ratio of the amount of a MON described herein to the amount of an agent encapsulated in the MON is at least 1:1, at least 2:1, at least 5:1, at least 10:1, at least 20:1, at least 50:1, at least 100:1, at least 200:1, or at least 500:1 mol/mol. In certain embodiments, the ratio of the MON or BCPMON to the agent is not more than 500:1, not more than 200:1, not more than 100:1, not more than 50:1, not more than 20:1, not more than 10:1, not more than 5:1, not more than 2:1, or not more than 1:1 mol/mol. Combinations of the above ranges (e.g., at least 1:1 and not more than 100:1) are also within the scope of the disclosure.

A MON and agent described herein may form an adduct. An adduct may be formed by covalently attaching an agent to a MON or by non-covalent interactions (e.g., electrostatic interactions, hydrophobic interactions, hydrogen bonding, van der Waals interactions, and/or xt-n stacking) between an agent and a MON. An agent may be contacted with a MON, or the components thereof (e.g., ligands of Formula (A), (C), or (B) and transition metal ions, and optionally anionic counterions), under conditions suitable to form an adduct.

Micelles, Liposomes, and Lipoplexes

A composition including a MON and agent described herein may be in the form of a micelle or liposome. In certain embodiments, the MONs are in the form of a micelle or liposome. An agent described herein may be inside a micelle or liposome, and a MON described herein may be inside the micelle or liposome. In certain embodiments, in a micelle or liposome, an agent is encapsulated in a MON. Micelles and liposomes are typically useful in delivering an agent, such as a hydrophobic agent, to a subject, tissue, or cell. When the micelle or liposome is complexed with (e.g., encapsulates or covers) a polynucleotide, the resulting complex may be referred to as a "lipoplex." Many techniques for preparing micelles and liposomes are known in the art, and any such method may be used to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This may prevent interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of lipsomes may involve preparing a MON described herein for hydration, hydrating the MONs with agitation, and sizing the vesicles to achieve a homogenous distribution of liposomes. A MON described herein may be first dissolved in a solvent in a container to result in a homogeneous mixture. The solvent is then removed to form a film. This film is thoroughly dried to remove residual amount of the solvent, e.g., by placing the container in vacuo for a period of time. Hydration of the film may be accomplished by adding an aqueous medium and agitating the resulting mixture. Disruption of LMV suspensions using sonic energy typically produces small unilamellar vesicles (SUV) with diameters in the range of 15-50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm. In certain embodiments, the amount of a MON described herein in the liposome is between about 30 mol % and about 80 mol %, between about 40 mol % and about 70 mol %, or between about 60 mol % and about 70 mol %, inclusive. In certain embodiments, the MONs further complexes an agent, such as a small molecule.

Liposomes and micelles may also be prepared according to methods in the following scientific papers: Narang et al., "Cationic Lipids with Increased DNA Binding Affinity for Nonviral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis, Activity, and Structure—Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem.* 12:251-57, 2001; Lukyanov et al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids," *J. Gene Med.* 6:S24-S35, 2004; van Balen et al., "Liposome/Water Lipophilicity: Methods, Information Content, and Pharmaceutical Applications," *Medicinal Research Rev.* 24(3):299-324, 2004.

Gels

Gels are different from classical mechanics of materials, in that the timescale associated with the imposed stress or strain can affect the mechanical response by several orders of magnitude. These viscoelastic characteristics of gels are significant to many applications, and better understanding of the spatial and temporal mechanisms which effect desirable mechanical properties will lead to better materials designs. In gels, the timescales over which mechanical interactions occur are highly important; materials can have apparent fluid-like properties at long timescales yet apparent solid-like properties at short timescales. Typically, gels possess little long-range spatial ordering. Instead, the molecules in the gels arrange themselves in a wide array of spatial conformations. This spatial heterogeneity effects a corresponding temporal heterogeneity: upon application of a stress, the material begins to relax by deforming. Each of the local conformations relax at a distinct timescale. The mechanical properties (e.g., viscoelastic properties) of gels are important for the gels to be used in various applications. For example, it has been shown that substrate elasticity can determine mesenchymal stem cell differentiation (Engler et al. Cell, 2006, 126, 677-689). There is a need for gels with "designer viscoelasticity," the ability to create gels with a specifically engineered viscoelastic spectrum. Conventional methods for designing the mechanical properties of gels include changing the molecular weight or molecular weight distribution of the polymer matrix, increasing the degree of crosslinking between polymer chains, changing the stiffness of the polymer backbone, and changing the bulkiness of the side groups. However, these conventional techniques alter the properties of the polymer matrix such that they add other features which may be undesirable.

Coordination chemistry typically features bonds between metals and ligands that are intermediate in bond-energy between covalent bonds and non-covalent interactions (e.g., van der Waals interactions and H-bonding). Such bonds can be reversible or dynamic under appropriate conditions; they have been extensively used for the formation of a class of gel networks—metallogels—that features stimuli-responsive properties.[1-32] Due to their low branch functionality and dynamic bonds, most metallogels are soft elastic materials (storage moduli of G'≤20 kPa at ~2 to 10 wt. % polymer network) that often display viscous flow behavior at low shear strain frequencies.[6,7,21,26,29] These weak mechanical properties severely limit the possible applications of metallogels; the desirable dynamic properties inevitably come at the expense of structural integrity.

Recently, transition metal-organic ligand complexes have been suggested to reinforce the mechanical properties and self-healing nature of marine mussel adhesion fibers ("byssi") (Harrington et al. *Science,* 2010, 328, 216-220;

Harrington et al. *The Journal of Experimental Biology*, 2007, 210, 4307-4318; Holten-Andersen et al. *Nature Materials*, 2007, 6, 669-672; Lee et al. *Proceedings of the National Academy of Sciences of the United States of America*, 2006, 103, 12999-13003). Efforts have been made to mimic the extraordinary mechanical properties of the byssi using simplified synthetic analogs (Holten-Andersen et al. *Proceedings of the National Academy of Sciences of the United States of America*, 2011, 108, 2651-2655; Holten-Andersen et al., *Journal of Materials Chemistry B*, 2014, 2, 2467-2472; Lee et al. *Annual Review of Materials Research*, 2011, 41, 99-132; Barrett et al. *Advanced functional materials*, 2013, 23, 1111-1119; Fullenkamp et al. *Macromolecules*, 2013, 46, 1167-1174). Craig et al. has reported the formation and dynamic mechanical properties of metallo-supramolecular networks formed by mixtures of bis-Pd(II) and Pt(II) cross-linkers with poly(4-vinylpyridine) in DMSO. These networks have relaxation timescales that vary across several orders of magnitude. Also reported are that the kinetics of metal-ligand dissociation could be used to tune the apparent mechanical properties of a metallogel within a relevant timescale.[24-26] Furthermore, it has been shown that the thermodynamics of coordination can serve as a partially complementary parameter to tune the mechanical properties of gels.[26] Though manipulation of the kinetic and thermodynamic properties of individual metal-ligand bonds offers one way to modulate bulk properties, this strategy is ultimately limited in terms of the magnitude of changes that can be induced. Furthermore, it requires the design and synthesis of an assortment of ligand architectures and/or the use of different metals to induce changes in network behavior, which may not be compatible with a given application.

Tetrazine derivatives are another ligand that is useful in transition metal-ligand complexes. Interest in tetrazine reactivity has recently resurged largely due to its use in bioconjugate and polymer chemistry (Wollack, J. W.; Monson, B. J.; Dozier, J. K.; Dalluge, J. J.; Poss, K.; Hilderbrand, S. A.; Distefano, M. D. Chemical Biology & Drug Design 2014, 84, 140; Darko, A.; Wallace, S.; Dmitrenko, O.; Machovina, M. M.; Mehl, R. A.; Chin, J. W.; Fox, J. M. *Chemical Science* 2014, 5, 3770; Wu, H.; Cisneros, B. T.; Cole, C. M.; Devaraj, N. K. *Journal of the American Chemical Society* 2014, 136, 17942; Hansell, C. F.; Espeel, P.; Stamenović, M. M.; Barker, I. A.; Dove, A. P.; Du Prez, F. E.; O'Reilly, R. K. *Journal of the American Chemical Society* 2011, 133, 13828; Blackman, M. L.; Royzen, M.; Fox, J. M. *Journal of the American Chemical Society* 2008, 130, 13518; Cok, A. M.; Zhou, H.; Johnson, J. A. *Macromolecular Symposia* 2013, 329, 108; Zhou, H.; Woo, J.; Cok, A. M.; Wang, M.; Olsen, B. D.; Johnson, J. A. *Proceedings of the National Academy of Sciences* 2012). Certain tetrazine species are known for their binding to various metal ions; specifically, 3,6-bis(2-pyridyl)-1,2,4,5-tetrazines (bptz), has been studied for additional purposes by several groups as ligands in self-assembled structures. The Dunbar group reported the synthesis of molecular triangles, squares, and pentagons using bptz and various metal ions including $Fe^{2+}$, $Ni^{2+}$, and $Ag^+$, respectively. Additional accounts of using bptz include gold surface modification and its use as a ligand for rhenium to use its MLCT for study in photoinduced charge separation (Skomski, D.; Tempas, C. D.; Smith, K. A.; Tait, S. L. *Journal of the American Chemical Society* 2014, 136, 9862; Li, G.; Parimal, K.; Vyas, S.; Hadad, C. M.; Flood, A. H.; Glusac, K. D. *J. Am. Chem. Soc.* 2009, 131, 11656).

It has previously reported that covalent $A_2+B_3$ type end-linked polymer networks was synthesized using a tris-bptz trifunctional crosslinker and norbornene-terminated poly (ethylene glycol) (PEG) telechelic polymers (Hansell, C. F.; Espeel, P.; Stamenović, M. M.; Barker, I. A.; Dove, A. P.; Du Prez, F. E.; O'Reilly, R. K. *Journal of the American Chemical Society* 2011, 133, 13828; Cok, A. M.; Zhou, H.; Johnson, J. A. *Macromolecular Symposia* 2013, 329, 108; Zhou, H.; Woo, J.; Cok, A. M.; Wang, M.; Olsen, B. D.; Johnson, J. A. *Proceedings of the National Academy of Sciences* 2012; Zhou, H.; Johnson, J. A. *Angew. Chem., Int. Ed.* 2013, 52, 2235). Strained alkenes and tetrazines undergo facile inverse-electron demand Diels-Alder reactions with the extrusion of nitrogen, which make them useful for efficiently synthesizing catalyst-free, two component polymer networks. Subsequent work by Anseth and coworkers used this chemistry to construct cytocompatible gels that could be photochemically patterned (Alge, D. L.; Azagarsamy, M. A.; Donohue, D. F.; Anseth, K. S. *Biomacromolecules* 2013, 14, 949). However, there are no known references of bptz-metal coordination as a mode of crosslinking for the formation of end-linked polymer networks and the applications thereof.

A key component of polymer network structures that cannot be readily addressed by traditional metallogels is the network branch functionality, f, which is the average number of chains that emanate from junctions within a network. According to the phantom network model of rubber elasticity, the modulus of a gel increases with f.[33] In traditional metallogels, the junctions are single metal centers; f is dictated by the number of ligands that can bind to that metal, which is typically limited to values between two and four. Thus, metallogels are typically very soft materials, and it is very difficult to tune f without complete redesign of the network components.

It was envisioned that dramatic enhancements in f could be realized if network junctions were created through metal-ligand self-assembly into higher-order cage-like structures. Such "suprametallogels" would retain the dynamic properties of metallogels while potentially featuring broadly tunable branch architectures and enhanced mechanical properties. Nature uses hierarchical, multivalent assembly of weakly interacting species to produce biological gels with robust mechanical properties and dynamic behavior. Similar concepts have been adopted to increase the mechanical stability of synthetic networks.[34] As demonstrated here, programmed metallosupramolecular assembly for gelation is attractive because it enables tuning of gel properties over a wide range using the same metal and polymer, and very simple ligand modifications.

Numerous examples of ligand-metal combinations are known to provide discrete self-assembled cage-like structures.[35-48] Reports of Fujita and coworkers on the formation of $M_{12}L_{24}$ spherical cages from the assembly of twenty-four phenyl-3,5-bis-(para-pyridine) ligands and 12 $Pd^{2+}$ atoms were inspiring. In several studies, these authors have shown that these assemblies can be synthesized in quantitative yield, that they are robust towards a diverse range of ligand substitutions,[49,50] and that they can serve as small molecule hosts and nano-reactors.[36] Thus, incorporation of these supramolecular cages as junctions within a polymer network could afford suprametallogels with additional advantages—aside from mechanical ones—over conventional metallogels such as the ability to encapsulate and release species within the junction cages, or conduct reactions in confined spaces within the gel.

Two questions were to be answered. First, if bis-pyridyl moieties similar to those used by Fujita et al.[36] are appended onto the ends of linear polymer chains, will those polymer chains form suprametallogels in the presence of $Pd^{2+}$ through the self-assembly of the polymer chain ends? This question is non-trivial, because gelation has the potential to dramatically perturb the dynamics of cage self-assembly. Second, if an isomeric bis-pyridyl ligand, one that does not generate spherical cages but an alternative assembly, can be used to tune the network branch functionality in a rational manner? For example, in contrast to the defined 120° bite angle of the para-pyridine isomers, the corresponding meta isomers have infinitely many possible bite angles between 0° and 240° depending on the relative orientation of the two pyridines. Ditopic ligands with similar geometry are known to self-assemble into $M_2L_4$ paddlewheels with several types of metal ions, including $Pd^{2+}$.[51-65] A 1-hydroxymethyl derivative was synthesized, and it was confirmed that it quantitatively forms $M_2L_4$ paddlewheels in the presence of Pd2+ ions. In other words, a small difference in macromonomer ligand structure may provide materials with different bulk properties. Notably, this approach stands in stark contrast to gels that are formed via pre-assembly of metal-ligand-derived MONs that feature orthogonal groups for subsequent crosslinking.[66-68] Presented here are examples of gelation induced through metal-ligand bond formation and concomitant metallosupramolecular assembly (e.g., induced exclusively through metal-ligand bond formation and concomitant metallosupramolecular assembly).

Therefore, in another aspect, the present disclosure provides compositions that are gels or in the form of a gel (e.g., hydrogel), the compositions including a BCPMON and optionally an agent described herein. The gels described herein are suprametallogels. A BCPMON described herein and/or an adduct of a BCPMON and an agent (supramolecule-agent adduct) may be able to form a gel upon contacting a fluid. In certain embodiments, the fluid is a suitable solvent described herein (e.g., water). In certain embodiments, the BCPMON and/or supramolecule-agent adduct form a gel at least through the complexation of ligands of Formula (A), (C), or (B) and transition metal ions and optionally also through other non-covalent interrelations (e.g., electrostatic interactions, hydrophobic interactions, hydrogen bonding, van der Waals interactions, and/or π-π stacking). A BCPMON and/or supramolecule-agent adduct described herein may form a gel upon contacting a fluid when the concentration of the BCPMON and/or supramolecule-agent adduct in the fluid is a suitable concentration described herein (e.g., between about 10 and about 500 millimoles of a reactant or reagent (e.g., a ligand of Formula (A), (C), or (B); a macromonomer of Formula (L) or (M); or a transition metal salt) per liter of the fluid, inclusive). The structure of a gel described herein includes the primary structure (e.g., the structure of the MON moieties of the gel) and secondary structure (e.g., the degree of entanglement of the BCPMONs in the gel). An instance of the BCPMON may entangle within itself, and two or more instances of the BCPMON may also entangle. The entangled BCPMON(s) form a molecular network that includes cavities, which may be filled with a fluid when the BCPMON(s) are contacted with the fluid, and the BCPMON(s) may retain the fluid and be swelled, rather than be dissolved, by the fluid to form a gel. A high degree of entanglement of the BCPMONs may be beneficial for the formation of a gel when the BCPMONs are contacted with a fluid. In certain embodiments, the fluid comprises water, DMSO, acetonitrile, or a mixture thereof. In certain embodiments, the fluid comprises water. In certain embodiments, wherein the fluid is water.

Conventional gels (e.g., gels formed by swelling a covalently cross-linked polymer with a fluid) are typically not able to flow under a suitable stress (a suitable shear stress) and to self-heal when damaged. The gels described herein are advantageous over the conventional gels at least in that the gels described herein are able to flow under a suitable stress and to self-heal when damaged. While a conventional gel is usually thermally irreversible, the gels described herein are thermoreversible. A change in physical and/or chemical conditions (e.g., stress, temperature, and/or concentration) from a first condition to a second condition may result in a change in the degree of gelation of a gel described herein from a first degree of gelation to a second degree of gelation. A change in physical and/or chemical conditions (e.g., stress, temperature, and/or concentration) from the second condition to the first condition may result in a change in the degree of gelation of a gel described herein from the second degree of gelation to the first degree of gelation. The molecular network of a gel described herein may reversibly deform at least through weakening or strengthening, or breaking or reforming, the coordination bonds between the ligands of Formula (A), (C), or (B) and the transition metal ions by changing physical and/or chemical conditions. In contrast, the covalent bonds in a conventional gel typically cannot be reversibly weakened or strengthened, or broken or reformed, by changing physical and/or chemical conditions. The aggregation of the molecules in a gel described herein is more dynamic, compared to the aggregation of the molecules in a conventional gel, and the more dynamic aggregation in a gel described herein is at least due to the non-covalent interactions between the molecules therein. Conventional gels typically cannot be easily characterized using spectroscopic techniques. In contrast, the gels described herein allow facile characterizations using readily available spectroscopic techniques (e.g., UV-vis absorption spectroscopy and Raman spectroscopy) under various conditions. Combination of chemical spectroscopy with mechanical tests will then beget spatial structure-temporal structure-mechanical property relationships; this allows for shape design criteria for engineering the mechanical properties of gels (vis-à-vis modulating the modes of the relaxation spectrum).

The gels described herein are also advantageous over conventional MONs (e.g., nanoparticles without the block-co-polymer moieties $(-L-(R)_p-(G)_q-(R)_u-(G)_v-E))$. Individual instances of a conventional MON are not covalently linked to each other, and therefore, the conventional MONs typically lack robustness and/or storage modulus. The covalent bonding between the individual MONs in a gel described herein is stronger than the non-covalent interactions, if any, between the individual MONs in conventional MONs. Therefore, compared to conventional MONs, the gels described herein show higher robustness and/or higher storage modulus.

The BCPMONs and compositions (e.g., gels) may also be able to absorb a large amount of a fluid (e.g., absorb at least 100 times by weight of the fluid, compared to the weight of the BCPMON or the dry weight of the composition (weight of the composition minus the weight of the fluid included in the composition) and, therefore, may be useful as super-absorbent materials.

In certain embodiments, each instance of the BCPMON is the same. In certain embodiments, two or more instances of the BCPMON are different from each other. In certain embodiments, each instance of the ligand of Formula (A) is the same. In certain embodiments, two or more instances of the ligand of Formula (A) are different from each other. In certain embodiments, each instance of the ligand of Formula (B) is the same. In certain embodiments, two or more instances of the ligand of Formula (B) are different from each other. In certain embodiments, each instance of the transition metal ion or transition metal salt is the same. In certain embodiments, two or more instances of the transition metal ion or transition metal salt are different from each other. In certain embodiments, at least an instance of G of a first instance of the BCPMON, and at least an instance of G of a second instance of the BCPMON are associated by non-covalent interactions. In certain embodiments, the non-covalent interactions are reversible. In certain embodiments, the non-covalent interactions are reversible at different temperatures.

Kits

Also described herein are kits (e.g., packs). The kits provided may comprise (1) a macromonomer, BCPMON, thermoplastic elastomer, gel, or composition described herein; and (2) a container (e.g., a vial, ampule, bottle, syringe, and/or dispenser package, or other suitable container). In certain embodiments, the macromonomer, BCPMON, thermoplastic elastomer, gel, or composition is included in the container. In some embodiments, a kit described herein further includes a second container comprising an excipient. In some embodiments, the macromonomer, BCPMON, thermoplastic elastomer, gel, or composition provided in the first container and the excipient provided in the second container are combined to form one unit dosage form.

In certain embodiments, the kits described herein are useful for delivering an agent to a subject, tissue, or cell. In certain embodiments, the kits are useful for delivering an agent to a target tissue described herein. In certain embodiments, the kits are useful for treating a disease described herein. In certain embodiments, the kits are useful for preventing a disease described herein.

In certain embodiments, the described kits further include instructions for administering a macromonomer, BCPMON, thermoplastic elastomer, gel, or composition described herein. The kits may also include information as required by a regulatory agency such as the U.S. Food and Drug Administration (FDA). In certain embodiments, the information included in the kits is prescribing information. In certain embodiments, the kits, including the instructions, provide for delivering an agent described herein to a subject, tissue, or cell. In certain embodiments, the kits, including the instructions, provide for treating a disease described herein. In certain embodiments, the kits, including the instructions, provide for preventing a disease described herein. The kit described herein may include one or more agents described herein as a separate composition.

Methods of Preparation and Products Prepared by Methods of Preparation

Another aspect of the present disclosure relates to methods of preparing a BCPMON described herein comprising complexing a macromonomer described herein with a transition metal salt.

Another aspect of the present disclosure relates to methods of preparing a thermoplastic elastomer described herein comprising annealing two or more instances of a BCPMON described herein.

Another aspect of the present disclosure relates to methods of preparing a gel described herein comprising contacting two or more instances of a BCPMON described herein with a fluid. In certain embodiments, the method of preparing a gel further comprises annealing the product formed by contacting the two or more instances of the BCPMON with the fluid.

Another aspect of the present disclosure relates to methods of preparing a composition described herein comprising complexing a macromonomer described herein with a transition metal salt in the presence of an agent. In certain embodiments, the method of preparing a composition further comprises annealing the product formed by complexing the macromonomer with the transition metal salt in the presence of the agent. In certain embodiments, two or more products formed by complexing the macromonomer with the transition metal salt in the presence of the agent are different.

Another aspect of the present disclosure relates to thermoplastic elastomers prepared by a method described herein.

Another aspect of the present disclosure relates to gels prepared by a method described herein.

In certain embodiments, each instance of the transition metal ion or transition metal salt is the same. In certain embodiments, two or more instances of the transition metal ion or transition metal salt are different from each other.

Methods of Treatment and Uses

One of the major problems in the development of formulations of pharmaceutical agents (e.g., anti-cancer agents) is the delivery of the pharmaceutical agents with adequately high bioavailability for therapeutic intentions. Using conventional delivery techniques, many pharmaceutical agents cannot be delivered effectively to the target tissues or target cells. Gels, such as hydrogels, have emerged as an important class of materials for biomedical applications due to their unique properties that bridge the gap between solid and liquid states. The gels described herein are advantageous over conventional gels that typically include a covalently cross-linked polymer network at least because the molecular network of a gel described herein is formed at least by non-covalent interactions, such as complexation of a ligand and a transition metal ion, and thus is thermoreversible, able to flow (e.g., under a high shear stress), and able to self-heal when damaged. An agent may be encapsulated in a gel described herein (e.g., encapsulated in a MON moiety of a BCPMON of the gel) and is delivered to a tissue or cell (e.g., a target tissue or target cell). The gel may dissociate in the tissue or cell to release the agent to the tissue or cell. In certain embodiments, a MON moiety of a BCPMON of the gel dissociates (e.g., by breaking the coordination bonds between (1) the ligands of Formula (A), (C), or (B) or macromonomers of Formula (L) or (M) and (2) the transition metal ions) to release the agent that was encapsulated in the MON moiety before the dissociation. The gels described herein may also be advantageous over conventional nanoparticles at least because the gels described herein may be more robust and may have higher storage modulus than the conventional nanoparticles.

In another aspect, the present disclosure provides methods of delivering an agent described herein (e.g., small molecule) to a subject, tissue, or cell. In certain embodiments, described herein are methods of delivering the agent to a target tissue or target cell described herein. In certain embodiments, described herein are methods of selectively delivering the agent to a target tissue, compared to a non-target tissue. In certain embodiments, described herein are methods of selectively delivering the agent to a target cell, compared to a non-target cell. In certain embodiments, the agent is delivered into the subject, tissue, or cell by the methods described herein. In certain embodiments, the agent is selectively delivered into the target tissue or target cell by the methods described herein, compared to a non-target tissue or non-target cell, respectively.

Another aspect of the present disclosure relates to methods of increasing the delivery of an agent to a subject, tissue, or cell. In certain embodiments, the delivery of the agent to the subject, tissue, or cell is increased by a method described herein. In certain embodiments, the delivery of the agent to the subject, tissue, or cell by a method described herein is increased compared to the delivery of the agent to the subject, tissue, or cell by a control method that does not involve a composition described herein.

In another aspect, the present disclosure provides methods of treating a disease described herein in a subject in need thereof.

In another aspect, the present disclosure provides methods of preventing a disease described herein in a subject in need thereof.

In certain embodiments, a disease described herein is a genetic disease. In certain embodiments, the disease is a proliferative disease. In certain embodiments, the disease is cancer. In certain embodiments, the disease is a benign neoplasm. In certain embodiments, the disease is pathological angiogenesis. In certain embodiments, the disease is an inflammatory disease. In certain embodiments, the disease is an autoimmune disease. In certain embodiments, the disease is a hematological disease. In certain embodiments, the disease is a neurological disease. In certain embodiments, the disease is a gastrointestinal disease. In certain embodiments, the disease is a liver disease. In certain embodiments, the disease is a spleen disease. In certain embodiments, the disease is a respiratory disease. In certain embodiments, the disease is a lung disease. In certain embodiments, the disease is a painful condition. In certain embodiments, the painful condition is inflammatory pain. In certain embodiments, the painful condition is associated with an inflammatory disorder and/or an autoimmune disorder. In certain embodiments, the disease is a genitourinary disease. In certain embodiments, the disease is a musculoskeletal condition. In certain embodiments, the disease is an infectious disease. In certain embodiments, the disease is a psychiatric disorder. In certain embodiments, the disease is a metabolic disorder. In certain embodiments, the disease is hepatic carcinoma. In certain embodiments, the disease is hypercholesterolemia. In certain embodiments, the disease is refractory anemia. In certain embodiments, the disease is familial amyloid neuropathy.

Another aspect of the present disclosure relates to methods of genetically engineering a subject. In certain embodiments, the subject is genetically engineered to increase the growth of the subject. In certain embodiments, the subject is genetically engineered to increase the subject's resistance to pathogenic organisms and/or microorganisms (e.g., viruses, bacteria, fungi, protozoa, and parasites).

In certain embodiments, a method described herein includes administering to the subject a composition described herein. In certain embodiments, a method described herein includes administering to the subject an effective amount of a composition described herein.

In certain embodiments, a method described herein includes contacting the tissue with a composition described herein. In certain embodiments, a method described herein includes contacting the tissue with an effective amount of a composition described herein.

In certain embodiments, a method described herein includes contacting the cell with a composition described herein. In certain embodiments, a method described herein includes contacting the cell with an effective amount of a composition described herein.

In certain embodiments, a subject described herein is a human. In certain embodiments, the subject is an animal. In certain embodiments, the subject is a non-human animal. The animal may be of either sex and may be at any stage of development. In certain embodiments, the subject is a fish. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a human with a disease described herein. In certain embodiments, the subject is a human suspected of having a disease described. In certain embodiments, the subject is a human at risk of developing a disease described herein.

In certain embodiments, a cell described herein is in vivo. In certain embodiments, a cell described herein is in vitro.

Another aspect of the present disclosure relates to uses of a MON described herein in a method described herein (e.g., uses for delivering an agent to a subject, tissue, or cell; uses for treating a disease in a subject in need thereof; and uses for preventing a disease in a subject).

Another aspect of the present disclosure relates to uses of a BCPMON described herein in a method described herein (e.g., uses for delivering an agent to a subject, tissue, or cell; uses for treating a disease in a subject in need thereof; and uses for preventing a disease in a subject).

Another aspect of the present disclosure relates to uses of a composition (e.g., gel) described herein in a method described herein (e.g., uses for delivering an agent to a subject, tissue, or cell; uses for treating a disease in a subject in need thereof; and uses for preventing a disease in a subject).

REFERENCES

1 Xing, B., Choi, M.-F. & Xu, B. A stable metal coordination polymer gel based on a calix[4]arene and its "uptake" of non-ionic organic molecules from the aqueous phase. *Chemical Communications*, 362-363, doi:10.1039/B 111245G (2002).

2 J. H. Hafkamp, R. et al. Organogel formation and molecular imprinting by functionalized gluconamides and their metal complexes. *Chemical Communications*, 545-546, doi:10.1039/A608266A (1997).

3 Xing, B., Choi, M.-F., Zhou, Z. & Xu, B. Spontaneous Enrichment of Organic Molecules from Aqueous and Gas Phases into a Stable Metallogel. *Langmuir* 18, 9654-9658, doi:10.1021/la0256580 (2002).

4 Xing, B., Choi, M.-F. & Xu, B. Design of Coordination Polymer Gels as Stable Catalytic Systems. *Chemistry—A European Journal* 8, 5028-5032, doi:10.1002/1521-3765 (20021104)8:21<5028::AID-CHEM5028>3.0.CO; 2-1 (2002).

Westhaus, E. & Messersmith, P. B. Triggered release of calcium from lipid vesicles: a bioinspired strategy for rapid gelation of polysaccharide and protein hydrogels. *Biomaterials* 22, 453-462, doi: dx.doi.org/10.1016/S0142-9612(00)00200-3 (2001).

6 Fullenkamp, D. E., He, L., Barrett, D. G., Burghardt, W. R. & Messersmith, P. B. Mussel-Inspired Histidine-Based Transient Network Metal Coordination Hydrogels. *Macromolecules* 46, 1167-1174, doi:10.1021/ma301791n (2013).

7. Holten-Andersen, N. et al. pH-induced metal-ligand cross-links inspired by mussel yield self-healing polymer networks with near-covalent elastic moduli. *Proceedings of the National Academy of Sciences* 108, 2651-2655, doi: 10.1073/pnas.1015862108 (2011).
8. Holten-Andersen, N. et al. Metal-coordination: using one of nature's tricks to control soft material mechanics. *Journal of Materials Chemistry B* 2, 2467-2472, doi: 10.1039/C3TB21374A (2014).
9. Harrington, M. J., Masic, A., Holten-Andersen, N., Waite, J. H. & Fratzl, P. Iron-Clad Fibers: A Metal-Based Biological Strategy for Hard Flexible Coatings. *Science* 328, 216-220, doi:10.1126/science.1181044 (2010).
10. Zhao, Y., Beck, J. B., Rowan, S. J. & Jamieson, A. M. Rheological Behavior of Shear-Responsive Metallo-Supramolecular Gels. *Macromolecules* 37, 3529-3531, doi: 10.1021/ma0497005 (2004).
11. Weng, W., Beck, J. B., Jamieson, A. M. & Rowan, S. J. Understanding the Mechanism of Gelation and Stimuli-Responsive Nature of a Class of Metallo-Supramolecular Gels. *Journal of the American Chemical Society* 128, 11663-11672, doi:10.1021/ja063408q (2006).
12. Weng, W., Jamieson, A. M. & Rowan, S. J. Structural origin of the thixotropic behavior of a class of metallo-supramolecular gels. *Tetrahedron* 63, 7419-7431, doi: dx.doi.org/10.1016/j.tet.2007.03.119 (2007).
13. Weng, W., Li, Z., Jamieson, A. M. & Rowan, S. J. Control of Gel Morphology and Properties of a Class of Metallo-Supramolecular Polymers by Good/Poor Solvent Environments. *Macromolecules* 42, 236-246, doi:10.1021/ma801046w (2008).
14. Weng, W., Li, Z., Jamieson, A. M. & Rowan, S. J. Effect of monomer structure on the gelation of a class of metallo-supramolecular polymers. *Soft Matter* 5, 4647-4657, doi:10.1039/B911166B (2009).
15. Beck, J. B. & Rowan, S. J. Multistimuli, Multiresponsive Metallo-Supramolecular Polymers. *Journal of the American Chemical Society* 125, 13922-13923, doi:10.1021/ja038521k (2003).
16. Rowan, S. J. & Beck, J. B. Metal-ligand induced supramolecular polymerization: A route to responsive materials. *Faraday Discussions* 128, 43-53, doi:10.1039/B403135K (2005).
17. Burnworth, M., Mendez, J. D., Schroeter, M., Rowan, S. J. & Weder, C. Decoupling Optical Properties in Metallo-Supramolecular Poly(p-phenylene ethynylene)s. *Macromolecules* 41, 2157-2163, doi:10.1021/ma702712e (2008).
18. McKenzie, B. M. & Rowan, S. J. in *Molecular Recognition and Polymers* 157-178 (John Wiley & Sons, Inc., 2008).
19. Buerkle, L. E. & Rowan, S. J. Supramolecular gels formed from multi-component low molecular weight species. *Chemical Society Reviews* 41, 6089-6102, doi: 10.1039/C2CS35106D (2012).
Xu, D. & Craig, S. L. Scaling Laws in Supramolecular Polymer Networks. *Macromolecules* 44, 5465-5472, doi: 10.1021/ma200096s (2011).
21. Xu, D. & Craig, S. L. Strain Hardening and Strain Softening of Reversibly Cross-Linked Supramolecular Polymer Networks. *Macromolecules* 44, 7478-7488, doi: 10.1021/ma201386t (2011).
22. Xu, D., Hawk, J. L., Loveless, D. M., Jeon, S. L. & Craig, S. L. Mechanism of Shear Thickening in Reversibly Cross-Linked Supramolecular Polymer Networks. *Macromolecules* 43, 3556-3565, doi:10.1021/ma100093b (2010).
23. Loveless, D. M., Jeon, S. L. & Craig, S. L. Chemoresponsive viscosity switching of a metallo-supramolecular polymer network near the percolation threshold. *Journal of Materials Chemistry* 17, 56-61, doi:10.1039/B614026B (2007).
24. Yount, W. C., Loveless, D. M. & Craig, S. L. Small-Molecule Dynamics and Mechanisms Underlying the Macroscopic Mechanical Properties of Coordinatively Cross-Linked Polymer Networks. *Journal of the American Chemical Society* 127, 14488-14496, doi:10.1021/ja054298a (2005).
Yount, W. C., Loveless, D. M. & Craig, S. L. Strong Means Slow: Dynamic Contributions to the Bulk Mechanical Properties of Supramolecular Networks. *Angewandte Chemie International Edition* 44, 2746-2748, doi: 10.1002/anie.200500026 (2005).
26. Loveless, D. M., Jeon, S. L. & Craig, S. L. Rational Control of Viscoelastic Properties in Multicomponent Associative Polymer Networks. *Macromolecules* 38, 10171-10177, doi:10.1021/ma0518611 (2005).
27. Kean, Z. S. et al. Increasing the Maximum Achievable Strain of a Covalent Polymer Gel Through the Addition of Mechanically Invisible Cross-Links. *Adv. Mater.* (Weinheim, Ger.), n/a-n/a, doi:10.1002/adma.201401570 (2014).
28. Nair, K. P., Breedveld, V. & Weck, M. Modulating mechanical properties of self-assembled polymer networks by multi-functional complementary hydrogen bonding. *Soft Matter* 7, 553-559, doi:10.1039/COSM00795A (2011).
29. Nair, K. P., Breedveld, V. & Weck, M. Multiresponsive Reversible Polymer Networks Based on Hydrogen Bonding and Metal Coordination. *Macromolecules* 44, 3346-3357, doi:10.1021/ma102462y (2011).
30. Hackelbusch, S., Rossow, T., van Assenbergh, P. & Seiffert, S. Chain Dynamics in Supramolecular Polymer Networks. *Macromolecules* 46, 6273-6286, doi:10.1021/ma4003648 (2013).
31. Hackelbusch, S., Rossow, T., Becker, H. & Seiffert, S. Multiresponsive Polymer Hydrogels by Orthogonal Supramolecular Chain Cross-Linking. *Macromolecules* 47, 4028-4036, doi:10.1021/ma5008573 (2014).
32. Zhang, Y. et al. Active Cross-Linkers that Lead to Active Gels. *Angewandte Chemie International Edition* 52, 11494-11498, doi:10.1002/anie.201304437 (2013).
33. Rubinstein, M. & Colby, R. *Polymers Physics*. (Oxford, 2003).
34. Cordier, P., Tournilhac, F., Soulie-Ziakovic, C. & Leibler, L. Self-healing and thermoreversible rubber from supramolecular assembly. *Nature* 451, 977-980, doi: www.nature.com/nature/journal/v451/n7181/suppinfo/nature06669_S1.html (2008).
35. Sun, W.-Y., Yoshizawa, M., Kusukawa, T. & Fujita, M. Multicomponent metal-ligand self-assembly. *Current Opinion in Chemical Biology* 6, 757-764, doi:_dx.doi.org/10.1016/S1367-5931(02)00358-7 (2002).
36. Harris, K., Fujita, D. & Fujita, M. Giant hollow MnL2n spherical complexes: structure, functionalisation and applications. *Chemical Communications* 49, 6703-6712, doi:10.1039/C3CC43191F (2013).
37. Leininger, S., Olenyuk, B. & Stang, P. J. Self-Assembly of Discrete Cyclic Nanostructures Mediated by Transition Metals. *Chem. Rev.* (Washington, D.C., U. S.) 100, 853-908, doi:10.1021/cr9601324 (2000).

38 Meyer, C. D. et al. The Dynamic Chemistry of Molecular Borromean Rings and Solomon Knots. *Chemistry—A European Journal* 16, 12570-12581, doi:10.1002/chem.201001806 (2010).

39 Forgan, R. S., Sauvage, J.-P. & Stoddart, J. F. Chemical Topology: Complex Molecular Knots, Links, and Entanglements. Chem. Rev. (Washington, D.C., U. S.) 111, 5434-5464, doi:10.1021/cr200034u (2011).

40 Chambron, J.-C. & Sauvage, J.-P. Topologically complex molecules obtained by transition metal templation: it is the presentation that determines the synthesis strategy. *New Journal of Chemistry* 37, 49-57, doi:10.1039/C2NJ40555E (2013).

41 Ronson, T. K., Zarra, S., Black, S. P. & Nitschke, J. R. Metal-organic container molecules through subcomponent self-assembly. *Chemical Communications* 49, 2476-2490, doi:10.1039/$C_2$CC36363A (2013).

42 Smulders, M. M. J., Riddell, I. A., Browne, C. & Nitschke, J. R. Building on architectural principles for three-dimensional metallosupramolecular construction. *Chemical Society Reviews* 42, 1728-1754, doi:10.1039/$C_2$CS35254K (2013).

43 Castilla, A. M., Ramsay, W. J. & Nitschke, J. R. Stereochemistry in Subcomponent Self-Assembly. *Accounts of Chemical Research* 47, 2063-2073, doi:10.1021/ar5000924 (2014).

44 Campos-Fernindez, C. S., Clérac, R. & Dunbar, K. R. A One-Pot, High-Yield Synthesis of a Paramagnetic Nickel Square from Divergent Precursors by Anion Template Assembly. *Angewandte Chemie International Edition* 38, 3477-3479, doi:10.1002/(SICI)1521-3773(19991203)38:23<3477::AID-ANIE3477>3.0.CO;2-P (1999).

45 Campos-Fernández, C. S., Clérac, R., Koomen, J. M., Russell, D. H. & Dunbar, K. R. Fine-Tuning the Ring-Size of Metallacyclophanes: A Rational Approach to Molecular Pentagons. *Journal of the American Chemical Society* 123, 773-774, doi:10.1021/ja002960r (2001).

46 Chifotides, H. T. & Dunbar, K. R. Anion-π Interactions in Supramolecular Architectures. *Accounts of Chemical Research* 46, 894-906, doi:10.1021/ar300251k (2013).

47 Holliday, B. J. & Mirkin, C. A. Strategies for the Construction of Supramolecular Compounds through Coordination Chemistry. *Angewandte Chemie International Edition* 40, 2022-2043, doi:10.1002/1521-3773(20010601)40:11<2022::AID-ANIE2022>3.0.CO;2-D (2001).

48 Yoshizawa, M. & Klosterman, J. K. Molecular architectures of multi-anthracene assemblies. *Chemical Society Reviews* 43, 1885-1898, doi:10.1039/C3CS60315F (2014).

49 Sun, Q.-F. et al. Self-Assembled M24L48 Polyhedra and Their Sharp Structural Switch upon Subtle Ligand Variation. *Science* (Washington, D.C., U. S.) 328, 1144-1147, doi:10.1126/science. 1188605 (2010).

50 Tominaga, M. et al. Finite, spherical coordination networks that self-organize from 36 small components. *Angew. Chem., Int. Ed.* 43, 5621-5625, doi:10.1002/anie.200461422 (2004).

51 Chand, D. K., Biradha, K. & Fujita, M. Self-assembly of a novel macrotricyclic Pd( ) metallocage encapsulating a nitrate ion. *Chemical Communications*, 1652-1653, doi:10.1039/B104853H (2001).

52 Owens, T. D., Hollander, F. J., Oliver, A. G. & Ellman, J. A. Synthesis, Utility, and Structure of Novel Bis(sulfinyl)imidoamidine Ligands for Asymmetric Lewis Acid Catalysis. *Journal of the American Chemical Society* 123, 1539-1540, doi:10.1021/ja005635c (2001).

53 Su, C.-Y., Cai, Y.-P., Chen, C.-L., Zhang, H.-X. & Kang, B.-S. Coordination-directed assembly of trigonal and tetragonal molecular boxes encapsulating anionic guests. *Journal of the Chemical Society, Dalton Transactions*, 359-361, doi:10.1039/B0101180 (2001).

54 Liu, Z.-M. et al. Assembly of Trigonal and Tetragonal Prismatic Cages from Octahedral Metal Ions and a Flexible Molecular Clip. *Inorganic Chemistry* 46, 5814-5816, doi:10.1021/ic062270+(2007).

55 Desmarets, C., Policar, C., Chamoreau, L.-M. & Amouri, H. Design, Self-Assembly, and Molecular Structures of 3D Copper(II) Capsules Templated by BF4-Guest Anions. *European Journal of Inorganic Chemistry* 2009, 4396-4400, doi:10.1002/ejic.200900606 (2009).

56 Liu, H.-K. et al. Discrete M2L2 metallacycle and M2L4 cage frameworks and anion competitive reactions of Cu2L4 type receptor. *Inorganic Chemistry Communications* 12, 457-460, doi:dx.doi.org/10.1016/j.inoche.2009.03.017 (2009).

57 Liao, P. et al. Two-component control of guest binding in a self-assembled cage molecule. *Chemical Communications* 46, 4932-4934, doi:10.1039/COCC00234H (2010).

58 Kishi, N., Li, Z., Yoza, K., Akita, M. & Yoshizawa, M. An $M_2L_4$ Molecular Capsule with an Anthracene Shell: Encapsulation of Large Guests up to 1 nm. *Journal of the American Chemical Society* 133, 11438-11441, doi: 10.1021/ja2037029 (2011).

59 Li, Z., Kishi, N., Hasegawa, K., Akita, M. & Yoshizawa, M. Highly fluorescent M2L4 molecular capsules with anthracene shells. *Chemical Communications* 47, 8605-8607, doi:10.1039/C1CC12946E (2011).

60 Li, Z., Kishi, N., Yoza, K., Akita, M. & Yoshizawa, M. Isostructural $M_2L_4$ Molecular Capsules with Anthracene Shells: Synthesis, Crystal Structures, and Fluorescent Properties. *Chemistry—A European Journal* 18, 8358-8365, doi:10.1002/chem.201200155 (2012).

61 Barbour, L. J., Orr, G. W. & Atwood, J. L. An intermolecular (H2O)10 cluster in a solid-state supramolecular complex. *Nature* 393, 671-673, doi: www.nature.com/nature/journal/v393/n6686/suppinfo/393671a0_S1.html (1998).

62 Yue, N. L. S., Eisler, D. J., Jennings, M. C. & Puddephatt, R. J. Macrocyclic and Lantern Complexes of Palladium (II) with Bis(amidopyridine) Ligands: Synthesis, Structure, and Host-Guest Chemistry. *Inorganic Chemistry* 43, 7671-7681, doi:10.1021/ic048893+(2004).

63 Amouri, H. et al. Host-Guest Interactions: Design Strategy and Structure of an Unusual Cobalt Cage That Encapsulates a Tetrafluoroborate Anion. *Angewandte Chemie International Edition* 44, 4543-4546, doi:10.1002/anie.200500786 (2005).

64 Clever, G. H., Tashiro, S. & Shionoya, M. Inclusion of Anionic Guests inside a Molecular Cage with Palladium (II) Centers as Electrostatic Anchors. *Angewandte Chemie International Edition* 48, 7010-7012, doi:10.1002/anie.200902717 (2009).

65 Hirakawa, T. et al. Removal of Perchlorate Anion from an Aqueous Solution by Encapsulation in an Anion-templated Self-assembled Molecular Capsule. *Chemistry Letters* 38, 290-291, doi:10.1246/cl.2009.290 (2009).

66 Yan, X. et al. Responsive Supramolecular Polymer Metallogel Constructed by Orthogonal Coordination-Driven Self-Assembly and Host/Guest Interactions. *Journal of the American Chemical Society* 136, 4460-4463, doi: 10.1021/ja412249k (2014).

67 Yan, X. et al. Hierarchical Self-Assembly: Well-Defined Supramolecular Nanostructures and Metallohydrogels via Amphiphilic Discrete Organoplatinum(II) Metallacycles. *Journal of the American Chemical Society* 135, 14036-14039, doi:10.1021/ja406877b (2013).
68 Yan, X. et al. Supramolecular polymers with tunable topologies via hierarchical coordination-driven self-assembly and hydrogen bonding interfaces. *Proceedings of the National Academy of Sciences* 110, 15585-15590, doi:10.1073/pnas.1307472110 (2013).
69 Crystals were obtained by vapor diffusion of ethyl acetate into DMSO-d6 at 23° C.
70 The chemical shifts and symmetric nature of the broad resonances mapped well onto the solution $^1$H NMR spectra of the Li-spheres and soluble polymer network fragments derived from B-3.
71 Yoneya, M., Tsuzuki, S., Yamaguchi, T., Sato, S. & Fujita, M. Coordination-Directed Self-Assembly of M12L24 Nanocage: Effects of Kinetic Trapping on the Assembly Process. *ACS Nano* 8, 1290-1296, doi:10.1021/nn404595j (2014).
72 Yoneya, M., Yamaguchi, T., Sato, S. & Fujita, M. Simulation of Metal-Ligand Self-Assembly into Spherical Complex M6L8. *J. Am. Chem. Soc.* 134, 14401-14407, doi:10.1021/ja303542r (2012).
73 Greater junction functionality translates into smaller for the same ν in the phantom network model equation G'phantom=RT(ν−μ)φ−⅓.

EXAMPLES

In order that the invention described herein may be more fully understood, the following examples are set forth. The synthetic and biological examples described herein are offered to illustrate the present disclosure and are not to be construed in any way as limiting their scope.

Example 1. Preparation and Characterization of BCPMONs of Formula (A) or (B)

For the realization of exemplary BCPMONs, poly(methyl methacrylate)-block-poly(n-butyl acrylate) (PMMA-b-PBA, or PMMA-PBA) bearing a pyridyl ligand at the chain end was used. PMMA-PBA is known to phase separate in the bulk state as well as in suitable solvents.[56-57] The ligands of choice are shown in FIG. 1B. In the presence of Pd ions, these ligands form $Pd_xL_y$ complexes with different geometries: ligand L1 forms a square planar $ML_4$ complex (this ligand may serve as a control for comparison to BCP-MONs), while ligands L2 and L3 are structural isomers of meta- and para-bispyridine that assemble into $M_2L_4$ paddlewheel and $M_{12}L_{24}$ Fujita sphere MONs, respectively. Schematics for these complexes are shown in FIG. 1C.

BCP Synthesis

Figure 2A:
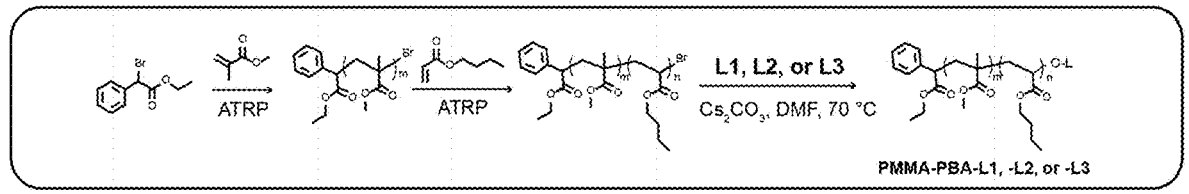
FIGS. 2A to 2C.
Figure 7:
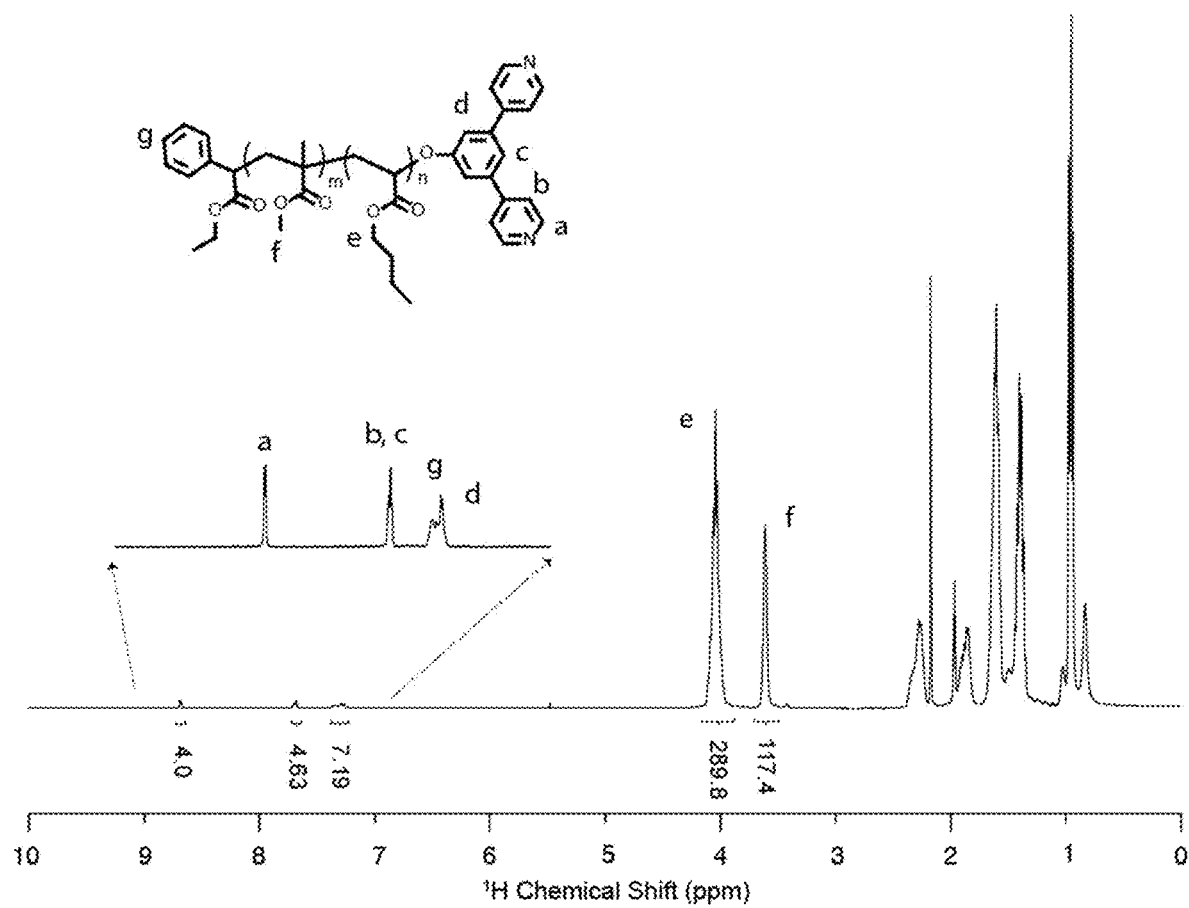
FIG. 7. $^1$H NMR spectrum showing an example of ligand-functionalized PMMA-PBA block copolymer. $PMMA_{4k}$-$PBA_{19k}$-L3 is shown. Solvent: acetonitrile-$d_3$.
Figures 8A, 8B, 8C, 8D:
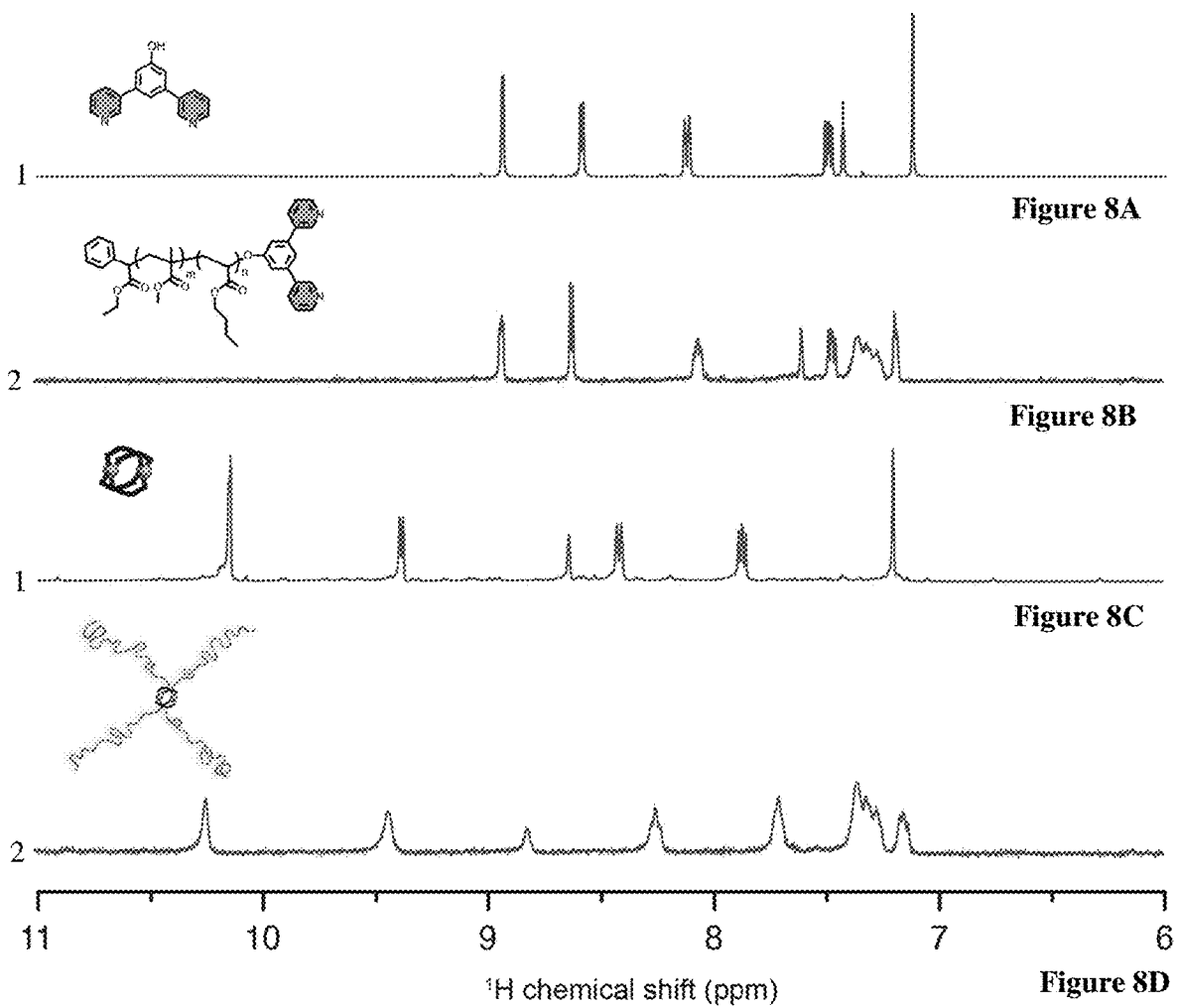
FIGS. 8A to 8D. $^1$H NMR spectra comparing the formation of paddle wheel-like $M_2L_4$ MON based on small molecules in DMSO-$d_6$ (1) and block copolymers in acetonitrile-$d_3$ (2). Spectra before (FIGS. 8A and 8B) and after (FIGS. 8C and 8D) assembly are shown. Block copolymer $PMMA_{4k}$-$PBA_{19k}$-L2 was used to obtain the spectra.

The BCPs were synthesized via atom transfer radical polymerization (ATRP), followed by post-polymerization functionalization (FIG. 2A). Using Ethyl α-bromophenylacetate (EBPA) as the initiator, the PMMA block could be synthesized with low dispersities (Đ=1.05-1.10) and controlled molecular weights.[58] The obtained PMMA then served as a macro-initiator for the synthesis of PMMA-PBA through chain extension. To install the desired ligand on the PBA chain end, a nucleophilic substitution reaction was used in which the appropriate pyridyl phenol ligand displaced the polymer chain end bromide to yield an ether product. The functionalized polymers were purified by silica gel chromatography. $^1$H nuclear magnetic resonance spectroscopy ($^1$H NMR) confirmed the presence of protons from both the EBPA initiator and the bispyridine chain end, as labeled in FIGS. 2B to 2C. The integration of characteristic peaks for all three macro-ligands matches the chemical structures, which suggests a high degree (>95%) of chain-end functionalization (FIG. 7). Apart from the difference in the ligands, BCPs of different molecular weights and block volume fractions were synthesized for comparison; detailed characterization data for all polymers studied are listed in Table 1. For nomenclature, $PMMA_{4k}$-$PBA_{19k}$-L1 stands for BCPs with a number-average molecular weight of 4 k Da and 19 k Da for each block and ligand L1 as the chain end (also abbreviated as -L1 in the same context).

TABLE 1

Characterization data for BCPs.

| [a]Polymer | [b]$M_n$ | Đ | [c]$N_{PMMA}$ | [d]$f_{PMMA}$ | [c]$N_{PBA}$ | [d]$f_{PBA}$ |
|---|---|---|---|---|---|---|
| $PMMA_{4k}$-$PBA_{19k}$ | 22.9k | 1.14 | 39 | 16.4 | 147 | 83.6 |
| $PMMA_{8k}$-$PBA_{27k}$ | 34.1k | 1.07 | 82 | 23.1 | 221 | 76.9 |
| $PMMA_{8k}$-$PBA_{48k}$ | 52.1k | 1.09 | 82 | 14.8 | 385 | 85.2 |

[a]Number-average molecular weight ($M_n$) and [c]degree of polymerization (N) determined by $^1$H NMR.
[b]$M_n$ measured by GPC (solvent, THF).
[d]Volumne fraction (f) is calculated based on N and the density of PMMA and PBA.

Metal-Coordination Driven MON Assembly

Figure 1C:
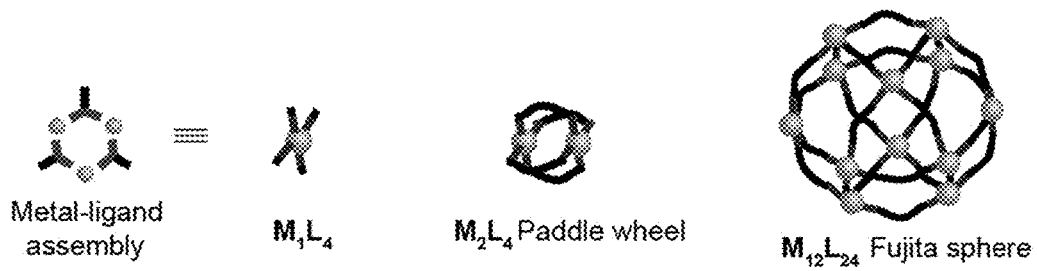
Figure 2B:
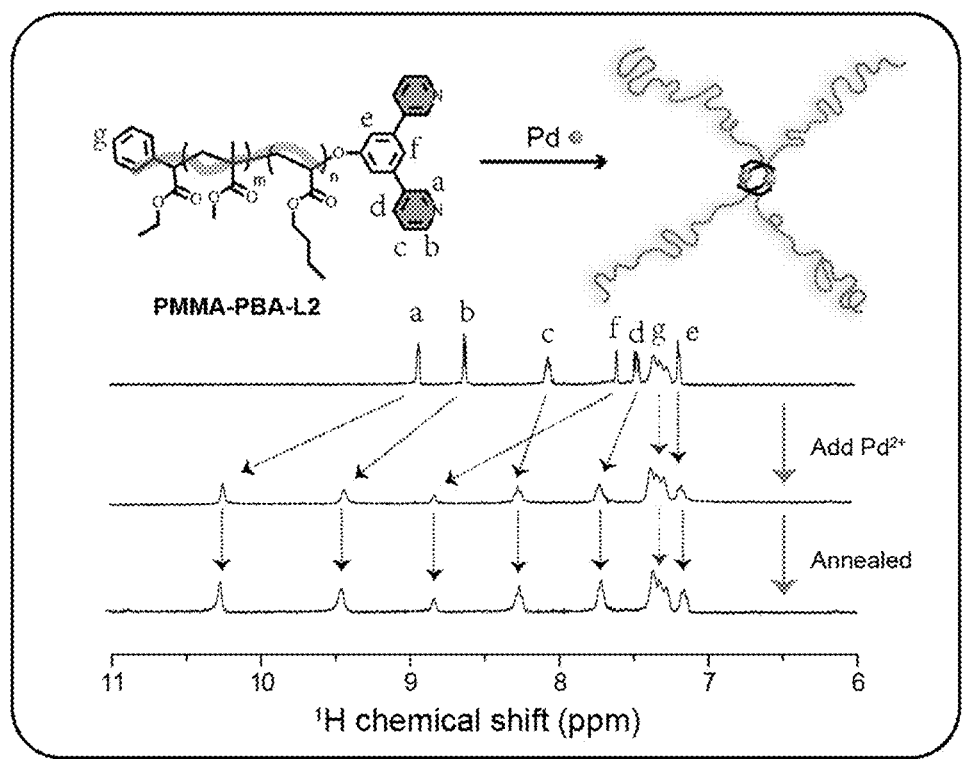

When palladium ions ($Pd^{2+}$) are introduced to a solution of PMMA-PBA-L in acetonitrile, Pd-pyridine metal-coordination occurs rapidly to give poorly defined coordination polymer networks. However, upon thermal annealing, the BCP-bound ligands and $Pd^{2+}$ ions assemble into the clusters shown schematically in FIG. 1C. $^1$H NMR was used to study the assembly process as well as the differences between polymers bearing various chain ends. $PMMA_{4k}$-$PBA_{19k}$ polymers are used as examples. The $^1$H NMR spectra for meta-bispyridyl L2 functionalized polymer ($PMMA_{4k}$-$PBA_{19k}$-L2) are shown in FIG. 2B. When $Pd^{2+}$ is added, most of the peaks corresponding to the ligand shift downfield. In particular, the peaks for the a pyridyl protons (labeled as a and b in FIG. 2B) shift from 8.9 to 10.5 ppm, and 8.6 to 9.4 ppm, respectively. The new chemical shifts agree with those obtained from a model study using small molecules (FIGS. 8A to 8D), which supports the assembly of paddlewheel junctions. Annealing of the sample at 80° C. for 4 h renders a sharper set of peaks, indicative of the formation of 4-arm polymers with well-defined cage structures. Because they are far from the MON junction, the peaks for the EBPA initiator (labeled as g in FIG. 2B) do not change before and after the assembly.

Figure 2C:
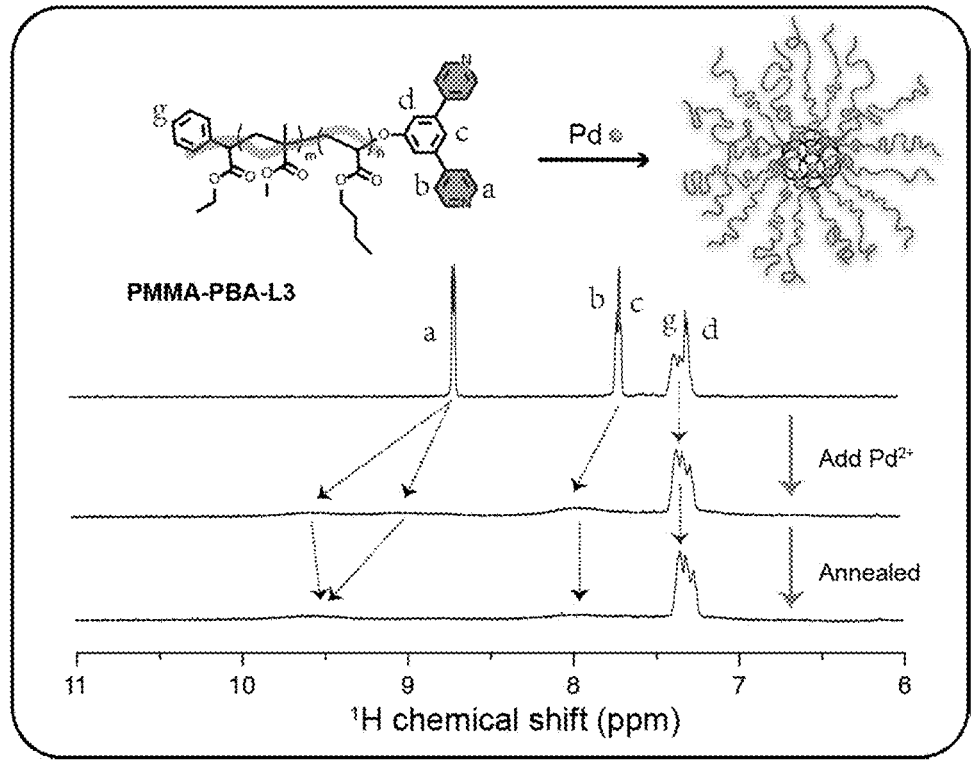

The para-bispyridyl L3 functionalized polymer ($PMMA_{4k}$-$PBA_{19k}$-L3) showed a completely different NMR spectrum in the aromatic region when assembled with $Pd^{2+}$ (FIG. 2C). The originally sharp peaks for the ligand turn to multiple broad peaks and shift downfield. For example, the peak at 8.7 ppm for the a pyridyl proton (labeled as a in FIG. 2C) is split to two peaks at 9.1 and 9.5 ppm. Prior to annealing, it is known that L3 as a small molecule can form kinetically trapped clusters with many different sizes and configurations when assembled with $Pd^{2+}$.[52, 59] These ill-defined structures significantly broaden the corresponding NMR peaks. After annealing, the peak at 9.1 ppm merges together with the peak at 9.5 ppm, indicating the system has reorganized. The fact that the final chemical shifts agree with ones obtained from the analogous non-polymeric ligand (FIGS. 9A to 9D) supports the formation of the $M_{12}L_{24}$ cage junctions. Because the $M_{12}L_{24}$ cage is buried in 24 polymer chains, it is difficult to resolve by $^1$H NMR (broad peaks) due to slowed relaxation. In contrast, the EBPA initiator residues located on the periphery of the star polymer are clearly observed (labeled as g in FIG. 2C).

Figure 3A:
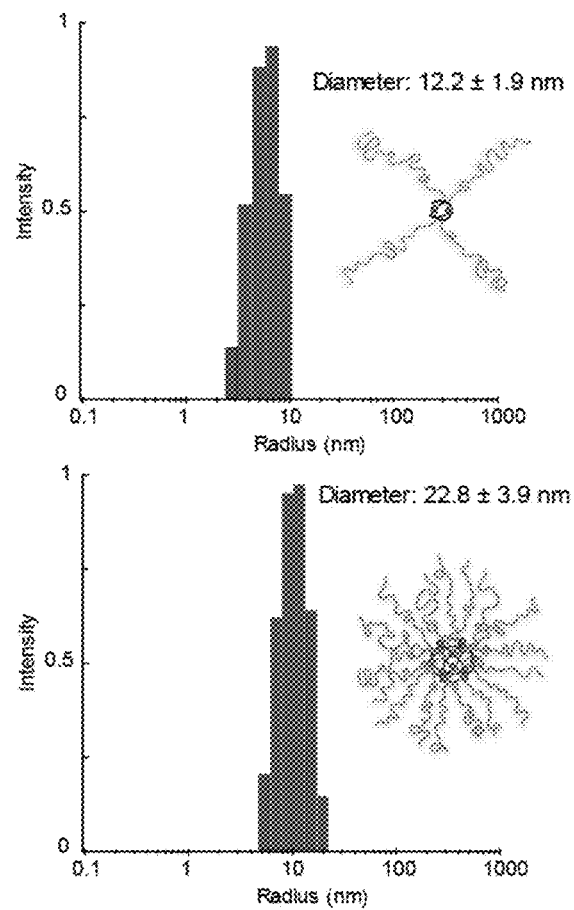
FIGS. 3A to 3C.

Dynamic light scattering (DLS) was used to confirm the formation of star polymers with each MON core. As shown in FIG. 3A, particles with a diameter of 12.2±1.9 nm were observed for star polymers with a paddlewheel core (top image). For polymers with the $M_{12}L_{24}$ cage junction, the diameter was 22.8±3.9 nm (bottom image). In both cases, the particles have a narrow size distribution. The radius of gyration ($R_g$) of these star polymers was estimated based on the molecular weight of the constitutive linear polymers and the number of arms using an ideal chain model.[60] The estimated values ($2R_g$) for 4-arm and 24-arm star polymers were 12.5 nm and 21.3 nm, respectively, which agree with the trend of hydrodynamic radius ($R_h$) measured by DLS. Thus, though the BCP component is the same in both systems, and the MONs themselves only differ in size by ~2 nm, the MON structure significantly impacts the star polymer size by forcing the chains into different conformations.

Figure 3B:
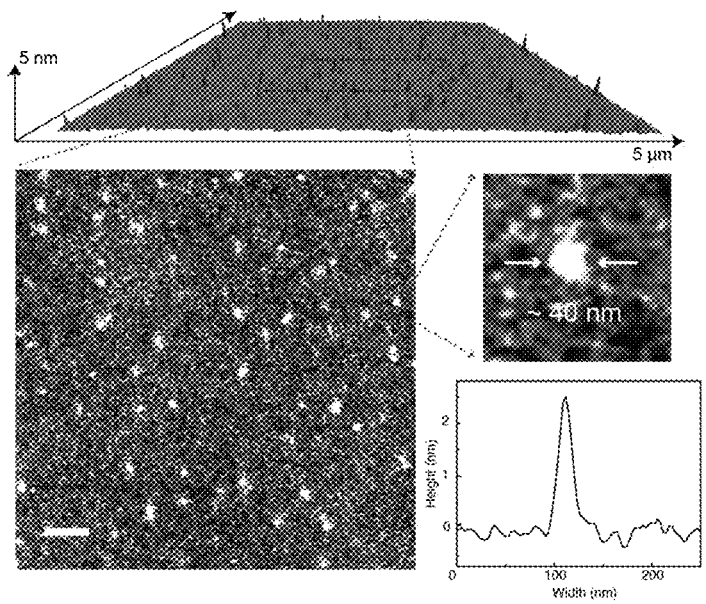
Figure 3C:
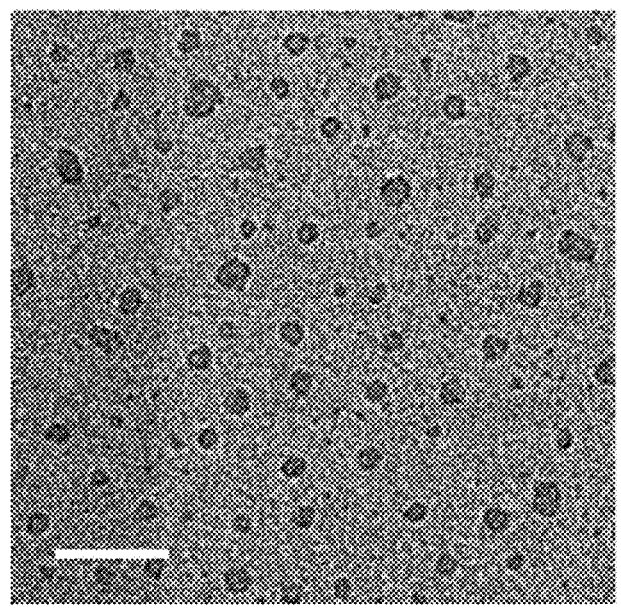

Atomic force microscopy (AFM) was employed to visualize the star polymers with the large $M_{12}L_{24}$ cores. FIG. 3B shows a typical 3D height image of $PMMA_{4k}$-$PBA_{19k}$-L3 after annealing with $Pd^{2+}$ and spin-coating on the surface of a silicon wafer. Relatively uniform particles of about 40±8 nm in diameter were observed (FIG. 3B). The heights of the particles ranged from 1.5 to 2.8 nm, slightly smaller than what has been measured for the Fujita spheres (~3.5 nm)[61], which is attributed to the fact that when the star polymer dries on the substrate, the cages collapse due to stretching of the tethered BCP chains. Polymer stretching and spreading on the surface also accounts for the discrepancy between the particles sizes measured using DLS and AFM. To rule out the possibility that the observed nanoparticles are the result of micelle formation of the BCP itself, a control experiment was carried with polymers at the same concentration but in the absence of $Pd^{2+}$. In this case, no particles were found (FIG. 10). These observations were further verified by transmission electron microscopy (TEM), which revealed ~35±6 nm nanoparticles for $M_{12}L_{24}$ star polymers derived from $PMMA_{4k}$-$PBA_{-19k}$-L3. Due to their small size, the four-arm star polymers bearing a paddlewheel MON core (from L2) were not observable using either AFM or TEM.

BCPMON Formation by BCP Phase Separation

Figure 1B:
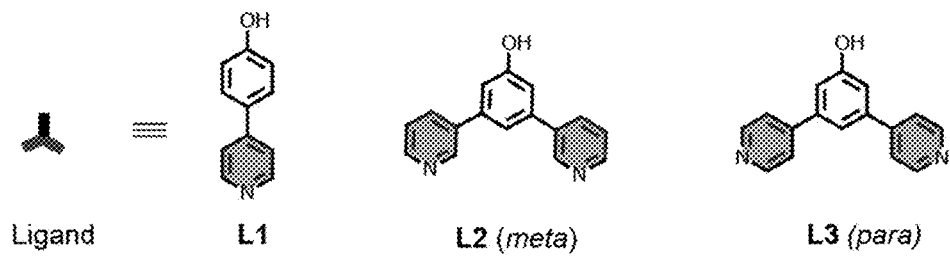

Having shown that MON assembly can be used to drive the formation of star polymers in solution with precise sizes and numbers of BCP arms, BCP phase separation and attractive interactions between the PMMA blocks were sought to be leveraged to crosslink these star polymers and provide BCPMONs (FIG. 1A). In the event, solvent was evaporated and the resulting bulk materials were thermally annealed to induce microphase separation of the BCPs and generate glassy PMMA micro domains. Together with the MON junctions, the PMMA micro domains serve as physical crosslinks to give elastic BCPMON networks, or BCPMON TPEs (FIG. 1A).

Figure 4A:
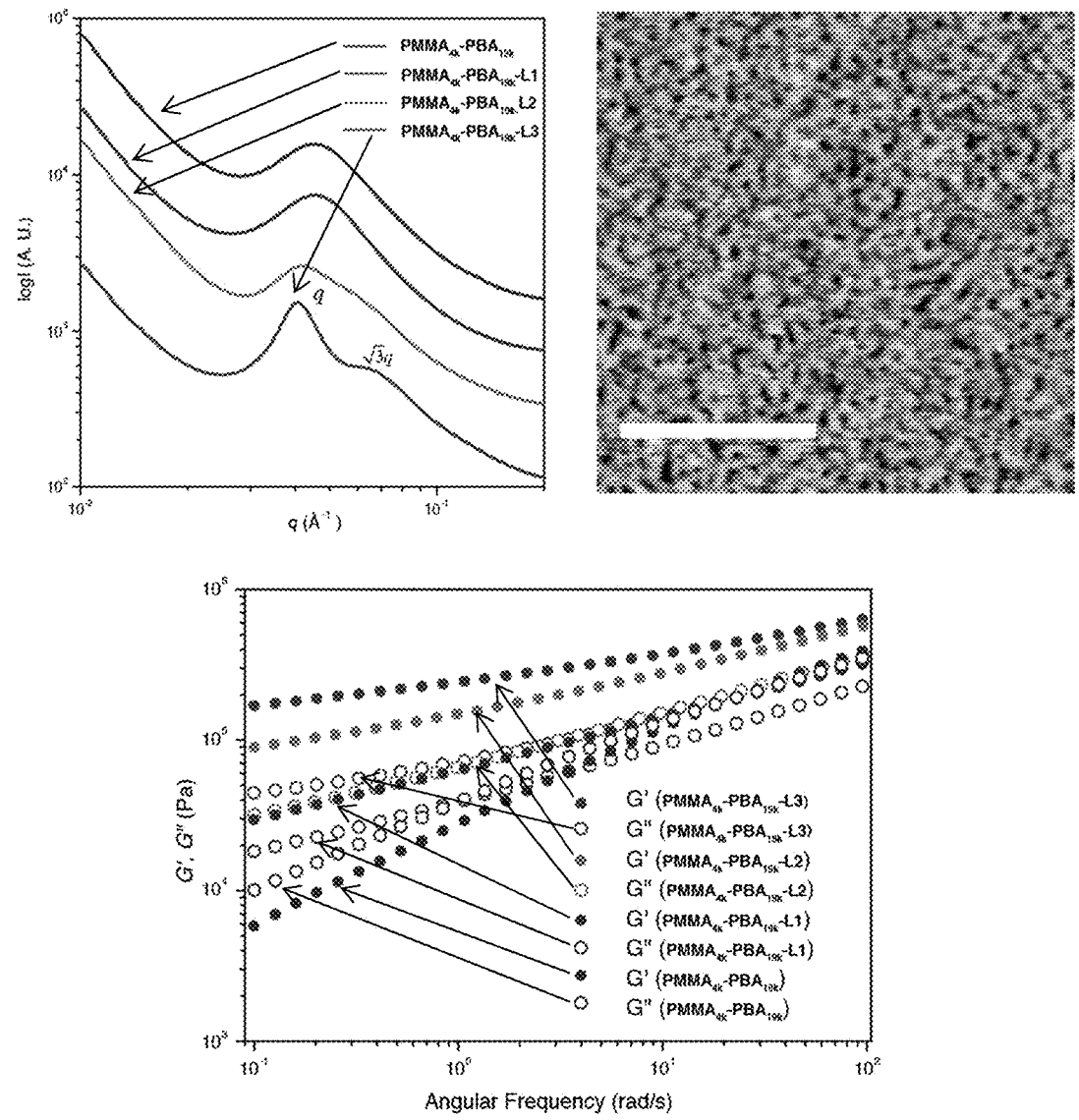
FIGS. 4A to 4C. Small angle X-ray scattering (top left), atomic force microscopy (top right), and rheology study of linear block copolymers and star block copolymers with MONs of different molecular weights and block volume fractions.

Small-angle X-ray scattering analysis (SAXS) was used to study the microphase separation. The SAXS diffractograms of the linear block copolymer $PMMA_{4k}$-$PBA_{19k}$ (~16% PMMA) without metal and $PMMA_{4k}$-$PBA_{19k}$-L1 with metal are shown in FIG. 4A (top left, upper two traces). For both samples, a single Bragg reflection peak located at $q=0.046$ Å$^{-1}$ is observed, indicating phase-separated structures with a d-spacing, i.e., the distance between adjacent PMMA-rich domains, equal to 13.7 nm. In this case, the coordination of Pd by mono-pyridine chain ends has little effect on the BCP assembly.

The scattering profiles for the BCPMONs consisting of identical polymer backbone but different MON cores (e.g., $PMMA_{4k}$-$PBA_{19k}$-L2 and -L3) are shown (FIG. 4A, top left). Two Bragg peaks are observed for each BCPMON, which suggests that the incorporation of MONs can facilitate phase separation and long range ordering of the materials. Similar phenomena have been observed in other types of star polymer systems.[62] The d-spacing calculated based on the position of the principal peak is 15.0 nm for both -L2 and -L3, an increase of 1.3 nm compared to the linear polymer due to polymer chain stretching in a star-like structure when the two blocks phase separate. The q ratio for the second peak to the primary peak is $q2/q1=1:\sqrt{3}$, suggesting a sphere or a hexagonally-packed cylinder morphology; the exact morphology of this BCPMON was not assigned due to limited number of higher order peaks.

AFM was used to visualize the phase-separated morphology. The linear $PMMA_{4k}$-$PBA_{19k}$ does not show appreciable contrast in the phase profile mainly because the molecular weight of the polymer is low (FIGS. 11A and 11B). While for $PMMA_{4k}$-$PBA_{19k}$-L3 bearing the spherical cages, contrast between the two blocks is observed (FIG. 4A, top right).

The mechanical properties of these materials were probed by oscillatory rheometry. For $PMMA_{4k}$-$PBA_{19k}$ alone, the storage modulus G' was similar to the loss modulus G". At lower angular frequencies, G' was smaller than G", while at higher frequencies ($\omega>20$ rad/s), G' was slightly greater than G"; the polymer appears as a very viscous fluid (FIG. 4A, bottom, bottom trace). In contrast, all of the metal-coordinated materials derived from $PMMA_{4k}$-$PBA_{19k}$-L were elastic at all frequencies; the G' values drastically increased and were significantly larger than G". The extent to which G' increased depended on the geometry of the core. For $PMMA_{4k}$-$PBA_{19k}$-L3 bearing the Fujita sphere cores, G' (at 0.1 rad/s, same thereafter) reached as high as 170 kPa, while the values for $PMMA_{4k}$-$PBA_{19k}$-L1 and -L2 were 29.4 kPa and 89.3 kPa, respectively. According to the phantom network theory[60], the difference in shear moduli can be attributed to the fact that the branch functionality in these BCPMONs is increasing, from f=4 for -L1 and -L2 to f=24 for -L3. Furthermore, networks prepared from -L3 may be more uniform as indicated by SAXS, and thus they may possess fewer elastically ineffective defects. Although in principle materials bearing ligand L1 and L2 have the same branch functionality, it was found that the material with L1 is much softer (smaller G). This observation suggests that the square-planar junctions in the L1-based material are more dynamic than the $M_2L_4$ junctions in the L2-based BCPMON.[63]

Figure 4B:
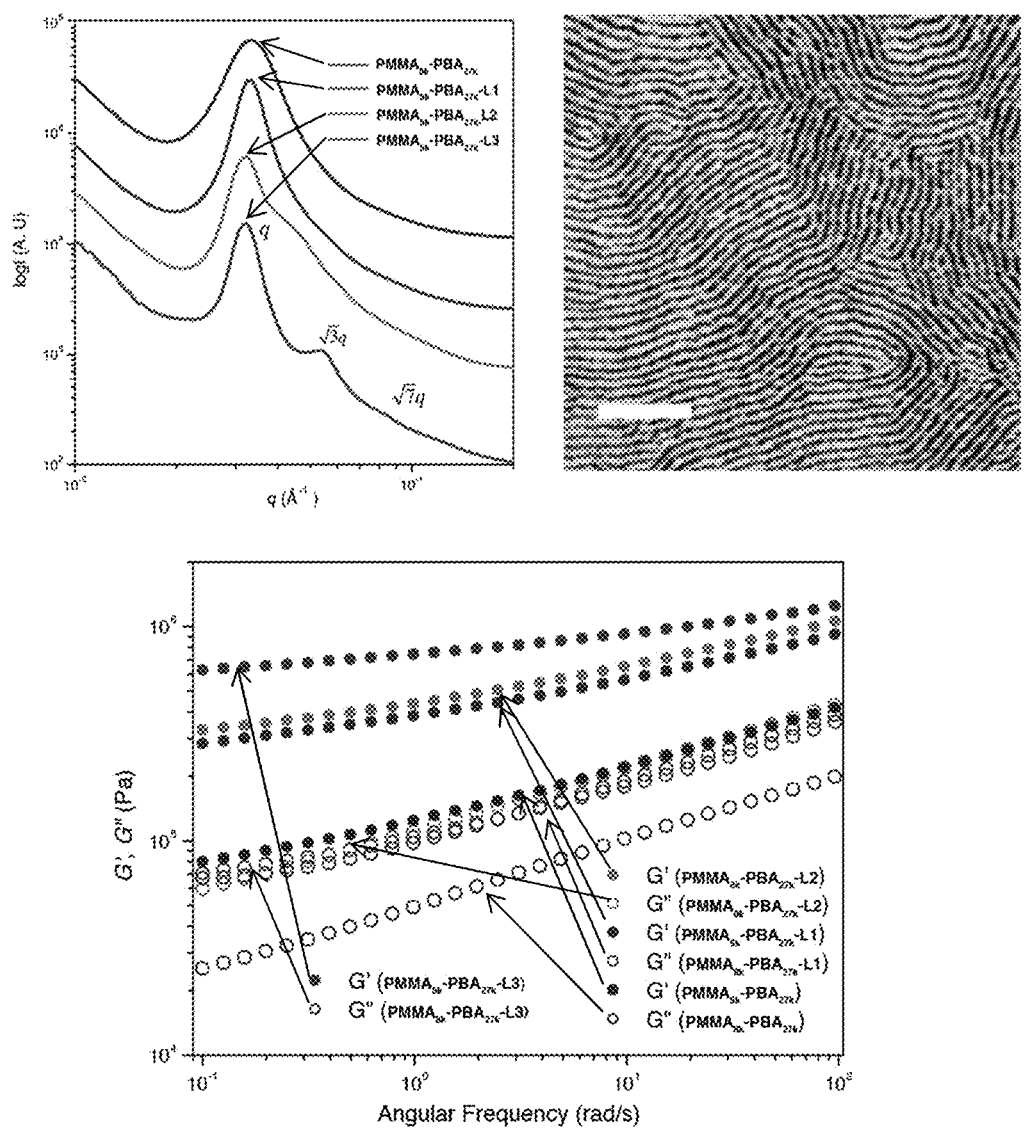
Figure 12A:
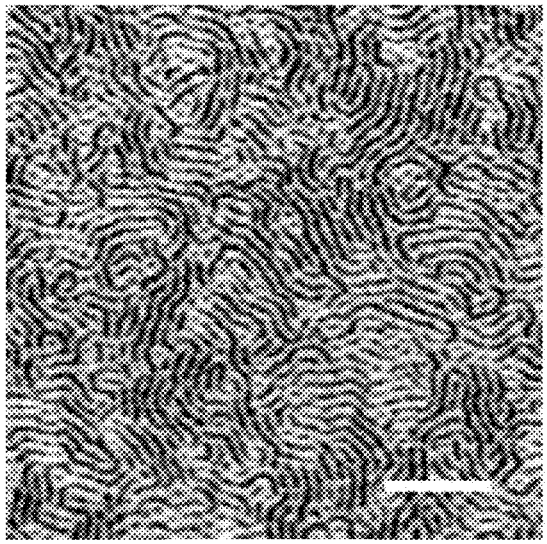
FIGS. 12A to 12D. Atomic force microscopy (AFM) phase images of (FIG. 12A) the linear block copolymer $PMMA_{8k}$-$PBA_{27k}$ and the star polymers $PMMA_{8k}$-$PBA_{27k}$-L1 (FIG. 12B), -L2 (FIG. 12C), and -L3 (FIG. 12D) with $M_1L_4$, $M_2L_4$, and $M_{12}L_{24}$ MON cores, respectively, showing the effect of MON core on the phase separation behavior.
Figure 12B:
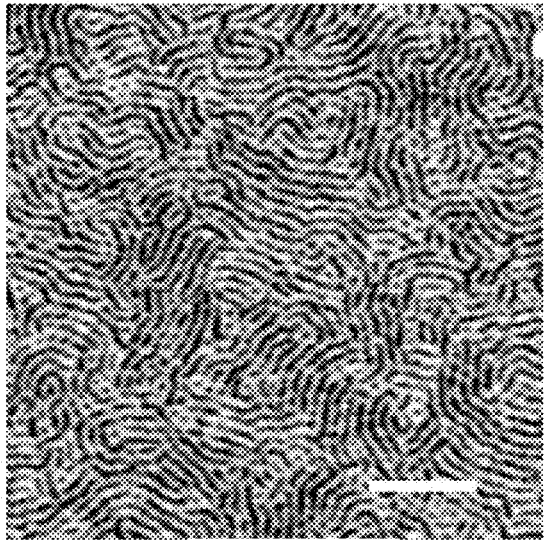
Figure 12C:
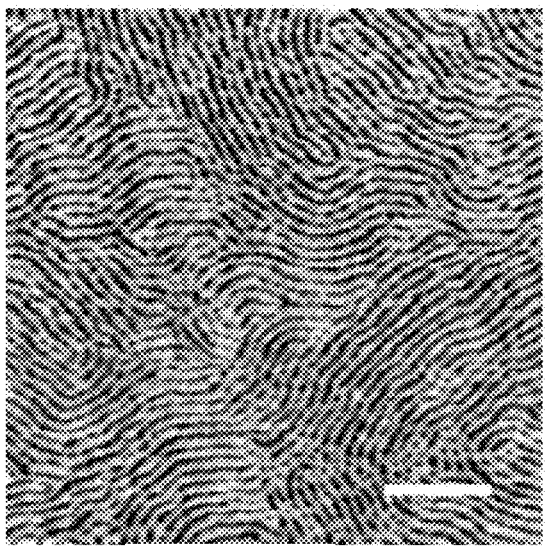
Figure 12D:
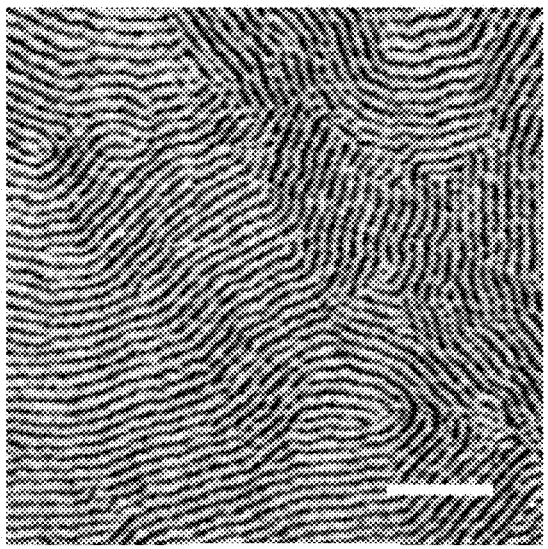
Figure 13A:
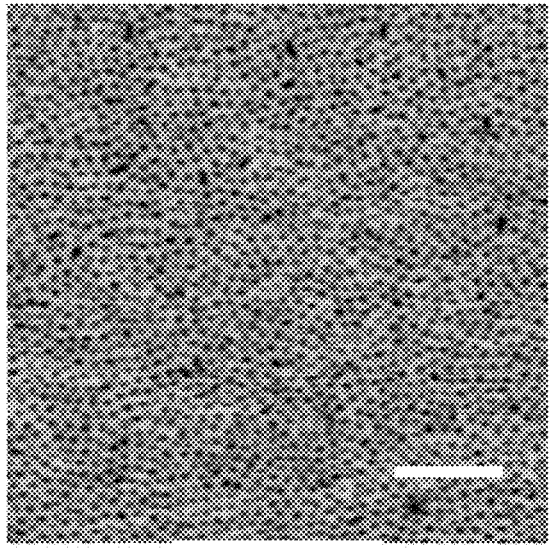
FIGS. 13A to 13D. Atomic force microscopy (AFM) phase images of (FIG. 13A) the linear block copolymer $PMMA_{8k}$-$PBA_{48k}$ and the star polymers $PMMA_{8k}$-$PBA_{48k}$-L1 (FIG. 13B), -L2 (FIG. 13C), and -L3 (FIG. 13D) with $M_1L_4$, $M_2L_4$, and $M_{12}L_{24}$ MON cores, respectively, showing the effect of MON core on the phase separation behavior.
Figure 13B:
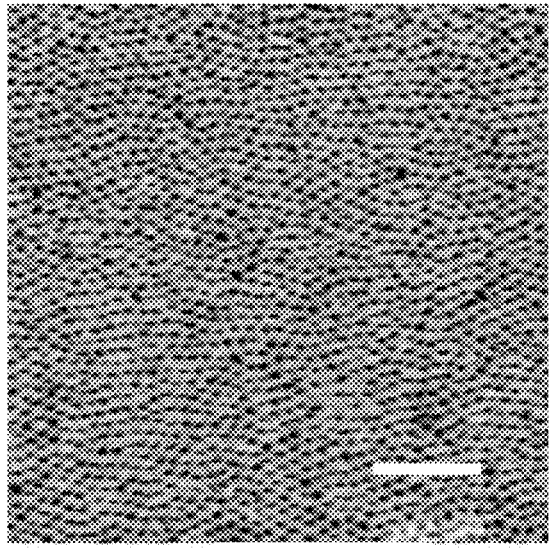
Figure 13C:
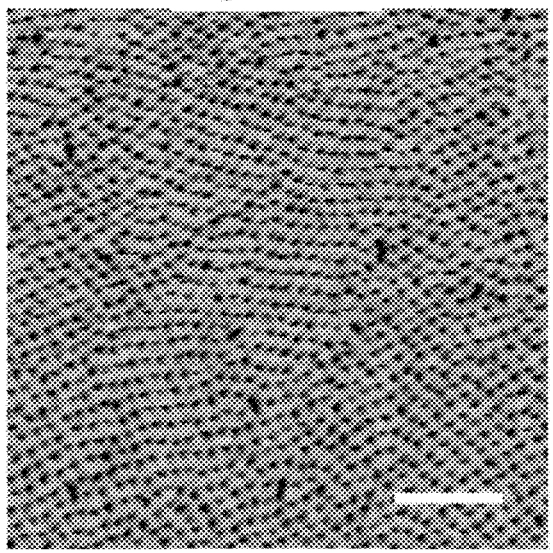
Figure 13D:
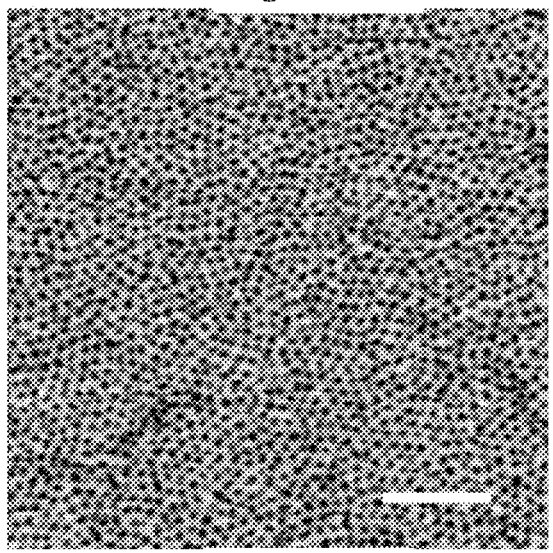

The role of the BCP composition, e.g., $PMMA_{8k}$-$PBA_{27k}$ and $PMMA_{8k}$-$PBA_{48k}$, on the BCPMON properties was also studied. For BCPMONs based on $PMMA_{8k}$-$PBA_{27k}$, which has a higher molecular weight and a slightly larger fraction of PMMA (~23% PMMA), a similar trend is observed where materials with a larger MON junction exhibit long-range ordering, as evidenced by the sharpening (for $PMMA_{8k}$-$PBA_{27k}$-L1) and the presence of higher order scattering peaks (for $PMMA_{8k}$-$PBA_{27k}$-L2 and -L3) in SAXS (FIG. 4B). The d-spacing for $PMMA_{8k}$-$PBA_{27k}$-L2, and -L3 with MON cores is 19.8 nm, which is 1.0 nm larger than the domain size of the linear $PMMA_{8k}$-$PBA_{27k}$ 18.8 nm (FIG. 4B, top left). For $PMMA_{8k}$-$PBA_{27k}$-L3 with the Fujita sphere MON core, the scattering pattern follows $q1:q2:q3=1:\sqrt{3}:\sqrt{7}$, indicating a hexagonally packed cylinder phase of PMMA in a PBA matrix. The AFM phase images of the $PMMA_{8k}$-$PBA_{27k}$ BCP and polyMONs are shown in FIG. 4B (top right) and FIGS. 12A to 12D. They all show the hexagonal cylinder phase, agreeing with the SAXS result. Compared to the BCP, which showed curved cylinders (FIG. 12A), the polyMONs, in particular the PMMA$_{8k}$-PBA$_{27k}$-L3, showed ordering in a longer range as indicated by the relatively straight cylinders observed (FIG. 4B, top right).

The mechanical properties of BCPMONs derived from PMMA$_{8k}$-PBA$_{27k}$ followed similar trends to those based on PMMA$_{4k}$-PBA$_{19k}$: the larger the MON core was, the higher the G' values were (FIG. 4B, bottom). The G' values at 0.1 rad/s for linear PMMA$_{8k}$-PBA$_{27k}$, and polyMONs PMMA$_{8k}$-PBA$_{27k}$-L1, -L2, and -L3 were 70.7 kPa, 284 kPa, 329 kPa, and 628 kPa, respectively.

Figure 4C:
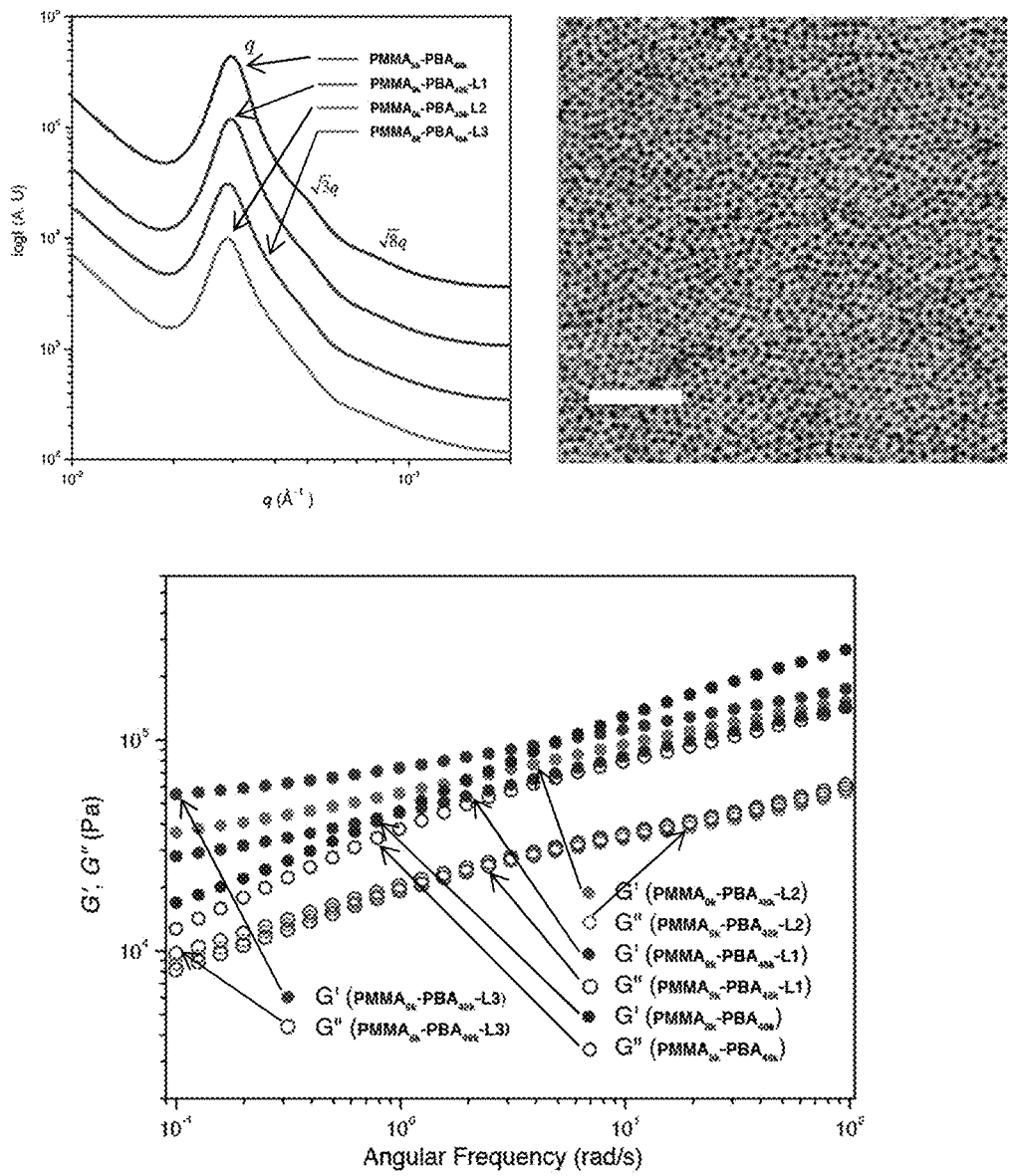

In the case of PMMA$_{8k}$-PBA$_{48k}$ materials, the volume fraction of the PBA block is increased while the molecular weight of PMMA is kept as 8 k (~15% PMMA). In contrast to the samples discussed above, the SAXS profiles for these materials show negligible differences between the polymer PMMA$_{8K}$-PBA$_{48k}$ and materials derived from PMMA$_{8k}$-PBA$_{48k}$-L1, -L2, or -L3. The scattering peaks for all the samples could be indexed as q1:q2:q3=1:√3:√8, implying a spherical morphology (FIG. 4C, top left). The d-spacing based on the principle peak is 21.2 nm. AFM phase images, as shown in FIG. 4C (top right) and FIGS. 13A to 13D, reveal the same morphology, that is, spherical PMMA domains distributed in a PBA matrix.

For these PMMA$_{8k}$-PBA$_{48k}$ materials, the degree of polymerization of PBA was increased to ~385 while the size of the PMMA block was kept constant. In this case, the PBA block is large enough to undergo significant chain entanglement (the entanglement molecular weight of PBA in melt is 29 k; DP: 226)[64], which leads to a steep increase of G' for the linear polymer at higher frequency. In the case of the BCPMONs derived from this polymer, the PBA chain ends are anchored together to MON cores. This clustering limits chain entanglement, as revealed by the rheology profile in which the G' values do not increase as rapidly with frequency. Again, the type of MON involved influences the mechanical properties of the BCPMON. The G' value for the BCPMON based on the M$_{12}$L$_{24}$ MON was greater than that of paddle wheels and mono-pyridine materials (FIG. 4C, bottom).

Collectively, the data indicate that the structure of the MON in each BCPMON dramatically affects the mechanical properties, and in two of three cases the BCP phase separation, compared to either free polymer or the square-planar system L1. To rationalize the role of MON in BCP phase separation, mean field theory was used with random phase approximation to calculate the spinodal boundaries of the BCPs taking into consideration the difference in the assembly architectures including linear and MON containing polymers.[65-66] According to the branch functionality, all polymers were generalized as (PMMA-PBA)$_n$, where n represents the number of BCPs attached to the each MON. For instance, in the case of star polymer with the spherical and the paddle wheel MON core, n=24 and 4, respectively, while in the case of linear polymer, n=1. The calculated spinodal curve is shown in FIGS. 5A and 5B, where χ is the Flory-Huggins interaction parameter, N is the total degree of polymerization of the star polymer, and f$_{PMMA}$ is the volume fraction of the PMMA block.

Figure 5A:
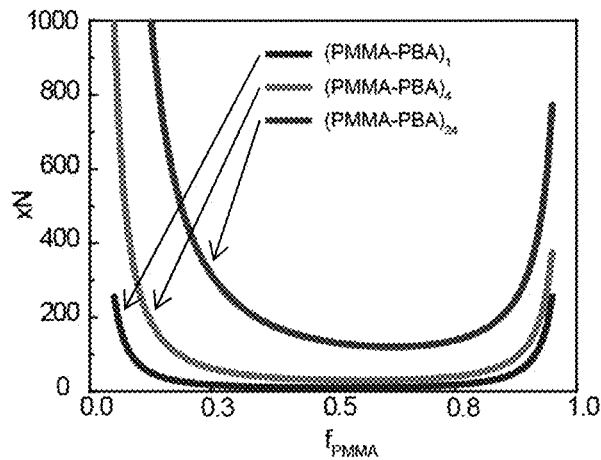
FIGS. 5A and 5B. Calculated spinodal curves of star polymer with 1, 4, and 24 PMMA-PBA arms.
Figure 5B:
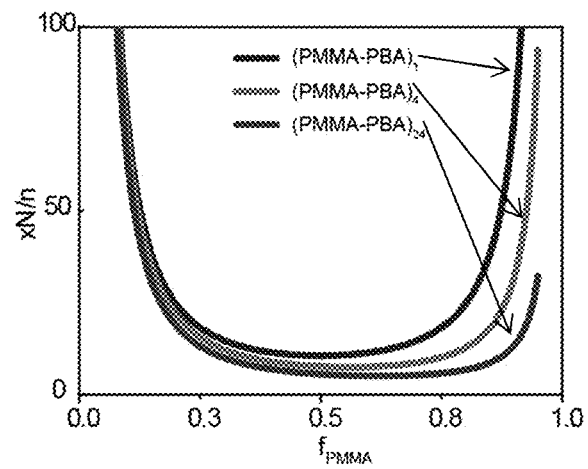

As shown in FIG. 5A, when n increases from 1 to 4 and then to 24, the curve boundary shifts upwards and it becomes asymmetric with the boundary more tilted to the higher f$_{PMMA}$ side. This shift means that microphase separation is more likely to occur at a higher f$_{PMMA}$ values for the BCPMONs with larger MONs. The tendency is more clearly presented when the spinodal curves are normalized by n (FIG. 5B).

The asymmetric spinodal boundary may arise from two factors. First, from the molecular architecture: the PBA blocks are anchored on both ends while the PMMA blocks are only anchored at one end. Second, since all the PBA blocks are anchored to a junction point, in this case the MONs, each PBA block tends to be significantly stretched to relieve the spatial crowding, known as "junction constraint".[67] Thus, the PBA blocks experience more conformational restrictions than the PMMA blocks. This effect is more pronounced when the PBA blocks are short and the number of constrained polymer chains is large. Therefore, the spinodal boundary shifts to lower values at the high f$_{PMMA}$ region (relatively shorter PBA) with increasing arm numbers.

According to this model, the star-shaped polymer architecture may facilitate the self-assembly of the block copolymers when a) the molecular weight of the arm is small, b) the fraction of the blocks linked to the star core is high, and c) the number of arms is large. This model qualitatively agrees with the experimental results. For BCPMONs based on PMMA$_{4k}$-PBA$_{19k}$ and PMMA$_{8k}$-PBA$_{48k}$, which have similar PMMA fractions, the smaller polymer PMMA$_{4k}$-PBA$_{19k}$ BCPMON showed increased long range ordering as shown by SAXS, while PMMA$_{8k}$-PBA$_{48k}$ BCPMON showed no such effect. Because PMMA$_{8k}$-PBA$_{27k}$ has a larger volume fraction of PMMA than PMMA$_{8k}$-PBA$_{48k}$, the BCPMON based on it also showed enhanced phase separation.

Figure 6A:
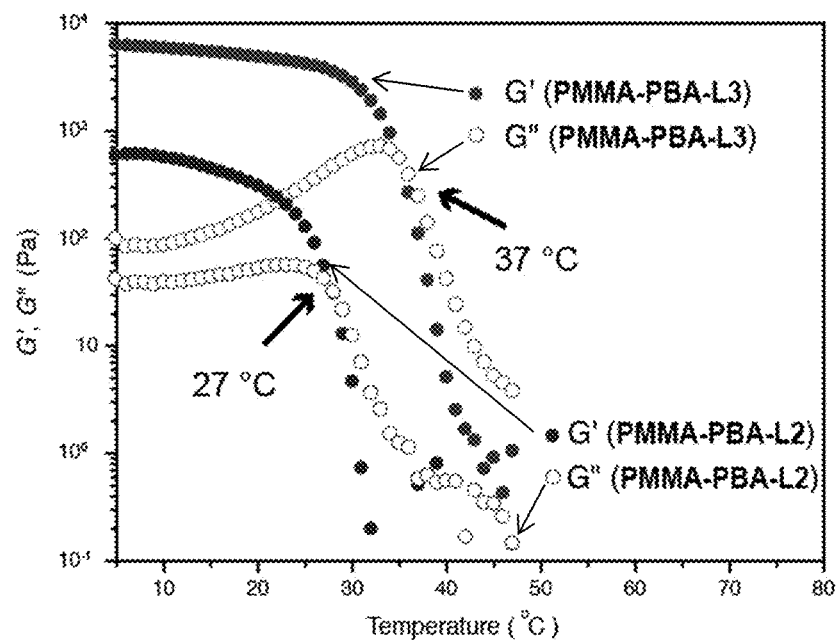
FIGS. 6A to 6D.
Figure 6B:
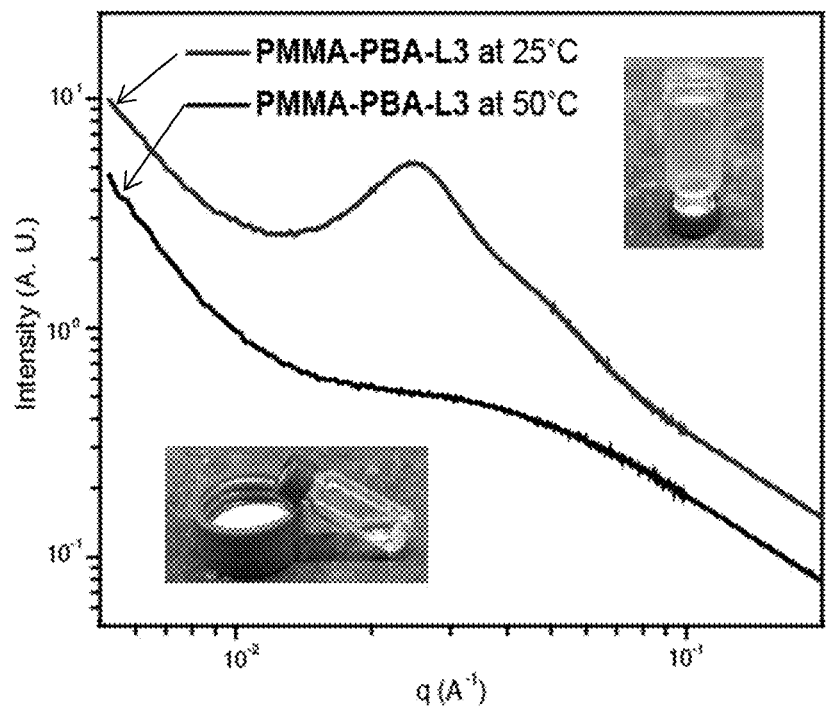

To further expand upon the functionality of BCPMONs, the formation of BCPMON organogels was investigated through the use of a selective solvent. Since PMMA has an upper critical solution temperature (UCST) in 2-ethyl hexanol solvent[57]—it dissolves when heated and aggregates when cooled—the formation of thermally responsive BCP-MON organogels was envisioned. For example, the mechanical properties of PMMA$_{8k}$-PBA$_{27k}$-L3 derived BCPMONs in 2-ethyl hexanol were studied as a function of temperature in FIG. 6A (upper traces, see key). At low temperatures, G' was greater than G"; the system was a transparent gel. Upon heating, G' significantly decreases and becomes smaller than G"; the system switches to a viscous solution. Depending on the type of MON core involved, the mechanical properties of the BCPMON gel vary significantly. When prepared with the same polymer mass fraction, gels with M$_{12}$L$_{24}$ MON junctions had a much higher modulus (G'=6.3 kPa) than ones with M$_2$L$_4$ paddle wheel junctions (G'=0.9 kPa) due to the difference in branch functionality (FIG. 6A). These data are consistent with the trend described above for BCPMONs in the bulk state. The SAXS profile of the gel shows a Bragg peak indicative of the aggregated PMMA domains (d-spacing is 25.4 nm). This peak disappears when the gel is heated; the process is fully reversible (FIG. 6B). Pictures of BCPMONs at 25 and 50° C. are also shown in FIG. 6B, inset.

Figure 6C:
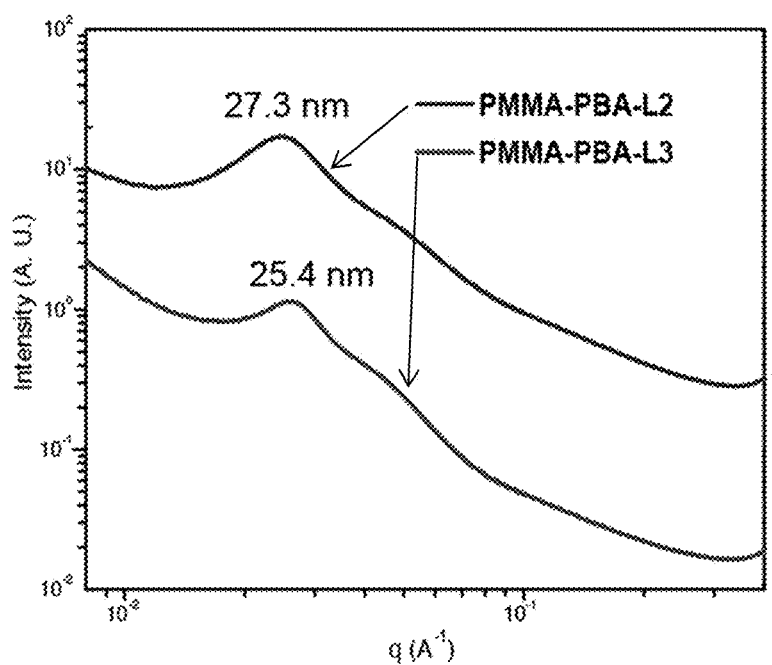

The difference in branch functionalities (e.g., 24 vs. 4) also influenced the spacing between the aggregated PMMA domains in the BCPMON gels (FIG. 6C), which directly affected the UCST. The L2-based BCPMON gels had a d-spacing of 27.3 nm while the L3-based BCPMON gels had a d-spacing of 25.4 nm. Moreover, the sol-gel transition occurred at different temperatures: 27° C. vs. 37° C. for the paddlewheel- and sphere-containing BCPMON gels, respectively.

Figure 6D:
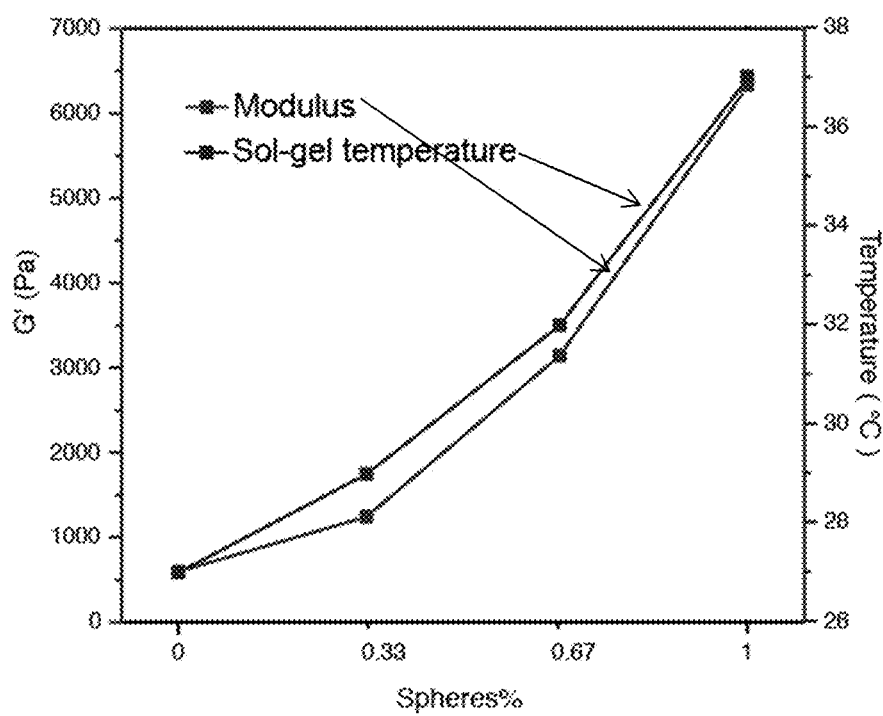
Figure 14:
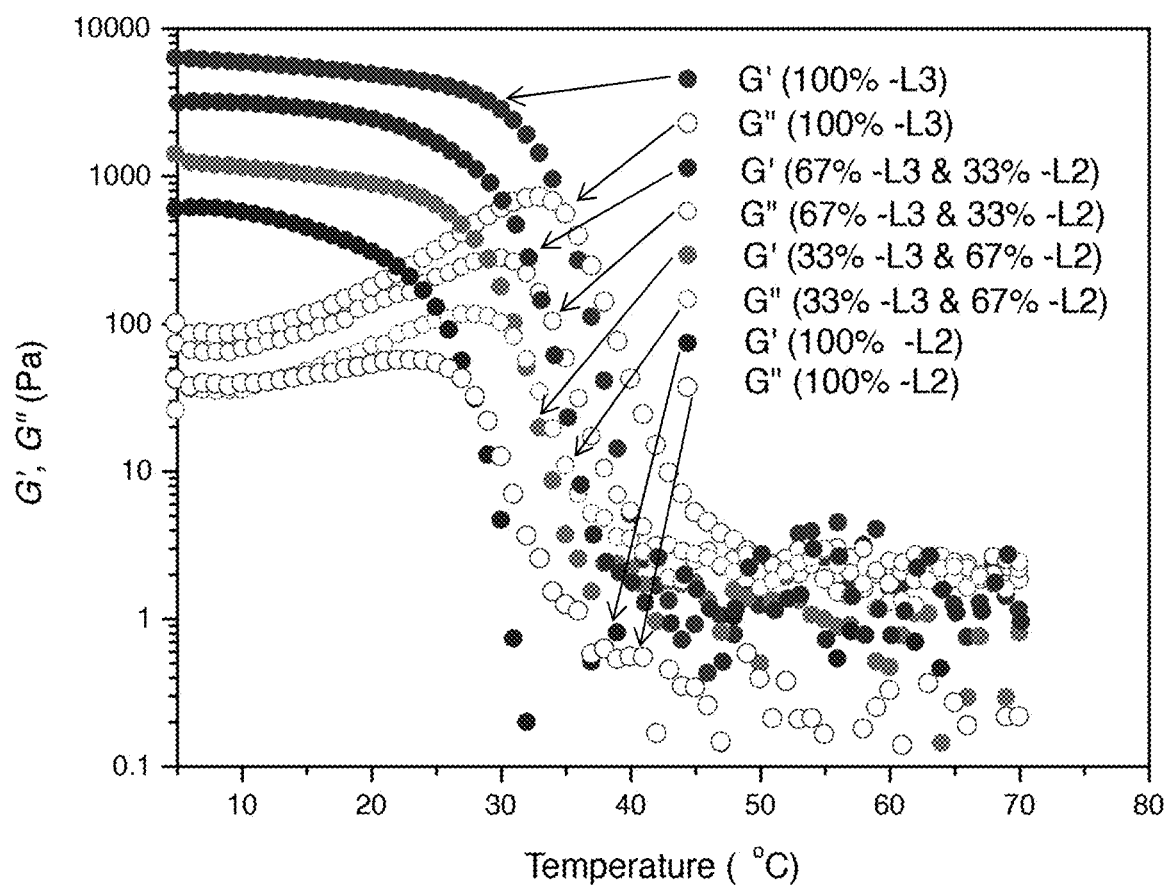
FIG. 14. Temperature sweep experiments of BCPMON organogels with various ratios of $M_2L_4$ and $M_{12}L_{24}$ MON junctions shows the moduli and so-gel transition as a function of temperature.
Figures 15A, 15B, 15C, 15D, 15E:
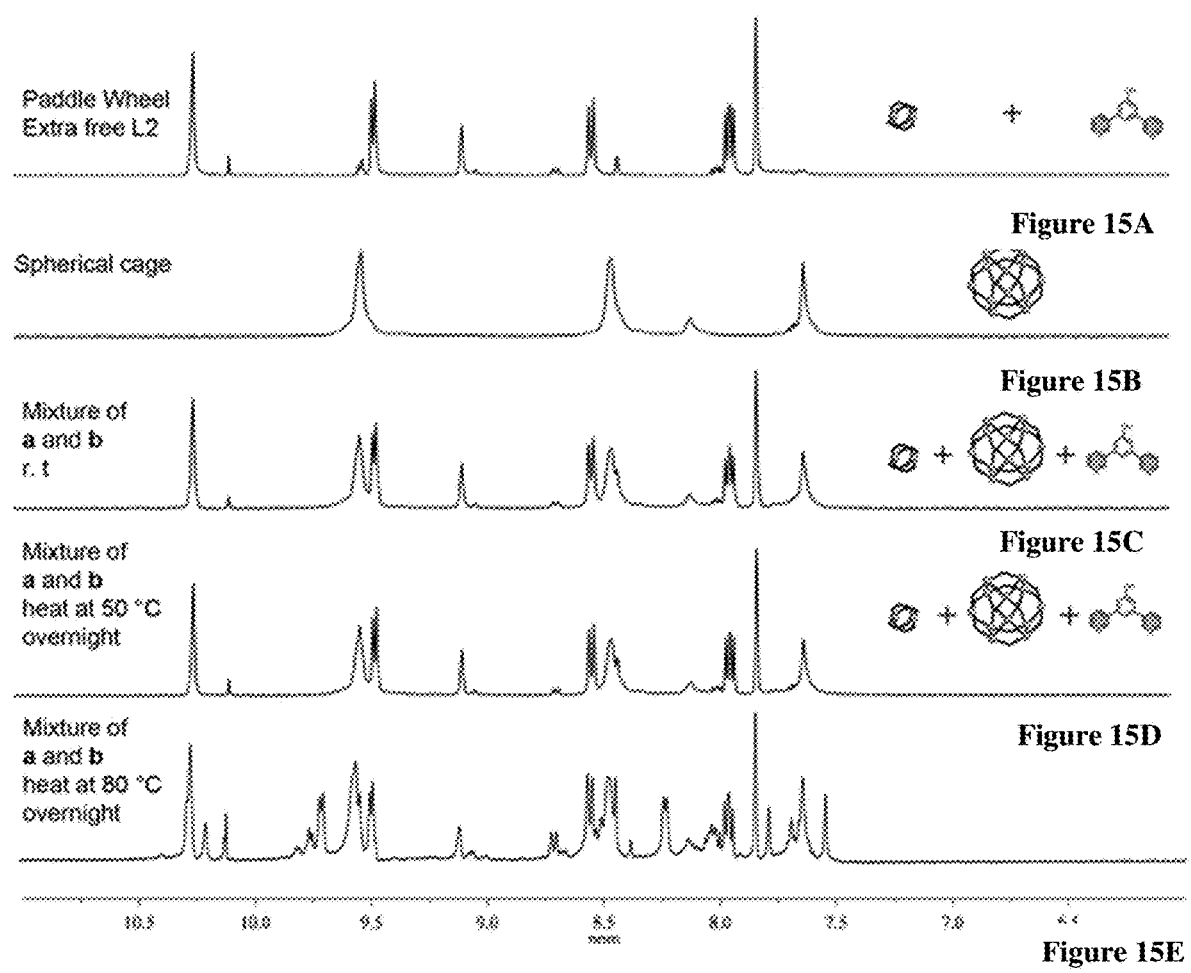
FIGS. 15A to 15E. $^1$H NMR spectra showing the $M_2L_4$ and $M_{12}L_{24}$ MONs separately and as a mixture at room temperature and after heating at 50 and 80° C. overnight.
Figure 16:
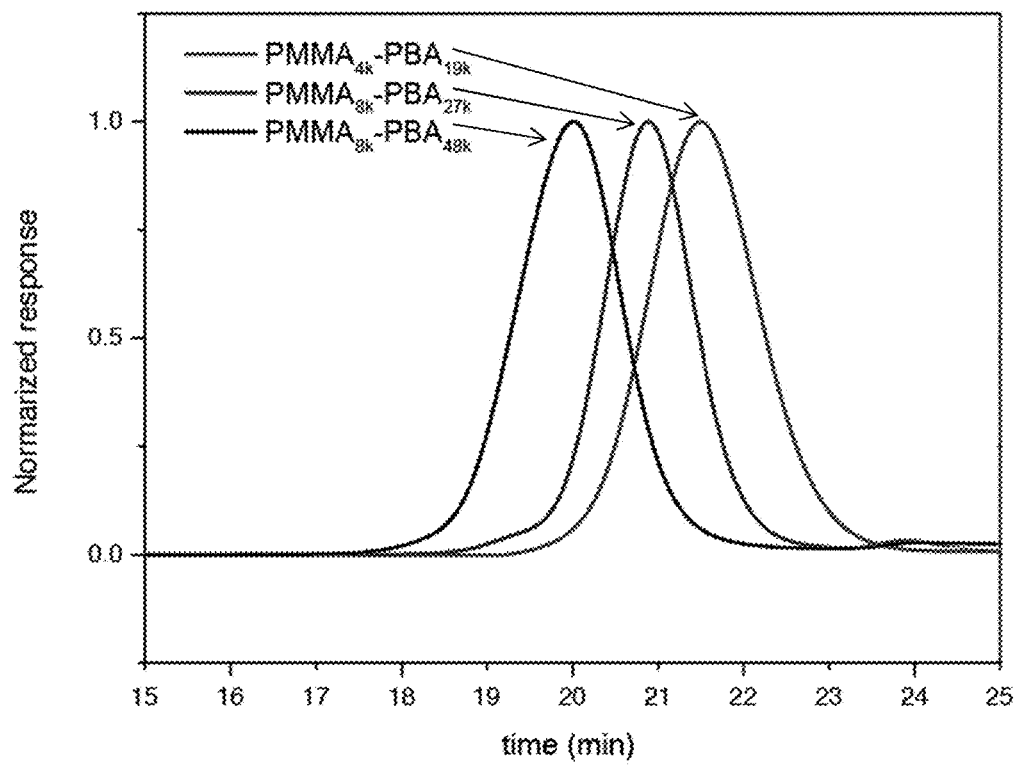
FIG. 16. Gel permeation chromatography (GPC) traces of the PMMA-PBA block copolymer synthesized.

The stepwise assembly strategy employed herein makes it possible to incorporate different MON junctions into one BCPMON by simply mixing the pre-assembled star polymers. Because the type and geometry of the MON structure may dominate the mechanical properties and the UCST, it was hypothesized that the materials' properties could be finely tuned by adjusting the percentage of different MON junctions in mixed BCPMONs. This idea is demonstrated by mixing, at different ratios, star polymers with the spherical MON junctions and the paddlewheel junctions. As can be seen in FIG. 6D ("Modulus" in key), the stiffness of the mixed BCPMON gels increased almost linearly as the percentage of spherical MON core increased. The sol-gel transition temperature also changed with the ratio of different MON junctions (FIG. 6D, "Sol-gel temperature" in key, FIG. 14). To confirm the presence and integrity of both sphere cages and paddle wheel cages in the gel, and to rule out thermally induced exchange of ligands from one MON type with the other, a model study was carried out with MONs derived from ligands L2 and L3 without BCPs attached. When mixed at room temperature, $^1$H NMR showed separate sets of peaks that corresponded to the spherical cages and the paddlewheel cages (FIGS. 15A to 15E). After heating at 50° C., well above the sol-gel transition temperature, the NMR spectra do not show appreciable changes; heating at 80° C. is required to induce any changes in the cage structure.

CONCLUSION

Herein, Block Co-PolyMONs (BCPMONs), which are a class of hierarchically structured materials formed via stepwise metallosupramolecular assembly of MONs followed by BCP microphase separation, are introduced. It is demonstrated that the choice of the MON, as determined by small differences in the ligand structures, may lead to large differences in the microscopic and mesoscopic structures and mechanical properties of BCPMONs. Due to the diverse range of MONs and BCPs that could be employed in the BCPMON paradigm, it is expected that BCPMONs may offer a numerous opportunities for functional materials design.

REFERENCES (1) Leininger, S.; Olenyuk, B.; Stang, P. J., *Chem. Rev.* 2000, 100, 853-908.
(2) Chakrabarty, R.; Mukherjee, P. S.; Stang, P. J., *Chem. Rev.* 2011, 111, 6810-6918.
(3) Cook, T. R.; Zheng, Y.-R.; Stang, P. J., *Chem. Rev.* 2013, 113, 734-777.
(4) Nitschke, J. R., *Acc. Chem. Res.* 2007, 40, 103-112.
(5) Smulders, M. M. J.; Riddell, I. A.; Browne, C.; Nitschke, J. R., *Chem. Soc. Rev.* 2013, 42, 1728-1754.
(6) Fujita, M., *Chem. Soc. Rev.* 1998, 27, 417-425.
(7) Fujita, M.; Tominaga, M.; Hori, A.; Therrien, B., *Acc. Chem. Res.* 2005, 38, 369-378.
(8) Oliveri, C. G.; Ulmann, P. A.; Wiester, M. J.; Mirkin, C. A., *Acc. Chem. Res.* 2008, 41, 1618-1629.
(9) Eryazici, I.; Moorefield, C. N.; Newkome, G. R., *Chem. Rev.* 2008, 108, 1834-1895.
(10) Stang, P. J.; Olenyuk, B., *Acc. Chem. Res.* 1997, 30, 502-518.
(11) Ronson, T. K.; Zarra, S.; Black, S. P.; Nitschke, J. R., *Chem. Commun.* 2013, 49, 2476-2490.
(12) Meng, W.; Clegg, J. K.; Thoburn, J. D.; Nitschke, J. R., *J. Am. Chem. Soc.* 2011, 133, 13652-13660.
(13) Smulders, M. M. J.; Jiménez, A.; Nitschke, J. R., *Angew. Chem., Int. Ed.* 2012, 51, 6681-6685.
(14) Wood, C. S.; Ronson, T. K.; Belenguer, A. M.; Holstein, J. J.; Nitschke, J. R., *Nat. Chem.* 2015, 7, 354-358.
(15) McConnell, A. J.; Wood, C. S.; Neelakandan, P. P.; Nitschke, J. R., *Chem. Rev.* 2015, 115, 7729-7793.
(16) Fujita, M.; Oguro, D.; Miyazawa, M.; Oka, H.; Yamaguchi, K.; Ogura, K., *Nature* 1995, 378, 469-471.
(17) Sun, W.-Y.; Yoshizawa, M.; Kusukawa, T.; Fujita, M., *Curr. Opin. Chem. Biol.* 2002, 6, 757-764.
(18) Harris, K.; Fujita, D.; Fujita, M., *Chem. Commun.* 2013, 49, 6703-6712.
(19) Lehn, J.-M., *Chem. Soc. Rev.* 2007, 36, 151-160.
(20) Chambron, J.-C.; Sauvage, J.-P., *New J. Chem.* 2013, 37, 49-57.
(21) Brown, A. M.; Ovchinnikov, M. V.; Stern, C. L.; Mirkin, C. A., *J. Am. Chem. Soc.* 2004, 126, 14316-14317.
(22) Newkome, G. R.; Cho, T. J.; Moorefield, C. N.; Baker, G. R.; Cush, R.; Russo, P. S., *Angew. Chem., Int. Ed.* 1999, 38, 3717-3721.
(23) Xie, T.-Z.; Li, J.-Y.; Guo, Z.; Ludlow, J. M.; Lu, X.; Moorefield, C. N.; Wesdemiotis, C.; Newkome, G. R., *Eur. J. Inorg. Chem.* 2016, 2016, 1671-1677.
(24) Xie, T.-Z.; Guo, K.; Guo, Z.; Gao, W.-Y.; Wojtas, L.; Ning, G.-H.; Huang, M.; Lu, X.; Li, J.-Y.; Liao, S.-Y.; Chen, Y.-S.; Moorefield, C. N.; Saunders, M. J.; Cheng, S. Z. D.; Wesdemiotis, C.; Newkome, G. R., *Angewandte Chemie* 2015, 127, 9356-9361.
(25) Xie, T.-Z.; Liao, S.-Y.; Guo, K.; Lu, X.; Dong, X.; Huang, M.; Moorefield, C. N.; Cheng, S. Z. D.; Liu, X.; Wesdemiotis, C.; Newkome, G. R., *J. Am. Chem. Soc.* 2014, 136, 8165-8168.
(26) Stadler, A.-M.; Kyritsakas, N.; Graff, R.; Lehn, J.-M., *Chem. Eur. J.* 2006, 12, 4503-4522.
(27) Cook, T. R.; Stang, P. J., *Chem. Rev.* 2015, 115, 7001-7045.
(28) Zhou, H.-C.; Long, J. R.; Yaghi, O. M., *Chem. Rev.* 2012, 112, 673-674.
(29) Furukawa, H.; Cordova, K. E.; O'Keeffe, M.; Yaghi, O. M., *Science* 2013, 341, 1230444.
(30) Furukawa, S.; Reboul, J.; Diring, S.; Sumida, K.; Kitagawa, S., *Chem. Soc. Rev.* 2014, 43, 5700-5734.
(31) Stock, N.; Biswas, S., *Chem. Rev.* 2012, 112, 933-969.
(32) Cook, T. R.; Vajpayee, V.; Lee, M. H.; Stang, P. J.; Chi, K.-W., *Acc. Chem. Res.* 2013, 46, 2464-2474.
(33) Olenyuk, B.; Whiteford, J. A.; Fechtenkotter, A.; Stang, P. J., *Nature* 1999, 398, 796-799.
(34) Riddell, I. A.; Smulders, M. M. J.; Clegg, J. K.; Nitschke, J. R., *Chem. Commun.* 2011, 47, 457-459.
(35) Sun, Q.-F.; Iwasa, J.; Ogawa, D.; Ishido, Y.; Sato, S.; Ozeki, T.; Sei, Y.; Yamaguchi, K.; Fujita, M., *Science* 2010, 328, 1144-1147.
(36) Zhao, C.; Sun, Q.-F.; Hart-Cooper, W. M.; DiPasquale, A. G.; Toste, F. D.; Bergman, R. G.; Raymond, K. N., *J. Am. Chem. Soc.* 2013, 135, 18802-18805.
(37) Pluth, M. D.; Bergman, R. G.; Raymond, K. N., *Acc. Chem. Res.* 2009, 42, 1650-1659.
(38) Wang, Z. J.; Clary, K. N.; Bergman, R. G.; Raymond, K. N.; Toste, F. D., *Nat. Chem.* 2013, 5, 100-103.
(39) Fujita, D.; Ueda, Y.; Sato, S.; Yokoyama, H.; Mizuno, N.; Kumasaka, T.; Fujita, M., *Chem* 2016, 1, 91-101.
(40) Jansze, S. M.; Cecot, G.; Wise, M. D.; Zhurov, K. O.; Ronson, T. K.; Castilla, A. M.; Finelli, A.; Pattison, P.; Solari, E.; Scopelliti, R.; Zelinskii, G. E.; Vologzhanina, A. V.; Voloshin, Y. Z.; Nitschke, J. R.; Severin, K., *J. Am. Chem. Soc.* 2016, 138, 2046-2054.

(41) Yan, X.; Li, S.; Pollock, J. B.; Cook, T. R.; Chen, J.; Zhang, Y.; Ji, X.; Yu, Y.; Huang, F.; Stang, P. J., *Proc. Natl. Acad. Sci. U.S.A* 2013, 110, 15585-15590.
(42) Li, Z.-Y.; Zhang, Y.; Zhang, C.-W.; Chen, L.-J.; Wang, C.; Tan, H.; Yu, Y.; Li, X.; Yang, H.-B., *J. Am. Chem. Soc.* 2014, 136, 8577-8589.
(43) Hardy, J. G.; Cao, X.-y.; Harrowfield, J.; Lehn, J.-M., *New J. Chem.* 2012, 36, 668-673.
(44) Burnworth, M.; Tang, L.; Kumpfer, J. R.; Duncan, A. J.; Beyer, F. L.; Fiore, G. L.; Rowan, S. J.; Weder, C., *Nature* 2011, 472, 334-337.
(45) Yan, X.; Cook, T. R.; Pollock, J. B.; Wei, P.; Zhang, Y.; Yu, Y.; Huang, F.; Stang, P. J., *J. Am. Chem. Soc.* 2014, 136, 4460-4463.
(46) Yan, X.; Li, S.; Cook, T. R.; Ji, X.; Yao, Y.; Pollock, J. B.; Shi, Y.; Yu, G.; Li, J.; Huang, F.; Stang, P. J., *J. Am. Chem. Soc.* 2013, 135, 14036-14039.
(47) Chifotides, H. T.; Dunbar, K. R., *Acc. Chem. Res.* 2013, 46, 894-906.
(48) Kawamoto, K.; Grindy, S. C.; Liu, J.; Holten-Andersen, N.; Johnson, J. A., *ACS Macro Lett.* 2015, 4, 458-461.
(49) Foster, J. A.; Parker, R. M.; Belenguer, A. M.; Kishi, N.; Sutton, S.; Abell, C.; Nitschke, J. R., *J. Am. Chem. Soc.* 2015, 137, 9722-9729.
(50) Zheng, W.; Chen, L.-J.; Yang, G.; Sun, B.; Wang, X.; Jiang, B.; Yin, G.-Q.; Zhang, L.; Li, X.; Liu, M.; Chen, G.; Yang, H.-B., *J. Am. Chem. Soc.* 2016, 138, 4927-4937.
(51) Hosono, N.; Gochomori, M.; Matsuda, R.; Sato, H.; Kitagawa, S., *J. Am. Chem. Soc.* 2016, 138, 6525-6531.
(52) Zhukhovitskiy, A. V.; Zhong, M.; Keeler, E. G.; Michaelis, V. K.; Sun, J. E. P.; Hore, M. J. A.; Pochan, D. J.; Griffin, R. G.; Willard, A. P.; Johnson, J. A., *Nat. Chem.* 2016, 8, 33-41.
(53) BATES, F. S., *Science* 1991, 251, 898-905.
(54) Mai, Y.; Eisenberg, A., *Chem. Soc. Rev.* 2012, 41, 5969-5985.
(55) Bates, F. S.; Fredrickson, G. H., *Phys. Today* 1999, 52, 32-38.
(56) Nese, A.; Mosnaek, J.; Juhari, A.; Yoon, J. A.; Koynov, K.; Kowalewski, T.; Matyjaszewski, K., *Macromolecules* 2010, 43, 1227-1235.
(57) Seitz, M. E.; Burghardt, W. R.; Faber, K. T.; Shull, K. R., *Macromolecules* 2007, 40, 1218-1226.
(58) Magenau, A. J. D.; Kwak, Y.; Matyjaszewski, K., *Macromolecules* 2010, 43, 9682-9689.
(59) Yoneya, M.; Tsuzuki, S.; Yamaguchi, T.; Sato, S.; Fujita, M., *ACS Nano* 2014, 8, 1290-1296.
(60) Rubinstein, M.; Colby, R. H., *Polymers Physics*. Oxford Univ. Press, 2003.
(61) Kikuchi, T.; Sato, S.; Fujita, D.; Fujita, M., *Chem. Sci.* 2014, 5, 3257-3260.
(62) Pakula, T.; Koynov, K.; Boerner, H.; Huang, J.; Lee, H.-i.; Pietrasik, J.; Sumerlin, B.; Matyjaszewski, K., *Polymer* 2011, 52, 2576-2583.
(63) Sato, S.; Ishido, Y.; Fujita, M., *J. Am. Chem. Soc.* 2009, 131, 6064-6065.
(64) Yamazaki, H.; Takeda, M.; Kohno, Y.; Ando, H.; Urayama, K.; Takigawa, T., *Macromolecules* 2011, 44, 8829-8834.
(65) Shi, W.; Tateishi, Y.; Li, W.; Hawker, C. J.; Fredrickson, G. H.; Kramer, E. J., *ACS Macro Letters* 2015, 4, 1287-1292.
(66) Delaney, K. T.; Fredrickson, G. H., *Comput. Phys. Commun.* 2013, 184, 2102-2110.
(67) Olvera de la Cruz, M.; Sanchez, I. C., *Macromolecules* 1986, 19, 2501-2508.

Materials

Methyl methacrylate (MMA) and n-butyl acrylate (BA) were purchased from Sigma-Aldrich and were allowed to pass through a basic alumina column to remove the inhibitor before use. Tris(2-(dimethylamino)ethyl)amine (Me$_6$Tren), Copper(II) bromide (CuBr$_2$) and ethyl α-bromophenylacetate (EBPA) were purchased from Sigma-Aldrich and were used as received. 3,5-Dibromoanisole, 3-pyridylboronic acid pinacol ester, 4-pyridylboronic acid pinacol ester, and tetrakis(triphenylphosphine) palladium(0) (Pd(Ph$_3$)$_4$) were purchased from Ark Pharm, Inc. and were used as received. All other reagents and solvents were purchased from Sigma-Aldrich and used without further purification.

Synthetic Methods

Ligand Synthesis

Ligands L1 and L3 were synthesized following literature procedures.[1-2] L2 was synthesized using a similar protocol[1] and is described below.

Synthesis of 3,5-di(pyridin-3-yl)phenol (L2)

1,3-dibromo-5-methoxybenzene (2.66 g, 10.0 mmol), 4-Pyridineboronic acid pinacol ester (5.0 g, 24.4 mmol), tetrakis(triphenylphosphine) palladium(0) (1.16 g, 1 mmol), and potassium carbonate (13.8 g, 0.1 mol) were added into a 100 ml single-neck equipped with a magnetic stir bar and capped with a septum. Under nitrogen atmosphere, 60 ml of DMF along with 2 ml of H$_2$O was added and the resulting mixture was stirred for 60 h at 100° C. After cooling to room temperature, the reaction residue was diluted with chloroform/methanol (10/1, v/v) and filtered through CELITE. The filtrate was extracted with brine, dried over anhydrous Na$_2$SO$_4$, and concentrated under vacuum. Using silica gel column chromatography, the crude product was purified to yield a light yellow solid. The solid was further dried under high vacuum, and was dissolved in 100 mL anhydrous dichloromethane (DCM) in a 250 mL round bottom flask equipped with a star bar. The solution was cooled to −78° C., and BBr$_3$ (50.0 mL, 1.0 M in CH$_2$Cl$_2$, 50 mmol) was added slowly to the flask over the course of 30 min. The reaction was stirred for another 10 min before it was gradually warmed up to room temperature and stirred for 8 h. The reaction residue was poured to 400 mL of iced sodium bicarbonate saturated aqueous solution to quench. Light yellow precipitation formed and was collected by filtration. The solid was further purified by washing with DI water, ethyl ether, and large amount of CH$_2$Cl$_2$ to yield 1.1 g of L$_2$ as white solid (65%). $^1$H NMR (DMSO-d$_6$): δ 8.92 (2H, d, J=2.0 Hz), 8.57 (2H, dd, J=4.8 Hz, J=2.0 Hz), 8.10 (2H, dt, J=8.0 Hz, J=2.0 Hz), 7.47 (2H, dd, J=8.0 Hz, J=4.4 Hz), 7.41 (1H, t, J=2.0 Hz), 7.10 (2H, d, J=8.0 Hz). $^{13}$C NMR (DMSO-d$_6$): δ 149.09, 148.25, 139.73, 136.09, 134.76, 124.29, 116.45, 114.16. HRMS (m/z): [M+H]$^+$ calculated for C$_{16}$H$_{12}$N$_2$O, 249.1022; found, 249.1016.

Synthesis of PMMA

PMMA polymers were synthesized via atom transfer radical polymerization (ATRP) following a literature procedure.[3] Specifically, to a long-neck Schlenk flask equipped with a magnetic stir bar were charged with 16.0 mL of MMA, 8.0 mL of 0.095 M EBPA in anisole, 1 mL of 0.076 M CuBr$_2$ and 0.149 M 4,4'-Dinonyl-2,2'-bipyridine (dNbpy) in DMF. The system was then degassed with three freeze-pump-thaw cycles. After the last cycle, a copper wire (L=3 cm, d=1 mm) cleaned by rinsing with aqueous HCl was added into the flask under nitrogen. The flask was then stopped and purged with three vacuum/nitrogen cycles. The system was allowed to thaw and the flask was heated at 35° C. in an oil bath. Reaction aliquots were withdrawn at timed intervals to calculate the conversion based on $^1$H NMR analysis. The reaction was quenched at ~3.5 h (35% to 50% conversion) by opening the flask to air and cooling to room temperature. Immediately after that, the reaction mixture was diluted in THF and passed through a column of neutral alumina. The polymer was then precipitate three times against hexanes, and was collected as white solids by filtration and dried under vacuum.

Synthesis of PMMA-PBA Block Copolymer

PMMA-PBA was synthesized via activator regenerated by electron transfer (ARGET) ATRP. A representative procedure is as follows. To a long-neck Schlenk flask equipped with a magnetic stir bar were charged with 1.0 g of PMMA, 10 mL of n-butyl acrylate, 2 mL of 0.047 M Me$_6$Tren in anisole, and 300 µL of 0.076 M CuBr$_2$ in DMF. The resulting solution was degassed by bubbling nitrogen for 45 min. After that, 1.0 mL of tin(II) 2-ethylhexanoate in anisole (0.1 M, degassed) was added. The reaction mixture was then submerged in an oil bath that was maintained at 70° C. Reaction aliquots were withdrawn at timed intervals to calculate the conversion based on $^1$H NMR analysis. The reaction was quenched at 4 h by opening the flask to air and cooling down to room temperature. Immediately after that, the reaction mixture was diluted in THF and passed through a column of neutral alumina to remove the copper catalyst. The resulting solution was then concentrated and dried under high vacuum at 50° C.

Block Copolymer Functionalization (Synthesis of PMMA-PBA-L)

To a long-neck Schlenk flask equipped with a magnetic stir bar were charged with 1.0 g of PMMA-PBA block copolymer, 200 mg of Ligand L1, L2, or L3, 300 mg Cs$_2$CO$_3$, and catalytic amount of KI. The Schlenk flask was then evacuated and back-filled with nitrogen for three cycles. Under nitrogen, 3.0 mL of DMF was added and the reaction mixture was heated to and maintained at 60° C. in an oil bath. After 8 h, the DMF was removed under high vacuum. The functionalized block copolymer was isolated via silica gel column chromatography (3% methanol in DCM). Due to the polar pyridine group, the functionalized block copolymers have a higher polarity, making it possible to purify the polymer using silica gel chromatography. $^1$H NMR spectrum of PMMA$_{4k}$-PBA$_{19k}$-L3 is shown in FIG. 7 as an example.

Characterization Methods

Atomic Force Microscopy (AFM)

Tapping mode AFM experiments were conducted on an Asylum Research MFP-3D AFM system (Oxford Instruments). All experiments were done in air using silicon tips (AC160TS-R3, Asylum Research) with a spring constant of 26 N/m and a resonance frequency of 300 kHz. For block copolymer microphase-separation imaging, a filtered polymer solution in toluene (20 mg/mL) was drop-cast onto the surface of silicon wafer (1 cm×1 cm). Before polymer casting, the wafer was cleaned by rinsing with acetone, hexanes, and isopropanol and dried under nitrogen. For imaging of the star polymer containing the MON core, a dilute solution (0.1 mg/mL) of the star polymer was spin-coated on the surface a cleaned silicon wafer.

Small Angle X-Ray Scattering (SAXS)

SAXS experiments were performed at the Sector 12 beamline of Advanced Photon Source (APS) of Argonne National Laboratory. X-rays of wavelength 0.89 Å (14 keV) were used. The system was calibrated using silver behenate as the standard. For the bulk rubber sample, the exposure time was 0.5 s; for the gel sample, the exposure time was 1 s. For variable temperature (VT) experiment, the samples were mounted on a Linkam temperature control stage and were heated or cooled in situ. 2-dimensional scattering data were recorded and were converted to 1-dimensional plot via radial averaging of the 2D pattern. The background scattering (for example the Kapton tape) was subtracted.

Nuclear Magnetic Resonance Spectroscopy (NMR)

$^1$H NMR and $^{13}$C NMR were recorded using a Bruker AVANCE-400 NMR spectrometer. Chemical shifts are reported in parts per million (ppm), and are referenced to residual solvent peaks. Scalar coupling constant J was reported in Hertz (Hz).

Gel Permeation Chromatography (GPC)

GPC analyses were carried out in tetrahydrofuran (THF) at a flow rate of 1.0 mL/min using an Agilent 1260 Infinity system with variable-wavelength diode array (254, 450, and 530 nm) and a refractive index detector. The instrument was calibrated with low-dispersity poly(styrene) (PS) standards between 1.7 and 3150 kg/mol. The number-averaged molar mass, weight-averaged molar mass, and dispersity index were abbreviated as $M_n$, $M_w$, and Đ (Đ=$M_w$/$M_n$).

Rheometry

Rheology studies of the bulk rubber samples were measured on an Anto Paar MCR 301 rheometer. A disposable parallel-plate geometry (radius=12 mm) and a disposable bottom plate were used together; and the gap between the two plates was about 2 mm. Frequency sweep experiments were conducted from 0.1 to 100 rad/s at 1% strain, which was in the linear viscoelastic regime as confirmed using strain sweep experiments. The rubber samples were molded at 120° C. using a TEFLON mode with a radius of 12 mm and a height of 2 mm. This process also anneals the polymers to induce phase separation. Rheology experiments of the gel samples were performed on a TA Discovery HR-2 rheometer. A parallel-plate with a radius of 20 mm was used and coupled with a bottom plate capable of varying temperatures using a Peltier heating system. When loading the sample, a piece of gel (~30 mg) was transferred on the bottom plate and the plate temperature was raised to 50° C. When the gel turned to a liquid, the top plate was lowered until the sample was fully sandwiched. The gap between the top and bottom plates is 0.5 to 1.0 mm. Temperature sweep experiments were performed where the moduli were measured as a function of temperature (5 to 70° C.). The strain and the angular frequency were kept at 1% and 10 rad/s, respectively. The temperature step was 1° C. per measurement.

Transmission Electron Microscopy (TEM)

TEM images were obtained using a FEI Tecnai multipurpose scope (G2 Spirit TWIN). The samples were prepared by spin-coating a dilute acetonitrile solution (0.1 mg/mL) of the star polymers containing the MON core on to a carbon coated copper grid. After drying under vacuum for 10 min, the sample-coated grids were placed in a small jar saturated with RuO$_4$ vapor prepared by mixing 30 mg of RuCl$_3$ and 15 mL of sodium hypochlorite solution (10 to 15%, Sigma). The polymer samples were allowed to stain for 45 min, and scoped at an electron accelerating voltage of 120 kV.

Dynamic Light Scattering (DLS)

DLS experiments were performed on a Wyatt Dawn Heleo-II instrument at 20° C. An acetonitrile solution of the linear or star polymers is filtered right before each measurement.

Estimation of the Radius of Gyration of the Linear and Star Polymers4

The radii of gyration ($R_g$) was calculated to compare the size difference between the star-shaped polyMON with different number of arms.

The radius of gyration of an ideal linear chain can be calculated by:

$$\langle R_g^2 \rangle = \frac{b^2 N}{6}$$

where $\langle R_g^2 \rangle$ is the mean-square radius of gyration, b is the Kuhn length of the polymer, and N is the number of the Kuhn segments in the polymer chain. For a linear di-block copolymer, adjustment can be made so that:

$$\langle R_g^2 \rangle = \frac{b_1^2 N_1}{6} + \frac{b_2^2 N_2}{6}$$

where $b_1$, $N_1$, $b_2$, and $N_2$, are specific values for each of the blocks in the copolymer—in this case, PMMA-PBA. For the simplicity of calculation, =the interaction between PMMA and PBA was neglected.

The Kuhn length for PMMA is 1.7 nm and the molecular mass for a Kuhn segment is 655 g/mol. The Kuhn length for PBA is 1.96 nm, and the molecular mass for the Kuhn segment is 960 g/mol. In the case of PMMA$_{4k}$-PBA$_{19k}$, $$\langle R_g^2 \rangle = \frac{b_1^2 N_1}{6} + \frac{b_2^2 N_2}{6} = \frac{1.7^2 \times 4000/655}{6} + \frac{1.96^2 \times 19000/960}{6} = 15.6\,\text{nm}^2$$

so that $2R_g$=7.9 nm.

For the star polymers with n arms, the radius of gyration of an ideal linear chain is:

$$\langle R_g^2 \rangle = \frac{b_1^2 N_{1\,total}/n}{6} \times \left(3 - \frac{2}{n}\right) + \frac{b_2^2 N_{2\,total}/n}{6} \times \left(3 - \frac{2}{n}\right)$$

where $N_{total}$ is the number of Kuhn segments from all arms. For the 4-arm PMMA$_{4k}$-PBA$_{19k}$ star polymer possessing a $M_2L_4$ paddle wheel MON core, n=4, and $2R_g$ can be calculated to be 12.5 nm.

For the 24-arm star polymer possessing a $M_{12}L_{24}$ MON core based on PMMA$_{4k}$-PBA$_{9k}$, n=24. Considering that the polymer chains might be stretched due to the junction constraint[5], it was assumed that polymers are in a good solvent, instead of a θ solvent). In this case, $$\langle R_g^2 \rangle = \frac{b_1^2 N_{1\,total}^{1.2}/n}{6} \times \left(3 - \frac{2}{n}\right) + \frac{b_2^2 N_{2\,total}/n}{6} \times \left(3 - \frac{2}{n}\right)$$

and therefore $2R_g$=17.8 nm. Because the MON core is about 3.5 nm in diameter, the size of the star polymer is 21.3 nm.

Calculation of Spinodal Curve the thermal unstability limit of the disordered melt of a star-shape polymer with AB block copolymer—in this case PMMA-PBA as arms, denoted as (AB)$_n$, where n is the number of arms, was predicted. For a star-like architecture, all the AB arms are connected at each B block end. If the A and B blocks have degree of polymerization (DP) of NA and $N_B$, respectively, the total DP is N=n($N_A$+$N_B$). The average segment length is set to a for both A and B segments. The structure factor for the (AB)$_n$ star-shaped block copolymer is $$\overline{S} = [S/W - 2\chi]^{-1}$$

where $$S = S_{AA} + S_{BB} + 2S_{AB}$$

$$W = S_{AA} * S_{BB} - S_{AB}^2$$

$$S_{AA} = nS_{AA}^{ii} + n(n-1)S_{AA}^{ij}$$

$$S_{BB} = nS_{BB}^{ii} + n(n-1)S_{BB}^{ij}$$

$$S_{AB} = nS_{AB}^{ii} + n(n-1)S_{AB}^{ij}$$

$$S_{AA}^{ii} = n(N_A + nN_B)^{-1} g(N_A)$$

$$S_{AA}^{ij} = \frac{1}{2}(nN_A + nN_B)^{-1}[g(2N_A + 2N_B) - 2g(N_A + 2N_B) + g(2N_B)]$$

$$S_{BB}^{ii} = (nN_A + nN_B)^{-1} g(N_B)$$

$$S_{BB}^{ij} = \frac{1}{2}(nN_A + nN_B)^{-1}[g(2N_B) - 2g(N_B)]$$

$$S_{AB}^{ii} = \frac{1}{2}(nN_A + nN_B)^{-1}[g(N_A + N_B) - g(N_A) - g(N_B)]$$

$$S_{AB}^{ij} = \frac{1}{2}(nN_A + nN_B)^{-1}[g(N_A + 2N_B) - g(N_A + N_B) - g(2N_B) + g(N_B)]$$

-continued $$g(f, x) = \frac{2}{y^2}[fxy + \exp(-fxy) - 1]$$

$$y = \frac{q^2 a^2}{6}$$

The structure factor is divergent at the spinodal point, which is equal to $\overline{S}^{-1}$=0. Based on the structure factor, a spinodal curve can be drawn to present the thermal unstability limit of the disordered melt (see main text).

REFERENCES (1) Jiang, F.; Wang, N.; Du, Z.; Wang, J.; Lan, Z.; Yang, R., *Chemistry—An Asian Journal* 2012, 7, 2230-2234.
(2) Seredyuk, M.; Gaspar, A. B.; Ksenofontov, V.; Galyametdinov, Y.; Verdaguer, M.; Villain, F.; Gütlich, P., *Inorganic Chemistry* 2010, 49, 10022-10031.
(3) Magenau, A. J. D.; Kwak, Y.; Matyjaszewski, K., *Macromolecules* 2010, 43, 9682-9689.
(4) Rubinstein, M.; Colby, R. H., *Polymers Physics*. Oxford Univ. Press, 2003.
(5) Olvera de la Cruz, M.; Sanchez, I. C., *Macromolecules* 1986, 19, 2501-2508.

Example 2. Preparation and Characterization of BCPMONs of Formula (C)

Herein, the synthesis of uniform oligomeric polyMOF ligands with alkyne end groups via an iterative exponential growth (IEG) strategy is reported. These ligands were used to prepare a diblock copolymer via copper-catalyzed azide-alkyne cycloaddition "click" chemistry with azide-terminated polystyrene (PS). In the presence of Zn ions, this novel block copolymer forms a BCPMON comprised of crystalline polyMOF domains embedded in an amorphous PS matrix.

Block copolymer (BCP) assemblies and metal-organic frameworks (MOFs) are two classes of self-assembled matter with vastly different structures and properties. The former may be derived from covalently linked, flexible polymer chains that may undergo phase separation on length scales typically ranging from ~10-100 nm.[1,2] BCPs may be useful for separations, micropatterning, battery, and electronics technologies. 1,2 On the other hand, MOFs are crystalline networks, optionally with angstrom-scale order and permanent porosity. These features may enable functions such as gas and energy storage, catalysis, and selective separation.[3]

There are exciting opportunities to merge the chemistry of well-defined networks based on metal-ligand coordination (such as MOFs and metal-organic cages/polyhedra (M-OCs))[4-9] and amorphous materials.[10-36] For example, Cohen[23] and coworkers recently showed that benzene dicarboxylate (BDC) ligands could be linked together to form oligomers/polymers that could form "polyMOFs", wherein the ligand struts of MOF-5 were connected by polymer backbone linkers.[23,34] Cohen's polyMOFs were structurally similar to the parent MOF-5, but they featured greater ambient stability and recyclability due the polymeric components.

The merger of amorphous polymer networks with multicomponent supramolecular assembly to generate soft materials with novel properties is of interest. For example, "polyMOCs", which are a class of hybrid materials that feature MOCs embedded in networks of flexible polymer chains, are reported.[26-30] As part of these efforts, it was recently shown that addition of $Pd^{2+}$ to BCPs with MOC-forming ligands on their chain ends could induce MOC assembly and subsequent phase separation to yield polyMOC elastomers where the mechanical properties depend strongly on the MOC geometry.[28]

With an interest in further expanding these types of hybrid materials, herein we report a novel BCP wherein one block is a uniform BDC-based oligomer synthesized by iterative exponential growth (IEG)[37-40] and the other is polystyrene (PS) prepared by atom transfer radical polymerization (ATRP).[41,42] In the presence of Zn ions, this BCP forms a BCPMON comprised of polyMOF domains embedded in a PS matrix. This work represents the first demonstration that a BCP with a suitably designed polyMOF-forming block can form a composite material with both highly crystalline polyMOF domains and amorphous polymer domains. BCPMONs could find applications as robust and easily processable materials for gas separations.

Preparation of BCPMONs of Formula (C)

Figure 17:
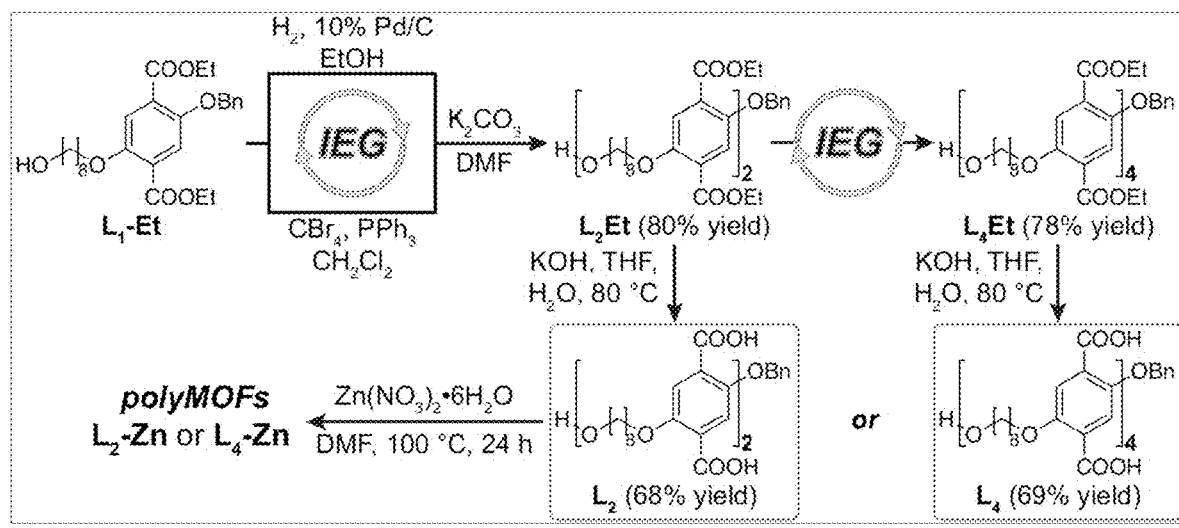
FIG. 17. IEG synthesis of uniform BDC dimer ($L_2$) and tetramer ($L_4$) ligands as precursors to IEG-polyMOFs.

The present study includes the design of a BDC oligomer suitable for BCP synthesis (FIG. 17). To date, Cohen's BDC-based polyMOF precursors have been synthesized via step-growth polymerizations.[23,34] Though operationally simple, such polymerizations suffer from poor control over the degree of polymerization and broad molar mass distributions. Moreover, they are not readily amenable to the formation of BCPs. In an effort to develop a uniform BDC oligomer with defined end functionality, the IEG approach outlined in FIG. 17 was developed (see Example 2). IEG is a molecular-doubling strategy that enables the efficient synthesis of uniform sequence- and stereo-defined oligomers/polymers with absolute control over molecular structure.[37,38] The approach described in FIG. 17 provides BDC-based oligomers with precise structures that can subsequently be modified to tune polyMOF functionality.

Figure 23:
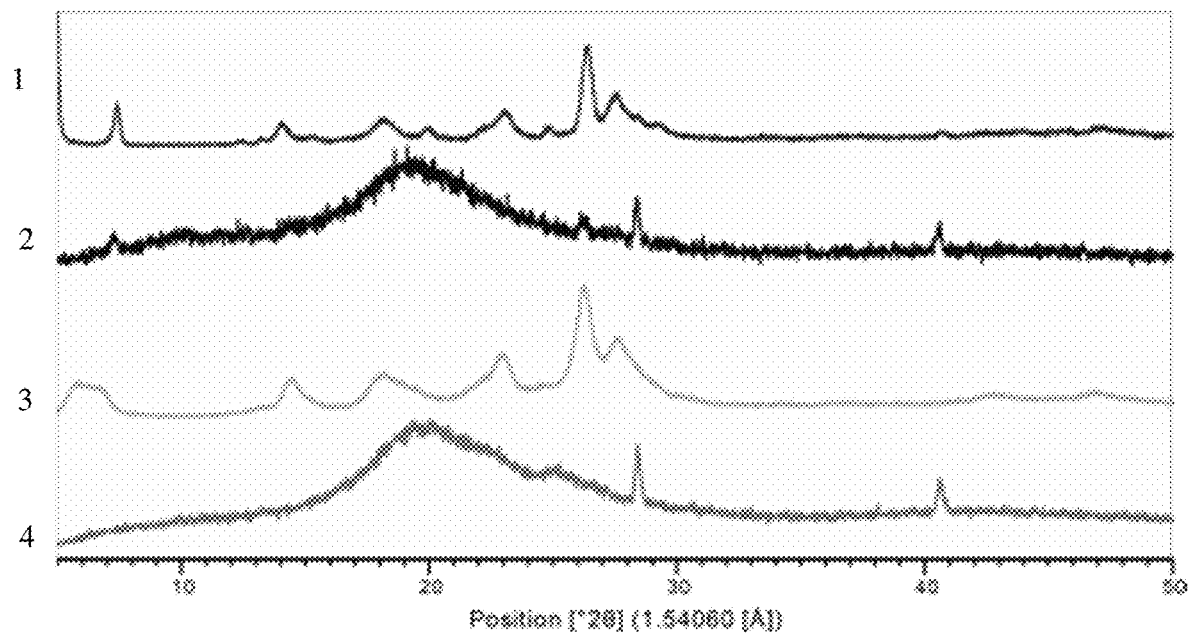
FIG. 23. PXRD spectra for BDC-based polyMOF and BCPMON ligands. 1 is $L_2$, 2 is $L_2$PS, 3 is $L_4$ and 4 is $L_4$PS. Note that $L_4$ is highly hygroscopic.

Mono-benzylation of commercially available diethyl 2,5-dihydroxyterephthalate followed by alkylation with 8-bromo-1-octanol provided the IEG "monomer" $L_1Et$ (FIG. 17, 53% yield over two steps).[23] In the first IEG cycle (FIG. 17), $L_1Et$ was subjected to divergent $CBr_4/PPh_3$ bromination and Pd/C debenzylation reactions followed by convergent alkylation to provide $L_2Et$ (1.4 g, 80% over three steps). Repeating this sequence with $L_2Et$ as the starting material (FIG. 17) provided the uniform tetramer $L_4Et$ (2.3 g, 78% over three steps). Treatment of $L_2Et$ or $L_4Et$ with KOH at 80° C. provided $L_2$ (390 mg, 68%) or $L_4$ (220 mg, 69%), respectively. The structures of these ligands were confirmed by $^1H$ NMR, $^{13}C$ NMR, and high-resolution mass spectrometry (HRMS) (see Example 2). $L_2$ and $L_4$ were crystalline, which attests to their uniformity and contrasts with Cohen's oligomers (FIG. 23). The octamer $L_8Et$ could be readily synthesized via another IEG cycle.

Figure 18A:
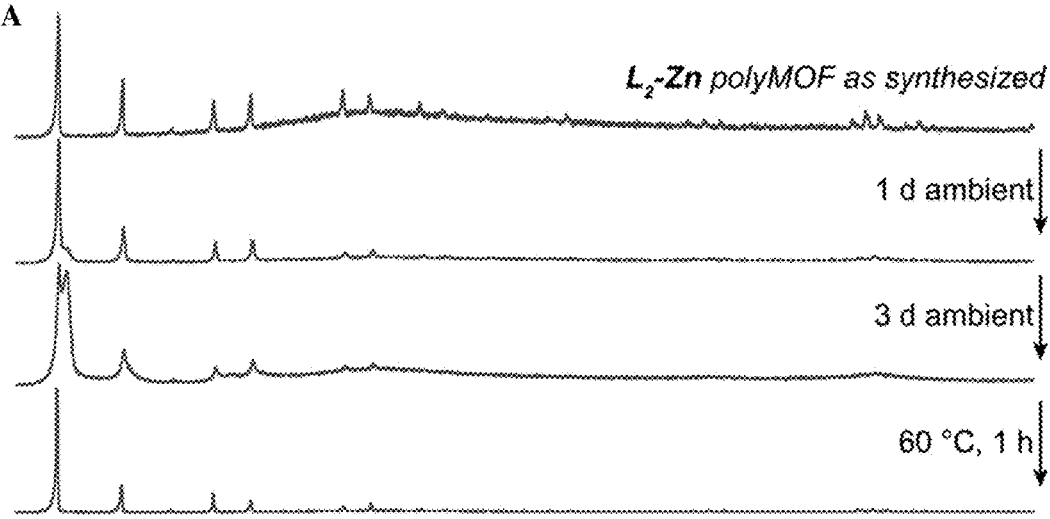
FIGS. 18A to 18B. PXRD spectra of polyMOFs derived from $L_2$ and $L_4$ and Zn.
Figure 18B:
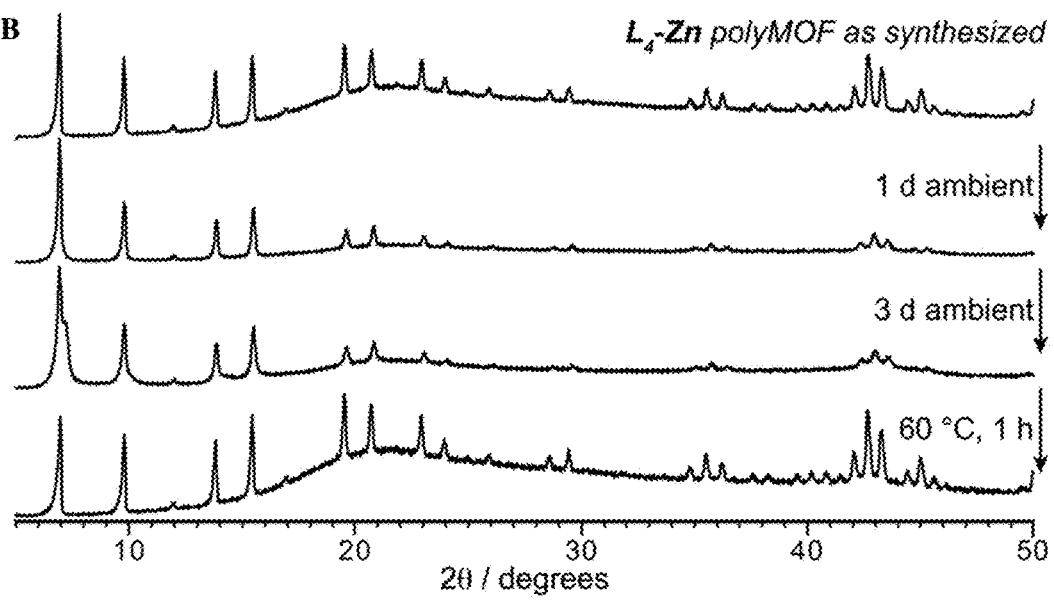

To confirm that $L_2$ and $L_4$ could form polyMOFs analogous to Cohen's, mixtures of each ligand and $Zn(NO_3)_2 \cdot 6H_2O$ in DMF were heated at 100° C. for 24 h. Powder X-ray diffraction (PXRD) confirmed the formation of two new materials, $L_2$-Zn and $L_4$-Zn, with reflections that matched those of Cohen's polyMOFs and the parent MOF-5 (FIGS. 18A and 18B). Both materials exhibited longer-term stability towards ambient conditions than MOF-5.[23] Similar to Cohen's polyMOFs, the partial shift observed in the principle PXRD peak after 1 d and 3 d exposure to ambient conditions for $L_2$-Zn and $L_4$-Zn, respectively, is attributed to the formation of a non-native polyMOF and not decomposition (the analogous decomposition of MOF-5 to MOF 69c is not observed via XRD).[23] Notably, the IEG polyMOF crystal structure can be regenerated by heating the samples in DMF for 1 h at 60° C. (FIG. 18B); the minor peak broadening observed is similar to Cohen's findings for regenerated polyMOFs.

Figure 24:
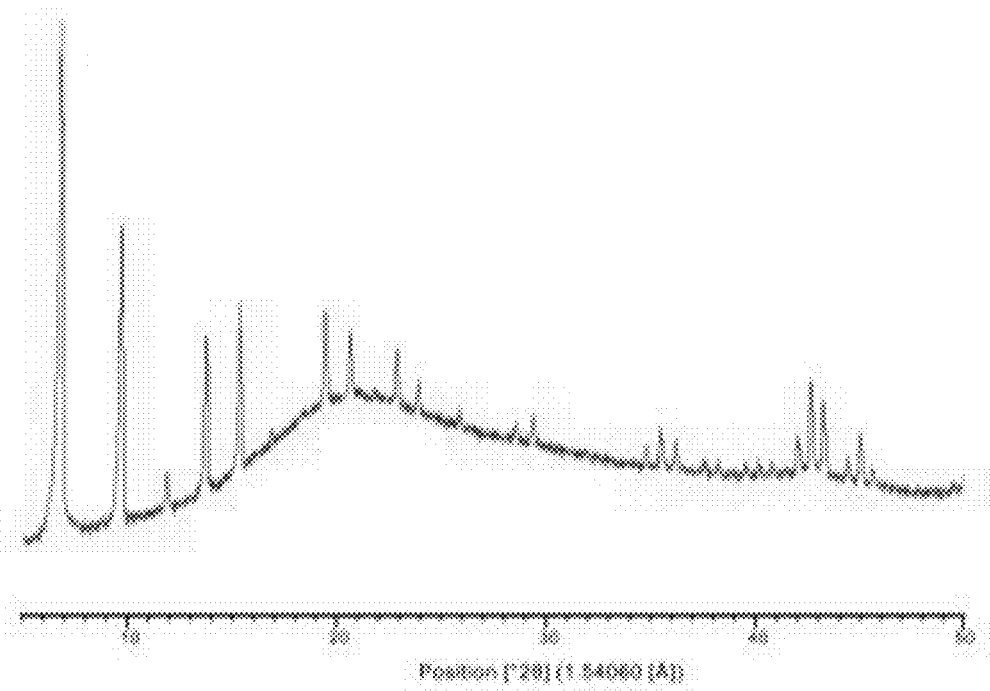
FIG. 24. PXRD spectrum for $L_4$Bn-Zn.

Next, it was sought to install functionality selectively at one end of the $L_2$ and $L_4$, and investigate the impact of this new functionality on polyMOF formation. A terminal alkyne, which was planned to be exploited in subsequent copper-catalyzed azide-alkyne cycloaddition (CuAAC) reactions, was targeted.[43-45] Attempts to directly propargylate the hydroxyl end of $L_2Et$ or $L_4Et$ led to low yields and mixtures of products; however, debenzylation followed by selective propargylation of the resulting phenol (FIG. 19A) provided $L_2Et$-alkyne and $L_4Et$-alkyne in good yields (89% and 86%, respectively). A new polyMOF ligand $L_4Bn$ was prepared (see Example 2) via CuAAC coupling of $L_4Et$-alkyne and benzyl azide followed by saponification of the BDC sidechains. The PXRD spectrum of the $L_4Bn$-derived polyMOF ($L_4Bn$-Zn) was equivalent to that of $L_4$-Zn (FIG. 24), which suggests that the triazole product of CuAAC coupling does not disrupt polyMOF formation. This is the first example of a CuAAC-modified polyMOF material; in principle, $L_4Et$-alkyne could be used to generate a wide variety of new polyMOFs depending on the azide used.

Figure 19A:
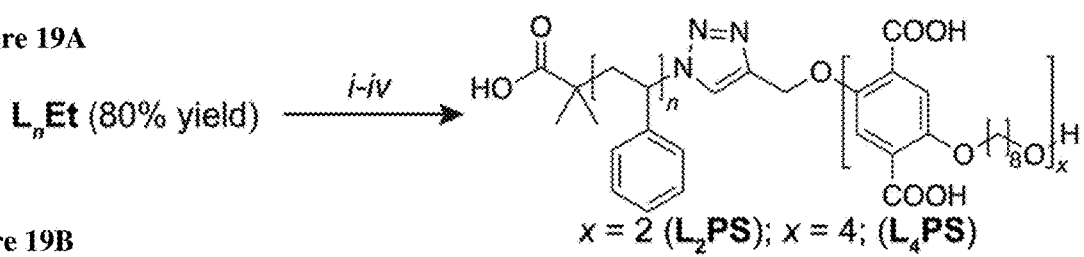
FIGS. 19A to 19C.
Figure 19B:
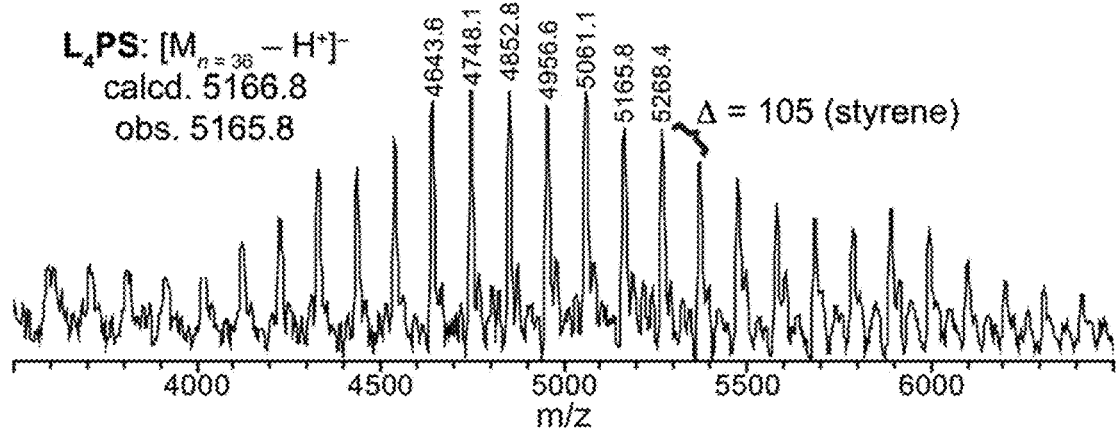
Figure 19C:
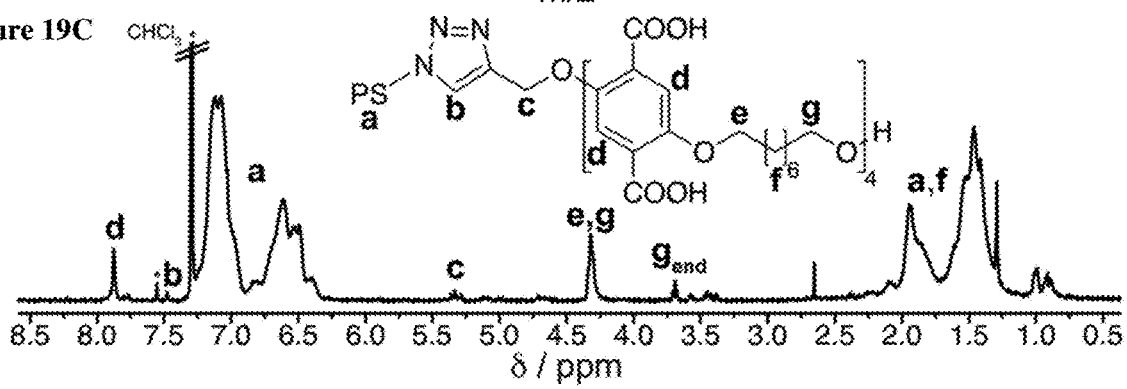

Turning to the target BCPMONs, azide-terminated PS ($PS-N_3$ prepared by ATRP and end group substitution, see Supplmentary Information; $M_n$=3.7 kg $mol^{-1}$; Đ=1.08) was coupled to $L_2Et$-alkyne and $L_4Et$-alkyne via CuAAC to yield $L_2EtPS$ and $L_4EtPS$, respectively (FIG. 19A). The BCA groups were revealed by saponification to produce ligands $L_2PS$ and $L_4PS$. Matrix-assisted laser desorption ionization time-of-flight (MALDI-TOF) mass spectrometry (FIG. 19B for L$_4$PS) and 1H NMR spectroscopy (FIG. 19C for L$_4$PS) confirmed the structures of these BCPs. PXRD spectra for L$_2$PS and L$_4$PS exhibited broad amorphous peaks centered at 19° attributed to PS as well as crystalline features from the BCA blocks (FIG. 23).

Figure 20:
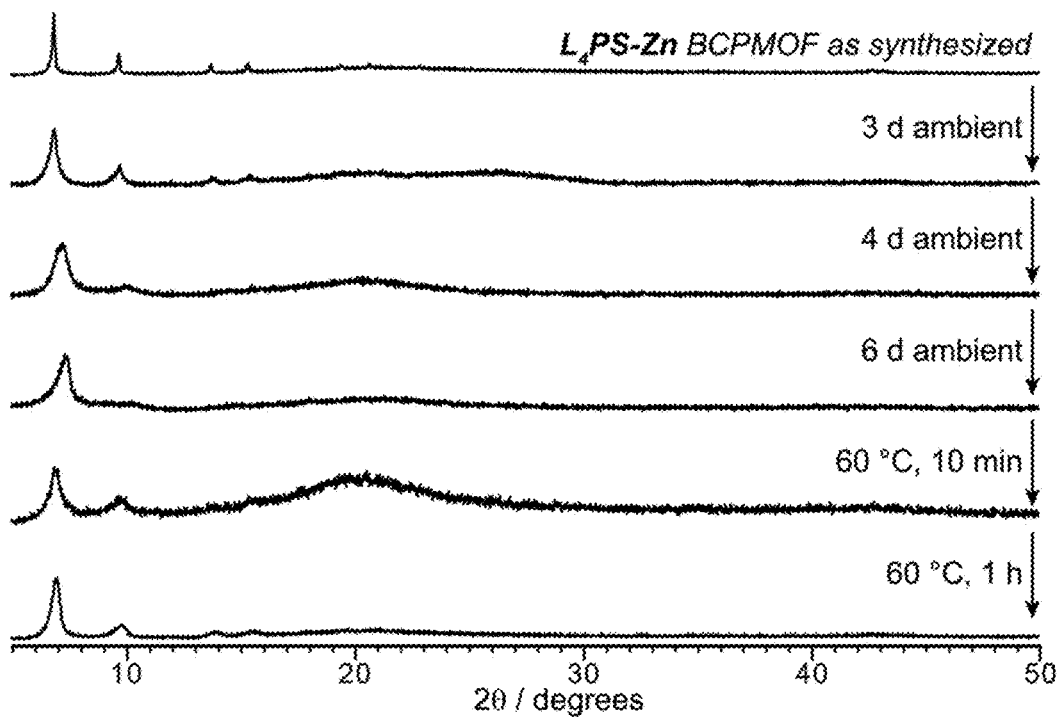
FIG. 20. PXRD spectra for BCPMON $L_4$PS—Zn.
Figure 25:
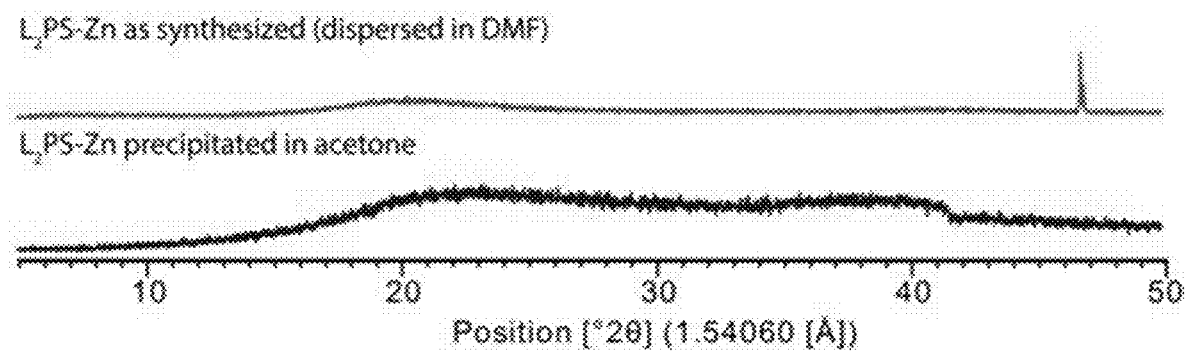
FIG. 25. PXRD spectra for $L_2$PS—Zn.

When L$_2$PS was exposed to a variety of conditions that are typically used to generate MOF-5 and related poly-MOFs, crystalline solids were not formed (FIG. 25). Presumably, the very short ligand block in this copolymer precludes the formation of crystalline polyMOFs. In future studies, it may be possible to form polyMOFs with L$_2$PS and BDC mixtures, where additional BDC ligands could facilitate the formation of MOF domains and L$_2$PS could link these domains to PS domains. When L$_4$PS was allowed to react with Zn(NO$_3$)$_2$.6H$_2$D a precipitate (L$_4$PS—Zn) formed that displayed PXRD reflections similar to those of poly-MOF L$_4$-Zn and MOF-5, thus confirming the formation of the target BCPMON (FIG. 20). L$_4$PS—Zn was partially soluble in CHCl$_3$, which is a non-solvent for MOF-5 and L$_4$-Zn but is a good solvent for PS. L$_4$PS—Zn appeared to be stable under ambient conditions for 3 d with no shift in the PXRD peaks (FIG. 20). After 4 d, a slight shift of the principle peak to a higher angle was observed. As noted above, Cohen's polyMOFs displayed a similar shift after 1 d, which is indicative of the formation of a non-native polyMOF.[23] These data also suggest that the BCPMON is more stable under ambient conditions than the IEG poly-MOF. The hydrophobic PS chains of L$_4$PS likely coat the MOF domains within L$_4$PS—Zn thereby providing superior stability towards moisture. In addition, L$_4$PS—Zn could be regenerated by heating the non-native L$_4$PS—Zn at 60° C. for 1 h. Again, though the peaks of the regenerated material were broadened, the peak locations match those of the pristine material.

Material/General Methods/Instrumentation

All reagents were purchased from commercial suppliers and used without further purification unless stated otherwise. Polystyrene azide was synthesized as previously reported using ethyl α-bromoisobutyrate initiator (O. Altintas, T. Josse, M. Abbasi, J. De Winter, V. Trouillet, P. Gerbaux, M. Wilhelm and C. Barner-Kowollik Polym. Chem., 2015, 6, 2854-2868). Column chromatography was performed on a Biotage® Isolera One with Accelerated Chromatographic Isolation flash chromatography system, using Biotage® KP-Sil SNAP cartridges at the recommended flow rates. High-resolution mass spectra (HRMS) were measured on a Bruker Daltonics APEXIV 4.7 Tesla Fourier Transform Ion Cyclotron Resonance Mass Spectrometer (FT-ICR-MS) using an electrospray ionization (ESI) source. X-ray diffraction was performed using a Rigaku Smartlab Multipurpose Diffracteter with an incident beam Ge (022) double bounce monochromator and a diffracted beam graphite monochromator using the variable-slit Bragg Brentano method. No corrections were made. Samples were cast as powder or from residual DMF or acetone onto zero background plates. The samples were air dried for 10 minutes before measurements began. SAXS and WAXS were preformed using Rigaku H3r Source/Bruker Nanostar SAXS system with a two-dimensional CCD detector and a beam path length of 60.4 cm. Samples were prepared in Kapton tape. The Kapton tape scattering was subtracted. Nuclear magnetic resonance spectroscopy (NMR), $^1$H NMR and $^{13}$C NMR were recorded using a Bruker AVANCE-400 NMR spectrometer or a VARIAN Inova-500 NMR spectrometer. Chemical shifts are reported in parts per million (ppm), and are referenced to residual solvent peaks. The data were analyzed using MestReNova or Topspin software. Gel permeation chromatography (GPC) analyses were carried out in tetrahydrofuran (THF) at a flow rate of 1.0 mL/min using an Agilent 1260 Infinity system with a variable-wavelength diode array (254, 450, and 530 nm) and a refractive index detector for PS—N$_3$. Matrix-absorption laser desorption ionization time-of-flight (MALDI-TOF) mass spectra were recorded with a Bruker model MicroFlex MALDI-TOF at the Koch Institute for Integrative Cancer Research at MIT. Dithranol in THF was used as the matrix in negative ion mode. Thermogravimetric analysis (TGA) was performed using a TA Instruments Discovery TGA. Samples were run in platinum TGA pans at a ramp rate of 10° C. per minute from 30 to 600° C. Differential scanning calorimetry (DSC) was performed on a TA Instruments Discovery DSC, where each sample was run with a Tzero aluminum pan sealed with a hermetic lid. Scanning electron microscopy (SEM) was performed in a Zeiss Merlin high-resolution SEM. Samples were prepared by drop casting a solution of the desired material on silicon wafers from dichloromethane suspensions. The samples were allowed to dry overnight. Transmission electron microscopy (TEM) images were obtained using a FEI Tecnai multipurpose scope (G2 Spirit TWIN). The samples were prepared by drop-casting a dilute dichloromethane suspension (0.1 mg/mL) of the BCPMON onto a carbon coated copper grid. Consequently, uniform thin films were difficult to obtain. For positively stained samples, after casting the samples were dried for 30 minutes, the sample-coated grids were placed in a four mL vial which was placed in a sealed 20 mL vial containing 1 mL RuO$_4$. It was allowed to rest for 30 minutes. The sample was then removed and allowed to rest for 30 minutes. Gas adsorption measurements were measured with an ASAP 2020 surface area and pore size analyzer. ~50 mg of L$_4$-Zn was soaked in CHCl$_3$ for 2 days, decanting and refreshing CHCl$_3$ every 12 hours. ~100 mg of L$_4$PS—Zn was soaked in CHCl$_3$ for 12 h and was centrifuged down to isolate ~20 mg of sample. The samples were dried on a vacuum line for ~10 min at room temperature, and transferred to pre-weighed sample tubes with a filler rods and degassed at 160° C. for 10 h. The sample tube was reweighed to obtain a consistent mass for the degassed sample. UHP grade (99.999%) N$_2$ were used for all measurements and the sample temperature was maintained at 77 K.

Preparation of Compound A

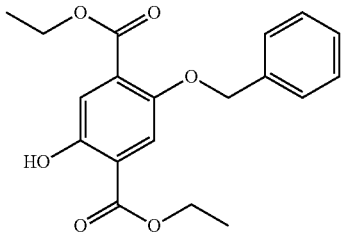 [SMILES: CCOC(=O)c1cc(OCc2ccccc2)c(C(=O)OCC)cc1O]

10 g (39.3 mmol, 1.0 eq.) of diethyl 2,5-dihydroxyterephthalate, 2.7 g (19.7 mmol, 0.50 eq.) K$_2$CO$_3$, 2.3 mL (19.7 mmol, 0.50 eq.) benzyl bromide and 39 mL acetone were added to a pressure vessel. The vessel was sealed and the reaction was stirred at 80° C. overnight. The reaction was cooled and water was added. The solution was neutralized with 1 M HCl and then extracted with dichloromethane three times. The extracts were dried with Na$_2$SO$_4$, filtered and concentrated under vacuum. The solid collected was loaded with minimal DCM and purified by silica gel chromatography using 0-5% ethyl acetate in hexanes. Unreacted starting material elutes at 1-2% ethyl acetate in hexanes and can be reisolated. The product elutes at 2-3% ethyl acetate in hexanes in 61% yield. 1H (CDCl$_3$, 400 Hz): 1.32 (2H, t), 1.40 (2H, t), 4.35 (2H, q), 4.39 (2H, q), 5.07 (2H, s), 7.24-7.54 (7H, m), 10.41 (1H, s). $^{13}$C (CDCl3, 400 Hz): 14.33, 61.60, 62.07, 72.13, 115.00, 115.05, 120.20, 127.45, 128.07, 128.64, 129.45, 149.74, 155.62, 165.53, 169.31. HRMS: calcd: for $C_{19}H_{21}O_6[M+H]^+$, most abundant m/z=345.1333; found, 345.1338.

Preparation of Compound L$_1$Et

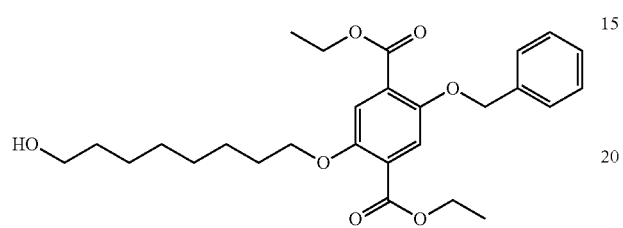

1.2 g (8.7 mmol, 1.5 eq.) of potassium carbonate, 0.15 g (0.58 mmol, 0.10 eq.) 18-crown-6, 2.0 g (5.8 mmol, 1.0 eq.) of 1 and 0.95 mL (6.3 mmol, 1.1 eq.) of 8-bromo-1-octanol were dissolved in a 18 mL of 50:50 DMF/ethanol mixture. The mixture was heated at 80° C. for 16 h in a sealed pressure vessel. The reaction was then cooled. 70 mL of DI water were added and the reaction was neutralized with 1 M HCl and then extracted with dichloromethane three times. The extracts were dried with Na$_2$SO$_4$, filtered and concentrated under vacuum. The oil collected was loaded with minimal DCM and columned using 0 to 40% ethyl acetate in hexanes on silica (eluting at 35%) in 86% yield. 1H (CDCl$_3$, 400 Hz): 1.24-1.40 (12H, m), 1.40-1.58 (4H, m), 1.77 (2H, dt), 3.58 (2H, t), 3.98 (2H, t), 4.34 (4H, q), 5.09 (2H, s), 7.24-7.49 (7H, m). $^{13}$C (CDCl$_3$, 400 Hz): 14.16, 14.22, 25.63, 25.68, 29.15, 29.21, 29.27, 32.66, 61.26, 61.39, 62.72, 69.67, 71.64, 76.83, 77.15, 77.47, 116.56, 117.38, 124.53, 125.10, 127.19, 127.82, 128.37, 136.57, 151.07, 152.13, 165.85, 165.90. HRMS: calcd. for $C_{27}H_{37}O_7[M+H]^+$, most abundant m/z=473.2534; found, 473.2549.

Preparation of Compound L$_1$EtBr

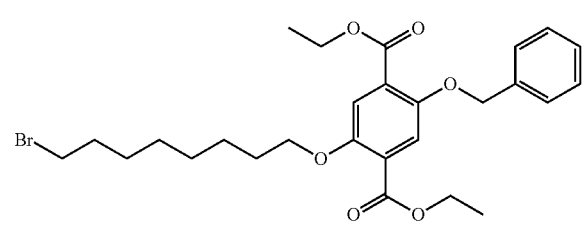 [SMILES: CCOC(=O)c1cc(OCc2ccccc2)c(C(=O)OCC)cc1OCCCCCCCCBr]

A solution of L$_1$Et 4.3 g (9.0 mmol, 1.0 eq.) and tetrabromomethane 3.3 g (9.9 mmol, 1.1 eq.) in 39 mL of DCM was cooled to 0° C. 2.6 g (9.9 mmol, 1.1 eq.) of triphenyl phosphine was added in four portions every 5-10 minutes. The reaction was stirred at RT for 1 h. Then an additional 0.25 eq. of CBr$_4$ and PPh$_3$ were added and the reaction was stirred for an additional 2 h. The reaction was concentrated and subjected to silica gel chromatography (0 to 20% ethyl acetate in hexanes, eluting at 10%) to provide the product in 89% yield. $^1$H (CDCl$_3$, 400 Hz): 1.30-1.53 (14H, m), 1.75-1.90 (4H, m), 3.40 (2H, t), 4.01 (2H, t), 4.37 (4H, q), 5.12 (2H, s), 7.28-7.40 (4H, m), 7.43-7.50 (3H, m). $^{13}$C (CDCl3, 400 Hz): 14.32, 14.38, 25.95, 28.18, 28.78, 29.22, 29.30, 32.86, 34.02, 61.37, 61.51, 69.81, 71.85, 116.76, 117.59, 124.75, 125.32, 127.35, 127.98, 128.53, 136.74, 151.26, 152.29, 165.93, 166.01. HRMS: calcd. for $C_{27}H_{36}BrO_6 [M+H]^+$, most abundant m/z=535.1690; found, 535.1684.

Preparation of Compound L$_1$EtOH

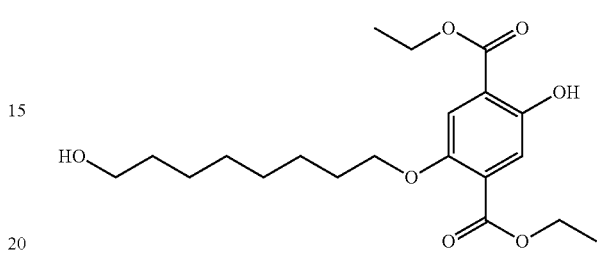

A solution of L$_1$Et 3.8 g (8.0 mmol, 1.0 eq.) and 10% palladium on carbon 0.85 g (8.0 mmol, 1.0 eq.) in 40 mL ethanol was sparged with nitrogen for 10 minutes. The solution was then sparged with hydrogen for 5 minutes and stirred under hydrogen atmosphere for 18 h at RT. The reaction was filtered to remove the palladium, concentrated, purified by silica gel chromatography (0 to 50% ethyl acetate in hexanes, eluting at 30%) and isolated in 99% yield. $^1$H (CDCl$_3$, 400 Hz): 1.27-1.61 (16H, m), 1.79 (2H, tt), 3.60 (2H, t), 3.96 (2H, t), 4.35 (2H, q), 4.41 (2H, q), 7.27 (1H, s), 7.33 (1H, s), 10.36 (1H, s). $^{13}$C (CDCl3, 400 Hz): 14.32, 14.48, 25.95, 28.18, 28.78, 29.22, 29.30, 32.96, 34.02, 61.36, 61.50, 69.81, 71.85, 116.75, 117.58, 124.75, 125.32, 127.34, 127.97, 128.53, 136.74, 151.26, 152.29, 165.93, 166.01. HRMS: calcd. for $C_{20}H_{31}O_7 [M+H]^+$, most abundant m/z=383.2064; found, 383.2078.

Preparation of Compound L$_2$Et

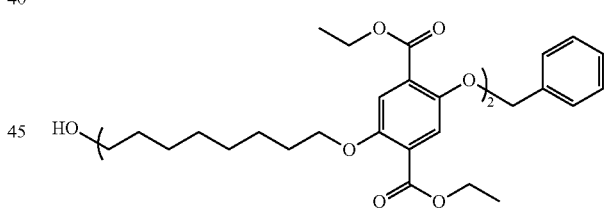

0.39 g (2.8 mmol, 1.5 eq.) of potassium carbonate, 0.47 g (0.18 mmol, 0.10 eq.) 18-crown-6, 0.68 g (1.8 mmol, 0.95 eq.) of L$_1$EtOH and 1.0 g (1.9 mmol, 1.0 eq.) of L$_1$EtBr were dissolved in a 22 mL of 50:50 DMF/ethanol mixture. The mixture was heated at 80° C. for 25 h in a sealed pressure vessel. The reaction was then cooled to RT. 50 mL of DI water were added and the reaction was neutralized with 1 M HCl and then extracted with dichloromethane three times. The extracts were dried with Na$_2$SO$_4$, filtered and concentrated under vacuum. The solid collected was loaded with minimal DCM and was purified by silica gel chromatography (0 to 60% Ethyl acetate in hexanes, eluting at 30%). Note: if moisture content is high, a side product will form that elutes at 60% ethyl acetate. It can be treated with ethanol and a catalytic amount of HCl under reflux conditions to convert it back to the desired product. L$_2$Et isolated in 91% yield. 1H (CDCl$_3$, 400 Hz): 1.27-1.61 (30H, m), 1.75-1.85 (6H, m), 3.63 (2H, t), 4.00 (6H, m), 4.36 (8H, q), 5.12 (2H, s), 7.27-7.51 (9H, m). $^{13}$C (CDCl3, 400 Hz): 14.31, 14.37, 25.73, 25.94, 26.03, 29.31, 29.34, 29.36, 29.40, 32.83, 61.38, 61.52, 63.06, 69.83, 69.89, 71.82, 116.67, 116.71, 117.56, 124.70, 124.78, 125.27, 127.34, 127.98, 128.54, 136.72, 151.23, 151.80, 152.29, 165.98, 166.02, 166.19. HRMS: calcd. for $C_{47}H_{64}NaO_{13}$ [M+Na]$^+$, most abundant m/z 859.4239; found, 859.4255.

Preparation of Compound $L_2$

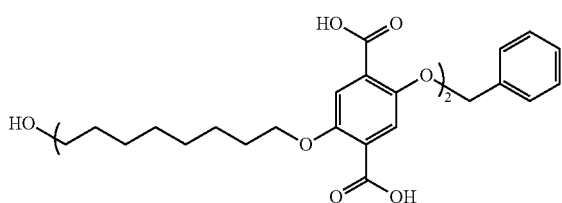

Figure 31:
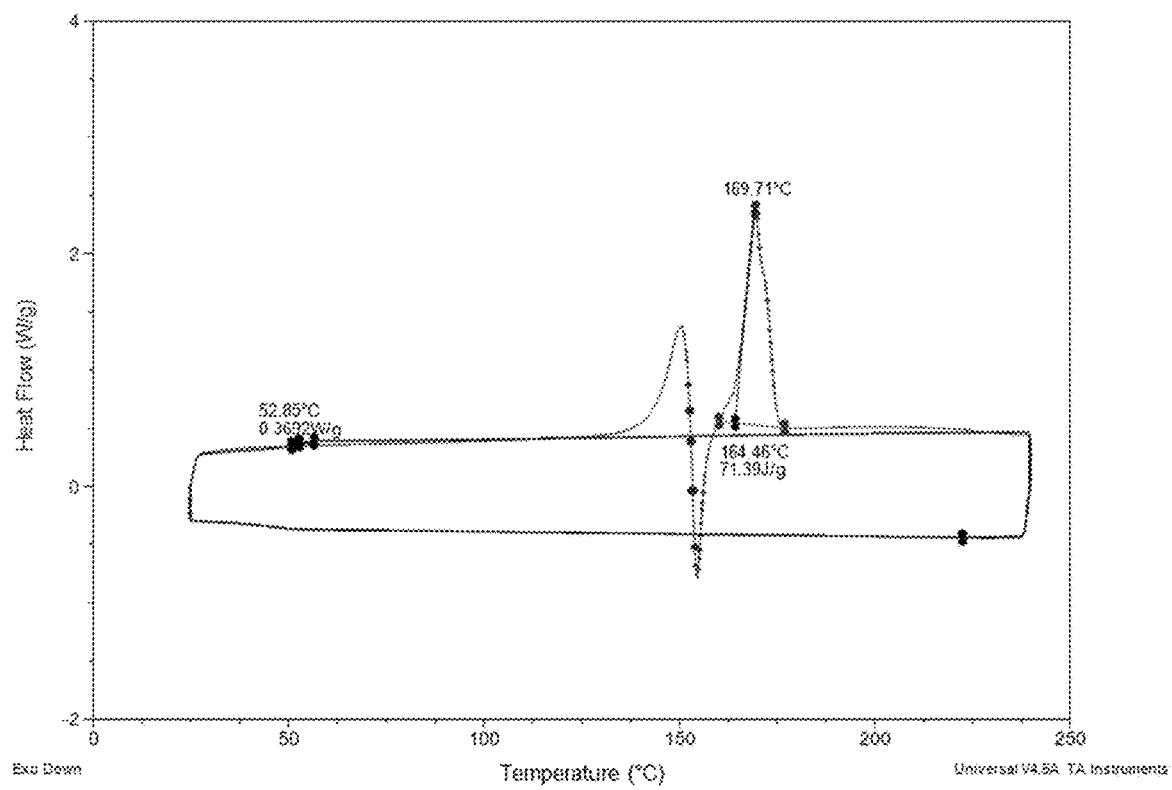
FIG. 31. DSC trace of $L_2$.

670 mg (0.80 mmol, 1.0 eq.) $L_2$Et and 100 eq. of potassium hydroxide were dissolved in 29.0 mL of DMF. 15 mL of water were added and the mixture was heated at 80° C. for 8 hrs. The reaction was acidified with 1 M HCl to a pH of 2. The product precipitated from solution as a white solid and was centrifuged at 6000 rpm. The solvent was decanted. The sample was washed with water three times and dried under vacuum overnight to give 68% yield. $^1$H (d6-DMSO, 400 Hz): 1.21-1.47 (23H, m), 1.62-1.72 (6H, m), 3.37 (2H, t), 3.98 (6H, m), 5.15 (2H, s), 7.24-7.41 (7H, m), 7.45-7.50 (2H, m), 12.93 (4H, s). $^{13}$C (d$_6$-DMSO, 400 Hz): 25.28, 25.30, 25.44, 60.70, 69.15, 70.48, 115.50, 115.57, 115.99, 125.45, 125.63, 127.16, 127.64, 128.30, 137.02, 149.97, 150.43, 150.71, 166.76, 166.82. HRMS: calcd. for $C_{39}H_{48}NaO_{13}$ [M+Na]$^+$, most abundant m/z=747.2987; found, 747.2975. See FIG. 31.

Preparation of Compound $L_2$EtBr

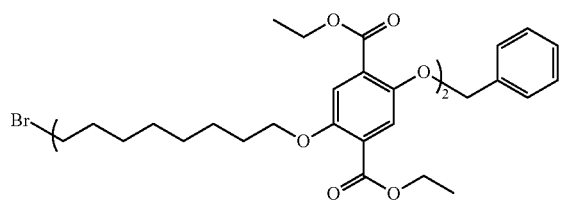

A solution of $L_2$Et 2.4 g (2.9 mmol, 1.0 eq.) and tetrabromomethane 1.1 g (3.2 mmol, 1.1 eq) in 24 mL of DCM was cooled to 0° C. 0.84 g (3.2 mmol, 1.1 eq.) of triphenyl phosphine was added in four portions every 5-10 minutes. The reaction was stirred at RT for 1 hr. Then an additional 0.25 eq of CBr$_4$ and PPh$_3$ were added and the reaction was stirred for an additional 2 h. The reaction was concentrated and the product was purified by silica gel chromatography (0 to 60% ethyl acetate in hexanes, eluting at 17%) and isolated in 88% yield. $^1$H (CDCl$_3$, 400 Hz): 1.31-1.55 (28H, m), 1.72-1.92 (8H, m), 3.41 (2H, t), 4.00 (6H, m), 4.37 (8H, q), 5.12 (2H, s), 7.28-7.41 (6H, m), 7.42-7.51 (3H, m). $^{13}$C (CDCl3, 400 Hz): 14.35, 14.41, 25.99, 26.07, 28.22, 28.82, 29.28, 29.36, 29.39, 29.41, 29.44, 32.90, 34.07, 61.40, 61.54, 69.92, 69.97, 71.90, 77.34, 116.73, 116.78, 117.63, 124.78, 124.86, 125.36, 127.39, 128.01, 128.57, 137.68, 151.29, 151.84, 152.35, 166.01, 166.06, 166.19, 166.22. HRMS: calcd. For $C_{47}H_{63}BrNaO_{12}$ [M+Na]$^+$, most abundant m/z=923.3406; found, 923.3416.

Preparation of Compound $L_2$EtOH

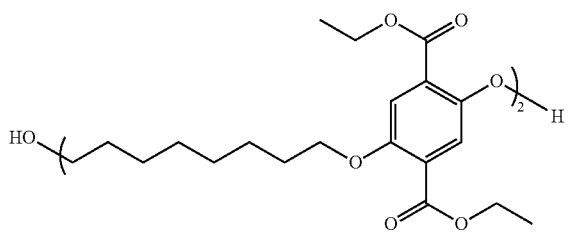

A solution of $L_2$Et 2.1 g (2.5 mmol, 1.0 eq.) and palladium on carbon 0.27 g (2.5 mmol, 1.0 eq.) in 38 mL of a 50:50 mixture of ethyl acetate:ethanol was sparged with nitrogen for 10 minutes. The solution was then sparged with hydrogen for 5 minutes and then stirred under hydrogen atmosphere for 18 h at 50° C. The reaction was filtered to remove the catalyst, concentrated, and subjected to silica gel chromatography (0 to 60% ethyl acetate in hexanes, eluting at 40%) to yield the product in 98% yield. $^1$H (CDCl$_3$, 400 Hz): 1.28-1.57 (30H, m), 1.71-1.83 (6H, m), 3.59 (2H, t), 3.96 (6H, m), 4.29-4.37 (6H, m), 4.40 (2H, q), 7.26 (1H, s), 7.31 (1H, s), 7.32 (1H, s), 10.33 (1H, s). $^{13}$C (CDCl$_3$, 400 Hz): 14.25, 14.32, 25.70, 25.90, 25.97, 29.28, 29.29, 29.31, 29.35, 32.77, 61.31, 61.33, 61.36, 61.94, 62.94, 69.87, 69.97, 113.78, 114.82, 116.64, 119.78, 124.77, 128.96, 150.14, 151.76, 155.08, 165.61, 166.12, 166.15, 169.30. HRMS: calcd. for $C_{40}H_{58}NaO_{13}$ [M+Na]$^+$, most abundant m/z=769.3770; found, 769.3768.

Preparation of Compound $L_4$Et

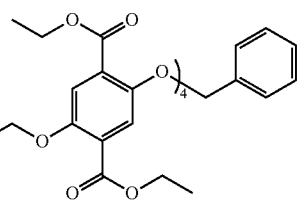

0.35 g (2.5 mmol, 1.5 eq.) of potassium carbonate, 21 mg (0.08, 0.05 eq.) 18-crown-6, 1.2 g (1.6 mmol, 0.95 eq.) of $L_2$EtOH and 1.5 g (1.7 mmol, 1.0 eq.) of $L_2$EtBr were dissolved in a 12.5 mL of 50:50 DMF/ethanol mixture. The mixture was heated at 80° C. for 29 h in a sealed pressure vessel. The reaction was then cooled. The solvent was removed under vacuum. The solid was dissolved in a 100 mL of a 50:50 mixture of DCM:DI water, neutralized with 1 M HCl and then extracted with dichloromethane three times. The extracts were dried with Na$_2$SO$_4$, filtered and concentrated under vacuum. The solid collected was dissolved with minimal DCM and purified by silica gel chromatography (0 to 8% methanol in DCM, eluting at 5%) and isolated in 90% yield. $^1$H (CDCl$_3$, 400 Hz): 1.30-1.58 (58H, m), 1.79 (14H, m), 3.61 (2H, t), 3.98 (14H, t), 4.35 (16H, q), 5.11 (2H, s), 7.27-7.50 (13H, m). $^{13}$C (CDCl$_3$, 400 Hz): 14.28, 14.34, 25.72, 25.91, 26.00, 29.34, 29.37, 32.80, 61.34, 61.48, 63.00, 69.82, 69.89, 71.81, 116.65, 117.55, 124.70, 124.78, 125.27, 127.32, 127.95, 128.50, 136.70, 151.21, 151.79, 152.26, 165.94, 165.99, 166.15. HRMS: calcd. for $C_{87}H_{124}NO_{25}$ [M+NH$_4$]$^+$, most abundant m/z=1582.8457; found, 1582.8489.

Preparation of Compound L₄

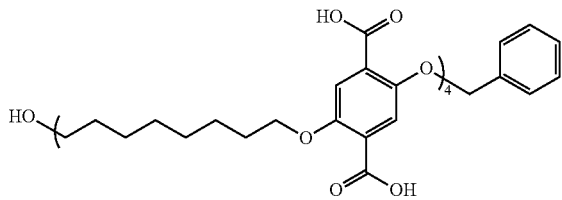

Figure 33:
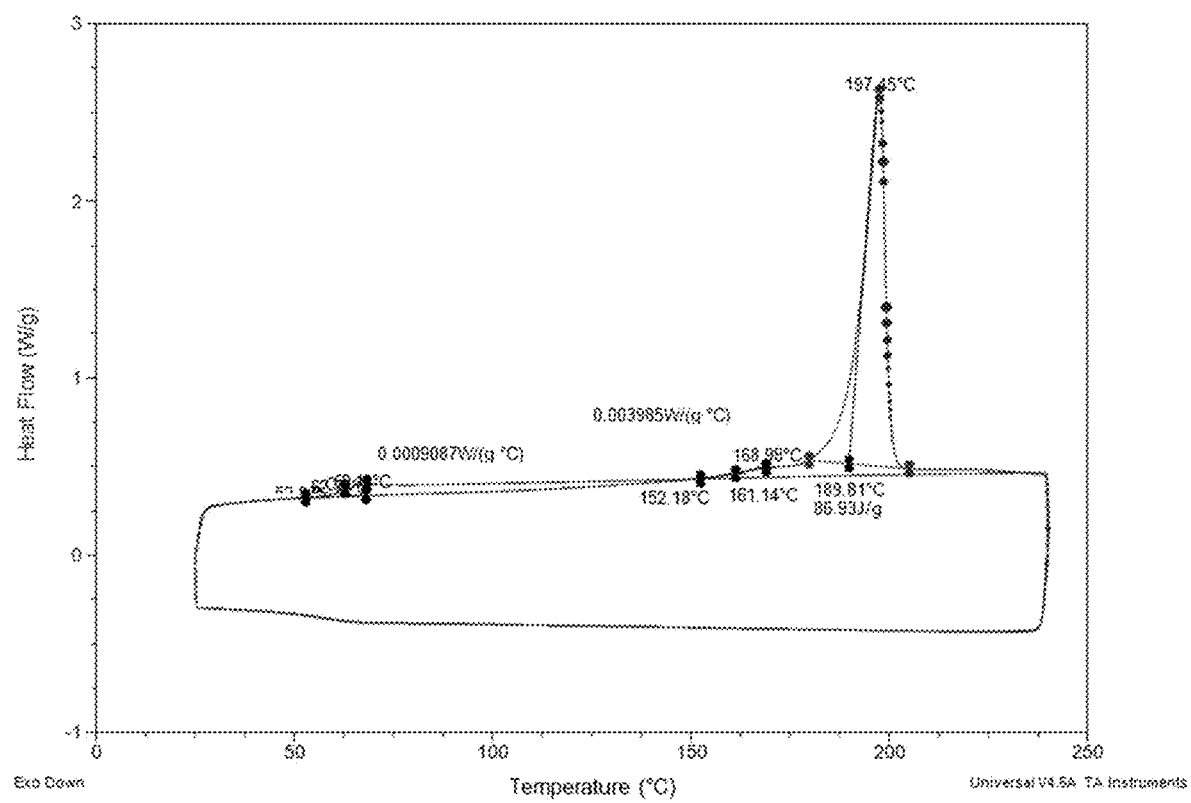
FIG. 33. DSC trace of $L_4$.
Figure 34:
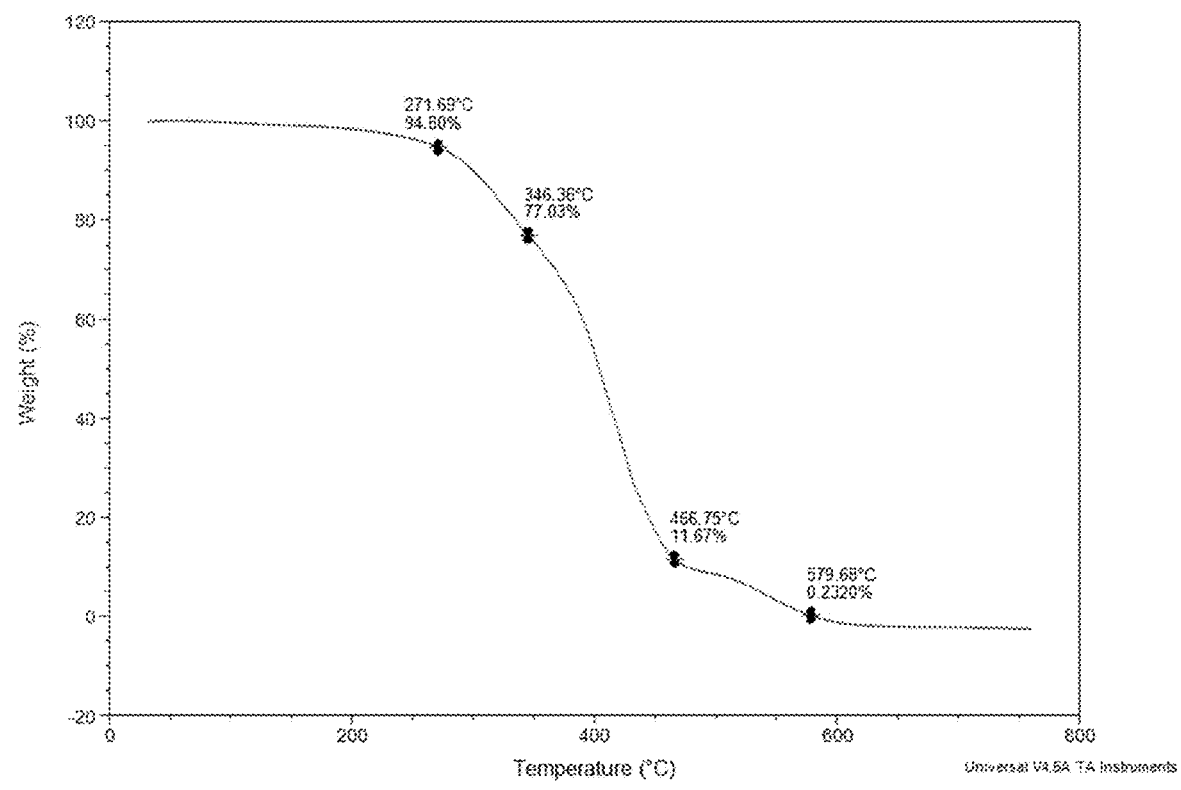
FIG. 34. TGA data for $L_2$.
Figure 35:
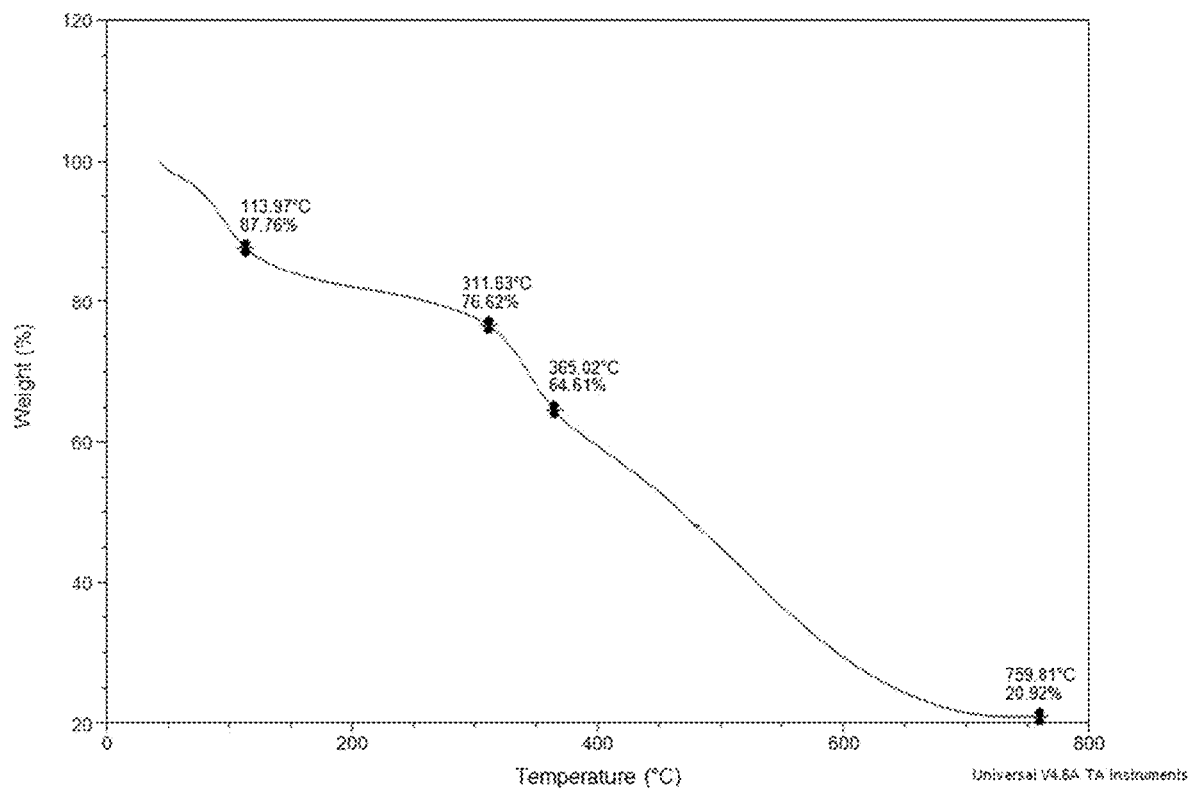
FIG. 35. TGA data for $L_2$-Zn.
Figure 36:
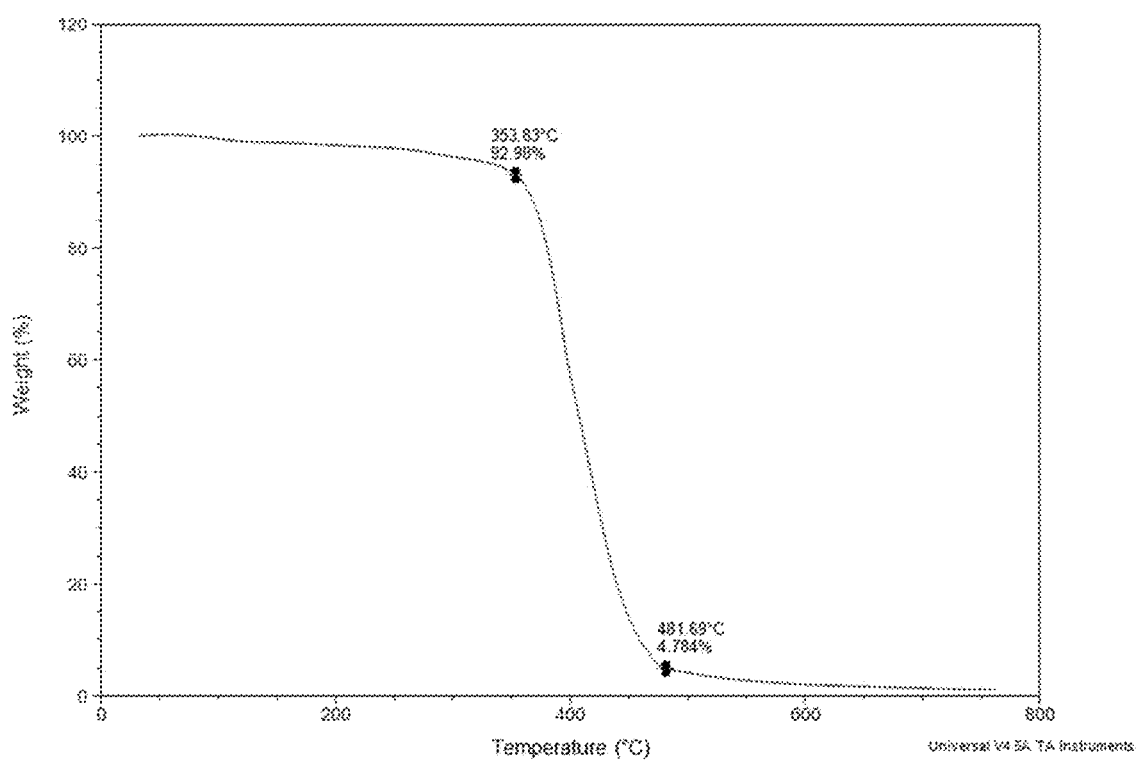
FIG. 36. TGA data for $L_2$PS.
Figure 37:
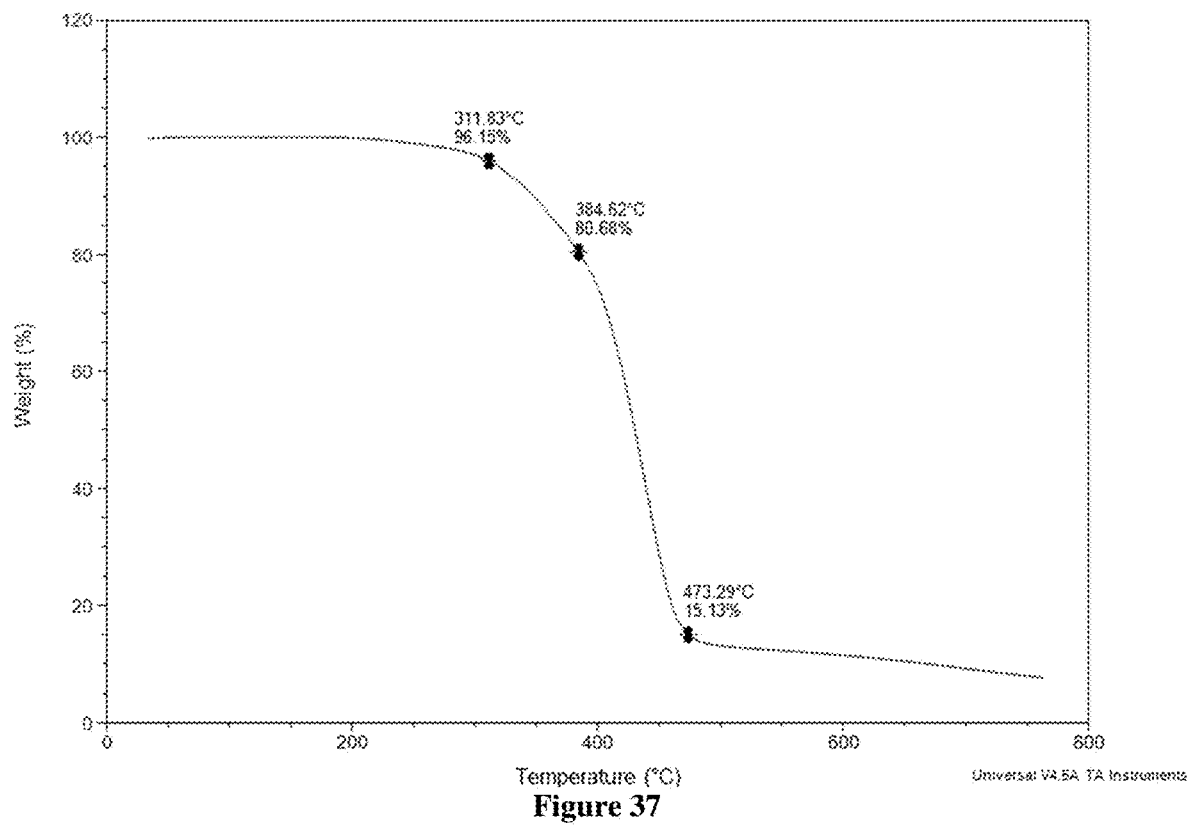
FIG. 37. TGA data for $L_4$.
Figure 38:
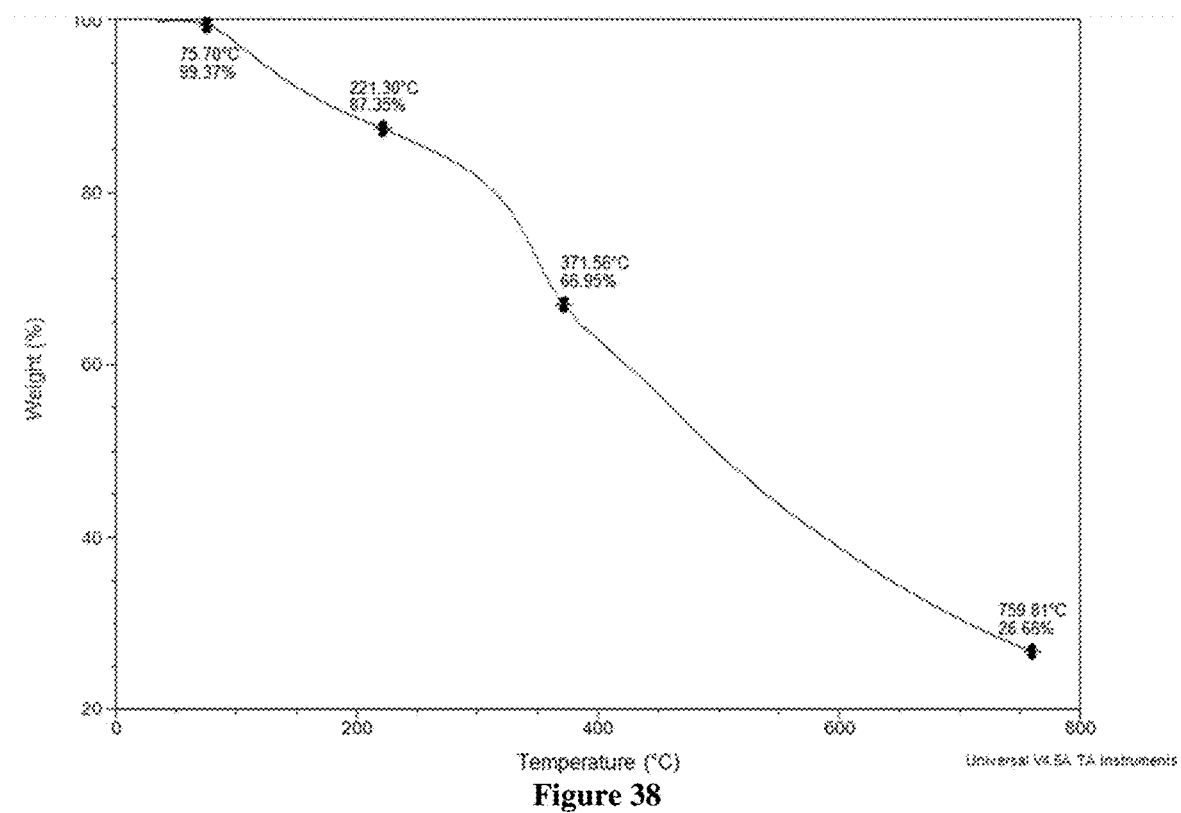
FIG. 38. TGA data for $L_4$-Zn.

360 mg (0.23 mmol, 1 eq.) L₄Et and 150 eq. of potassium hydroxide were dissolved in 8 mL DMF. 3 mL of water were added and the mixture was heated at 80° C. for 8 hrs. The reaction was acidified with 1 M HCl to a pH of 2. The product crashed out of solution as a white solid and was centrifuged at 6000 rpm. The solvent was decanted. The sample was washed with water three times and dried under vacuum overnight to give 69% yield. $^1$H (d₆-DMSO, 400 Hz): 1.23-1.45 (34H, m), 1.61-1.73 (14H, m), 3.37 (2H, t), 3.93-4.02 (14H, m), 5.15 (2H, s), 7.24-7.34 (8H, m), 7.35-7.41 (3H, m), 7.45-7.49 (2H, m), 12.90 (8H, s). $^{13}$C (d₆-DMSO, 400 Hz): 25.28, 25.44, 28.69, 28.76, 28.92, 32.52, 60.70, 69.15, 70.48, 115.50, 116.03, 125.46, 125.64, 127.16, 127.64, 128.30, 137.02, 149.96, 150.43, 150.72, 166.77, 166.83. HRMS: calcd. for $C_{71}H_{88}NaO_{25}$ [M+Na]⁺, most abundant m/z=1363.5507; found, 1363.5522. See FIG. 33.

Preparation of Compound L₄EtOH

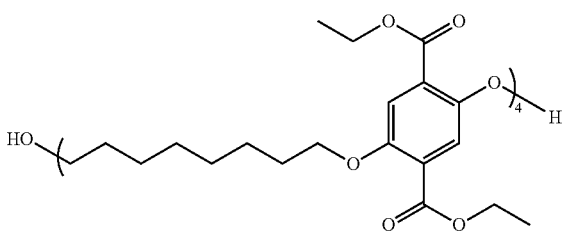

A solution of L₄Et 3.1 g (2.0 mmol, 1.0 eq.) and palladium on carbon 0.21 g (2.0 mmol, 1.0 eq.) in 240 mL of 50:50 mixture of toluene and ethanol was sparged with nitrogen for 10 minutes. The solution was then sparged with hydrogen for 5 minutes and then stirred under hydrogen atmosphere for 18 h at 6° C. The reaction was filtered to remove the catalyst, concentrated, and subject to silica gel chromatography (0 to 8% methanol in DCM, eluting at 6%). L₄EtOH was isolated in 96% yield. 1H (CDCl₃, 400 Hz): 1.32-1.58 (58H, m), 1.74-1.84 (14H, m), 3.63 (2H, t), 3.94-4.04 (14H, m), 4.31-4.39 (14H, m), 4.42 (2H, q), 7.29 (1H, s), 7.33 (6H, s), 7.34 (1H, s), 10.36 (1H, s). $^{13}$C (CDCl₃, 400 Hz): 14.32, 14.38, 25.73, 25.94, 26.03, 29.33, 29.37, 29.42, 32.83. 61.37, 61.42, 61.99, 63.08, 69.90, 70.00, 77.33, 113.78, 114.86, 116.66, 119.86, 124.77, 128.98, 150.28, 151.80, 155.13, 165.63, 166.15, 116.28, 116.20, 269.36. HRMS: calcd. for $C_{80}H_{114}NaO_{25}$ [M+Na]⁺, most abundant m/z=1497.7541; found, 1497.7594.

Preparation of Compound L₂Et-alkyne

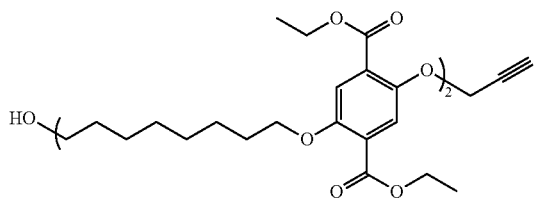

0.11 g (0.83 mmol, 1.5 eq.) of potassium carbonate, 0.41 g (0.55 mmol, 1.0 eq.) of L₂EtOH and 0.077 mL (0.72 mmol, 1.3 eq.) of propargyl bromide were dissolved in 5.5 mL of acetone and 2.75 mL ethanol. The mixture was heated at 80° C. for 14 h in a sealed pressure vessel. The reaction was then cooled. 50 mL of DI water were added and the reaction was neutralized with 1 M HCl and then extracted with dichloromethane three times. The extracts were dried with Na₂SO₄, filtered, and concentrated under vacuum. The solid collected was dissolved in a minimal amount of DCM and purified by silica gel chromatography (0 to 80% ethyl acetate in hexanes, eluting at 25%). The product was obtained in 89% yield. $^1$H (CDCl₃, 400 Hz): 1.29-1.59 (30H, m), 1.74-1.85 (6H, m), 2.52 (1H, t), 3.62 (2H, t), 3.95-4.03 (6H, mt), 4.31-4.40 (8H, m), 4.72 (2H, d), 7.32 (2H, s), 7.34 (1H, s), 7.52 (1H, s). $^{13}$C (CDCl₃, 400 Hz): 14.35, 14.49, 25.74, 25.95, 26.02, 29.34, 29.40, 32.84, 58.60, 61.39, 61.41, 61.59, 63.07, 69.78, 69.91, 76.15, 78.32, 116.36, 116.69, 119.44, 124.71, 124.81, 126.10, 150.13, 151.82, 153.08, 165.55, 165.77, 166.20. HRMS: calcd. for $C_{43}H_{60}NaO_{13}$ [M+Na]⁺, most abundant m/z=807.3926; found, 807.3906.

Preparation of Compound L₄Et-alkyne

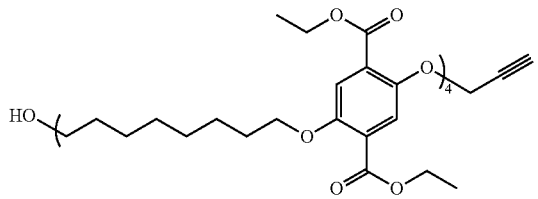

75 mg (0.54 mmol, 1.5 eq.) of potassium carbonate, 0.53 g (0.36 mmol, 1.0 eq.) of L₄EtOH and 0.050 mL (0.47 mmol, 1.3 eq.) of propargyl bromide were dissolved in 3.6 mL of acetone and 1.2 mL of ethanol. The mixture was heated at 80° C. for 14 h in a sealed pressure vessel. The reaction was then cooled. 30 mL of DI water were added and the reaction was neutralized with 1 M HCl and then extracted with dichloromethane three times. The extracts were dried with Na₂SO₄, filtered and concentrated under vacuum. The solid collected was dissolved in a minimal amount of DCM and purified by silica gel chromatography (0 to 6% methanol in DCM, 3%) to provide the product in 86% yield. 1H (CDCl3, 400 Hz): 1.37-1.44 (40H, m), 1.47-1.55 (16H, m), 1.78-1.88 (16H, m), 2.55 (1H, t), 3.67 (2H, dt), 4.03 (14H, t), 3.36-3.44 (16H, m), 4.76 (2H, d), 7.36 (1H, s), 7.39 (1H, s), 7.57 (1H, s). $^{13}$C (CDCl3, 400 Hz): 14.37, 14.40, 25.76, 25.97, 26.06, 29.36, 29.41, 29.45, 29.81, 32.87, 58.62, 61.39, 61.59, 63.11, 69.80, 69.96, 76.15, 116.39, 116.72, 119.47, 124.74, 124.84, 126.12, 150.15, 121.84, 161.56, 165.57, 165.57, 165.78, 166.20. HRMS: calcd. for $C_{83}H_{116}NaO_{25}$ [M+Na]⁺, most abundant m/z=1535.7698; found, 1535.7708.

Preparation of Compound L₂PS

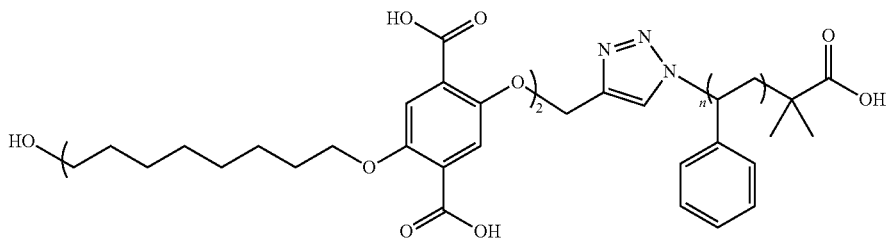

Figure 32:
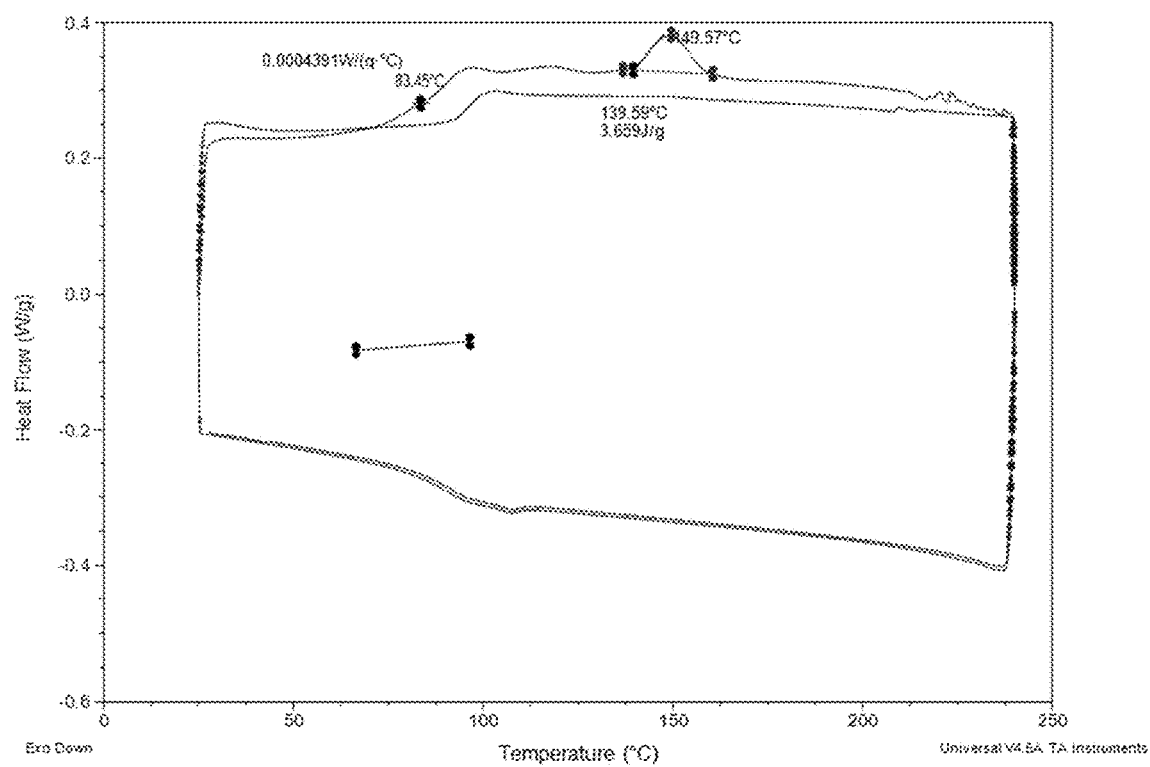
FIG. 32. DSC trace of $L_2$PS.

This reaction was set up in a nitrogen atmosphere glovebox. 0.13 g (0.17 mmol, 1 eq.) of L₂Etyne and 0.61 mg of polystyrene azide (0.16 mmol, 0.95 eq) were dissolved in 5 mL of THF. 0.005 mL (0.019 mmol, 0.11 eq) of Me₆Tren was added to 2.4 mg (0.017 mmol, 0.1 eq.) of CuBr dissolved in 1 mL of THF (prepared through iterative dilution) and added to the polystyrene mixture. The reaction was stirred at RT for 12 hrs and then concentrated. The mixture was purified by column chromatography (0-10% Methanol in DCM, eluting at 8%). The concentrated material was dissolved in 11 mL of DMSO and 100 eq. KOH were added. A few drops of water were added (the material precipitates if too much water is added) and was heated at 80° C. for 8 hours. The reaction was acidified with 1 M HCl to a pH of 2. The product precipitated from solution as a white solid and was centrifuged at 6000 rpm. The solvent was decanted. The sample was washed, centrifuged after each wash, with water three times and with acetone one time, and dried under vacuum overnight. $^1$H (CDCl3, 500 Hz): 0.82-0.90 (4H, m), 0.91-1.03 (11H, m), 1.18-1.97 (356H, m, *H₂O present), 2.00-2.11 (b), 3.6-3.70 (2H, t), 4.20-4.33 (6H, m), 5.24-5.35 (2H, b), 6.24-7.24 (161H, m, *overlap with CDCl3), 7.61 (1H, s), 7.72-7.77 (m, 1H), 7.81-7.87 (3H, s). Note peaks shift and broaden significantly depending on solvent used and solvent contamination. Carboxylic acid protons only visible in DMF. See FIG. 32.

Preparation of Compound L₄PS

Figure 39:
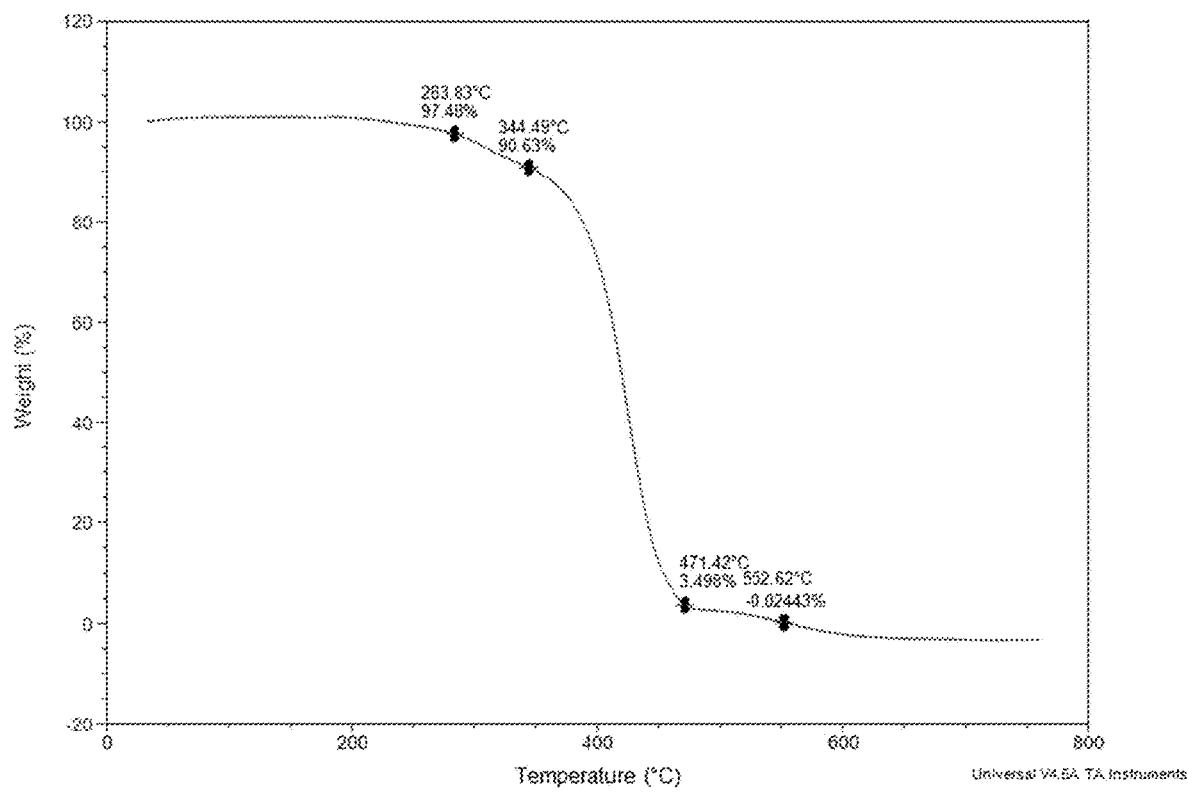
FIG. 39. TGA data for $L_4$PS.

This reaction was set up in a nitrogen atmosphere glovebox. 0.20 g (0.14 mmol, 1 eq.) of L₄Etyne and 0.49 mg of polystyrene azide (0.13 mmol, 0.95 eq) were dissolved in 5 mL of THF. 0.004 mL (0.015 mmol, 0.11 eq) of Me₆Tren was added to 1.9 mg (0.014 mmol, 0.1 eq.) of CuBr dissolved in 1 mL of THF (prepared via iterative dilution) and added to the polystyrene mixture. The reaction was stirred at RT for 12 hrs and then concentrated. The mixture was purified by silica gel chromatography (0-10% Methanol in DCM, eluting at 8%). The concentrated material was dissolved in 4.0 mL of DMF and 100 eq. KOH were added. A few drops of water were added (the material precipitates if too much water is added) and was heated at 80° C. for 8 hours. The reaction was acidified with 1 M HCl to a pH of 2. The product precipitated as a white solid and was centrifuged at 6000 rpm. The solvent was decanted. The sample was washed, centrifuging after each wash, with water three times and with acetone one time, and dried under vacuum overnight. $^1$H (CDCl₃, 400 Hz): 0.82-0.93 (12H, m), 0.93-1.00 (10H, m), 1.16-1.99 (257H, m, *H₂O present), 2.00-2.11 (5H, m), 2.11-2.26 (2H, m), 3.62-3.70 (2H, t), 4.20-4.33 (14H, m), 5.23-5.34 (2H, m), 6.27-7.21 (285H, m, *overlap with CDCl₃), 7.44 (1H, s), 7.71-7.79 (m, 2H), 7.81-7.86 (6H, s). Note peaks shift and broaden significantly depending on solvent used. Carboxylic acid protons only visible in DMF. See FIG. 39.

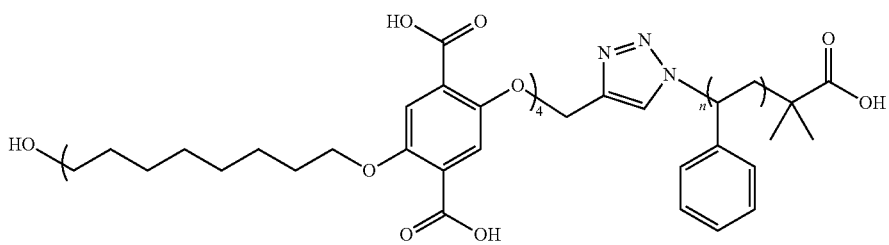

Preparation of Compound L$_4$Bn

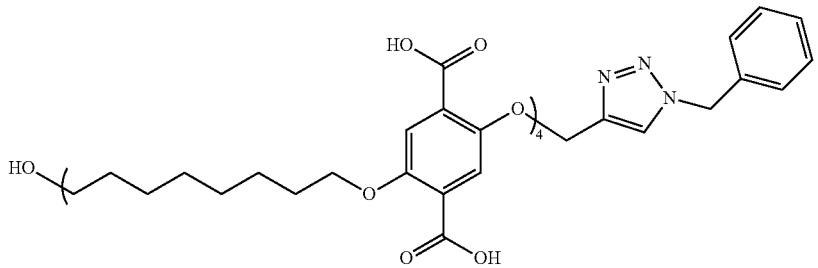

L$_4$Bn was synthesized using the same conditions as those for L$_4$PS except benzyl azide was used instead of polystyrene azide. $^1$H (d6-DMSO 3, 400 Hz): 1.23-147 (34H, m), 1.63-1.72 (14H, m), 3.37 (2H, t), 3.97 (14H, t), 5.16 (2H, s), 5.61 (2H, s), 7.24-7.40 (12H, m), 7.44 (1H, s), 8.18 (1H, s), 12.89 (8H, s). $^{13}$C (d$_6$-DMSO, 400 Hz): 25.29, 25.45, 28.70, 28.78, 28.93, 32.53, 52.79, 60.71, 69.16, 115.52, 125.46, 125.53, 127.84, 128.11, 128.76, 150.43, 166.84. HRMS: calcd. for C$_{74}$H$_{91}$N$_3$NaO$_{25}$ [M+Na]$^+$, most abundant m/z=1444.5834; found, 1444.5811.

Characterization of BCPMONs of Formula (C)

Next, small- and wide-angle X-ray scattering (SAXS and WAXS, respectively) was used to characterize these materials. For polyMOF L$_4$-Zn, the SAXS region was devoid of peaks suggesting a lack of nanoscale order. In contrast, the WAXS region of L$_4$-Zn displayed several sharp peaks indicative of crystallinity. The SAXS/WAXS curves for BCP L$_4$PS displayed the opposite pattern: no sharp peaks were observed in the WAXS region while a broad peak was observed in the SAXS region that corresponded to a domain spacing (d) of 9.85 nm. BCP assembly is driven by the Flory-Huggins interaction parameter, $\chi$, and the degree of polymerization, N.[2,46,47] Stronger phase segregation occurs when $\chi$N is large. Though x is unknown for L$_4$PS, N is low; therefore, $\chi$N is likely small, which may explain why the SAXS peak is broad and relatively weak for this BCP.

Figure 21:
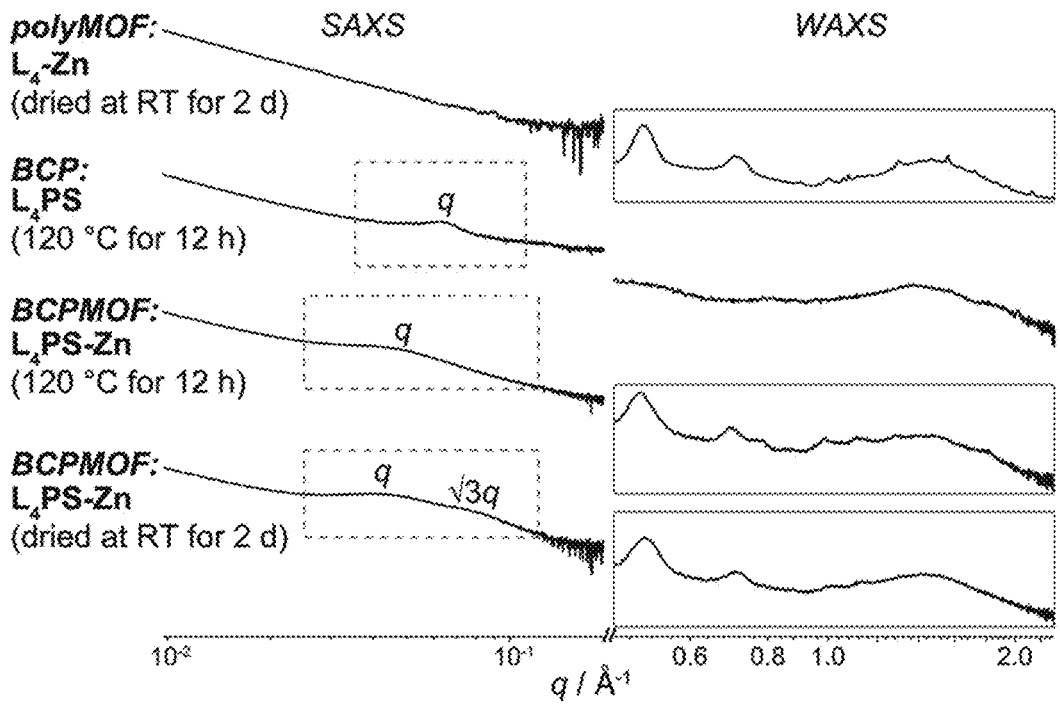
FIG. 21. SAXS and WAXS data for BCPMON $L_4$PS—Zn, BCP $L_4$PS, and polyMOF $L_4$-Zn.
Figure 26:
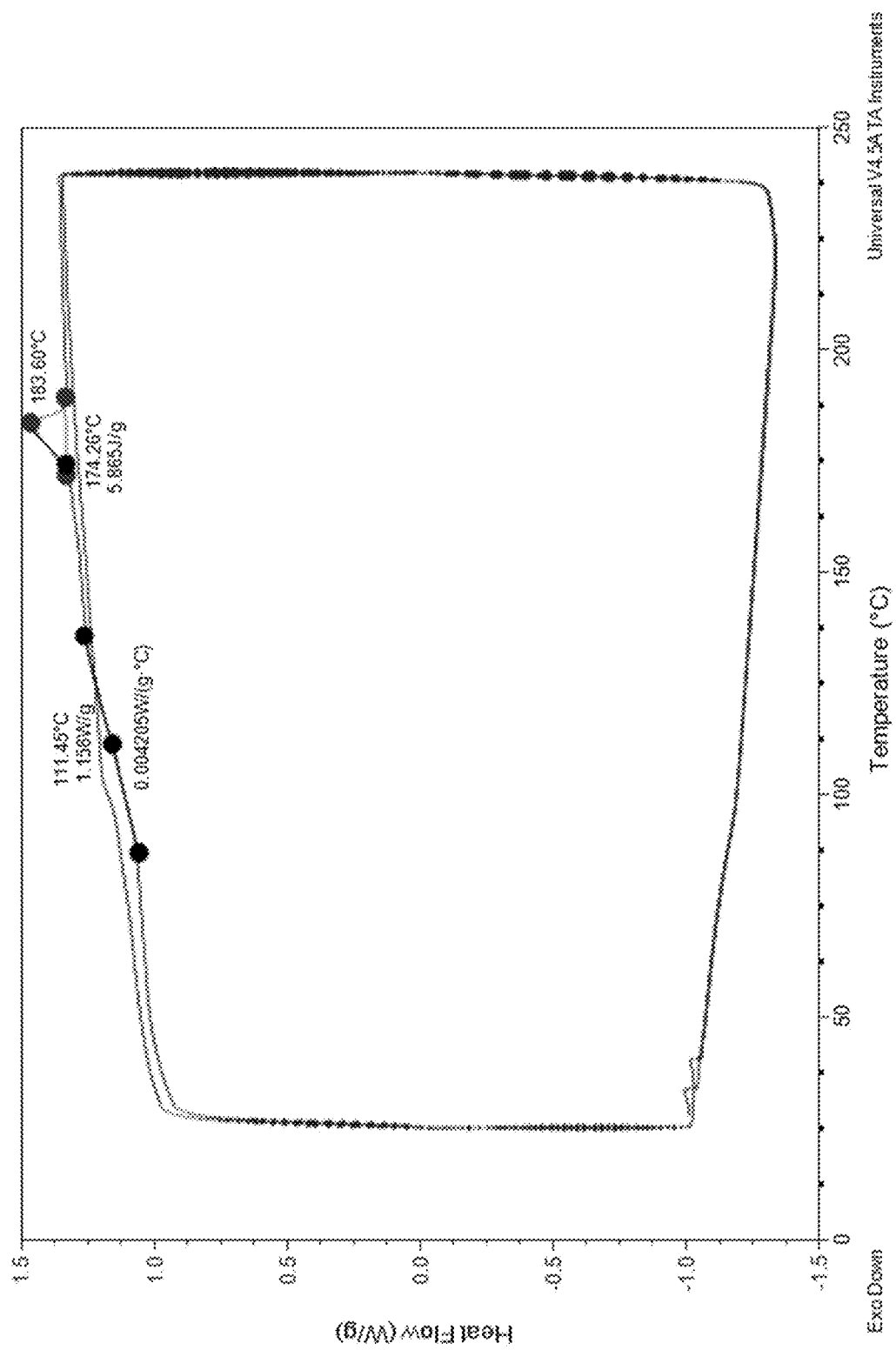
FIG. 26. DSC data for $L_4$PS.

BCPMON L$_4$PS—Zn displayed broad peaks in the SAXS region and sharp peaks in the WAXS region (FIG. 21), suggesting that this material contains a combination of distinct PS and polyMOF domains as well as polyMOF crystallinity. The SAXS pattern and domain spacing depended on the sample preparation. When L$_4$PS—Zn was annealed at 120° C. for 12 h (above the T$_g$ of L$_4$PS as determined by differential scanning calorimetry, FIG. 26), the SAXS curve displayed a single peak with a q-value of 0.040 Å$^{-1}$, which corresponds to a d of 15.7 nm. When L$_4$PS—Zn was dried under vacuum at RT for 2 d, two broad peaks were found in the SAXS curve. The principle peak had a d of 16.1 nm, and the q-ratio of the two peaks was q$_2$/q$_1$=1:√3, which corresponds to either a hexagonalcylinder or body-centered cubic morphology. The larger d values for L$_4$PS—Zn relative to L$_4$PS reflect a combination of stretching of the PS chains at the dense polymer-polyMOF interface and an increase in the size of the polyMOF regions relative to L$_4$PS. Though L$_4$PS has exactly four MOF-forming ligands per chain, the polyMOF domains can incorporate several L$_4$PS molecules. Though there may be a minimum length of the polyMOF ligand block required for BCPMON formation (L$_2$PS did not yield a polyMOF), there is no reason to suspect that the polyMOF domain size within a BCPMON should be uniform or directly determined by the length of the polyMOF ligand block. Thus, the broadness of the SAXS peaks for L$_4$PS—Zn likely reflects size dispersity of the polyMOF domains.[48,49] In addition, as BCPMON formation is driven by MOF crystallization, the factors affecting BCP phase segregation (i.e., $\chi$N) are not necessarily relevant; the weak segregation of parent ligand L$_4$PS does not indicate that the BCPMON should also have weak segregation. Nevertheless, the data conclusively validate the proposed BCPMON design: BCPs with a polyMOF-forming block and an amorphous polymer block can generate crystalline BCPMONs with both nano- and angstrom-scale domain spacings.

Figure 22A:
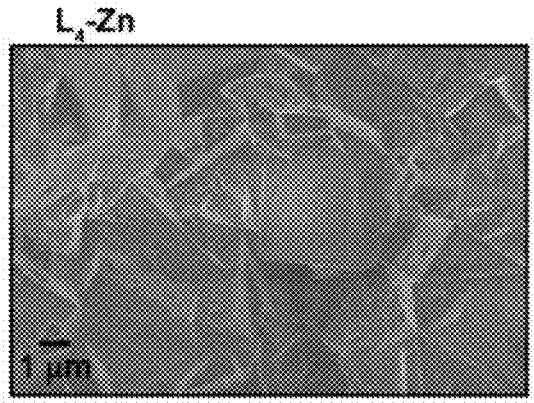
FIGS. 22A to 22D.
Figure 22B:
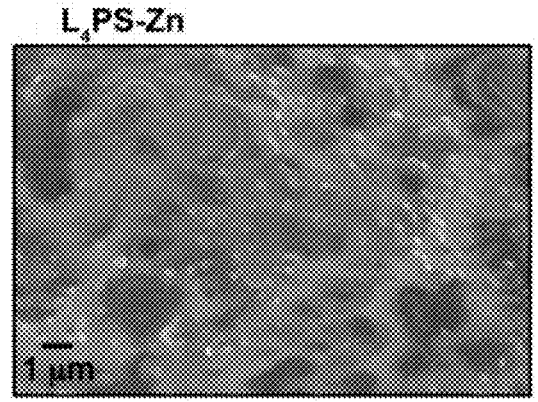
Figure 22C:
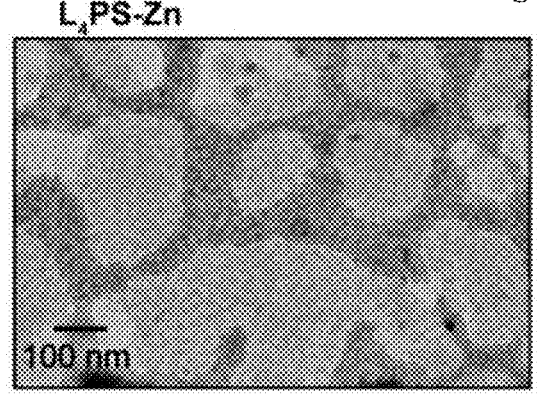
Figure 22D:
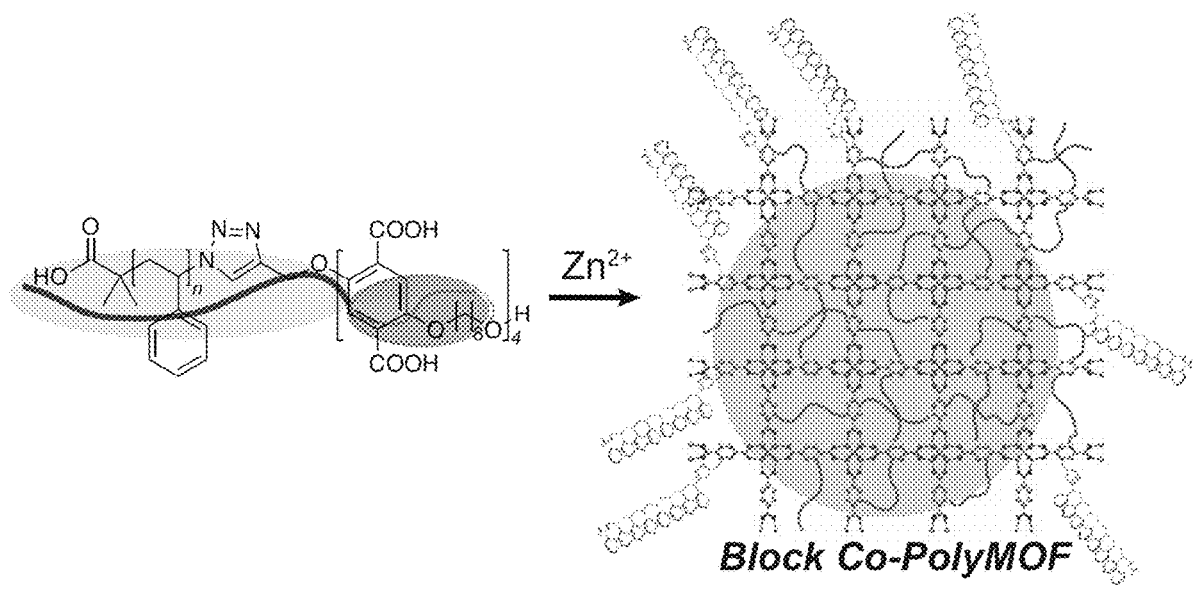

These materials were further characterized using scanning electron microscopy (SEM) and transmission electron microscopy (TEM). SEM images of polyMOF L$_4$-Zn revealed oblong, faceted, and inter-grown crystalline superstructures measuring tens of microns in size (FIG. 22A). SEM images of BCPMON L$_4$PS—Zn revealed a thin polymer film with de-wetted regions due to solvent evaporation (FIG. 22B); no crystals are observed. These data suggest that the BCPMON ligand structure limits the growth of polyMOF crystals to nanoscale dimensions, which is reasonable given that each ligand possesses a PS chain that must be accommodated within or on the surface of the polyMOF domain. TEM imaging of L$_4$PS—Zn stained with RuO$_4$ (a positive stain for PS) revealed a multilayer structure with evidence of nanoscale ordering. Considering all of the above data, it is proposed that the BCPMON L$_4$PS—Zn herein has the structure shown schematically in FIG. 22D, which features polyMOF domains embedded within a PS matrix.

Figure 27:
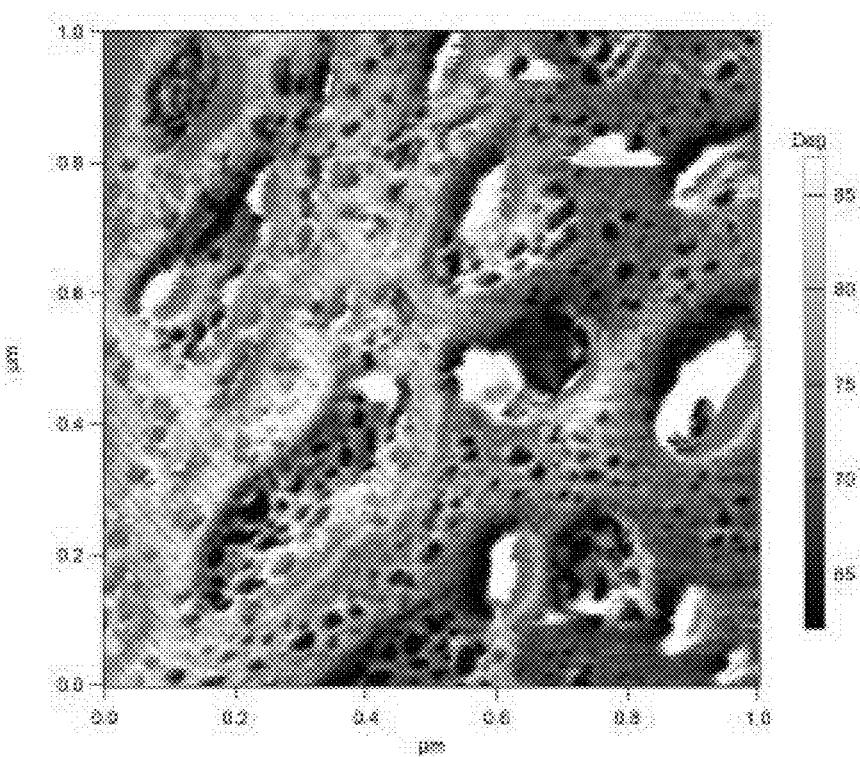
FIG. 27. AFM image of $L_4$PS—Zn annealed at 120° C. for 12 hours.
Figure 28:
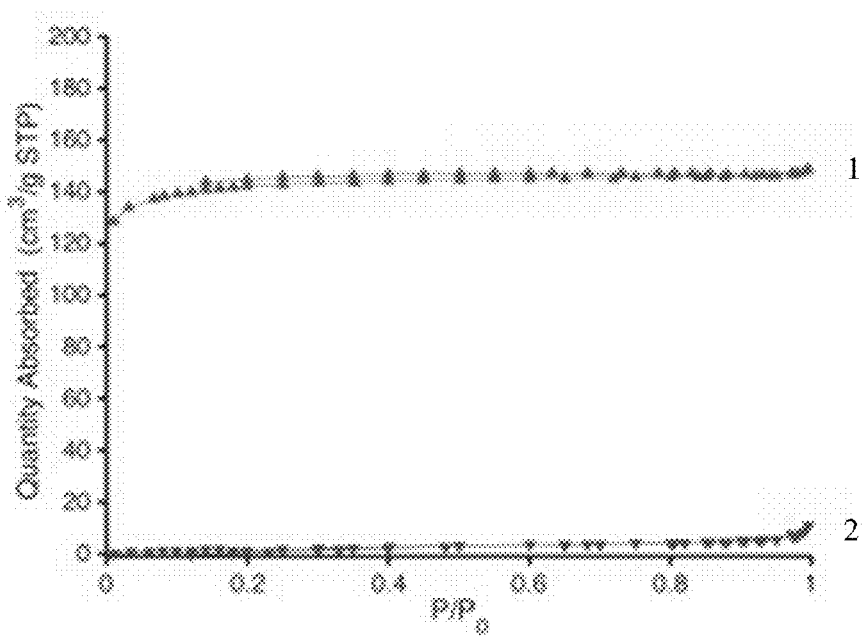
FIG. 28. $N_2$ sorption isotherms for $L_4$-Zn (1) and $L_4$PS—Zn (2). Note: we obtained reasonable surface area not controlling water content which was found to be the optimal synthetic protocols for MOF-5's gas storage (S. S. Kaye, A. Dailly, O. M. Yaghi and J. R. Long J. Am. Chem. Soc., 2007, 129, 14176-14177). The low value for $L_4$PS—Zn is not unexpected due to the high content of nonporous polymer and high solubility in organic solvents which made solvent exchange difficult. The activation at 160° C., above the $T_g$ of polystyrene, could also lead to incorporation of polymers in to the polyMOF pores.
Figure 29:
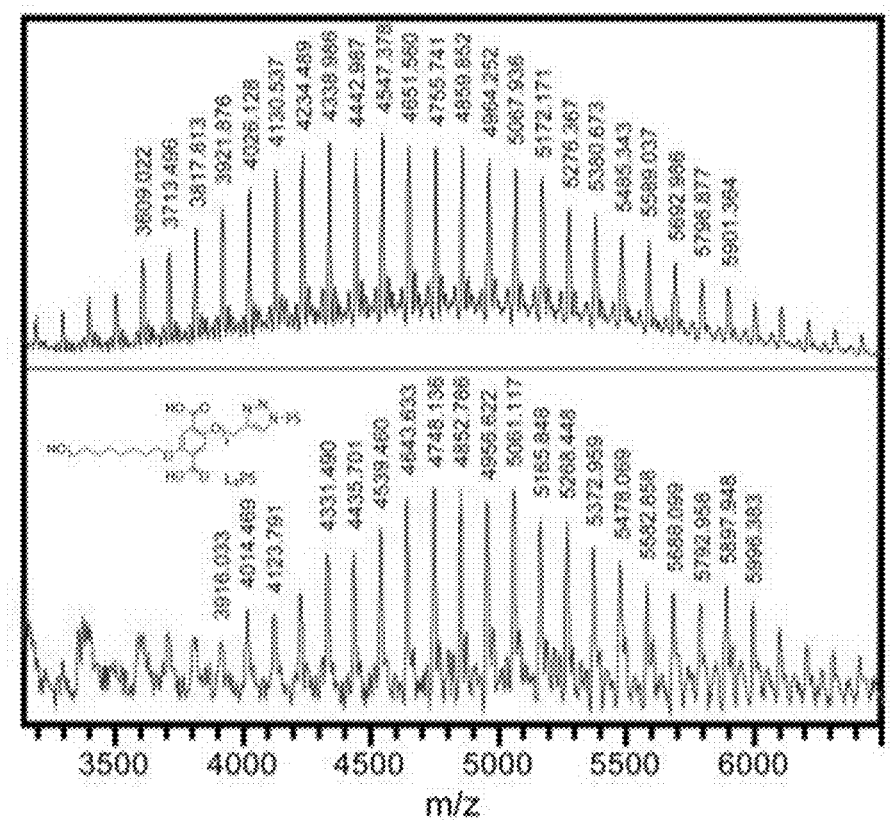
FIG. 29. MALDI-TOF spectra in negative ion mode. Top trace is $L_2$PS and bottom trace is $L_4$PS. Within a 0.1% margin of error, calculated m/z is 4445.53 for $L_2$PS and 5063.79 for $L_4$PS (35 units of styrene).
Figure 30:
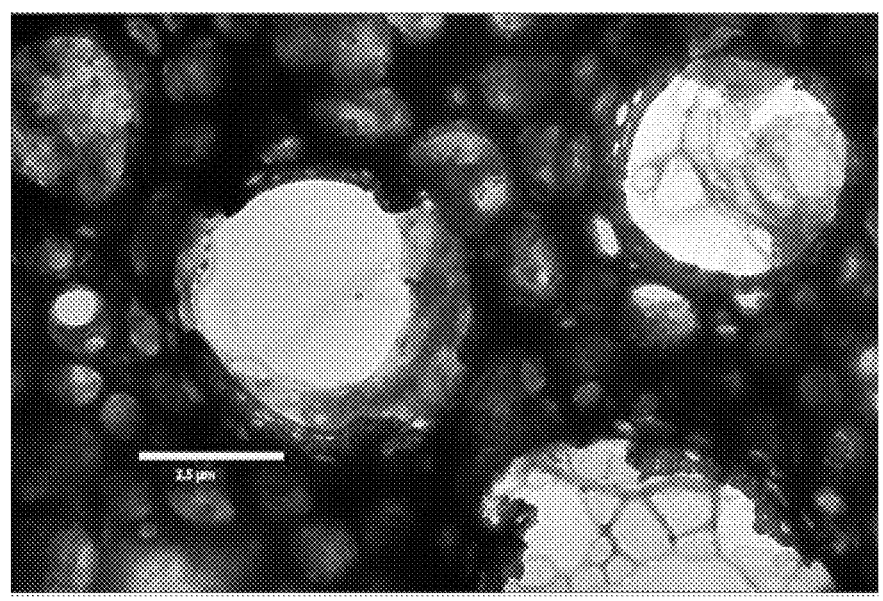
FIG. 30. TEM image of $L_4$PS—Zn annealed at 120° C. for 12 hours.

Atomic force microscopy (AFM) was used to study the surface morphology of L$_4$PS—Zn. AFM images could not be obtained for L$_4$PS—Zn films dried at room temperature due to tip contamination by the very soft films; however, when the films were dried at 120° C. for 2 h, AFM phase images revealed the presence of large and small pores with irregular oval shapes (FIG. 27). The large pores are likely the results of de-wetting, while the smaller pores, which ranged from 10-25 nm in size, may correspond to phase-segregated PS and polyMOF domains. Lastly, the surface areas of these materials were studied using N$_2$ adsorption methods. The BET and Langmuir surface areas of L$_4$-Zn were 476 m$^2$ g$^{-1}$ and 630 m$^2$ g$^{-1}$, respectively, while the BET and Langmuir surface areas of L$_4$PS—Zn were two orders of magnitude lower: 5.68 m$^2$ g$^{-1}$ and 8.48 m$^2$ g$^{-1}$, respectively (FIG. 28). The observation of the porosity is encouraging, and suggests that these materials could find utility in gas separations. Furthermore, both L$_4$-Zn and L$_4$PS—Zn could be digested and the ligands re-used for polyMOF or BCPMON synthesis, respectively, with no loss in surface area, suggesting potential recyclability of these materials.

CONCLUSIONS

Herein, the iterative exponential growth synthesis of uniform oligomeric ligands for polyMOFs that contain an end-functionality (an alkyne) for further structural diversification has been demonstrated. Coupling of a tetrameric ligand to azide-terminated polystyrene followed by exposure to Zn ions under traditional conditions for the formation of MOF-5 yielded a BCPMOF. This work represents the first demonstration that it is possible to generate a crystalline polyMOF-amorphous polymer hybrid material from a single diblock copolymer. As a result, BCPMONs represent a new composite material that possesses the processability of polymers, enhanced stability towards ambient conditions compared to the parent MOF-5 and polyMOFs, and gas absorption capacity. The BCPMONs may have other advantageous properties, such as robust mechanical properties, high surface areas, and/or tunable, well-defined domain sizes.

REFERENCES (1) M. C. Orilall and U. Wiesner, Chem. Soc. Rev., 2011, 40, 520-535.
(2) F. S. Bates, M. A. Hillmyer, T. P. Lodge, C. M. Bates, K. T. Delaney and G. H. Fredrickson, Science, 2012, 336, 434-440.
(3) R. J. Kuppler, D. J. Timmons, Q. R. Fang, J. R. Li, T. A. Makal, M. D. Young, D. Q. Yuan, D. Zhao, W. J. Zhuang and H. C. Zhou, Coord. Chem. Rev., 2009, 253, 3042-3066.
(4) T. R. Cook, Y. R. Zheng and P. J. Stang, Chem. Rev., 2013, 113, 734-777.
(5) S. Leininger, B. Olenyuk and P. J. Stang, Chem. Rev., 2000, 100, 853-908.
(6) H. Furukawa, K. E. Cordova, M. O'Keeffe and O. M. Yaghi, Science, 2013, 341, 1230444.
(7) H. C. Zhou, J. R. Long and O. M. Yaghi, Chem. Rev., 2012, 112, 673-674.
(8) A. J. McConnell, C. S. Wood, P. P. Neelakandan and J. R. Nitschke, Chem. Rev., 2015, 115, 7729-7793.
(9) Q.-F. Sun, J. Iwasa, D. Ogawa, Y. Ishido, S. Sato, T. Ozeki, Y. Sei, K. Yamaguchi and M. Fujita, Science, 2010, 328, 1144-1147.
(10) T. Uemura, N. Yanai and S. Kitagawa, Chem. Soc. Rev., 2009, 38, 1228-1236.
(11) J. Zhang and C.-Y. Su, Coord. Chem. Rev., 2013, 257, 1373-1408.
(12) H. Li and L. Wu, Soft Matter, 2014, 10, 9038-9053.
(13) L. L. Yang, X. X. Tan, Z. Q. Wang and X. Zhang, Chem. Rev., 2015, 115, 7196-7239.
(14) Y. Y. Zhang, X. Feng, S. Yuan, J. W. Zhou and B. Wang, Inorg. Chem. Front., 2016, 3, 896-909.
(15) X. W. Liu, T. J. Sun, J. L. Hu and S. D. Wang, J. Mater. Chem. A, 2016, 4, 3584-3616.
(16) J. B. Beck and S. J. Rowan, J. Am. Chem. Soc., 2003, 125, 13922-13923.
(17) J. M. Pollino, K. P. Nair, L. P. Stubbs, J. Adams and M. Weck, Tetrahedron, 2004, 60, 7205-7215.
(18) J. Reboul, S. Furukawa, N. Horike, M. Tsotsalas, K. Hirai, H. Uehara, M. Kondo, N. Louvain, O. Sakata and S. Kitagawa, Nat. Mater., 2012, 11, 717-723.
(19) C. A. Allen, J. A. Boissonnault, J. Cirera, R. Gulland, F. Paesani and S. M. Cohen, Chem. Commun., 2013, 49, 3200-3202.
(20) X. Yan, S. Li, J. B. Pollock, T. R. Cook, J. Chen, Y. Zhang, X. Ji, Y. Yu, F. Huang and P. J. Stang, Proc. Natl. Acad. Sci. U.S.A, 2013, 110, 15585-15590.
(21) X. Yan, S. Li, T. R. Cook, X. Ji, Y. Yao, J. B. Pollock, Y. Shi, G. Yu, J. Li, F. Huang and P. J. Stang, J. Am. Chem. Soc., 2013, 135, 14036-14039.
(22) C. A. Allen and S. M. Cohen, Inorg. Chem., 2014, 53, 7014-7019.
(23) Z. J. Zhang, H. T. H. Nguyen, S. A. Miller and S. M. Cohen, Angew. Chem., Int. Ed., 2015, 54, 6152-6157.
(24) J. A. Foster, R. M. Parker, A. M. Belenguer, N. Kishi, S. Sutton, C. Abell and J. R. Nitschke, J. Am. Chem. Soc., 2015, 137, 9722-9729.
(25) K. A. McDonald, J. I. Feldblyum, K. Koh, A. G. Wong-Foy and A. J. Matzger, Chem. Commun., 2015, 51, 11994-11996.
(26) K. Kawamoto, S. C. Grindy, J. Liu, N. Holten-Andersen and J. A. Johnson, ACS Macro Lett., 2015, 4, 458-461.
(27) A. V. Zhukhovitskiy, M. Z. Zhong, E. G. Keeler, V. K. Michaelis, J. E. P. Sun, M. J. A. Hore, D. J. Pochan, R. G. Griffin, A. P. Willard and J. A. Johnson, Nat. Chem., 2016, 8, 33-41.
(28) Y. Wang, M. Zhong, J. V. Park, A. V. Zhukhovitskiy, W. Shi and J. A. Johnson, J. Am. Chem. Soc., 2016, 138, 10708-10715.
(29) A. V. Zhukhovitskiy, J. Zhao, M. J. Zhong, E. G. Keeler, E. A. Alt, P. Teichen, R. G. Griffin, M. J. A. Hore, A. P. Willard and J. A. Johnson, Macromolecules, 2016, 49, 6896-6902.
(30) Y. Wang, Y. Gu, E. G. Keeler, J. V. Park, R. G. Griffin and J. A. Johnson, Angew. Chem., Int. Ed., 2017, 56, 188-192.
(31) N. D. H. Gamage, K. A. McDonald and A. J. Matzger, Angew. Chem., Int. Ed., 2016, 55, 12099-12103.
(32) R. Semino, N. A. Ramsahye, A. Ghoufi and G. Maurin, ACS Appl. Mater. Interfaces, 2016, 8, 809-819.
(33) C. Le Calvez, M. Zouboulaki, C. Petit, L. Peeva and N. Shirshova, RSC Adv., 2016, 6, 17314-17317.
(34) Z. J. Zhang, H. T. H. Nguyen, S. A. Miller, A. M. Ploskonka, J. B. DeCoste and S. M. Cohen, J. Am. Chem. Soc., 2016, 138, 920-925.
(35) Z.-Y. Li, Y. Zhang, C.-W. Zhang, L.-J. Chen, C. Wang, H. Tan, Y. Yu, X. Li and H.-B. Yang, J. Am. Chem. Soc., 2014, 136, 8577-8589.
(36) T. Rodenas, I. Luz, G. Prieto, B. Seoane, H. Miro, A. Corma, F. Kapteijn, F. X. L. I. Xamena and J. Gascon, Nat. Mater., 2015, 14, 48-55.
(37) S. Binauld, D. Damiron, L. A. Connal, C. J. Hawker and E. Drockenmuller, Macromol. Rapid Commun., 2011, 32, 147-168.
(38) J. C. Barnes, D. J. C. Ehrlich, A. X. Gao, F. A. Leibfarth, Y. Jiang, E. Zhou, T. F. Jamison and J. A. Johnson, Nat. Chem., 2015, 7, 810-815.
(39) F. A. Leibfarth, J. A. Johnson and T. F. Jamison, Proc. Natl. Acad. Sci. U.S.A, 2015, 112, 10617-10622.
(40) Y. Jiang, M. R. Golder, H. V.-T. Nguyen, Y. Wang, M. Zhong, J. C. Barnes, D. J. C. Ehrlich and J. A. Johnson, J. Am. Chem. Soc., 2016, 138, 9369-9372.
(41) J. F. Lutz, J. M. Lehn, E. W. Meijer and K. Matyjaszewski, Nat. Rev. Mater., 2016, 1, 1-14.
(42) K. Matyjaszewski and N. V. Tsarevsky, Nat. Chem., 2009, 1, 276-288.
(43) O. Altintas, T. Josse, M. Abbasi, J. De Winter, V. Trouillet, P. Gerbaux, M. Wilhelm and C. Barner-Kowollik, Polym. Chem., 2015, 6, 2854-2868.
(44) J. A. Johnson, M. G. Finn, J. T. Koberstein and N. J. Turro, Macromol. Rapid Commun., 2008, 29, 1052-1072.
(45) J. A. Johnson, D. R. Lewis, D. D. Diaz, M. G. Finn, J. T. Koberstein and N. J. Turro, J. Am. Chem. Soc., 2006, 128, 6564-6565.

(46) F. S. Bates and G. H. Fredrickson, Phys. Today, 1999, 52, 32-38.
(47) F. S. Bates, Science, 1991, 251, 898-905.
(48) N. A. Lynd and M. A. Hillmyer, Macromolecules, 2005, 38, 8803-8810.
(49) B. van Genabeek, B. F. M. de Waal, M. M. J. Gosens, L. M. Pitet, A. R. A. Palmans and E. W. Meijer, J. Am. Chem. Soc., 2016, 138, 4210-4218.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:

1. A (block co-polymer)-(metal organic nanostructure) conjugate (BCPMON) comprising:
   (i) y instances of a transition metal ion, wherein y is an integer between 1 and 1,000, inclusive;
   (ii) z instances of a ligand of Formula (C):

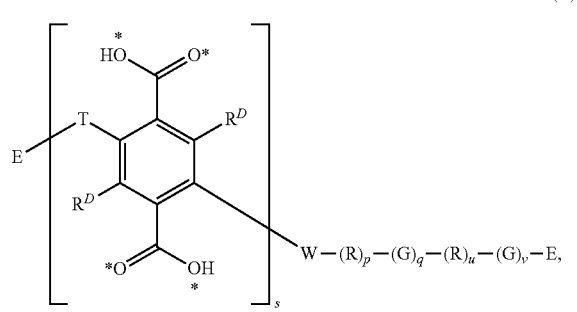

wherein:
   z is an integer between 2 and 200, inclusive;
   s is an integer between 2 and 10, inclusive;
   each instance of $R^D$ is hydrogen;
   each instance of T is independently —O—$(CH_2)_t$—O—, wherein t is an integer between 4 and 16, inclusive;
   each instance of W is substituted or unsubstituted, $C_{2-200}$ heteroalkylene, wherein one carbon atom or one heteroatom, of the substituted or unsubstituted, $C_{2-200}$ heteroalkylene, is replaced with

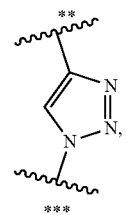

wherein —$(R)_p$-$(G)_q$-$(R)_u$-$(G)_v$-E is closer to the attachment point labeled with "*" than the attachment point labeled with "";
   each instance of R is independently a diradical of a first polymer, wherein:
      the glass transition temperature ($T_g$) of each instance of the first polymer is not higher than 20° C.; and
      the number-average molecular weight ($M_n$) of the first polymer is between 1,000 g/mol and 1,000,000 g/mol, inclusive;
   each instance of G is independently a diradical of a second polymer, wherein:
      the $T_g$ of each instance of the second polymer is higher than 20° C.; and the $M_n$ of the second polymer is between 300 g/mol and 100,000 g/mol, inclusive;
each instance of p is independently 0 or 1;
each instance of q is independently 0 or 1, provided that at least one instance of p and q is 1;
each instance of u is 0;
each instance of v is 0; and
each instance of E is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and
unless otherwise provided, each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;
wherein each instance of the transition metal ion and at least one instance of the ligand of Formula (C) form through one or more coordination bonds a coordination complex; and
wherein each of the coordination bonds is formed between an instance of the transition metal ion and an instance of the oxygen atom labeled with "*"; and
(iii) at least one instance of an anionic counterion;
wherein the BCPMON is electrically neutral.

2. The BCPMON of claim 1, wherein at least one instance of the coordination complex is substantively of the MOF-5 framework.

3. A composition comprising a BCPMON of claim 1; and optionally an excipient.

4. The composition of claim 3 further comprising an agent.

5. A method of delivering an agent to a cell, the method comprising contacting the cell with a composition of claim 4.

6. A kit comprising:
a BCPMON of claim 1; and
instructions for using the BCPMON.

7. A method of preparing a composition of claim 4 comprising complexing the ligand of Formula (C) with a salt comprising the transition metal ion, in the presence of an agent.

8. A method of preparing a BCPMON of claim 1 comprising complexing the ligand of Formula (C) with a salt comprising the transition metal ion.

9. The BCPMON of claim 1, wherein the transition metal ion is Zn(II).

10. The BCPMON of claim 1, wherein the transition metal ion is Cu(II) or Fe(III).

11. The BCPMON of claim 1, wherein y is an integer between 100 and 1,000, inclusive.

12. The BCPMON of claim 1, wherein z is an integer between 50 and 200, inclusive.

13. The BCPMON of claim 1, wherein s is 2, 3, 4, or 5.

14. The BCPMON of claim 1, wherein each instance of W is of the formula:

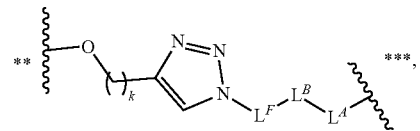

wherein:
each instance of k is independently an integer from 1 to 10, inclusive;
each instance of L$^F$ is independently substituted or unsubstituted, C$_{2-180}$ heteroalkylene;
each instance of -L$^B$-L$^A$- is independently —C(=O)O—, —OC(=O)—, —C(=O)NR$^E$—, or —NR$^E$C(=O)—, wherein each instance of R$^E$ is independently hydrogen, substituted or unsubstituted, C$_{1-6}$ alkyl, or a nitrogen protecting group; and
—(R)$_p$-(G)$_q$-(R)$_u$-(G)$_v$-E is closer to the attachment point labeled with "*" than the attachment point labeled with "".

15. The BCPMON of claim 1, wherein at least one instance of the first polymer is a poly(alkyl acrylate), poly(hydroxyalkyl acrylate), poly(haloalkyl acrylate), polymethacrylate, poly(alkyl methacrylate), poly(hydroxyalkyl methacrylate), poly(haloalkyl methacrylate), polydimethylsiloxane, polybutadiene, or polyisoprene.

16. The BCPMON of claim 1, wherein the number-average molecular weight of the first polymer is between 3,000 g/mol and 100,000 g/mol, inclusive.

17. The BCPMON of claim 1, wherein at least one instance of the second polymer is poly(alkyl acrylate), poly(hydroxyalkyl acrylate), poly(haloalkyl acrylate), polymethacrylate, poly(alkyl methacrylate), poly(hydroxyalkyl methacrylate), poly(haloalkyl methacrylate), polystyrene, or polyethylene.

18. The BCPMON of claim 1, wherein at least one instance of the second polymer is polystyrene.

19. The BCPMON of claim 1, wherein the number-average molecular weight of the second polymer is between 1,000 g/mol and 30,000 g/mol, inclusive.

20. The BCPMON of claim 1, wherein at least one instance of the metal organic nanostructure is in a square planar molecular geometry or pseudo square planar molecular geometry.

21. The BCPMON of claim 1, wherein at least one instance of the metal organic nanostructure has cuboctahedral symmetry.

22. A method of delivering an agent to a subject, the method comprising administering to the subject a composition of claim 4.

23. The BCPMON of claim 1, wherein s is 4.

24. The BCPMON of claim 1, wherein t is 8.

25. The BCPMON of claim 1, wherein each q is 1, and each p is 0.

26. The BCPMON of claim 1, wherein each p is 1, and each q is 0.

27. The BCPMON of claim 1, wherein each instance of W is of the formula:

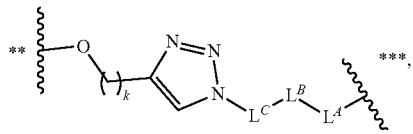

wherein:
  each instance of k is independently an integer from 1 to 10, inclusive;
  each instance of $L^C$ is independently substituted or unsubstituted, $C_{1-180}$ alkylene;
  each instance of -$L^B$-$L^A$- is independently —C(=O)O—, —OC(=O)—, —C(=O)$NR^E$—, or —$NR^E$C(=O)—, wherein each instance of $R^E$ is independently hydrogen, substituted or unsubstituted, $C_{1-6}$ alkyl, or a nitrogen protecting group; and
  —$(R)_p$-$(G)_q$-$(R)_u$-$(G)_v$-E is closer to the attachment point labeled with "*" than the attachment point labeled with "".

* * * * *